United States Patent
Wyrich et al.

(10) Patent No.: US 10,144,952 B2
(45) Date of Patent: *Dec. 4, 2018

(54) STABILIZATION AND ISOLATION OF EXTRACELLULAR NUCLEIC ACIDS

(71) Applicant: QIAGEN GmbH, Hilden (DE)

(72) Inventors: Ralf Wyrich, Hilden (DE); Thorsten Voss, Leverkusen (DE); Daniel Grölz, Hilden (DE)

(73) Assignee: QIAGEN GmbH, Hilden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/777,878

(22) PCT Filed: Mar. 18, 2014

(86) PCT No.: PCT/EP2014/000724
§ 371 (c)(1),
(2) Date: Sep. 17, 2015

(87) PCT Pub. No.: WO2014/146780
PCT Pub. Date: Sep. 25, 2014

(65) Prior Publication Data
US 2016/0281132 A1    Sep. 29, 2016

(30) Foreign Application Priority Data

Mar. 18, 2013  (EP) .................................... 13159834
Aug. 12, 2013  (EP) .................................... 13180086

(51) Int. Cl.
C12N 15/10      (2006.01)
C12Q 1/6806     (2018.01)

(52) U.S. Cl.
CPC ........... *C12Q 1/6806* (2013.01); *C12N 15/10* (2013.01)

(58) Field of Classification Search
None
See application file for complete search history.

(56) References Cited

U.S. PATENT DOCUMENTS

| | | | |
|---|---|---|---|
| 3,389,133 A | 6/1968 | Gutcho | |
| 3,903,179 A | 9/1975 | Bacha et al. | |
| 4,555,487 A * | 11/1985 | Yamada | C12N 1/20 435/129 |
| 4,938,961 A | 7/1990 | Collins et al. | |
| 5,459,073 A | 10/1995 | Ryan | |
| 5,460,797 A | 10/1995 | Ryan | |
| 5,705,628 A | 1/1998 | Hawkins | |
| 5,811,286 A * | 9/1998 | Fallon | C12N 9/78 435/228 |
| 5,860,397 A | 1/1999 | Schafer | |
| 5,898,071 A | 4/1999 | Hawkins | |
| 6,379,930 B1 | 4/2002 | Dattagupta et al. | |
| 6,407,107 B1 * | 6/2002 | Gilbert | C07C 219/06 514/237.8 |
| 6,534,262 B1 | 3/2003 | McKernan et al. | |
| 6,602,718 B1 | 8/2003 | Augello et al. | |
| 6,617,170 B2 | 9/2003 | Augello et al. | |
| 6,673,364 B1 | 1/2004 | Holland et al. | |
| 6,776,959 B1 | 8/2004 | Helftenbein | |
| 7,270,953 B2 | 9/2007 | Holländer et al. | |
| 7,332,277 B2 | 2/2008 | Dhallan | |
| 7,442,506 B2 | 10/2008 | Dhallan | |
| 2002/0081619 A1 | 6/2002 | Bastian et al. | |
| 2003/0118980 A1 | 6/2003 | Taylor | |
| 2004/0043505 A1 | 3/2004 | Walenciak et al. | |
| 2004/0167165 A1 * | 8/2004 | Shankar | A61K 31/445 514/317 |
| 2004/0253661 A1 | 12/2004 | Goldrick et al. | |
| 2005/0158699 A1 | 7/2005 | Kadkade et al. | |
| 2006/0014177 A1 | 1/2006 | Hogan et al. | |
| 2006/0212020 A1 | 9/2006 | Rainen et al. | |
| 2007/0208166 A1 * | 9/2007 | Baly | C07C 237/22 534/766 |
| 2008/0176209 A1 | 7/2008 | Muller et al. | |
| 2008/0187924 A1 | 8/2008 | Korfhage et al. | |
| 2008/0257207 A1 | 10/2008 | Rengaswamy et al. | |
| 2009/0274765 A1 | 11/2009 | Beduneau et al. | |
| 2010/0009349 A1 | 1/2010 | Holländer | |
| 2010/0137575 A1 | 6/2010 | Connolly et al. | |
| 2010/0184069 A1 | 7/2010 | Fernando et al. | |
| 2010/0209930 A1 | 8/2010 | Fernando | |
| 2010/0255524 A1 | 10/2010 | Holländer | |
| 2010/0280233 A1 | 11/2010 | Connolly et al. | |
| 2010/0285468 A1 | 11/2010 | Xin | |
| 2010/0311166 A1 | 12/2010 | Florio et al. | |
| 2011/0027771 A1 | 2/2011 | Deng | |

(Continued)

FOREIGN PATENT DOCUMENTS

| | | |
|---|---|---|
| AU | 2011253662 A1 | 12/2011 |
| EP | 0 578 885 A2 | 1/1994 |

(Continued)

OTHER PUBLICATIONS

Baechler et al., "Expression levels for many genes in human peripheral blood cells are highly sensitive to ex vivo incubation," *Genes and Immunity* 5:347-353 (2004).

Caserta et al., "Q-VD-Oph, a broad spectrum caspase inhibitor with potent antiapoptotic properties," *Apoptosis* 8(4):345-352 (2003).

Chiu et al., "Effects of Blood-Processing Protocols on Fetal and Total DNA Quantification in Maternal Plasma," *Clinical Chemistry* 47(9):1607-1613 (2001).

DeAngelis et al., "Solid-phase reversible immobilization for the isolation of PCR products," *Nucleic Acids Research* 23(22):4742-4743 (1995).

Fan et al., "Analysis of the Size Distributions of Fetal and Maternal Cell-Free DNA by Paired-End Sequencing," *Clinical Chemistry* 56(8):1-8 (2010).

(Continued)

*Primary Examiner* — Aaron A Priest
(74) *Attorney, Agent, or Firm* — Seed IP Law Group LLP

(57) ABSTRACT

The present invention provides methods, compositions and devices for stabilizing the extracellular nucleic acid population in a cell-containing biological sample using butanamide.

14 Claims, 35 Drawing Sheets
Specification includes a Sequence Listing.

(56) References Cited

U.S. PATENT DOCUMENTS

| | | | |
|---|---|---|---|
| 2011/0111410 A1 | 5/2011 | Ryan et al. | |
| 2011/0306668 A1* | 12/2011 | Yu | C07C 235/78 514/616 |
| 2012/0064021 A1 | 3/2012 | Leplanquais et al. | |
| 2012/0253071 A1 | 10/2012 | Rau et al. | |
| 2013/0323793 A1 | 12/2013 | Tanner et al. | |
| 2014/0227687 A1 | 8/2014 | Horlitz et al. | |
| 2014/0227688 A1 | 8/2014 | Horlitz et al. | |
| 2015/0056604 A1 | 2/2015 | Sehgal | |

FOREIGN PATENT DOCUMENTS

| | | | |
|---|---|---|---|
| EP | 0 880 537 B1 | | 12/1998 |
| EP | 2 256 196 A1 | | 12/2010 |
| GB | 2 496 969 A | | 5/2013 |
| JP | 2009-521949 A | | 6/2009 |
| JP | 2009-522542 A | | 6/2009 |
| JP | 2011-109987 A | | 6/2011 |
| WO | 95/21849 A1 | | 8/1995 |
| WO | 97/34015 A1 | | 9/1997 |
| WO | 97/35589 A1 | | 10/1997 |
| WO | 97/035589 A1 | | 10/1997 |
| WO | 98/29126 A1 | | 7/1998 |
| WO | 98/41651 A1 | | 9/1998 |
| WO | 99/57318 A2 | | 11/1999 |
| WO | 01/60517 A2 | | 8/2001 |
| WO | 01/70279 A1 | | 9/2001 |
| WO | 03/086480 A1 | | 10/2003 |
| WO | 2004/024958 A1 | | 3/2004 |
| WO | 2004/032750 A1 | | 4/2004 |
| WO | 2004/072228 A2 | | 8/2004 |
| WO | 2005/067388 A2 | | 7/2005 |
| WO | 2005/081867 A2 | | 9/2005 |
| WO | 2006/017295 A2 | | 2/2006 |
| WO | 2006/097806 A1 | | 9/2006 |
| WO | 2007/077199 A2 | | 7/2007 |
| WO | 2007/077560 A2 | | 7/2007 |
| WO | 2008/081166 A1 | | 7/2008 |
| WO | 2008/145710 A1 | | 12/2008 |
| WO | 2009/016255 A1 | | 2/2009 |
| WO | 2010/096323 A1 | | 8/2010 |
| WO | 2011/026027 A1 | | 3/2011 |
| WO | 2011/026028 A1 | | 3/2011 |
| WO | 2011/057061 A1 | | 5/2011 |
| WO | 2011/057184 A1 | | 5/2011 |
| WO | 2011/157678 A1 | | 12/2011 |
| WO | 2012/151450 A1 | | 11/2012 |
| WO | 2013/045432 A1 | | 4/2013 |
| WO | 2013/045434 A1 | | 4/2013 |
| WO | 2013/045457 A1 | | 4/2013 |
| WO | 2013/045458 A1 | | 4/2013 |
| WO | 2013/053855 A1 | | 4/2013 |
| WO | 2014/049022 A1 | | 4/2014 |
| WO | 2014/055936 A1 | | 4/2014 |
| WO | 2014/131906 A1 | | 9/2014 |
| WO | 2014/146780 A1 | | 9/2014 |
| WO | 2014/146781 A1 | | 9/2014 |
| WO | 2014/146782 A1 | | 9/2014 |
| WO | 2015/140218 A1 | | 9/2015 |
| WO | 2016/022433 A1 | | 2/2016 |

OTHER PUBLICATIONS

Fleischhacker et at, "Circulating nucleic acids (CNAs) and cancer—a survey," *Biochimica et Biophysica Acta* 1775:181-232 (2007).
Fleischhacker, "Biology of Circulating mRNA—Still More Questions Than Answers?" *Ann. N.Y. Acad. Sci.* 1075:40-49 (2006).
Hromadnikova et al., "Quantification of Fetal and Total Circulatory DNA in Maternal Plasma Samples Before and After Size Fractionation by Agarose Gel Electrophoresis," *DNA and Cell Biology* 25(11):635-640 (2006).
Kruhøffer et al., "Isolation of Microarray-Grade Total RNA, MicroRNA, and DNA from a Single PAXgene Blood RNA Tube," *Journal of Molecular Diagnostics* 9(4):452-458 (Sep. 2007).
Lis et al., "Size fractionation of double-stranded DNA by precipitation with polyethylene glycol," *Nucleic Acids Research* 2(3):383-389 (Mar. 1975).
Pahl et al., "Gene expression changes in blood after phlebotomy: implications for gene expression profiling," *Blood* 100(3):1-2 (Aug. 1, 2002).
Rainen et al., "Stabilization of mRNA Expression in Whole Blood Samples," *Clinical Chemistry* 48(11):1883-1890 (2002).
Swarup et al., "Circulating (cell-free) nucleic acids—a promising, non-invasive tool for early detection of several human diseases," *FEBS Letters* 581:795-799 (2007).
Marino et al., "Lysosomal and mitochondrial permeabilization mediates zinc(II) cationic phthalocyanine phototoxicity," *The International Journal of Biochemistry & Cell Biology* 45:2553-2562 (2013).
Mosbah et al., "Effects of Polyethylene Glycol and Hydroxyethyl Starch in University of Wisconsin Preservation Solution on Human Red Blood Cell Aggregation and Viscosity," *Transplantation Proceedings* 38:1229-1235 (2006).
Anonymous, "Caspase Inhibitor," BD™ ApoBlock—Technical Data Sheet (2 pages) (2008).
Dupuis et al., "Molecular-crowding effects on single-molecule RNA folding/unfolding thermodynamics and kinetics," *PNAS* 111(23):8464-8469 (Jun. 10, 2014).
Ekert et al., "Caspase inhibitors," *Cell Death and Differentiation* 6:1081-1086, 1999.
Fernando et al., "Preservation and Amplification of Fetal Cell-Free DNA in Maternal Plasma for Noninvasive Prenatal Diagnosis," *Streck*, First Presented at AACC/ASCLS Clinical Lab Expo on Jul. 23, 2009.
Fernando et al., "Stabilization of Cell-Free RNA in Plasma for Noninvasive Diagnosis," *Streck*, Presented at AACC Annual Meeting Jul. 2010, Anaheim, CA.
Goldstein et al., "Caspase-independent cytochrome c release is a sensitive measure of low-level apoptosis in cell culture models," *Aging Cell* 4(4):217-222 (2005).
Jani et al., "Caspase Inhibition Prevents the Increase in Caspase-3, -2, -8 and -9 Activity and Apoptosis in the Cold Ischemic Mouse Kidney," *American Journal of Transplantation* 4:1246-1254, 2004.
Karimata et al., "Stabilization of a DNA duplex under molecular crowding conditions of PEG," *Nucleic Acids Symposium Series* No. 48:107-108 (2004).
Ke et al., "Characterizing DNA Condensation and Conformational Changes in Organic Solvents," *PLoS One* 5(10):e13308, 2010, 8 pages.
MP Biomedicals, "Q-VD-OPH (OPH109), a new generation broad spectrum caspase inhibitor from innovators of Z-VAD(OMe)-FMK Caspase Inhibitor / Apoptosis Inhibitor," downloaded from https://www.mpbio.com/detailed_info.php?family_key=03OPH109&country=223 on Sep. 5, 2017, 5 pages.
Mukae et al., "Molecular cloning and characterization of human caspase-activated DNase," Proc. Natl. Acad. Sci. USA 95:9123-9128 (1998).
Müller et al., "Improvement of molecular monitoring of residual disease in leukemias by bedside RNA stabilization," *Leukemia* 16:2395-2399 (2002).
Notice of Reasons for Refusal with English Translation, dated Jun. 1, 2016, for Japanese Application No. 2014-532357, 11 pages.
Paithankar et al., "Precipitation of DNA by polyethylene glycol and ethanol," Nucleic Acids Research 19(6):1346 (Feb. 6, 1991).
QIAamp® Circulating Nucleic Acid Handbook, QIAGEN®—Sample & Assay Technologies (44 pages) (May 2009).
Samejima et al., "Trashing the Genome: The Role of Nucleases During Apoptosis," *Nature Reviews* 6:677-688, 2005.
Sethu et al., "Microfluidic Isolation of Leukocytes from Whole Blood for Phenotype and Gene Expression Analysis," *Anal. Chem.* 76:5453-5461 (2006).

\* cited by examiner

SEQUENCE LISTING

```
<160> NUMBER OF SEQ ID NOS: 83

<210> SEQ ID NO 1
<211> LENGTH: 5
<212> TYPE: PRT
<213> ORGANISM: Unknown
<220> FEATURE:
<223> OTHER INFORMATION: Bax-Inhibiting peptide, V5

<400> SEQUENCE: 1

Val Pro Met Leu Lys
1               5

<210> SEQ ID NO 2
<211> LENGTH: 6
<212> TYPE: PRT
<213> ORGANISM: Unknown
<220> FEATURE:
<223> OTHER INFORMATION: STAT3 Inhibitor peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: PHOSPHORYLATION

<400> SEQUENCE: 2

Pro Tyr Leu Lys Thr Lys
1               5

<210> SEQ ID NO 3
<211> LENGTH: 4
<212> TYPE: PRT
<213> ORGANISM: Artificial
<220> FEATURE:
<223> OTHER INFORMATION: Group III Caspase Inhibitor I
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (4)..(4)
<223> OTHER INFORMATION: BLOCKED

<400> SEQUENCE: 3

Ile Glu Pro Asp
1

<210> SEQ ID NO 4
<211> LENGTH: 4
<212> TYPE: PRT
<213> ORGANISM: Artificial
<220> FEATURE:
<223> OTHER INFORMATION: Caspase 3, 7 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 4

Asp Glu Val Asp
1

<210> SEQ ID NO 5
<211> LENGTH: 4
<212> TYPE: PRT
<213> ORGANISM: Artificial
<220> FEATURE:
<223> OTHER INFORMATION: Caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 5

Leu Glu Thr Asp
1

<210> SEQ ID NO 6
<211> LENGTH: 4
<212> TYPE: PRT
<213> ORGANISM: Artificial
<220> FEATURE:
<223> OTHER INFORMATION: Caspase 1, 4 inhibitor
```

```
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 6

Tyr Val Ala Asp
1

<210> SEQ ID NO 7
<211> LENGTH: 4
<212> TYPE: PRT
<213> ORGANISM: Artificial
<220> FEATURE:
<223> OTHER INFORMATION: Caspase 10 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 7

Ala Glu Val Asp
1

<210> SEQ ID NO 8
<211> LENGTH: 4
<212> TYPE: PRT
<213> ORGANISM: Artificial
<220> FEATURE:
<223> OTHER INFORMATION: Caspase 12 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 8

Ala Thr Ala Asp
1

<210> SEQ ID NO 9
<211> LENGTH: 4
<212> TYPE: PRT
<213> ORGANISM: Artificial
<220> FEATURE:
<223> OTHER INFORMATION: Caspase 4 inhibitor
```

```
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 9

Leu Glu Val Asp
1

<210> SEQ ID NO 10
<211> LENGTH: 4
<212> TYPE: PRT
<213> ORGANISM: Artificial
<220> FEATURE:
<223> OTHER INFORMATION: Caspase 13 inhibitor, reversible
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 10

Leu Glu Glu Asp
1

<210> SEQ ID NO 11
<211> LENGTH: 4
<212> TYPE: PRT
<213> ORGANISM: Artificial
<220> FEATURE:
<223> OTHER INFORMATION: Caspase 13 inhibitor, irreversible
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 11

Leu Glu Glu Asp
1

<210> SEQ ID NO 12
<211> LENGTH: 4
```

```
<212> TYPE: PRT
<213> ORGANISM: Artificial
<220> FEATURE:
<223> OTHER INFORMATION: inhibitor of anti-APO-1 induced apoptosis in
      L929-APO-1 cells
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 12

Tyr Val Ala Asp
1

<210> SEQ ID NO 13
<211> LENGTH: 20
<212> TYPE: PRT
<213> ORGANISM: Artificial
<220> FEATURE:
<223> OTHER INFORMATION: Caspase 1 Inhibitor I, cell-permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 13

Ala Ala Val Ala Leu Leu Pro Ala Val Leu Leu Ala Leu Leu Ala Pro
1               5                   10                  15

Tyr Val Ala Asp
            20

<210> SEQ ID NO 14
<211> LENGTH: 4
<212> TYPE: PRT
<213> ORGANISM: Artificial
<220> FEATURE:
<223> OTHER INFORMATION: Caspase 1 Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 14

Tyr Val Ala Asp
1

<210> SEQ ID NO 15
<211> LENGTH: 4
<212> TYPE: PRT
<213> ORGANISM: Artificial
<220> FEATURE:
<223> OTHER INFORMATION: Caspase 1 inhibitor IV, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED
```

-continued

<400> SEQUENCE: 15

Tyr Val Ala Asp
1

<210> SEQ ID NO 16
<211> LENGTH: 4
<212> TYPE: PRT
<213> ORGANISM: Artificial
<220> FEATURE:
<223> OTHER INFORMATION: Caspase 1 Inhibitor VI, cell permeable
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 16

Tyr Val Ala Asp
1

<210> SEQ ID NO 17
<211> LENGTH: 5
<212> TYPE: PRT
<213> ORGANISM: Artificial
<220> FEATURE:
<223> OTHER INFORMATION: Caspase 2 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (5)..(5)
<223> OTHER INFORMATION: BLOCKED

<400> SEQUENCE: 17

Val Asp Val Ala Asp
1               5

<210> SEQ ID NO 18
<211> LENGTH: 5
<212> TYPE: PRT
<213> ORGANISM: Artificial
<220> FEATURE:
<223> OTHER INFORMATION: Caspase 2 Inhibitor II
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: BLOCKED

<400> SEQUENCE: 18

Leu Asp Glu Ser Asp

```
1               5

<210> SEQ ID NO 19
<211> LENGTH: 4
<212> TYPE: PRT
<213> ORGANISM: Artificial
<220> FEATURE:
<223> OTHER INFORMATION: Caspase 3 Inhibitor I
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 19

Asp Glu Val Asp
1

<210> SEQ ID NO 20
<211> LENGTH: 20
<212> TYPE: PRT
<213> ORGANISM: Artificial
<220> FEATURE:
<223> OTHER INFORMATION: Caspase 3 Inhibitor I, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 20

Ala Ala Val Ala Leu Leu Pro Ala Val Leu Leu Ala Leu Leu Ala Pro
1               5                   10                  15
Asp Glu Val Asp
            20

<210> SEQ ID NO 21
<211> LENGTH: 4
<212> TYPE: PRT
<213> ORGANISM: Artificial
<220> FEATURE:
<223> OTHER INFORMATION: Caspase 3 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 21

Asp Glu Val Asp
1
```

```
<210> SEQ ID NO 22
<211> LENGTH: 4
<212> TYPE: PRT
<213> ORGANISM: Artificial
<220> FEATURE:
<223> OTHER INFORMATION: Caspase 3 Inhibitor III
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 22

Asp Glu Val Asp
1

<210> SEQ ID NO 23
<211> LENGTH: 4
<212> TYPE: PRT
<213> ORGANISM: Artificial
<220> FEATURE:
<223> OTHER INFORMATION: Caspase 3 Inhibitor IV
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 23

Asp Met Gln Asp
1

<210> SEQ ID NO 24
<211> LENGTH: 4
<212> TYPE: PRT
<213> ORGANISM: Artificial
<220> FEATURE:
<223> OTHER INFORMATION: Caspase 3 Inhibitor V
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 24

Asp Gln Met Asp
1

<210> SEQ ID NO 25
<211> LENGTH: 4
<212> TYPE: PRT
<213> ORGANISM: Artificial
<220> FEATURE:
<223> OTHER INFORMATION: Caspase 4 Inhibitor I
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 25

Leu Glu Val Asp
1

<210> SEQ ID NO 26
<211> LENGTH: 20
<212> TYPE: PRT
<213> ORGANISM: Artificial
<220> FEATURE:
<223> OTHER INFORMATION: Caspase 4 Inhibitor I, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 26

Ala Ala Val Ala Leu Leu Pro Ala Val Leu Leu Ala Leu Leu Ala Pro
1               5                   10                  15

Leu Glu Val Asp
            20

<210> SEQ ID NO 27
<211> LENGTH: 4
<212> TYPE: PRT
<213> ORGANISM: Artificial
<220> FEATURE:
<223> OTHER INFORMATION: Caspase 5 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 27

Trp Glu His Asp
1

<210> SEQ ID NO 28
<211> LENGTH: 4
<212> TYPE: PRT
<213> ORGANISM: Artificial
<220> FEATURE:
<223> OTHER INFORMATION: Caspase 6 Inhibitor I
<220> FEATURE:
<221> NAME/KEY: MOD_RES
<222> LOCATION: (1)..(1)
<223> OTHER INFORMATION: BLOCKED
<220> FEATURE:
```

```
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 28

Val Glu Ile Asp
1

<210> SEQ ID NO 29
<211> LENGTH: 20
<212> TYPE: PRT
<213> ORGANISM: Artificial
<220> FEATURE:
<223> OTHER INFORMATION: Caspase 6 Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 29

Ala Ala Val Ala Leu Leu Pro Ala Val Leu Leu Ala Leu Leu Ala Pro
1               5                   10                  15

Val Glu Ile Asp
            20

<210> SEQ ID NO 30
<211> LENGTH: 20
<212> TYPE: PRT
<213> ORGANISM: Artificial
<220> FEATURE:
<223> OTHER INFORMATION: Caspase 8 Inhibitor I, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 30

Ala Ala Val Ala Leu Leu Pro Ala Val Leu Leu Ala Leu Leu Ala Pro
1               5                   10                  15

Ile Glu Thr Asp
            20

<210> SEQ ID NO 31
<211> LENGTH: 4
<212> TYPE: PRT
<213> ORGANISM: Artificial
<220> FEATURE:
<223> OTHER INFORMATION: Caspase 8 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
```

```
<223> OTHER INFORMATION: METHYLATION
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 31

Ile Glu Thr Asp
1

<210> SEQ ID NO 32
<211> LENGTH: 4
<212> TYPE: PRT
<213> ORGANISM: Artificial
<220> FEATURE:
<223> OTHER INFORMATION: Caspase 9 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 32

Leu Glu His Asp
1

<210> SEQ ID NO 33
<211> LENGTH: 20
<212> TYPE: PRT
<213> ORGANISM: Artificial
<220> FEATURE:
<223> OTHER INFORMATION: Caspase 9 Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 33

Ala Ala Val Ala Leu Leu Pro Ala Val Leu Leu Ala Leu Leu Ala Pro
1               5                   10                  15

Leu Glu His Asp
            20

<210> SEQ ID NO 34
<211> LENGTH: 4
<212> TYPE: PRT
<213> ORGANISM: Artificial
<220> FEATURE:
<223> OTHER INFORMATION: Caspase 9 Inhibitor III
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (4)..(4)
<223> OTHER INFORMATION: BLOCKED

<400> SEQUENCE: 34

Leu Glu His Asp
1

<210> SEQ ID NO 35
<211> LENGTH: 19
<212> TYPE: PRT
<213> ORGANISM: Artificial
<220> FEATURE:
<223> OTHER INFORMATION: Pan-Caspase Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (19)..(19)
<223> OTHER INFORMATION: BLOCKED

<400> SEQUENCE: 35

Ala Ala Val Ala Leu Leu Pro Ala Val Leu Leu Ala Leu Leu Ala Pro
1               5                   10                  15

Val Ala Asp

<210> SEQ ID NO 36
<211> LENGTH: 5
<212> TYPE: PRT
<213> ORGANISM: Artificial
<220> FEATURE:
<223> OTHER INFORMATION: Caspase Inhibitor VIII
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: BLOCKED

<400> SEQUENCE: 36

Val Asp Val Ala Asp
1               5

<210> SEQ ID NO 37
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 37

Tyr Val Ala Asp
1
```

<210> SEQ ID NO 38
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 38

Trp Glu His Asp
1

<210> SEQ ID NO 39
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 39

Tyr Val Ala Asp
1

<210> SEQ ID NO 40
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 40

Tyr Val Ala Asp
1

<210> SEQ ID NO 41
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

```
<400> SEQUENCE: 41

Tyr Val Ala Asp
1

<210> SEQ ID NO 42
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 42

Tyr Val Lys Asp
1

<210> SEQ ID NO 43
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 43

Tyr Val Ala Asp
1

<210> SEQ ID NO 44
<211> LENGTH: 5
<212> TYPE: PRT
<213> ORGANISM: Artificial
<220> FEATURE:
<223> OTHER INFORMATION: caspase 2 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: BLOCKED

<400> SEQUENCE: 44

Val Asp Val Ala Asp
1               5

<210> SEQ ID NO 45
<211> LENGTH: 5
<212> TYPE: PRT
<213> ORGANISM: Artificial
<220> FEATURE:
<223> OTHER INFORMATION: caspase 2 inhibitor
<220> FEATURE:
<221> NAME/KEY: MOD_RES
<222> LOCATION: (1)..(1)
<223> OTHER INFORMATION: BLOCKED
```

```
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (5)..(5)
<223> OTHER INFORMATION: BLOCKED
<220> FEATURE:
<221> NAME/KEY: MOD_RES
<222> LOCATION: (5)..(5)
<223> OTHER INFORMATION: METHYLATION

<400> SEQUENCE: 45

Val Asp Val Ala Asp
1               5

<210> SEQ ID NO 46
<211> LENGTH: 4
<212> TYPE: PRT
<213> ORGANISM: Artificial
<220> FEATURE:
<223> OTHER INFORMATION: caspase 3 precursor inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 46

Glu Ser Met Asp
1

<210> SEQ ID NO 47
<211> LENGTH: 4
<212> TYPE: PRT
<213> ORGANISM: Artificial
<220> FEATURE:
<223> OTHER INFORMATION: caspase 3 precursor inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 47

Ile Glu Thr Asp
1

<210> SEQ ID NO 48
<211> LENGTH: 4
<212> TYPE: PRT
<213> ORGANISM: Artificial
<220> FEATURE:
<223> OTHER INFORMATION: caspase 3 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 48

Asp Glu Val Asp
```

```
<210> SEQ ID NO 49
<211> LENGTH: 4
<212> TYPE: PRT
<213> ORGANISM: Artificial
<220> FEATURE:
<223> OTHER INFORMATION: caspase 3 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 49

Asp Met Gln Asp
1

<210> SEQ ID NO 50
<211> LENGTH: 4
<212> TYPE: PRT
<213> ORGANISM: Artificial
<220> FEATURE:
<223> OTHER INFORMATION: Caspase 3/7 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 50

Asp Gln Met Asp
1

<210> SEQ ID NO 51
<211> LENGTH: 4
<212> TYPE: PRT
<213> ORGANISM: Artificial
<220> FEATURE:
<223> OTHER INFORMATION: Caspase 3/7 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 51

Asp Glu Val Asp
1

<210> SEQ ID NO 52
<211> LENGTH: 4
<212> TYPE: PRT
<213> ORGANISM: Artificial
<220> FEATURE:
```

<223> OTHER INFORMATION: Caspase 3/7 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 52

Asp Glu Val Asp
1

<210> SEQ ID NO 53
<211> LENGTH: 4
<212> TYPE: PRT
<213> ORGANISM: Artificial
<220> FEATURE:
<223> OTHER INFORMATION: caspase 4 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 53

Leu Glu Val Asp
1

<210> SEQ ID NO 54
<211> LENGTH: 4
<212> TYPE: PRT
<213> ORGANISM: Artificial
<220> FEATURE:
<223> OTHER INFORMATION: caspase 4 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 54

Tyr Val Ala Asp
1

<210> SEQ ID NO 55
<211> LENGTH: 4
<212> TYPE: PRT
<213> ORGANISM: Artificial
<220> FEATURE:
<223> OTHER INFORMATION: caspase 6 inhibitor
<220> FEATURE:
<221> NAME/KEY: MOD_RES
<222> LOCATION: (1)..(1)

```
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 55

Val Glu Ile Asp
1

<210> SEQ ID NO 56
<211> LENGTH: 4
<212> TYPE: PRT
<213> ORGANISM: Artificial
<220> FEATURE:
<223> OTHER INFORMATION: caspase 6 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 56

Val Glu Ile Asp
1

<210> SEQ ID NO 57
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 57

Ile Glu Pro Asp
1

<210> SEQ ID NO 58
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 58
```

Ala Glu Val Asp
1

<210> SEQ ID NO 59
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 59

Ile Glu Thr Asp
1

<210> SEQ ID NO 60
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 60

Leu Glu Thr Asp
1

<210> SEQ ID NO 61
<211> LENGTH: 4
<212> TYPE: PRT
<213> ORGANISM: Artificial
<220> FEATURE:
<223> OTHER INFORMATION: caspase 9 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 61

Leu Glu His Asp
1

<210> SEQ ID NO 62
<211> LENGTH: 4
<212> TYPE: PRT
<213> ORGANISM: Artificial
<220> FEATURE:
<223> OTHER INFORMATION: caspase 9 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 62

Leu Glu His Asp
1

<210> SEQ ID NO 63
<211> LENGTH: 4
<212> TYPE: PRT
<213> ORGANISM: Artificial
<220> FEATURE:
<223> OTHER INFORMATION: caspase 10 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 63

Ala Glu Val Asp
1

<210> SEQ ID NO 64
<211> LENGTH: 4
<212> TYPE: PRT
<213> ORGANISM: Artificial
<220> FEATURE:
<223> OTHER INFORMATION: Granzyme B Inhibitor II
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 64

Ile Glu Thr Asp
1

<210> SEQ ID NO 65
<211> LENGTH: 4
<212> TYPE: PRT
<213> ORGANISM: Artificial
<220> FEATURE:
<223> OTHER INFORMATION: Granzyme B Inhibitor IV
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES

```
<222> LOCATION: (4)..(4)
<223> OTHER INFORMATION: BLOCKED

<400> SEQUENCE: 65

Ile Glu Pro Asp
1

<210> SEQ ID NO 66
<211> LENGTH: 22
<212> TYPE: DNA
<213> ORGANISM: Artificial
<220> FEATURE:
<223> OTHER INFORMATION: human ribosomal DNA forward primer

<400> SEQUENCE: 66
gccgctagag gtgaaattct tg                                          22

<210> SEQ ID NO 67
<211> LENGTH: 21
<212> TYPE: DNA
<213> ORGANISM: Artificial
<220> FEATURE:
<223> OTHER INFORMATION: human ribosomal DNA reverse primer

<400> SEQUENCE: 67
cattcttggc aaatgctttc g                                           21

<210> SEQ ID NO 68
<211> LENGTH: 21
<212> TYPE: DNA
<213> ORGANISM: Artificial
<220> FEATURE:
<223> OTHER INFORMATION: human ribosomal DNA probe

<400> SEQUENCE: 68
accggcgcaa gacggaccag a                                           21

<210> SEQ ID NO 69
<211> LENGTH: 22
<212> TYPE: DNA
<213> ORGANISM: Artificial
<220> FEATURE:
<223> OTHER INFORMATION: human ribosomal DNA forward primer

<400> SEQUENCE: 69
gtcgctcgct cctctcctac tt                                          22

<210> SEQ ID NO 70
<211> LENGTH: 19
<212> TYPE: DNA
<213> ORGANISM: Artificial
<220> FEATURE:
<223> OTHER INFORMATION: human ribosomal DNA reverse primer

<400> SEQUENCE: 70
ggctgctggc accagactt                                              19

<210> SEQ ID NO 71
<211> LENGTH: 25
<212> TYPE: DNA
<213> ORGANISM: Artificial
<220> FEATURE:
<223> OTHER INFORMATION: human ribosomal DNA probe

<400> SEQUENCE: 71
ctaatacatg ccgacgggcg ctgac                                       25
```

```
<210> SEQ ID NO 72
<211> LENGTH: 4
<212> TYPE: PRT
<213> ORGANISM: Artificial Sequence
<220> FEATURE:
<223> OTHER INFORMATION: Caspase-3 Inhibitor II
<220> FEATURE:
<221> NAME/KEY: MOD_RES
<222> LOCATION: 1
<223> OTHER INFORMATION: Blocked
<220> FEATURE:
<221> NAME/KEY: MOD_RES
<222> LOCATION: 4
<223> OTHER INFORMATION: Blocked

<400> SEQUENCE: 72

Asp Glu Val Asp
1

<210> SEQ ID NO 73
<211> LENGTH: 4
<212> TYPE: PRT
<213> ORGANISM: Artificial Sequence
<220> FEATURE:
<223> OTHER INFORMATION: Caspase-3 Inhibitor IV
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 4
<223> OTHER INFORMATION: Blocked

<400> SEQUENCE: 73

Val Glu Ile Asp
1

<210> SEQ ID NO 74
<211> LENGTH: 4
<212> TYPE: PRT
<213> ORGANISM: Artificial Sequence
<220> FEATURE:
<223> OTHER INFORMATION: Caspase-8 Inhibitor II
<220> FEATURE:
<221> NAME/KEY: MOD_RES
<222> LOCATION: 1,4
<223> OTHER INFORMATION: Blocked

<400> SEQUENCE: 74

Ile Glu Thr Asp
1

<210> SEQ ID NO 75
<211> LENGTH: 4
<212> TYPE: PRT
<213> ORGANISM: Artificial Sequence
<220> FEATURE:
<223> OTHER INFORMATION: Caspase-9 Inhibitor I
<220> FEATURE:
<221> NAME/KEY: MOD_RES
<222> LOCATION: 1,4
<223> OTHER INFORMATION: Blocked

<400> SEQUENCE: 75

Leu Glu His Asp
1

<210> SEQ ID NO 76
```

```
<211> LENGTH: 4
<212> TYPE: PRT
<213> ORGANISM: Artificial Sequence
<220> FEATURE:
<223> OTHER INFORMATION: Caspase-1 Inhibitor
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 3,4
<223> OTHER INFORMATION: BLOCKED

<400> SEQUENCE: 76

Tyr Val Lys Asp
1

<210> SEQ ID NO 77
<211> LENGTH: 4
<212> TYPE: PRT
<213> ORGANISM: Artificial Sequence
<220> FEATURE:
<223> OTHER INFORMATION: Caspase-1 Inhibitor
<220> FEATURE:
<221> NAME/KEY: MOD_RES
<222> LOCATION: 1,4
<223> OTHER INFORMATION: BLOCKED

<400> SEQUENCE: 77

Tyr Val Ala Asp
1

<210> SEQ ID NO 78
<211> LENGTH: 4
<212> TYPE: PRT
<213> ORGANISM: Artificial Sequence
<220> FEATURE:
<223> OTHER INFORMATION: Caspase-1 Inhibitor
<220> FEATURE:
<221> NAME/KEY: MOD_RES
<222> LOCATION: 1
<223> OTHER INFORMATION: BLOCKED
<220> FEATURE:
<221> NAME/KEY: MOD_RES
<222> LOCATION: 4
<223> OTHER INFORMATION: METHYLATION
<220> FEATURE:
<221> NAME/KEY: MOD_RES
<222> LOCATION: 4
<223> OTHER INFORMATION: BLOCKED

<400> SEQUENCE: 78

Tyr Val Ala Asp
1

<210> SEQ ID NO 79
<211> LENGTH: 4
<212> TYPE: PRT
<213> ORGANISM: Artificial Sequence
<220> FEATURE:
<223> OTHER INFORMATION: Caspase-1 Inhibitor
<220> FEATURE:
<221> NAME/KEY: MOD_RES
<222> LOCATION: 1,4
<223> OTHER INFORMATION: BLOCKED

<400> SEQUENCE: 79

Tyr Val Ala Asp
1
```

```
<210> SEQ ID NO 80
<211> LENGTH: 4
<212> TYPE: PRT
<213> ORGANISM: Artificial Sequence
<220> FEATURE:
<223> OTHER INFORMATION: Caspase-3 Inhibitor
<220> FEATURE:
<221> NAME/KEY: MOD_RES
<222> LOCATION: 1,4
<223> OTHER INFORMATION: BLOCKED

<400> SEQUENCE: 80

Asp Glu Val Asp
1

<210> SEQ ID NO 81
<211> LENGTH: 4
<212> TYPE: PRT
<213> ORGANISM: Artificial Sequence
<220> FEATURE:
<223> OTHER INFORMATION: Caspase-3 Inhibitor
<220> FEATURE:
<221> NAME/KEY: MOD_RES
<222> LOCATION: 1
<223> OTHER INFORMATION: METHYLATION
<220> FEATURE:
<221> NAME/KEY: MOD_RES
<222> LOCATION: 1
<223> OTHER INFORMATION: BLOCKED
<220> FEATURE:
<221> NAME/KEY: MOD_RES
<222> LOCATION: 2
<223> OTHER INFORMATION: METHYLATION
<220> FEATURE:
<221> NAME/KEY: MOD_RES
<222> LOCATION: 4
<223> OTHER INFORMATION: METHYLATION
<220> FEATURE:
<221> NAME/KEY: MOD_RES
<222> LOCATION: 4
<223> OTHER INFORMATION: BLOCKED

<400> SEQUENCE: 81

Asp Glu Val Asp
1

<210> SEQ ID NO 82
<211> LENGTH: 4
<212> TYPE: PRT
<213> ORGANISM: Artificial Sequence
<220> FEATURE:
<223> OTHER INFORMATION: Caspase-9 Inhibitor
<220> FEATURE:
<221> NAME/KEY: MOD_RES
<222> LOCATION: 1
<223> OTHER INFORMATION: BLOCKED
<220> FEATURE:
<221> NAME/KEY: MOD_RES
<222> LOCATION: 2
<223> OTHER INFORMATION: METHYLATION
<220> FEATURE:
<221> NAME/KEY: MOD_RES
<222> LOCATION: 4
<223> OTHER INFORMATION: METHYLATION
<220> FEATURE:
<221> NAME/KEY: MOD_RES
<222> LOCATION: 4
<223> OTHER INFORMATION: BLOCKED

<400> SEQUENCE: 82

Leu Glu His Asp
1
```

```
<210> SEQ ID NO 83
<211> LENGTH: 4
<212> TYPE: PRT
<213> ORGANISM: Artificial Sequence
<220> FEATURE:
<223> OTHER INFORMATION: Caspase-10 Inhibitor
<220> FEATURE:
<221> NAME/KEY: MOD_RES
<222> LOCATION: 1
<223> OTHER INFORMATION: BLOCKED
<220> FEATURE:
<221> NAME/KEY: MOD_RES
<222> LOCATION: 2
<223> OTHER INFORMATION: METHYLATION
<220> FEATURE:
<221> NAME/KEY: MOD_RES
<222> LOCATION: 4
<223> OTHER INFORMATION: METHYLATION
<220> FEATURE:
<221> NAME/KEY: MOD_RES
<222> LOCATION: 4
<223> OTHER INFORMATION: BLOCKED

<400> SEQUENCE: 83

Ala Glu Val Asp
1
```

STABILIZATION AND ISOLATION OF EXTRACELLULAR NUCLEIC ACIDS

The work leading to this invention has received funding from the European Community's Seventh Framework Programme (FP7/2007-2013) under grant agreement no 222916.

FIELD OF THE INVENTION

The technology disclosed herein relates to methods and compositions suitable for stabilizing the extracellular nucleic acid population in a cell-containing sample, in particular a blood sample, and to a method for isolating extracellular nucleic acids from respectively stabilized biological samples.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 771025_412USPC_SEQUENCE_LISTING.txt. The text file is 25.2 KB, was created on Sep. 8, 2015, and is being submitted electronically via EFS-Web.

BACKGROUND

Extracellular nucleic acids have been identified in blood, plasma, serum and other body fluids. Extracellular nucleic acids that are found in respective samples are to a certain extent degradation resistant due to the fact that they are protected from nucleases (e.g. because they are secreted in form of a proteolipid complex, are associated with proteins or are contained in vesicles). The presence of elevated levels of extracellular nucleic acids such as DNA and/or RNA in many medical conditions, malignancies, and infectious processes is of interest inter alia for screening, diagnosis, prognosis, surveillance for disease progression, for identifying potential therapeutic targets, and for monitoring treatment response. Additionally, elevated fetal DNA/RNA in maternal blood is being used to determine e.g. gender identity, assess chromosomal abnormalities, and monitor pregnancy-associated complications. Thus, extracellular nucleic acids are in particular useful in non-invasive diagnosis and prognosis and can be used e.g. as diagnostic markers in many fields of application, such as non-invasive prenatal genetic testing, oncology, transplantation medicine or many other diseases and, hence, are of diagnostic relevance (e.g. fetal- or tumor-derived nucleic acids). However, extracellular nucleic acids are also found in healthy human beings. Common applications and analysis methods of extracellular nucleic acids are e.g. described in WO97/035589, WO97/34015, Swarup et al, FEBS Letters 581 (2007) 795-799, Fleischhacker Ann. N.Y. Acad. Sci. 1075: 40-49 (2006), Fleischhacker and Schmidt, Biochmica et Biophysica Acta 1775 (2007) 191-232, Hromadnikova et al (2006) DNA and Cell biology, Volume 25, Number 11 pp 635-640; Fan et al (2010) Clinical Chemistry 56:8.

Traditionally, the first step of isolating extracellular nucleic acids from a cell-containing biological sample such as blood is to obtain an essentially cell-free fraction of said sample, e.g. either serum or plasma in the case of blood. The extracellular nucleic acids are then isolated from said cell-free fraction, commonly plasma, when processing a blood sample. However, obtaining an essentially cell-free fraction of a sample can be problematic and the separation is frequently a tedious and time consuming multi-step process as it is important to use carefully controlled conditions to prevent cell breakage during centrifugation which could contaminate the extracellular nucleic acids with cellular nucleic acids released during breakage. Furthermore, it is often difficult to remove all cells. Thus, many processed samples that are often and commonly classified as "cell-free" such as plasma or serum in fact still contain residual amounts of cells that were not removed during the separation process. Another important consideration is that after the sample was collected, cellular nucleic acid are released from the cells contained in the sample due to cell breakage during ex vivo incubation, typically within a relatively short period of time from a blood draw event. Once cell lysis begins, the lysed cells release large amounts of additional nucleic acids which become mixed with the extracellular nucleic acids and it becomes increasingly difficult to recover the extracellular nucleic acids for testing. These problems are discussed in the prior art (see e.g. Chiu et al (2001), Clinical Chemistry 47:9 1607-1613; Fan et al (2010) and US2010/0184069). Further, the amount and recoverability of available extracellular nucleic acids can decrease substantially over a period of time due to degradation.

Thus, plasma and serum samples can serve as important sample materials for diagnostic purposes, because they contain free circulating nucleic acids from different origins. It is e.g. possible to detect DNA from tumors in the plasma sample. It is also possible to detect DNA from a fetus in maternal plasma and analyse if for genetic disorders (e.g trisomy). This is much less invasive and therefore much less hazardous for the mother and the baby than an amnioncynthesis. However, as discussed above, a major problem regarding the analysis of circulating, cell-free nucleic acids (cfNA) from tumors or of foetal origin is—besides the degradation that occurs in serum and probably also plasma—the possible dilution of extracellular DNA (and RNA) by genetic material from damaged or decaying blood cells after blood collection. In particular the lysis of white blood cells is a problem as they release large amounts of genomic DNA in addition to RNA. Red blood cells do not contain genomic DNA. Therefore, stabilization of circulating nucleic acids in whole blood must include mechanism to stabilize blood cells in order to prevent during stabilization a contamination of the extracellular nucleic acid population by cellular genomic DNA and also RNA.

Besides mammalian extracellular nucleic acids that derive e.g. from tumor cells or the fetus, cell-containing samples may also comprise other nucleic acids of interest that are not comprised in cells. An important, non-limiting example is pathogen nucleic acids such as viral nucleic acids. Preservation of the integrity of viral nucleic acids in cell-containing samples such as in particular in blood specimens during shipping and handling is also crucial for the subsequent analysis and viral load monitoring.

Extracellular nucleic acids are often only comprised in a low concentration in the samples. E.g. free circulating nucleic acids are present in plasma in a concentration of 1-100 ng/ml plasma. Furthermore, extracellular nucleic acids often circulate as fragments of a size of 500 nt, 300 nt (when indicating the size and hence the chain length the term "nt" also includes "bp" in case of DNA) or even less (circulating nucleosomes). Additionally, the actual target extracellular nucleic acid that is supposed to be identified for diagnostic purposes usually also represents only a small fraction among the total extracellular nucleic acids. E.g.

tumor specific DNA fragments are very rare and often are comprised in a concentration that is 1000-fold less than the "normal" extracellular nucleic acid background. Thus, a further dilution of these rare nucleic acids by intracellular nucleic acids must be prevented after the sample was collected.

The above discussed problems particularly are an issue, if the sample comprises a high amount of cells as is the case e.g. with whole blood samples. Thus, in order to avoid respectively reduce the above described problems it is common to separate an essentially cell-free fraction of the sample from the cells contained in the sample basically immediately after the sample is obtained. E.g. it is recommended to obtain blood plasma from whole blood basically directly after the blood is drawn and/or to cool the whole blood and/or the obtained plasma or serum in order to preserve the integrity of the extracellular nucleic acids and to avoid contaminations of the extracellular nucleic acid population with intracellular nucleic acids that are released from the contained cells. However, the need to directly separate e.g. the plasma from the blood is a major disadvantage because many facilities wherein the blood is drawn (e.g. a doctor's practice) do not have a centrifuge that would enable the efficient separation of blood plasma. Furthermore, plasma that is obtained under regular conditions often comprises residual amounts of cells which accordingly, may also become damaged or may die during handling of the sample, thereby releasing intracellular nucleic acids, in particular genomic DNA, as is described above. These remaining cells also pose a risk that they become damaged during the handling so that their nucleic acid content, particularly genomic (nuclear) DNA and cytoplasmic RNA, would merge with and thereby contaminate respectively dilute the extracellular, circulating nucleic acid fraction. To remove these remaining contaminating cells and to avoid/reduce the aforementioned problems, it was known to perform a second centrifugation step at higher speed. However, again, such powerful centrifuges are often not available at the facilities wherein the blood is obtained. Furthermore, even if plasma is obtained directly after the blood is drawn, it is recommended to freeze it at −80° C. in order to preserve the nucleic acids contained therein if the nucleic acids can not be directly isolated. This too imposes practical constraints upon the processing of the samples as e.g. the plasma samples must be shipped frozen. This increases the costs and furthermore, poses a risk that the sample gets compromised in case the cold chain is interrupted.

Besides extracellular nucleic acids also intracellular nucleic acids are of interest for many applications. E.g. profiles of transcripts of the genome (in particular mRNA and miRNA) are widely used as biomarkers in molecular in vitro diagnostics and provide inside into normal biological and pathological processes with the hope of predicting disease outcome and indicating individualised courses of therapy. Therefore, also the profiling of intracellular nucleic acids, in particular RNA, is becoming important in disease diagnosis, prognosis and in clinical trials for biomarker discovery. Without precaution in the stabilisation of the sample to be analysed, the sample will undergo changes during transport and storage that may alter the expression profile of the targeted molecules. If the transcriptome is significantly altered due to the handling of the sample, the subsequent analysis does not reflect the original situation of the sample and hence of the patient but rather measure an artificial profile generated during sample handling, transport and storage. Therefore, optimized stabilisation processes are needed which stabilise the gene expression profile.

Blood samples are presently usually collected in blood collection tubes containing spray-dried or liquid EDTA (e.g. BD Vacutainer $K_2$EDTA). EDTA chelates magnesium, calcium and other bivalent metal ions, thereby inhibiting enzymatic reactions, such as e.g. blood clotting or DNA degradation due to DNases. However, even though EDTA is an efficient anticoagulant, EDTA does not efficiently prevent the dilution respectively contamination of the extracellular nucleic acid population by released intracellular nucleic acids during storage. Thus, the extracellular nucleic acid population that is found in the cell-free portion of EDTA stabilised samples changes during the storage and becomes contaminated with large amounts of intracellular nucleic acids, in particular genomic DNA. Accordingly, EDTA is not capable of sufficiently stabilizing the extracellular nucleic acid population in particular because it can not avoid the contamination of the extracellular nucleic acid population with e.g. genomic DNA fragments which are generated after blood draw by cell degradation and cell instability during sample transportation and storage.

Furthermore, blood collection tubes are known that contain reagents for an immediate stabilization of the RNA gene expression profile and thus the transcriptome at the point of sample collection (see for example U.S. Pat. No. 6,617,170, U.S. Pat. No. 7,270,953, Kruhoffer et al, 2007). However, these methods are based on the immediate lysis of the cells contained in the sample. Therefore, these methods and other methods that induce cell lysis are unsuitable for stabilizing the extracellular nucleic acid population in a cell-containing sample, because they induce the release of intracellular nucleic acids which become thereby mixed with the extracellular nucleic acid population.

Furthermore, methods are known in the prior art for stabilizing cell-containing samples, such as blood or tissue samples, which stabilize e.g. the cells, the transcriptome, genome and proteome. Such a method is e.g. disclosed in WO 2008/145710. Said method is based on the use of specific stabilizing compounds, such as N,N-Dimetyhlacetamide. However, N,N-dimetyhlacetamide is a toxic agent. Therefore, there is a need to provide alternative stabilization methods which avoid the use of toxic agents.

Further methods are known in the prior art that specifically aim at stabilizing circulating nucleic acids contained in whole blood. One method employs the use of formaldehyde to stabilize the cell membranes, thereby reducing the cell lysis and furthermore, formaldehyde inhibits nucleases. Respective methods are e.g. described in U.S. Pat. No. 7,332,277 and U.S. Pat. No. 7,442,506. To address the need of simultaneous cell stabilization and nucleic acid stabilization, stabilization systems were developed that are based on the use of formaldehyde releasers. Respective stabilization agents are commercially available from Streck Inc. under the name of cell-free RNA BCT (blood collection tube). The 10 ml blood collection tube is intended for the preservation and stabilization of cell-free RNA in plasma for up to 3 days at room temperature. The preservative stabilizes cell-free RNA in plasma and prevents the release of non-target background RNA from blood cells during sample processing and storage. US 2011/0111410 describes the use of formaldehyde releasing components to achieve cell and RNA stabilization in the same blood sample. Therefore, this document describes a technique wherein the stabilization agent stabilises the blood cells in the drawn blood thereby preventing contamination of cellular RNA with cell-free RNA or globin RNA, inhibits the RNA synthesis for at least 2 hours and cellular RNA that is within the blood cells is preserved to keep the protein expression pattern of the blood cells substantially unchanged to the time of the blood draw. The white blood cells can be isolated from the respectively stabilised sample and cellular RNA is than extracted from the white blood cells. However, the use of formaldehyde or formaldehyde-releasing substances has drawbacks, as they compromise the efficacy of extracellular nucleic acid isolation by induction of crosslinks between nucleic acid molecules or between proteins and nucleic acids. Methods to stabilize blood samples are also described e.g. in US 2010/0184069 and US 2010/0209930. These rather recently developed methods demonstrate the great need for providing means to stabilise cell-containing biological samples, to allow the efficient recovery of e.g. extracellular nucleic acids contained in such samples.

Unpublished PCT/EP2012/070211 and PCT/EP2012/068850 describe different methods for stabilizing the extracellular nucleic acid population in a cell-containing biological sample such as a whole blood sample. The stabilization compositions described in these unpublished applications are effective in stabilizing the extracellular nucleic acid population, in particular by preventing the release of intracellular nucleic acids into the extracellular nucleic acid population.

There is a continuous need to develop processing techniques which stabilize cell-containing samples such as in particular blood samples. In particular, methods are needed that result in a stabilization of the extracellular nucleic acid population comprised in a cell-containing biological sample, including samples suspected of containing cells, in particular whole blood, plasma or serum, thereby making the handling, respectively processing of such samples easier (e.g. by avoiding the need to directly separate plasma from whole blood or to cool or even freeze the isolated plasma). By providing efficient and reliable sample stabilization technologies which do not hamper the subsequent nucleic acid isolation, the isolation and testing of extracellular nucleic acids contained in such samples becomes more reliable and consequently, the diagnostic and prognostic application/use of extracellular nucleic acids is improved by such stabilization technologies. In particular, there is a continuous need for a solution for preserving the extracellular nucleic acid population in whole blood samples, e.g. for prenatal testing and/or for screening for diseases such as e.g. neoplastic, in particular premalignant or malignant diseases.

It is the object of the present invention to provide methods and composition for stabilizing the extracellular population comprised in a cell-containing sample. In particular, it is the object to overcome at least one of the drawbacks of the prior art sample stabilization methods. Furthermore, it is in particular an object of the present invention to provide a method suitable for stabilizing a cell-containing biological sample, in particular a whole blood sample, at room temperature. Furthermore, it is an object of the present invention to provide a sample collection container, in particular a blood collection tube, that is capable of effectively stabilizing a cell-containing biological sample and in particular is capable of stabilizing the extracellular nucleic acid population comprised in the sample. Furthermore, it is one object of the present invention to provide a stabilization technology which allows the subsequent isolation of nucleic acids comprised in the sample with good yield.

SUMMARY OF THE INVENTION

The present invention is based on the surprising finding that butanamide is effective in stabilizing cell-containing biological samples comprising extracellular nucleic acids, in particular whole blood samples or samples derived from blood such as e.g. plasma or serum. It was found that butanamide can stabilize the extracellular nucleic acid population and in particular is capable to reduce the risk that the extracellular nucleic acid population becomes contaminated with genomic DNA, in particular fragmented genomic DNA, after the sample was collected. Therefore, using butanamide as stabilizer reduces the risk that the extracellular nucleic acid population becomes diluted by intracellular nucleic acids what significantly contributes to the preservation of the profile of the extracellular nucleic acid population. Advantageously, butanamide is not classified as toxic, harmful or irritant agent. Furthermore, nucleic acids can be efficiently isolated from butanamide stabilized samples using standard nucleic acid isolation methods.

According to a first aspect, a method suitable for stabilizing an extracellular nucleic acid population comprised in a cell-containing sample is provided, wherein the cell-containing sample is contacted with butanamide.

According to a second aspect, a method for isolating nucleic acids from a stabilized cell-containing biological sample is provided, wherein said method comprises
  a) stabilizing the cell-containing biological sample according to the method defined in the first aspect of the present invention; and
  b) isolating nucleic acids from the stabilized sample.

Stabilization in step a) is achieved according to the first aspect of the present invention as described above which involves the use of butanamide as stabilizing agent. The stabilization according to the present invention has the effect that the extracellular nucleic acid population contained in the cell-containing biological sample is substantially preserved in the state it had shown at the time the biological sample was obtained, respectively was collected and stabilized using butanamide. The release of genomic DNA and other intracellular nucleic acids is significantly reduced as is shown by the examples. Extracellular nucleic acids isolated from respectively stabilized samples comprise significantly less contamination with intracellular nucleic acids, in particular fragmented genomic DNA, compared to extracellular nucleic acids that are isolated from unstabilized samples. Extracellular nucleic acids isolated from unstabilized samples comprise large amounts of intracellular nucleic acids such as genomic DNA and intracellular RNA that is released during the storage period by decaying cells comprised in the sample. Such dilution and alteration of the extracellular nucleic acid population can be significantly reduced when using the stabilization technologies described herein. The substantial preservation of the extracellular nucleic acid population that is achieved with the stabilization technology described herein is an important advantage because this stabilization/preservation of the extracellular nucleic acid population enhances the accuracy of any subsequent tests that aims at analysing extracellular nucleic acids. This allows for standardizing the isolation and subsequent analysis of the extracellular nucleic acid population, thereby making diagnostic or prognostic applications that are based on the extracellular nucleic acid fraction more reliable and more independent from the used storage/handling conditions. Thereby, the diagnostic and prognostic applicability of the respectively isolated extracellular nucleic acids is improved. In particular, stabilizations described herein have the advantage that the ratio of certain extracellular nucleic acid molecules comprised in the population of extracellular nucleic acids can be kept substantially constant and thus comparable to the ratio present at the time the biological sample was collected. Thus, advantageously, the profile of the extracellular nucleic acid population can be preserved.

According to a third aspect, a composition suitable for stabilizing a cell-containing biological sample is provided wherein the composition comprises butanamide and at least one further additive selected from the group consisting of
an apoptosis inhibitor,
an anticoagulant and
a compound according to formula 1

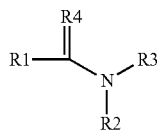

formula 1 wherein R1 is a hydrogen residue or an alkyl residue, preferably a C1-C5 alkyl residue, a C1-C4 alkyl residue or a C1-C3 alkyl residue, preferably a C1-C2 alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue, preferably R4 is oxygen.

A respective stabilizing composition is particularly effective in stabilizing a cell-containing biological sample, in particular whole blood, plasma and/or serum, by stabilizing cells and the extracellular nucleic acid population comprised in said sample. A respective stabilizing composition allows the storage and/or handling, e.g. shipping, of the stabilized sample, e.g. whole blood, at room temperature for at least two, or preferably at least three days without substantially compromising the quality of the sample, respectively the extracellular nucleic acid population contained therein. Thus, when using the stabilization composition according to the present invention, the time between sample collection, e.g. blood collection, and nucleic acid extraction can vary without substantial effect on the extracellular nucleic acid population contained in the sample. This is an important advantage as it reduces variabilities in the extracellular nucleic acid population attributable to different handling procedures. For example, when using said stabilizing composition for stabilizing a blood sample, the cell fraction can be separated from the stabilized sample to provide a plasma or serum sample which comprises the preserved extracellular nucleic acid population.

According to a fourth aspect, the present invention is related to the use of the composition according to third aspect for stabilizing the extracellular nucleic acid population in a cell-containing biological sample, preferably a blood sample.

According to a fifth aspect, a container for collecting a cell-containing biological sample is provided, wherein the container comprises butanamide and at least one further additive selected from the group consisting of
an apoptosis inhibitor,
an anticoagulant and
a compound according to formula 1

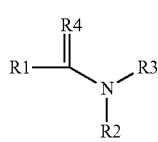

formula 1 wherein R1 is a hydrogen residue or an alkyl residue, preferably a C1-C5 alkyl residue, a C1-C4 alkyl residue or a C1-C3 alkyl residue, preferably a C1-C2 alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue, preferably R4 is oxygen. The container for collecting a cell-containing biological sample, preferably a blood sample, may comprise a stabilizing composition according to the third aspect of the present invention. Providing a respective container, e.g. a sample collection tube, comprising the stabilizing composition has the advantage that the cell-containing biological sample is immediately stabilized as soon as the sample is collected in the respective container. Furthermore, a respective sample collection container, in particular a blood collection tube, is capable of stabilizing blood cells, extracellular nucleic acids and optionally, viruses respectively viral nucleic acids, contained in the blood sample.

According to a sixth aspect, a method is provided comprising the step of collecting, preferably drawing, a biological sample, preferably blood, from a patient directly into a chamber of a container according to the fifth aspect of the present invention.

According to a seventh aspect, a method of producing a composition according to the third aspect of the present invention is provided, wherein the components of the composition are mixed, preferably are mixed in a solution. The term "solution" as used herein in particular refers to a liquid composition, preferably an aqueous composition. It may be a homogenous mixture of only one phase but it is also within the scope of the present invention that a solution comprises solid components such as e.g. precipitates.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only.

DETAILED DESCRIPTION OF THIS INVENTION

Figure 1:
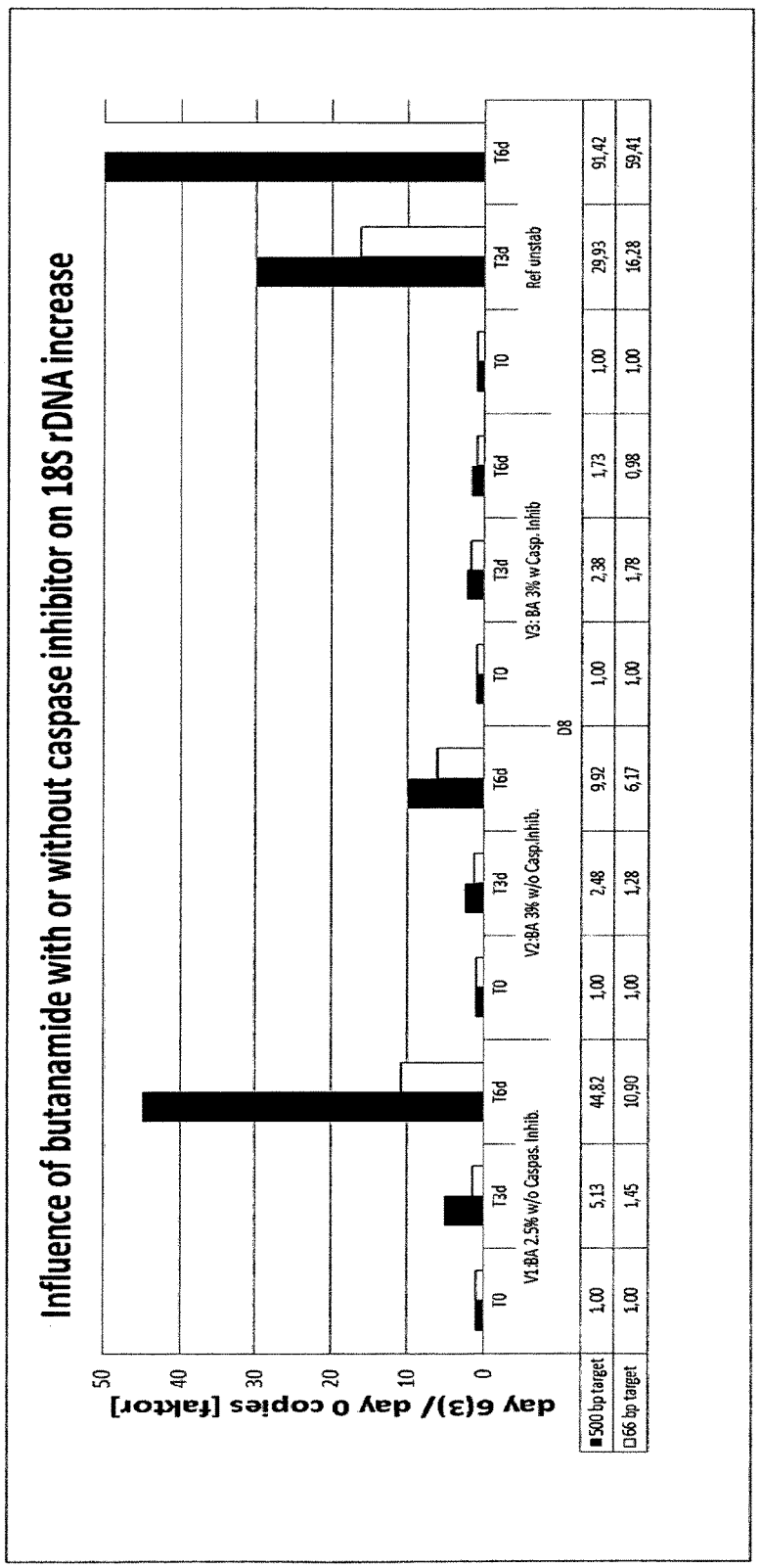
FIGS. 1 and 2 show the influence of butanamide with or without caspase inhibitor on 18S rDNA increase as described in Example 1.

The present invention is directed to methods, compositions and devices and thus to technologies for stabilizing a cell-containing biological sample and in particular for stabilizing the extracellular nucleic acid population comprised in the cell-containing biological sample that are based on the use of butanamide as stabilizer. Furthermore, advantageous combinations of butanamide with other stabilizing agents are described. The stabilization technologies disclosed herein reduce the risk that the extracellular nucleic acid population comprised in the cell-containing sample becomes contaminated and thus becomes diluted with intracellular nucleic acids, in particular fragmented genomic DNA, originating from damaged and/or dying cells contained in the sample. The stabilization that is achieved with the methods and compositions of the present invention allows the storage and/or handling of the stabilized sample for a prolonged period of time at room temperature without jeopardizing the quality of the sample, respectively the composition of the extracellular nucleic acid population contained therein. As the composition of the extracellular nucleic acid population is stabilized and thus is substantially preserved at the time the sample is obtained, the time between sample collection and nucleic acid isolation can vary within the suitable stabilization period without significant negative effect on the composition of the extracellular nucleic acid population. This e.g. simplifies a standardization of diagnostic or prognostic extracellular nucleic acid analyses because variations in the handling/storage of the samples have less influence on the quality, respectively the composition and thus profile of the extracellular nucleic acid population comprised in the cell-containing biological sample. Hence, the analysis of respective cell containing biological samples, respectively the extracellular nucleic acids obtained from respectively stabilized samples, becomes more comparable. Furthermore, the teachings of the present invention obviate the necessity to directly separate cells contained in the biological sample from the cell-free portion of the sample in order to avoid, respectively reduce, contaminations of the extracellular nucleic acids with intracellular nucleic acids, in particular fragmented genomic DNA, that is otherwise released from cells that die or decay during storage/shipping. This advantage considerably simplifies the handling of cell-containing biological samples, such as whole blood samples. E.g. whole blood samples obtained in a clinic and stabilized according to the teachings of the present invention can be shipped at room temperature and the plasma containing the extracellular nucleic acids can be conveniently separated from the cell fraction of the sample in the receiving clinical lab. However, the teachings of the invention are also advantageous when processing cell-depleted biological samples, or samples commonly referred to as being "cell-free" such as e.g. blood plasma or serum. Respective cell-depleted or "cell-free" biological samples may still (also depending on the used separation process) comprise residual cells, in particular white blood cells which comprise genomic DNA. Said residual cells pose a risk that the extracellular nucleic acid population becomes increasingly contaminated with intracellular nucleic acids, in particular fragmented genomic DNA, if the (potentially) remaining cells are damaged or die during the shipping or storing process. This risk is considerably reduced when using the stabilization methods taught by the present invention. Because the technology of the present invention allows to efficiently preserve the extracellular nucleic acid population of the sample at the time the sample is collected and contacted with butanamide and optionally one or more additional stabilizing agents as taught herein, said samples can be properly worked up in the receiving facilities in order to isolate extracellular nucleic acids from said samples, while substantially avoiding respectively reducing contaminations of the extracellular nucleic population with intracellular nucleic acids. The facilities receiving the samples such as e.g. laboratories usually also have the necessary equipment such as e.g. high speed centrifuges (or other means, see also below) to efficiently remove cells comprised in the stabilized samples, including residual cells that might be present in cell-depleted samples such as e.g. in blood plasma. Such equipment is often not present in the facilities where the cell-containing biological sample is obtained. Thus, the present invention has many advantages when stabilizing biological samples which comprise large amounts of cells such as e.g. whole blood samples, but also has important advantages when stabilizing biological samples which comprise smaller or only a small amount of cells or which may only be suspected of containing cells such as e.g. plasma, serum, urine, saliva, synovial fluids, amniotic fluid, lachrymal fluid, lymphatic fluid, liquor, cerebrospinal fluid and the like.

A. Method of Stabilization

According to a first aspect, a method is provided suitable for stabilizing an extracellular nucleic acid population comprised in a cell-containing biological sample by contacting the cell-containing biological sample with butanamide.

As described above, said method that is based on the use of butanamide as stabilizing agent efficiently stabilizes cell-containing samples such as blood samples and in particular stabilizes the extracellular nucleic acid population comprised in the cell-containing sample. Said method reduces the risk that the extracellular nucleic acid population becomes heavily contaminated with intracellular nucleic acids, in particular fragmented genomic DNA, originating from contained cells, e.g. from damaged or dying cells. Thereby, the composition of the extracellular nucleic acid population comprised in said cell-containing sample is substantially preserved, respectively stabilized, at the time said cell-containing sample is collected and stabilized using the method according to the present invention. The preservation of the composition and thus profile of the extracellular nucleic acid population contained in the sample is in particular important when extracellular nucleic acids are subsequently analysed for diagnostic purposes. As is shown by the examples, the use of butanamide as stabilizer achieves a stabilization effect for up to three days. The use of butanamide as stabilizer is e.g. advantageous over methods that use e.g. the toxic agent N,N-dimethylacetamide, because butanamide is not toxic. This is an essential benefit as it simplifies the handling of the stabilization composition. Furthermore, nucleic acids can be efficiently isolated from butanamide stabilized samples using standard nucleic acid isolation methods because butanamide does not have cross-linking properties. This is an important advantage as it e.g. simplifies the further processing of the stabilized samples and also increases the chance that rare target nucleic acids comprised in the extracellular nucleic acid population can be subsequently detected.

The term "extracellular nucleic acids" or "extracellular nucleic acid" as used herein, in particular refers to nucleic acids that are not contained in cells. Respective extracellular nucleic acids are also often referred to as cell-free nucleic acids. These terms are used as synonyms herein. Hence, extracellular nucleic acids usually are present exterior of a cell or exterior of a plurality of cells within a sample. The term "extracellular nucleic acids" refers e.g. to extracellular RNA as well as to extracellular DNA. Examples of typical extracellular nucleic acids that are found in the cell-free fraction (respectively portion) of biological samples such as e.g. body fluids include but are not limited to mammalian extracellular nucleic acids such as e.g. extracellular tumor-associated or tumor-derived DNA and/or RNA, other extracellular disease-related DNA and/or RNA, epigenetically modified DNA, fetal DNA and/or RNA, small interfering RNA such as e.g. miRNA and siRNA, and non-mammalian extracellular nucleic acids such as e.g. viral nucleic acids, pathogen nucleic acids released into the extracellular nucleic acid population e.g. from prokaryotes (e.g. bacteria), viruses, eukaryotic parasites or fungi. The extracellular nucleic acid population usually comprises certain amounts of intracellular nucleic acids that were released from damaged or dying cells. E.g. the extracellular nucleic acid population present in blood usually comprises intracellular globin mRNA that was released from damaged or dying cells. This is a natural process that occurs in vivo. Such intracellular nucleic acid present in the extracellular nucleic acid population can even serve the purpose of a control in a subsequent nucleic acid detection method. The stabilization method described herein in particular reduces the risk that the amount of intracellular nucleic acids, such as genomic DNA, that is comprised in the extracellular nucleic acid population is significantly increased after the cell-containing sample was collected due to the ex vivo handling of the sample. Thus, alterations of the extracellular nucleic acid population because of the ex vivo handling are reduced and can even be prevented. According to one embodiment, the cell-containing biological sample is or is derived from a body fluid such as e.g. blood, plasma, serum, saliva, urine, liquor, cerebrospinal fluid, sputum, lachrymal fluid, sweat, amniotic fluid or lymphatic fluid. Herein, we refer to extracellular nucleic acids that are obtained from a circulating body fluid such as blood or lymphatic fluid as circulating extracellular nucleic acids or circulating cell-free nucleic acids. According to one embodiment, the term extracellular nucleic acids in particular refers to mammalian extracellular nucleic acids. Examples include but are not limited to disease-associated or disease-derived extracellular nucleic acids such e.g. as tumor-associated or tumor-derived extracellular nucleic acids, extracellular nucleic acids released due to inflammations or injuries, in particular traumata, extracellular nucleic acids related to and/or released due to other diseases, or extracellular nucleic acids derived from a fetus. The term "extracellular nucleic acids" or "extracellular nucleic acid" as described herein also refers to extracellular nucleic acids obtained from other cell-containing biological samples, in particular biological samples other than body fluids. Usually, a sample comprises more than one kind or type of extracellular nucleic acids. Extracellular nucleic acids encompass extracellular DNA as well as extracellular RNA.

The term "extracellular nucleic acid population" as used herein in particular refers to the collective of different extracellular nucleic acids that are comprised in a cell-containing sample. A cell-containing sample usually comprises a characteristic and thus unique extracellular nucleic acid population. Thus, the type, kind, ratio and/or the the amount of one or more extracellular nucleic acids comprised in the extracellular nucleic acid population of a specific sample may be important sample characteristics. As discussed above, it is therefore important to stabilize and thus to substantially preserve said extracellular nucleic acid population at the state wherein the sample is collected, as its composition and/or the amount of one or more extracellular nucleic acids comprised in the extracellular nucleic acid population of a sample can provide valuable medical, prognostic or diagnostic information. Therefore, it is advantageous if the profile of the extracellular nucleic acid population is efficiently stabilized. The stabilization technologies described herein reduce contaminations and hence a dilution of the extracellular nucleic acid population by intracellular nucleic acids, in particular by genomic DNA, after sample collection and stabilization. Thus, a substantial preservation of the extracellular nucleic acid population is achieved. As is shown by the examples, changes in the extracellular nucleic acid population with respect to the quantity, the quality and/or the composition of the comprised extracellular nucleic acids, in particular changes attributable to an increase of released genomic DNA, are over the stabilization period considerably reduced compared to an unstabilized sample or a corresponding sample that is e.g. stabilized by EDTA in case of a blood sample or a sample derived from blood. According to one embodiment the increase in genomic DNA from $T_0$ (stabilization point) to a end of the stabilization period (preferably 48 h, 72 h or 96 h after $T_0$) is reduced by at least 60%, at least 70%, at least 75%, at least 80%, at least 85%, at least 90% or at least 95% compared to an unstabilized sample or a corresponding sample that is e.g. stabilized by EDTA in case of a blood sample (e.g. 1.5 mg EDTA/ml stabilized blood sample) or a sample derived from blood.

The mixture that is obtained after contacting the cell-containing biological sample with butanamide and optionally further additives may comprise butanamide in a concentration of at least 0.1% (w/v), at least 0.2% (w/v), at least 0.3% (w/v), at least 0.4% (w/v), at least 0.5% (w/v), at least 0.6% (w/v), at least 0.75% (w/v), at least 1% (w/v), at least 1.25% (w/v), at least 1.5% (w/v), at least 1.75% (w/v), at least 1.85% (w/v), at least 2% (w/v), at least 2.1% (w/v), at least 2.2% (w/v), at least 2.3% (w/v), at least 2.4% (w/v), at least 2.5% (w/v), at least 2.6% (w/v), at least 2.7% (w/v), at least 2.8% (w/v), at least 2.9% (w/v) or at least 3% (w/v). Butanamide is used in a concentration, wherein it exerts a stabilizing effect on the cell-containing biological sample, in particular the extracellular nucleic acid population that is contained in the cell-free portion of the cell-containing sample. As is shown by the examples, butanamide is effective in various concentrations. Suitable concentrations of butanamide for different sample types can also be determined by the skilled person using routine experiments, e.g. by testing different concentrations of butanamide in the test assays described in the examples. As is shown by the examples, the suitable concentration range for butanamide also depends on whether one or more additional stabilizers are used in combination with butanamide. E.g. lower concentrations of butanamide can be used if one or more additional stabilizing additives as described herein, preferably at least one caspase inhibitor and/or a compound according to formula 1 (see below), are used in combination with butanamide for stabilizing a cell-containing biological sample such as e.g. blood. Suitable concentration ranges for butanamide when mixed with the cell-containing biological sample and optionally further additives, include but are not limited to 0.1% (w/v) up to 15%, 0.25% (w/v) to 13% (w/v), 0.4% (w/v) to 12% (w/v), 0.5% (w/v) to 10% (w/v), 0.75% (w/v) to 8% (w/v), 1% (w/v) to 7.5% (w/v), 1.25% (w/v) to 7% (w/v), 1.5% (w/v) to 6.5% (w/v), 1.75% (w/v) to 6% (w/v), 1.8% (w/v) to 5.5% (w/v), 1.9% (w/v) to 5.25% (w/v), 2% (w/v) to 5% (w/v), 2.1% (w/v) to 4.75% (w/v), 2.2% (w/v) to 4.5% (w/v), 2.3% (w/v) to 4.25% (w/v), 2.4% (w/v) to 4% (w/v), 2.5% (w/v) to 3.75% (w/v) or 2.5% (w/v) to 3.5% (w/v). According to one embodiment, said mixture that is obtained after contacting the cell-containing biological sample with butanamide and optionally further additives, comprises butanamide in a concentration that lies in the range of 0.5% (w/v) to 3.5% (w/v), preferably 0.75% (w/v) to 3.25% or 0.9% (w/v) to 3% (w/v). Such concentrations are particularly suitable for stabilizing blood samples. As is shown by the examples, using butanamide in a concentration that lies in these ranges provides an excellent stabilizing effect on blood samples and furthermore, prevents the hemolysis of the red blood cells contained in the blood sample. A lower butanamide concentration of ≤2% (w/v) is particularly effective when additionally using a further stabilizing agent such as preferably a caspase inhibitor and/or a compound according to formula 1. As is shown by the examples, using a combination of these stabilizing agents is particularly advantageous for stabilizing blood samples.

As is shown by the provided examples, butanamide alone is already effective in stabilizing a cell-containing sample and preserving the extracellular nucleic acid population from changes in its composition, in particular changes arising from a contamination with fragmented genomic DNA. Blood samples could be stabilized using butanamide for a stabilization period of up to three days. This is sufficient considering regular shipping and handling periods of e.g. blood samples. However, according to a preferred embodiment, the cell-containing biological sample is additionally contacted with at least one apoptosis inhibitor. The term "apoptosis inhibitor" as used herein in particular refers to a compound whose presence in a cell-containing biological sample provides a reduction, prevention and/or inhibition of apoptotic processes in the cells and/or makes the cells more resistant to apoptotic stimuli. Apoptosis inhibitors include but are not limited to proteins, peptides or protein- or peptide-like molecules, organic and inorganic molecules. Apoptosis inhibitors include compounds that act as metabolic inhibitors, inhibitors of nucleic acid degradation respectively nucleic acid pathways, enzyme inhibitors, in particular caspase inhibitors, calpain inhibitors and inhibitors of other enzymes involved in apoptotic processes. Respective apoptosis inhibitors are listed in Table 1. Preferably, the at least one apoptosis inhibitor that is used for stabilizing the cell-containing biological sample is selected from the group consisting of metabolic inhibitors, caspase inhibitors and calpain inhibitors. Examples for each class are listed in Table 1 in the respective category. Preferably, the apoptosis inhibitor is cell-permeable. It is also within the scope of the present invention to use a combination of different apoptosis inhibitors, either from the same or a different class of apoptosis inhibitors, respectively to use a combination of different apoptosis inhibitors which inhibit apoptosis either by the same or a different working mechanism.

In an advantageous embodiment of the present invention, the apoptosis inhibitor is a caspase inhibitor. Members of the caspase gene family play a significant role in apoptosis. The substrate preferences or specificities of individual caspases have been exploited for the development of peptides that successfully compete caspase binding. It is possible to generate reversible or irreversible inhibitors of caspase activation by coupling caspase-specific peptides to e.g. aldehyde, nitrile or ketone compounds. Suitable examples are described below. Therefore, according to a preferred embodiment; the cell-containing biological sample is contacted with butanamide and at least one caspase inhibitor. As is shown by the examples, using butanamide in combination with a caspase inhibitor significantly improves the achieved stabilization effect. In particular, the stabilization effect is achieved for a prolonged period of time. Furthermore, it was found that in particular with biological samples that contain large amounts of cells and furthermore, differ in their composition, such as e.g. blood samples, the achieved stabilization effect was stronger and more uniform. E.g. blood samples derived from different donors may differ in the changes in the extracellular nucleic acid population that occur during ex vivo handling. Some samples show strong alterations in the profile of the extracellular nucleic acid population (in particular strong increases in genomic DNA) while in other samples the effects are less prominent. Such samples can also react differently to stabilization. When using butanamide in combination with a caspase inhibitor for stabilizing blood samples obtained from different donors, a more equalized, uniform stabilization effect was achieved. Thus, variations in the original blood sample had less or even no influence on the achieved stabilization. Therefore, preferably, the cell-containing sample is contacted with butanamide and at least one caspase inhibitor. The caspase inhibitor present in the resulting mixture significantly supports the stabilization. The combination of butanamide and the caspase inhibitor inter alia stabilizes nucleated cells comprised in the biological sample, thereby preventing that intracellular nucleic acids, such as in particular genomic DNA, are released from cells comprised in the biological sample. It was found that a combination of a caspase inhibitor with butanamide is particularly effective in reducing the risk that the extracellular nucleic acid population is contaminated with intracellular nucleic acids, in particular fragmented genomic DNA, that originate from cells contained in the sample. As described, such contaminations are problematic as they dilute the extracellular nucleic acids and furthermore, alter the composition and thus profile of the extracellular nucleic acid population. To preserve the profile, however, is often important for diagnostic applications. Furthermore, the degradation of nucleic acids, in particular genomic DNA, present in the sample is reduced by said combination of stabilizers. Thus, using butanamide in combination with at least one caspase inhibitor significantly improves the stabilization effect thereby supporting that the extracellular nucleic acid population contained in the sample is substantially preserved in the state it had shown at the time the biological sample was obtained, respectively collected, even during prolonged storage periods. The reliable preservation of the extracellular nucleic acid population, in particular its composition/profile, makes an important contribution to the prior art. The combination according to the invention has a better stabilizing effect than the caspase inhibitor alone or butanamide alone. The results achieved with the combination of butanamide and the caspase inhibitor were comparable to the stabilization effect that is achieved with a combination of a caspase inhibitor and N,N dimethylacetamide (DMAA). Such a combination of stabilizing agents is described in unpublished PCT/EP2012/070211 and PCT/EP2012/068850. As these unpublished applications show, a combination of a caspase inhibitor and DMAA is very effective in stabilizing the extracellular nucleic acid population comprised in cell-containing biological samples such as whole blood samples. However, N,N-dimethylacetamide is a toxic agent. In contrast thereto, butanamide is not toxic and furthermore, is also not harmful or irritant. Therefore, stabilizing a cell-containing biological sample by using a combination of butanamide with a caspase inhibitor has important advantages over using a combination of a caspase inhibitor and N,N-dimethylacetamide. The present invention allows to efficiently stabilize the extracellular nucleic acid population comprised in a cell-containing biological sample without the use of toxic agents.

Preferably, the caspase inhibitor is cell-permeable. It is also within the scope of the present invention to use a combination of different caspase inhibitors. Members of the caspase gene family play a significant role in apoptosis. The substrate preferences or specificities of individual caspases have been exploited for the development of peptides that successfully compete caspase binding. It is possible to generate reversible or irreversible inhibitors of caspase activation by coupling caspase-specific peptides to e.g. aldehyde, nitrile or ketone compounds. E.g. fluoromethyl ketone (FMK) derivatized peptides such as Z-VAD-FMK act as effective irreversible inhibitors with no added cytotoxic effects. Inhibitors synthesized with a benzyloxycarbonyl group (BOC) at the N-terminus and O-methyl side chains exhibit enhanced cellular permeability. Further suitable caspase inhibitors are synthesized with a phenoxy group at the C-terminus. An example is Q-VD-OPh which is a cell permeable, irreversible broad-spectrum caspase inhibitor that is even more effective in preventing apoptosis and thus supporting the stabilization than the caspase inhibitor Z-VAD-FMK.

According to one embodiment, the caspase inhibitor used in combination with butanamide for stabilizing a cell-containing biological sample is a pancaspase inhibitor and thus is a broad spectrum caspase inhibitor. According to one embodiment, the caspase inhibitor comprises a modified caspase-specific peptide. Preferably, said caspase-specific peptide is modified by an aldehyde, nitrile or ketone compound. According to a preferred embodiment, the caspase specific peptide is modified, preferably at the carboxyl terminus, with an O-Phenoxy (OPh) or a fluoromethyl ketone (FMK) group. According to one embodiment, the caspase inhibitor is selected from the group consisting of Q-VD-OPh and Z-VAD(OMe)-FMK. In one embodiment, Z-VAD(OMe)-FMK, a pancaspase inhibitor, is used, which is a competitive irreversible peptide inhibitor and blocks caspase-1 family and caspase-3 family enzymes. In a preferred embodiment, Q-VD-OPh, which is a broad spectrum inhibitor for caspases, is used for stabilization. Q-VD-OPh is cell permeable and inhibits cell death by apoptosis. Q-VD-OPh is not toxic to cells even at extremely high concentrations and comprises a carboxy terminal phenoxy group conjugated to the amino acids valine and aspartate. It is equally effective in preventing apoptosis mediated by the three major apoptotic pathways, caspase-9 and caspase-3, caspase-8 and caspase-10, and caspase-12 (Caserta et al, 2003). Further caspase inhibitors that can be used according to the teachings of the present invention are listed in Table 1. According to one embodiment, the caspase inhibitor that is used for stabilizing the cell-containing sample is one which acts upon one or more caspases located downstream in the intracellular cell death pathway of the cell, such as caspase-3. In one embodiment of the present invention the caspase inhibitor is an inhibitor for one or more caspases selected from the group consisting of caspase-3, caspase-8, caspase-9, caspase-10 and caspase-12. As described, it is also within the scope of the present invention to use a combination of caspase inhibitors.

The mixture that is obtained after contacting the biological sample with butanamide and the at least one caspase inhibitor (and optionally further additives) may comprise the caspase inhibitor (or combination of caspase inhibitors) in a concentration of at least 0.01 NM, at least 0.05 µM, at least 0.1 µM, at least 0.5 µM, at least 0.6 µM, at least 0.7 µM, at least 0.75 µM at least 0.8 µM, at least 0.9 µM, at least 1 µM, at least 1.25 µM, at least 1.5 µM, at least 1.75 µM, at least 2 µM, at least 2.25 µM, at 2.5 µM, at least 2.75 µM, at least 3 µM, at least 3.25 µM or at least 3.5 µM. Of course, also higher concentrations can be used if a stabilization effect is maintained. Suitable concentration ranges for the caspase inhibitor(s) when mixed with the cell-containing biological sample and butanamide (and optionally further additives) include but are not limited to 0.01 µM to 100 µM, 0.1 µM to 75 µM, 0.25 µM to 50 µM, 0.5 µM to 40 µM, 0.6 µM to 30 µM, 0.7 µM to 35 µM, 0.8 µM to 30 µM, 0.9 µM to 25 µM, 1 µM to 20 µM, 1.1 µM to 17.5 µM, 1.25 µM to 15 µM or 1.5 µM to 12.5 µM. The higher concentrations were found to be more effective, however, good stabilizing results were also achieved at lower concentrations. Hence, an efficient stabilization is also achieved at lower concentrations e.g. in a range selected from 0.25 µM to 10 µM, 0.5 µM to 7.5 µM, 0.75 µM to 5 µM or 1 µM to 3 µM. The above mentioned concentrations apply to the use of a single caspase inhibitor as well as to the use of a combination of caspase inhibitors. If a combination of caspase inhibitors is used, the concentration of an individual caspase inhibitor that is used in said mixture of caspase inhibitors may also lie below the above mentioned concentrations, if the overall concentration of the combination of apoptosis inhibitors fulfils the above mentioned features. Using a lower concentration of a caspase inhibitor that still efficiently stabilizes cells and/or reduces the degradation of nucleic acids in present in the sample has the advantage that the costs for stabilization can be lowered. Lower concentrations can be used inter alia because the caspase inhibitor is used in combination with butanamide and optionally in combination with one or more other stabilizing additives as described herein. The aforementioned concentrations are in particular suitable when using a pancaspase inhibitor, in particular a modified caspase specific peptide such as Q-VD-OPh and/or Z-VAD(OMe)-FMK. The above mentioned concentrations are e.g. very suitable for stabilizing whole blood. Suitable concentration ranges for individual caspase inhibitors and/or for other cell-containing biological samples can be determined by the skilled person using routine experiments, e.g. by testing different concentrations of the respective caspase inhibitor in the test assays described in the examples. According to one embodiment, the caspase inhibitor will, in an effective amount, decrease or reduce apoptosis in a cell-containing biological sample by at least 25 percent, at least 30 percent, at least 40 percent, at least 50 percent, preferably, by at least 75 percent, more preferably, by at least 85 percent as compared to a control sample which does not contain a respective caspase inhibitor.

According to one embodiment, the cell-containing biological sample to be stabilized is contacted with butanamide and at least one compound according to formula 1

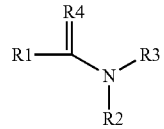

formula 1 wherein R1 is a hydrogen residue or an alkyl residue, preferably a C1-C5 alkyl residue, a C1-C4 alkyl residue or a C1-C3 alkyl residue, more preferred a C1-C2 alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue, preferably R4 is oxygen.

As is shown by the examples, a compound according to formula 1 as defined above is effective in achieving a stabilizing effect either alone or when being used in addition to butanamide. Also a mixture of one or more compounds according to formula 1 can be used in addition to butanamide for stabilization. Using one or more compounds according to formula 1 in addition to butanamide is advantageous, as it allows reducing the concentration of butanamide necessary for stabilization. This is advantageous, because the storage stability of a stabilizing composition comprising butanamide and a compound according to formula 1 is increased, in particular at lower temperatures. This allows to use a small volume of stabilising composition for stabilising a large amount of cell-containing biological sample such as blood.

According to one embodiment, the cell-containing biological sample is contacted for stabilization with butanamide, at least one caspase inhibitor and at least one compound according to formula 1. Preferably, the cell-containing sample is a blood sample. In the resulting mixture, butanamide is according to one embodiment comprised in a concentration of 3% (w/v) or less, 2.5% (w/v) or less, preferably 2.25% (w/v) or less, more preferred 2% (w/v) or less. Suitable ranges include e.g. 0.1% to 3%, 0.3% to 2.5%, 0.5% to 2% and 0.6% to 1.75%-all (w/v).

R2 and/or R3 of the compound according to formula 1 are identical or different and are selected from a hydrogen residue and a hydrocarbon residue. Thus, the compound according to formula 1 can be a primary, secondary or tertiary amide. Preferably, the compound according to formula 1 is a carboxylic acid amide. According to one embodiment, R2 and R3 are identical or different hydrocarbon residues. The hydrocarbon residues R2 and/or R3 can be selected independently of one another from the group comprising alkyl, including short chain alkyl and long-chain alkyl, alkenyl, alkoxy, long-chain alkoxy, cycloalkyl, aryl, haloalkyl, alkylsilyl, alkylsilyloxy, alkylene, alkenediyl, arylene, carboxylates and carbonyl. General groups, for instance alkyl, alkoxy, aryl etc. are claimed and described in the description and the claims. Preferably, the following groups are used within the generally described groups within the scope of the present invention:

(1) alkyl: preferably short chain alkyls, in particular linear and branched C1-C5 alkyls or long-chain alkyls: linear and branched C5-C20 alkyls;
(2) alkenyl: preferably C2-C6 alkenyl;
(3) cycloalkyl: preferably C3-C8 cycloalkyl;
(4) alkoxy: preferably C1-C6 alkoxy;
(5) long-chain alkoxy: preferably linear and branched C5-C20 alkoxy;
(6) alkylenes: preferably a divalent linear or branched aliphatic, cycloaliphatic or aromatic hydrocarbon residue with 2 to 18 carbon atoms optionally containing heteroatoms, e.g. selected from the group comprising: methylene; 1,1-ethylene; 1,1-propylidene; 1,2-propylene; 1,3-propylene; 2,2-propylidene; butan-2-ol-1,4-diyl; propan-2-ol-1,3-diyl; 1,4-butylene; 1,4-pentylene; 1,6-hexylene; 1,7-heptylene; 1,8-octylene; 1,9-nonylene; 1,10-decylene; 1,11-undecylene; 1,12-docedylene; cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and cyclopentane-1,3-diyl;
(7) alkenediyl: preferably selected from the group comprising: 1,2-propenediyl; 1,2-butenediyl; 2,3-butenediyl; 1,2-pentenediyl; 2,3-pentenediyl; 1,2-hexenediyl; 2,3-hexenediyl; and 3,4-hexenediyl;
(8) alkynediyl: is equal to C≡C—;
(9) aryl: preferably selected from aromatics with a molecular weight below 300 Da;
(10) arylenes: preferably selected from the group comprising: 1,2-phenylene; 1,3-phenylene; 1,4-phenylene; 1,2-naphtthalenylene; 1,3-naphtthalenylene; 1,4-naphtthalenylene; 2,3-naphtthalenylene; 1-hydroxy-2,3-phenylene; 1-hydroxy-2,4-phenylene; 1-hydroxy-2,5-phenylene; 1-hydroxy-2,6-phenylene;
(11) carboxylate: preferably the group —C(O)OR, where R is selected from: hydrogen; C1-C6 alkyl; phenyl; C1-C6 alkyl-C6H5; Li; Na; K; Cs; Mg; Ca;
(12) carbonyl: preferably the group —C(O)R, where R is selected from: hydrogen; C1-C6 alkyl; phenyl; C1-C6 alkyl-C6H5 and amine (resulting in an amide) selected from the group: —NR'2, where each R' is selected independently from: hydrogen; C1-C6 alkyl; C1-C6 alkyl-C6H5 and phenyl, where, if both Rs represent C1-C6 alkyl they can form an NC3 to NC5 heterocyclic ring with alkyl substituents of the ring forming the other alkyl chain;
(13) alkylsilyl: preferably the group —SiR1R2R3, where R1, R2 and R3 are selected independently of one another from: hydrogen; alkyl; long-chain alkyl; phenyl; cycloalkyl; haloalkyl; alkoxy; long-chain alkoxy;
(14) alkylsilyloxy: preferably the group —O—SiR1R2R3, where R1, R2 and R3 are selected independently of one another from: hydrogen; alkyl; long-chain alkyl; phenyl; cycloalkyl; haloalkyl; alkoxy; long-chain alkoxy.

The chain length n of R2 and/or R3 can in particular have the values 1, 2, 3, 4, 5, 6, 7, 8, 9, 10, 11, 12, 13, 14, 15, 16, 17, 18, 19 and 20. Preferably R2 and R3 have a length of the carbon chain of 1-10. In this case the chain length n can in particular have the values 1, 2, 3, 4, 5, 6, 7, 8, 9, and 10. Preferably, R2 and R3 have a length of the carbon chain of 1-5 and in this case the chain length can in particular have the values 1, 2, 3, 4 and 5. Particularly preferred is a chain length of 1 or 2 for R2 and R3. Preferably, R2 and R3 are both alkyl residues, preferably C1-C5 alkyl residues.

The chain length n of R1 preferably has the value 1,2,3,4 or 5. Particularly preferred is a chain length of 1 or 2 for R1. R4 preferably is oxygen.

According to a preferred embodiment, the compound according to formula 1 is a carboxylic acid amide. It can be a primary, secondary or tertiary carboxylic acid amide. In a particularly preferred embodiment, the compound according to formula 1 is a N,N-dialkyl-carboxylic acid amide. Preferred R1, R2, R3 and R4 groups are described above. Using a respective compound according to formula 1 has the advantage that additionally, intracellular nucleic acids such as in particular RNA, e.g. mRNA and/or miRNA transcripts can be stabilized in the cell-containing sample. The additional stabilization of intracellular nucleic acids, in particular gene transcript levels, is advantageous as it e.g. allows the subsequent analysis of target transcripts or transcript profiles in the contained cells. According to one embodiment, the compound according to formula 1 is selected from the group consisting of N,N-dimethylacetamide, N,N-diethylacetamide, N, N-dimethylformamide and N,N-diethylformamide. Also suitable are the respective thio analogues, which comprise sulphur instead of oxygen as R4. N,N-dimethylacetamide (DMAA) e.g. achieves good stabilization results, however, is a toxic agent. Preferably, a compound according to formula 1 is used for stabilizing the cell-containing biological sample in combination with butanamide which is not a toxic agent according to the GHS classification.

According to a particularly preferred embodiment, the cell-containing biological sample is contacted for stabilization with butanamide and a compound according to formula 1 which is a N,N-dialkylpropanamide, preferably the sample is contacted with butanamide and N,N-dimethylpropanamide. Preferably, a caspase inhibitor is additionally used for stabilisation. According to one embodiment, the cell-containing biological sample is contacted with butanamide, a caspase inhibitor and N,N-dimethylpropanamide. As is shown in the examples, stabilizing a cell-containing biological sample such as a blood sample with a caspase inhibitor, butanamide and N,N-dimethylpropanamide achieves excellent stabilization results. A stabilization of the extracellular nucleic acid population as well as a stabilization of intracellular nucleic acids can be achieved with a respective combination. Furthermore, advantageously, in contrast to DMAA, N,N-dimethylpropanamide is not classified as toxic agent. N,N-dimethylpropanamide is an expensive compound, however, using N,N-dimethylpropanamide in combination with butanamide (and preferably additionally a caspase inhibitor) allows to use low concentrations of N,N-dimethylpropanamide for stabilization, thereby allowing to reduce the costs for stabilizing the cell-containing sample.

The mixture that is obtained when contacting the cell-containing biological sample with butanamide and a compound according to formula 1 or a mixture of respective compounds (and optionally further additives such as preferably a caspase inhibitor) may comprise the compound according to formula 1 (or mixture of such compounds) in a concentration of at least 0.1%, at least 0.25%, at least 0.5%, at least 0.75%, at least 1%, at least 1.25% or at least 1.5%. Suitable concentration ranges include but are not limited to 0.1% to 30%, 0.25% to 20%, 0.5% to 15%, 0.7% to 10%, 0.8% to 7.5%, 0.9% to 6% and 1% to 5%. Concentrations or concentration ranges indicated in percentage values as used herein are in particular given as percentage weight per volume (w/v) for solid compounds, substances or compositions in a liquid composition, and as percentage volume per volume (v/v) for liquid compounds, substances or compositions in a liquid composition. Respective concentrations are particularly suitable when using a N,N-dialkyl-carboxylic acid amide, preferably a N—N-dialkylpropanamide such as N,N-dimethylpropanamide as additional stabilizing agent. The above mentioned concentrations are e.g. very suitable for stabilizing whole blood or blood products such as plasma. Suitable concentration ranges for other compounds according to formula 1 and/or other cell-containing biological samples for use in the method according to the present invention can also be determined by the skilled person using routine experiments, e.g. by testing the compound, respectively different concentrations thereof in the test assays described in the examples.

According to one embodiment, the cell-containing biological sample is contacted for stabilization with butanamide, at least one caspase inhibitor and at least one compound according to formula 1 as defined above. As described above, preferably, a compound according to formula 1 is used that is non-toxic. Particularly preferred is the use in combination with a N—N-dialkylpropanamide such as N,N-dimethylpropanamide, which is a non-toxic agent.

According to one embodiment, the cell-containing biological sample to be stabilized is contacted with butanamide and at least one poly(oxyethylene) polymer as stabilizing agent.

The term poly(oxyethylene) polymer in particular refers to an oligomer or polymer of ethylene oxide. It comprises at least two ethylene oxide units. Poly(oxyethylene) polymers are known in low and high molecular weights. Their molecular weight are usually multitutes of 44, the molecular weight of its monomer, and can range up to 100000. The respective molecular weights described herein are in Da. The poly(oxyethylene) polymer may be linear or branched or may have other geometries. A linear poly(oxyethylene) polymer is preferred. The poly(oxyethylene) polymer may be unsubstituted or substituted and preferably is a polyethylene glycol. As is demonstrated in the examples, polyethylene glycol has in various molecular weights and in various concentrations a stabilization effect on cells and therefore can be used in combination with butanamide and optionally other stabilization agents in order to support the stabilization of the extracellular nucleic acid population in a cell-containing sample, in particular by assisting to reduce the dilution of the extracellular nucleic acid population by intracellular nucleic acids such as in particular genomic DNA. However, also other poly(oxyethylene) polymers may be used that achieve a stabilization effect as was shown for polyethylene glycol. As mentioned, also substituted poly(oxyethylene) polymers having a stabilizing effect may be used such as alkyl poly(oxyethylene) polymers, e.g. alkylpolyethylene glycols, but also poly(oxyethylene) esters, poly(oxyethylene) amines, poly(oxyethylene) thiol compounds, poly(oxyethylene) glycerides and others. The preferred embodiment of the poly(oxyethylene) polymer that is used as stabilizing agent is polyethylene glycol. It preferably is unbranched and may be unsubstituted or substituted. Known substituted forms of polyethylene glycol include alkylpolyethylene glycols that are e.g. substituted at one or both ends with an C1-C5 alkyl group. Preferably, unsubstituted polyethylene glycol of the formula HO—$(CH_2CH_2O)_n$—H is used. All disclosures described in this application for the poly(oxyethylene) polymer in general, specifically apply and particularly refer to the preferred embodiment polyethylene glycol even if not explicitly stated. The poly(oxyethylene) polymer can be used in various molecular weights. Preferably, the term polyethylene glycol refers to oligo or polymers as is also evident from the molecular weights specified herein as suitable and preferred for the poly(oxyethylene) polymer which specifically also apply to the preferred embodiment polyethylene glycol.

A correlation was found between the stabilization effect of the poly(oxyethylene) polymer and its molecular weight. Higher molecular weight poly(oxyethylene) polymers were found to be more effective stabilizing agents than lower molecular weight poly(oxyethylene) polymers. To achieve an efficient supporting stabilization effect with a lower molecular weight poly(oxyethylene) polymer, generally higher concentrations are recommendable compared to a higher molecular weight poly(oxyethylene) polymer. For some applications such as blood samples it is preferred though to keep the amount of additives used for stabilization low. Therefore, in embodiments, higher molecular weight poly(oxyethylene) polymers are used as stabilizing agents, as they allow to use lower concentrations of the poly(oxyethylene) polymer while achieving a strong stabilization effect on the extracellular nucleic acid population.

Thus, according to one embodiment, a high molecular weight poly(oxyethylene) polymer having a molecular weight of at least 1500 is used as further stabilizing agent together with butanamide and is contacted with the cell-containing sample. The high molecular weight poly(oxyethylene) polymer may have a molecular weight that lies in a range selected from 1500 to 50000, 2000 to 40000, 2500 to 30000, 3000 to 20000, 3500 to 15000, 4000 to 10000, 4500 to 9000, 5000 to 8000 and 5500 to 7000. These molecular weights are particularly preferred for the use of a polyethylene glycol, in particular an unsubstituted polyethylene glycol. Unsubstituted polyethylene glycol was also used in the examples. The molecular weight of a poly(oxyethylene) polymer having a specific molecular weight may vary within certain ranges conditional to manufacturing as is well-known to the skilled person.

The high molecular weight poly(oxyethylene) polymer is used in a concentration, wherein it supports the stabilization of the extracellular nucleic acid population that is contained in the cell-containing sample. Suitable concentrations for different sample types can be determined by the skilled person, for example by testing different concentrations of a specific high molecular weight poly(oxyethylene) polymer in the test assays described in the examples. As is demonstrated by the examples, the high molecular weight poly(oxyethylene) polymer is effective in various concentrations and supports the stabilization effect of butanamide. The achieved stabilization effect and the preferred concentration also depends on whether besides butanamide one or more additional stabilizing agents are used. Preferred combinations are described herein. According to one embodiment, the mixture that is obtained after contacting the cell-containing biological sample with butanamide and the high molecular weight poly(oxyethylene) polymer and optionally further additives comprises the high molecular weight poly(oxyethylene) polymer in a concentration range that is selected from 0.05% to 4% (w/v), 0.1% to 3% (w/v), 0.2% to 2.5% (w/v), 0.25% to 2% (w/v), 0.3% to 1.75% (w/v) and 0.35% to 1.5% (w/v). According to one embodiment, the high molecular weight poly(oxyethylene) polymer is used in lower concentration ranges such as 0.25% to 1.5% (w/v), 0.3% to 1.25% (w/v), 0.35% to 1% (w/v) and 0.4% to 0.75% (w/v). The above concentrations ranges are particularly suitable for the stabilization of blood. Using a high molecular weight poly(oxyethylene) polymer in a concentration of 1.5% (w/v) or less, 1.25% (w/v) or less, 1% (w/v) or less and in particular in a concentration of 0.75% (w/v) or less is advantageous in certain embodiments. It was found in embodiments wherein a high molecular weight poly(oxyethylene) polymer was used in certain higher concentrations in the resulting mixture comprising the stabilizing agent and the cell-containing sample, such as a blood sample, the subsequent isolation of the extracellular nucleic acids may become impaired when using certain standard nucleic acid isolation procedures that involve e.g. the use of silica columns. It is however advantageous to use a stabilization technology that is compatible with most standard nucleic acid isolation methods and the use of silica columns for isolating extracellular nucleic acids is widely used and established. Using the high molecular weight poly(oxyethylene) polymer in a concentration of 1.5% (w/v) or less, 1.25% (w/v) or less, 1% (w/v) or less or 0.75% or less in the stabilization mixture containing the sample supports that the extracellular nucleic acids can be efficiently isolated from the stabilized samples using such standard methods with good yield even if higher volumes of stabilization composition is used. This is advantageous, because extracellular nucleic acids and in particular specific target nucleic acids comprised in the extracellular nucleic acid populations are often present in only few copies. As is demonstrated in the examples, the observed impairment also depends on the used volume of the the stabilization composition that contains the high molecular weight (polyoxyethylene) polymer. Using a lower volume of stabilizing composition for stabilization can compensate the impairment even if a high molecular weight poly(oxyethylene) polymer is used in higher concentrations so that the subsequent nucleic acid isolation is not impaired. Thus, reducing the overall concentration of the high molecular weight poly(oxyethylene) polymer in the mixture containing the sample and/or reducing the volume of stabilsation composition containing the high molecular weight poly(oxyethylene) polymer are alternative options to reduce or even avoid impairment. This volume dependent effect that is demonstrated in the examples is significant and was highly surprising as the overall concentration of the poly(oxyethylene) glycol in the mixture containing the sample was the same.

According to one embodiment, the poly(oxyethylene) polymer that is used in addition to butanamide for stabilization has a molecular weight below 1500 and may be a low molecular weight poly(oxyethylene) polymer having a molecular weight of 1000 or less. It is used in a concentration wherein it can support the stabilizing effect on the extracellular nucleic acid population of the cell-containing biological sample. Suitable concentrations for different sample types can be determined by the skilled person, e.g. by testing different concentrations in the test assays described in the examples. A respective poly(oxyethylene) polymer, such as a low molecular weight poly(oxyethylene) polymer having a molecular weight of 1000 or less, can be present in the mixture that is obtained after contacting the cell-containing biological sample with said poly(oxyethylene) polymer and optionally further additives in a concentration range that is selected from 0.5% to 10%, 1.5% to 9%, 2% to 8%, 2 to 7%, 2.5% to 7% and 3% to 6%. The percentage values refer to (w/v) in case the poly(oxyethylene) polymer is a solid and to (v/v) in case the poly(oxyethylene) polymer is a liquid. The indicated concentrations are particularly suitable for the use in case of blood samples. Higher concentration of at least 1%, preferably at least 1.5% are advantageous for a low molecular weight poly(oxyethylene) polymer to support the stabilization of the extracellular nucleic acid population in combination with butanamide. It was found that the low molecular weight poly(oxyethylene) polymer having a molecular weight of 1000 or less, preferably 700 or less, can be used in a substantially higher concentrations, because it does not substantially hinder the subsequent isolation of the extracellular nucleic acids from the stabilized sample even if a higher volume of the stabilizing composition is used. However, if the amount required to achieve a stabilization effect is too high, this can be inconvenient for the processing and handling of the samples. It is generally preferred to stabilize the sample with a rather low amount or volume of stabilizing agents. This particularly, as in case of certain samples such as blood samples, the amount of stabilizing agent that can be added to the sample is restricted by the standard collection tubes that are used. E.g. for a standard collection device that is used for collecting 10 ml blood, approx. 2 ml stabilizing agent can be added as maximum.

According to one embodiment, in addition to butanamide, at least two poly(oxyethylene) polymers are used for stabilization, which differ in their molecular weight. They may be of the same kind and preferably both are a polyethylene glycol such as an unsubstituted polyethylene glycol. According to one embodiment, the difference in the molecular weight is at least 100, at least 200, at least 300, at least 400, at least 500, at least 600, at least 700, at least 800, at least 900 or at least 1000. As is described subsequently in detail for specific embodiments of this embodiment, it is advantageous to use two poly(oxyethylene) polymers that differ in their molecular weight. As described herein, the stabilization effect of poly(oxyethylene) polymers appears to depend on their molecular weight. In the tested examples it was found that the higher the molecular weight, the higher the stabilization efficiency. However, poly(oxyethylene) polymers may differ in their effect on the subsequent nucleic acid isolation method depending on their molecular weight. As described above, it was found that in certain embodiments that involve the use of higher molecular weight poly(oxyethylene) polymers as stabilizing agents, in particular where a higher volume of stabilization composition and a higher concentration of the polymer in the stabilizing mixture containing the sample was used, that the nucleic acid isolation was less efficient with certain nucleic acid isolation methods. As is demonstrated by the examples, such issues that occur in certain scenarios can be overcome when using a mixture of poly(oxyethylene) polymers that differ in their molecular weight. Therefore, this embodiment wherein in addition to butanamide at least two poly(oxyethylene) polymers are used for stabilization that differ in their molecular weight is advantageous, because it allows to provide balanced compositions of poly(oxyethylene) polymers having the desired characteristics with respect to the stabilization effect to be achieved and the characteristics required e.g. for certain downstream uses.

According to one embodiment, a high molecular weight poly(oxyethylene) polymer as defined above which has a molecular weight of at least 1500 is used in combination with a low molecular weight poly(oxyethylene) polymer having a molecular weight of 1000 or less and the cell-containing sample is additionally contacted with both types of poly(oxyethylene) polymers. Using a high molecular weight poly(oxyethylene) polymer in combination with a low molecular weight poly(oxyethylene) polymer is advantageous, because the low molecular weight poly(oxyethylene) polymer allows to reduce the concentration of the high molecular weight poly(oxyethylene) polymer required to achieve an effective stabilization of the sample. Therefore, the high molecular weight poly(oxyethylene) polymer can be used in the mixture with the sample in a concentration wherein, e.g., it does not substantially impair the subsequent nucleic acid isolation using certain standard methods such as those involving silica columns. This embodiment is advantageous because it provides more freedom with respect to the volume or amount of stabilization composition that can be used. The low molecular weight poly(oxyethylene) polymer assists in the stabilization but in contrast to the high molecular weight poly(oxyethylene) polymer, in the tested examples was not found to significantly impair the subsequent isolation of the nucleic acids when using methods, such as those involving silica columns, where the higher molecular weight poly(oxyethylene) polymers showed in certain concentrations and/or volumes an impairing effect in the examples. Therefore, stabilizing the extracellular nucleic acid population in a cell-containing sample using a combination of butanamide and a high and a low molecular weight poly(oxyethylene) polymer is an advantageous embodiment. The low molecular weight poly(oxyethylene) polymer can be of the same kind as the high molecular weight poly(oxyethylene) polymer which was described above. Also for the low molecular weight poly(oxyethylene) polymer it is preferred that a polyethylene glycol is used, such as an unsubstituted polyethylene glycol. The low molecular weight poly(oxyethylene) polymer may have a molecular weight that lies in a range selected from 100 to 1000, 150 to 800, 150 to 700, preferably 200 to 600 and more preferably 200 to 500.

According to one embodiment, the mixture that is obtained after contacting the cell-containing biological sample, which preferably is blood, with butanamide and the high and the low molecular weight poly(oxyethylene) polymer and optionally further additives used for stabilization, comprises the high molecular weight poly(oxyethylene) polymer, which may have a molecular weight in the range of 3000 to 40000, preferably 4000 to 20000, more preferred 4500 to 10000, in a concentration that lies in a range of 0.2% to 1.5% (w/v), preferably 0.3% to 1.25% (w/v) and in certain embodiments in a range of 0.4 (w/v) to 0.75% (w/v) and the low molecular weight poly(oxyethylene) polymer, which preferably has a molecular weight that lies in a range of 200 to 800, preferably 200 to 600 in a concentration that lies in a range selected from 1.5% to 8%, preferably 2% to 7% or 2% to 6%. The high and low molecular weight poly(oxyethylene) polymer is preferably a polyethylene glycol, such as an unsubstituted polyethylene glycol. Suitable concentrations for butanamide are described above and also apply to this embodiment. The cell-containing biological sample may be blood in this embodiment and the blood sample is additionally contacted with an anticoagulant. Suitable examples for anticoagulants are described herein.

According to one embodiment, the cell-containing biological sample is contacted for stabilization with butanamide, at least one poly(oxyethylene) polymer, and furthermore, at least one caspase inhibitor and/or at least one compound according to formula 1 as defined above. In particular, the cell-containing biological sample may be contacted for stabilization with butanamide, at least one poly(oxyethylene) polymer and at least one caspase inhibitor. Optionally, at least one compound according to formula 1 as defined above may be used in addition to stabilize the extracellular nucleic acid population of a cell containing sample. As described above, preferably, the at least one poly(oxyethylene) polymer is a high molecular weight poly(oxyethylene) polymer or a combination of a high and a low molecular weight poly(oxyethylene) polymer. The high molecular weight poly(oxyethylene) polymer preferably has a molecular weight of at least 1500, more preferably in a range of 2000 to 40000, more preferred 3000 to 20000 or 4500 to 10000. The poly(oxyethylene) polymer is preferably a polyethylene glycol, such as an unsubstituted polyethylene glycol.

According to one embodiment, the cell-containing biological sample to be stabilized is contacted with butanamide and mono-ethylenglycol (1,2-ethanediol) as supporting stabilizing agent. In particular, the cell-containing biological sample to be stabilized may be contacted with butanamide, mono-ethylenglycol and any one or more of the other compounds described herein, including at least one poly(oxyethylene) polymer, and at least one caspase inhibitor and/or at least one compound according to formula 1 as defined above.

The stabilizing effect observed with combinations of stabilizing agents is stronger than the effect observed for any of the individual stabilizing agents when used alone and/or allows using lower concentrations of individual stabilizers, thereby making combinatorial use of stabilizing agents an attractive option. Furthermore, additional additives can be used for stabilization such as e.g. anticoagulants and chelating agents which are particularly useful when stabilizing a blood sample.

As discussed in the background of the invention, extracellular nucleic acids are usually not present "naked" in the extracellular portion of the cell-containing sample but are e.g. stabilized to a certain extent by being released protected in complexes or by being contained in vesicles and the like. This has the effect that extracellular nucleic acids are already to a certain extent stabilized by nature and thus, are usually not degraded rapidly by nucleases in cell-containing samples such as whole blood, plasma or serum. Thus, when intending to stabilize extracellular nucleic acids that are comprised in a cell-containing biological sample, one of the primary problems after obtaining or collecting the cell-containing biological sample is the contamination of the extracellular nucleic acid population comprised in the collected cell-containing biological sample by intracellular nucleic acids, in particular fragmented genomic DNA, that originates from damaged or dying cells that are contained in the cell-containing biological sample. This dilutes the extracellular nucleic acids and furthermore, changes the profile of the extracellular nucleic acid population. This also poses a problem when processing cell-depleted samples such as plasma or serum (which are sometimes also describes as being "cell-free" even though they may comprise minor amounts of residual cells). The stabilization technology according to the present invention is of particular advantage in this respect because it not only substantially preserves the extracellular nucleic acids present in the sample and e.g. inhibits degradation of the comprised extracellular nucleic acids (preferably at least by 60%, at least by 70%, at least by 75%, at least by 80%, at least by 85%, at least by 90% or most preferably at least by 95% over the stabilization period compared to an unstabilized sample or e.g. an EDTA stabilized sample in the case of blood) but furthermore, efficiently reduces the release of genomic DNA from cells contained in the obtained cell-containing biological sample and/or reduces the fragmentation of respective genomic DNA. According to one embodiment, using butanamide, optionally but preferably a caspase inhibitor, and optionally a compound according to formula 1 and optionally an anticoagulant for stabilizing a cell-containing biological sample has the effect that the increase of DNA that results from a release of genomic DNA from cells contained in the sample is reduced compared to a non-stabilized sample. According to one embodiment, said release of genomic DNA is reduced by at least 3-fold, at least 4-fold, at least 5-fold, at least 6-fold, at least 7-fold, at least 10-fold, at least 12-fold, at least 15-fold, at least 17-fold or at least 20-fold over the stabilization period compared to the non-stabilized sample or a corresponding sample that is stabilized with EDTA (in particular in case of a blood sample or a sample derived from blood such as plasma or serum). According to one embodiment, said release of genomic DNA is reduced by at least 60%, at least 70%, at least 75%, at least 80%, at least 85%, at least 90% or at least 95% over the stabilization period compared to the non-stabilized sample or a corresponding sample that is stabilized with EDTA (in particular in case of a blood sample or a sample derived from blood such as plasma or serum). The release of DNA can be determined e.g. by quantifying the ribosomal 18S DNA as is described herein in the example section. As is shown in the examples, the stabilization achievable with the teachings of the present invention remarkably reduces this release of DNA over the stabilization period. Thus, according to one embodiment, the stabilization effect that is achieved with butanamide, optionally in combination with a caspase inhibitor and/or the compound according to formula 1, results in that the release of DNA from cells contained in the stabilized sample is over the stabilization period reduced at least down to a maximum of 10-fold, preferably at least down to a maximum of 7-fold, more preferably at least down to a maximum of 5-fold, more preferably is reduced e.g. at least down to a maximum of 4-fold, more preferably is reduced at least down to a maximum of 3-fold or 2-fold as is e.g. determinable in the 18S DNA assay described in the examples. As is shown by the examples, an effective stabilization of the extracellular nucleic acid population is achievable with the method of the invention for a period of at least three days and when using a combination of stabilizing agents as described herein even up to 6 days. The stabilization effect can even be longer, e.g. in embodiments wherein additionally a poly(oxyethylene) polymer such as polyethylene glycol is used for stabilization, preferably in addition to a caspase inhibitor. During shorter storage, respectively stabilization periods e.g. up to a maximum of three days, the DNA release can be reduced at least down to a maximum of two-fold as is e.g. determinable in the 18S DNA assay described in the examples. Thus, according to one embodiment, the DNA release can be reduced down to 3fold or less or 2fold or less up to three days of storage when using the stabilizing methods according to the present invention. This is a remarkable improvement in the stabilization of the extracellular nucleic acid population compared to prior art methods. This significantly enhances the accuracy of any subsequent tests that analyses extracellular nucleic acids. In certain cases, for example if the sample material has to be transported for long distances or stored for longer periods e.g. at room temperature (as can be e.g. the case in certain countries), the process according to the invention makes it possible for these tests to be reliably carried out after such a period of time. However, of course, the samples may also be further processed earlier, if desired. It is not necessary to make use of the full achievable stabilization period. The stabilization that is achieved with the present invention, in particular when using butanamide in combination with a caspase inhibitor, reduces variations in the extracellular nucleic acid population that may result from a different handling/processing of the samples after collection (e.g. storage conditions and periods). Furthermore, nucleic acids can be efficiently isolated from respectively stabilized samples using standard methods as no cross-linking of the sample occurs. This greatly improves the standardization of molecular analysis that relies on the analysis of extracellular nucleic acids.

As described, further additives may be used in addition to butanamide. As described above, butanamide is preferably used in combination with a caspase inhibitor. Optionally, a compound according to formula 1 can be used in addition to butanamide or in addition to the combination of butanamide and the caspase inhibitor to further enhance the stabilization effect on the cell-containing biological sample and/or in order to allow reducing the concentration of butanamide. According to one embodiment, the compound according to formula 1 used in combination is a N—N-dialkylpropanamide, preferably N,N-dimethylpropanamide. Furthermore, as described above, a poly(oxyethylene) polymer may be used in addition to butanamide to support the stabilization effect. Particularly suitable is a combination of butanamide, a caspase inhibitor and at least one poly(oxyethylene) polymer which preferably is polyethylene glycol. A compound according to formula 1 may be used in addition.

The selection of suitable additives that may also contribute to the stabilization effect may also depend on the type of cell-containing sample to be stabilized. E.g. when processing blood as cell-containing biological sample, it is advantageous and also common to include an anticoagulant to prevent blood clotting. The anticoagulant is used in a concentration wherein it can prevent clotting of the amount of blood to be stabilized. The anticoagulant may be e.g. selected from the group consisting of heparin, chelating agents such as ethylenediamine tetraacetic acid, salts of carboxylic acids such as citrate or oxalate and any combination thereof. In an advantageous embodiment, the anticoagulant is a chelating agent. A chelating agent is an organic compound that is capable of forming coordinate bonds with metals through two or more atoms of the organic compound. Chelating agents according to the present invention include, but are not limited to diethylenetriaminepentaacetic acid (DTPA), ethylenedinitrilotetraacetic acid (EDTA), ethylene glycol tetraacetic acid (EGTA) and N,N-bis(carboxymethyl) glycine (NTA) and furthermore, e.g. citrate or oxalate. According to a preferred embodiment, EDTA is used as anticoagulant. As used herein, the term "EDTA" indicates inter alia the EDTA portion of an EDTA compound such as, for example, $K_2EDTA$, $K_3EDTA$ or $Na_2EDTA$. Using a chelating agent such as EDTA also has the advantageous effect that nucleases such as DNases and RNases are inhibited, thereby e.g. preventing a degradation of extracellular nucleic acids by nucleases. Therefore, the use of a chelating agent such as EDTA is also advantageous when using cell-containing samples different from blood. Furthermore, it was found that EDTA used/added in higher concentrations supports the stabilizing effect. However, EDTA alone does not achieve a sufficient stabilization effect for the purposes described herein. However, used in combination with the teachings of the present invention, in particular in combination with butanamide (and further additives as described herein), it can further improve the stabilization effect for the above discussed reasons.

According to one embodiment, the concentration of the chelating agent, preferably EDTA, in the mixture that is obtained when contacting the cell-containing biological sample with butanamide and optionally one or more additional additives lies in a range selected from the group consisting of 0.1 mM to 100 mM, 0.5 mM to 50 mM, 1 mM to 30 mM, 2.5 mM to 25 mM, 5 mM to 20 mM and 7.5 mM to 17.5 mM after the contacting step. According to one embodiment, the concentration of the chelating agent, preferably EDTA, in the mixture that is obtained when contacting the cell-containing biological sample with butanamide and optionally one or more additional additives lies in a range selected from the group consisting of 0.5 to 40 mg/ml, 1 to 30 mg/ml, 1.6 to 25 mg/ml, 5 to 20 mg/ml and 7.5 to 17.5 mg/ml. Respective concentrations are particularly effective when stabilizing blood, plasma and/or serum samples. Suitable concentrations can also be determined by the skilled person.

Additional additives can also be used in order to further support the stabilization of the cell-containing sample, respectively support the preservation of the extracellular nucleic acid population. Examples of respective additives include but are not limited to nuclease inhibitors, in particular RNase and DNase inhibiting compounds. Examples of RNase inhibitors include but are not limited to anti-nuclease antibodies or ribonucleoside-vanadyl-complexes. When choosing a respective further additive for supporting stabilization, care should be taken not to compromise and/or counteract the stabilizing effect. Thus, no additives such as e.g. chaotropic agents should be used in concentrations that result in or support the lysis and/or degradation of nucleated cells contained in the cell-containing biological sample that is stabilized and/or which support the degradation of the nucleic acids contained in the cell-free fraction of said biological sample. Therefore, preferably, the stabilization does not involve the use of additives (i) that induce or promote lysis of nucleated cells, (ii) that induce or promote lysis of cells in general and/or (iii) that lead to a degradation of nucleic acids contained in the cell-free fraction of the cell-containing biological sample. As the stabilization method described herein is not based on cell lysis but preserve cells, cells can be separated from the cell-containing sample after the stabilization period, thereby allowing to obtain a cell-free or cell-depleted fraction which comprises the extracellular nucleic acid population. Due to the butanamide based stabilization described herein, said extracellular nucleic acid population substantially corresponds to or at least closely resembles the extracellular nucleic acid population present at the time of sample collection and stabilization. Furthermore, nucleic acids can be isolated from the separated cells and are available for analysis. As described above, a combination comprising a compound according to formula 1 also has transcriptome stabilizing properties. The compounds according to formula 1 that are described as preferred above are particularly suitable for stabilizing the transcriptome of contaminated cells. For this purpose, preferably concentrations of at least 3%, at least 3.5%, preferably at least 4%, more preferred at least 5% are used to achieve a strong transcriptome stabilizing effect. Therefore, the methods which involve the use of such compounds according to formula 1 in addition to butanamide are suitable for additionally stabilizing intracellular nucleic acids, in particular RNA. By stabilizing the transcriptome in addition to the extracellular nucleic acid population, the respectively stabilized samples are also suitable for gene expression profiling. Furthermore, respectively stabilized samples allow, if desired, the separate analysis of the extracellular and intracellular nucleic acid populations from the same stabilized sample.

The stabilization methods as disclosed herein, provide a significant advantage over state-of-the-art stabilization methods that are used for stabilizing the extracellular nucleic acid population in a cell-containing sample which are based on the use of cross-linking reagents, such as formaldehyde, formaldehyde releasers and the like. Crosslinking reagents cause inter- or intra-molecular covalent bonds between nucleic acid molecules or between nucleic acids and proteins. This cross-linking effect can hamper the subsequent isolation of nucleic acids from such stabilized samples. As, for example, the concentration of circulating nucleic acids in a whole blood sample is already relatively low, any measure which further reduces the yield of such nucleic acids should be avoided. This may be of particular importance when detecting and analyzing very rare nucleic acid molecules derived e.g. from malignant tumors or from a developing fetus in the first trimester of pregnancy. As is shown by the examples, the method of the invention does not require cross-linking agents for stabilization. Therefore, according to one embodiment, the stabilization method according to the present invention does not involve the use of a cross-linking agent that induces protein-nucleic acid and/or protein-protein crosslinks. In particular, the stabilization does not involve the use of formaldehyde, formaline, paraformaldehyde or a formaldehyde releaser. Furthermore, as described above, according to one embodiment, the stabilization method according to the invention does not involve the use of additives that classify as toxic agents.

In an advantageous embodiment of the present invention, the cell-containing biological sample, which preferably is a blood sample or a sample derived from blood such as plasma or serum, is contacted with:
  a) butanamide, preferably in a concentration so that the concentration of butanamide in the mixture with the cell-containing biological sample lies in a range of 0.25% (w/v) to 7% (w/v), 0.4% (w/v) to 5% (w/v), 0.5% (w/v) to 4% (w/v), 0.75% (w/v) to 3.5% (w/v) or 1% (w/v) to 3% (w/v);
  b) at least one caspase inhibitor, preferably a pancaspase inhibitor, more preferred Q-VD-OPh, preferably in a concentration so that the concentration of the caspase inhibitor in the mixture with the cell-containing biological sample lies in a range of 0.5 µM to 30 µM, more preferred 0.75 µM to 25 µM, more preferred 1 µM to 10 µM; and
  c) optionally at least one compound according to formula 1 defined above (preferred embodiments such as N,N-dialkyl carboxylic acid amids, in particular N,N-dialkylpropanamids, preferably N,N-dimethylpropanamide and suitable and preferred concentrations are described above) and/or
  d) optionally a further additive, preferably a chelating agent, most preferably EDTA, preferably in a concentration so that the concentration of EDTA in the mixture with the cell-containing biological sample lies in a range of 1 mM to 50 mM, preferably 1.5 mM to 25 mM more preferred 2 mM to 20 mM.

Preferably, the above components a) and b) and optionally c) and d) are comprised in a stabilizing composition.

In an advantageous embodiment of the present invention, the cell-containing biological sample, which preferably is a blood sample or a sample derived from blood such as plasma or serum, is contacted with:
  a) butanamide, preferably in a concentration so that the concentration of butanamide in the mixture with the cell-containing biological sample lies in a range of 0.25% (w/v) to 7% (w/v), 0.4% (w/v) to 5% (w/v), 0.5% (w/v) to 4% (w/v), 0.75% (w/v) to 3.5% (w/v) or 1% (w/v) to 3% (w/v);
  b) at least one poly(oxyethylene) polymer;
  c) optionally at least one caspase inhibitor, preferably a pancaspase inhibitor, more preferred Q-VD-OPh, preferably in a concentration so that the concentration of the caspase inhibitor in the mixture with the cell-containing biological sample lies in a range of 0.5 µM to 30 µM, more preferred 0.75 µM to 25 µM, more preferred 1 µM to 10 µM;
  d) optionally at least one compound according to formula 1 defined above (preferred embodiments such as N,N- dialkyl carboxylic acid amids, in particular N,N-dialkylpropanamids, preferably N,N-dimethylpropanamide and suitable and preferred concentrations are described above and/or e) optionally a further additive, preferably a chelating agent, most preferably EDTA.

The poly(oxyethylene) polymer is according to one embodiment a high molecular weight poly(oxyethylene) polymer having a molecular weight of at least 1500, more preferably a polyethylene glycol such as an unsubstituted polyethylene glycol. Suitable molecular weights and concentrations were described above and it is referred to the above disclosure. According to one embodiment, it is used in a concentration so that the concentration of the poly(oxyethylene) polymer in the mixture with the cell-containing biological sample lies in a range of 0.2% to 1.5% (w/v), 0.25% to 1.25% (w/v), 0.3% to 1% (w/v) or 0.4% to 0.75% (w/v). According to one embodiment, the high molecular weight poly(oxyethylene) polymer has a molecular weight of at least 1500, preferably in a range of 2000 to 40000, more preferred 3000 to 20000 or 4500 to 10000. In an advantageous embodiment, the cell containing sample is contacted with butanamide, at least one poly(oxyethylene) glycol and at least one caspase inhibitor. According to one embodiment, a compound according to formula 1 is additionally used. For the stabilization of blood, the use of an anticoagulant such as an chelating agent, preferably EDTA, is advantageously used.

Preferably, a stabilizing composition according to the third aspect of the present invention is used for stabilization of the cell-containing biological sample. The components of the stabilizing composition can be comprised, respectively dissolved in a solvent, e.g. water, a buffer, e.g. a biological buffer such as MOPS, TRIS, PBS and the like. Furthermore, the components may be dissolved in or the stabilizing composition may comprise a polar aprotic solvent such as dimethyl sulfoxide (DMSO).

Butanamide, optionally at least one caspase inhibitor and optionally a compound according to formula 1, as well as optionally present further additives such as an anticoagulant, can be present in a device, preferably a container, for collecting the cell-containing biological sample. The same applies if at least one poly(oxyethylene) polymer is used in addition to butanamide. Butanamide and optionally the one or more compounds additionally used for stabilization can be present in a stabilizing composition that is present in a respective device or can be present as separate entities. Furthermore, they can be added to a respective collection device immediately prior to collection of the cell-containing biological sample, or can be added to the collection device immediately after the cell-containing biological sample was collected therein. It is also within the scope of the present invention to add the stabilizing agents and optionally, further additive(s) separately to the cell-containing biological sample. However, for the ease of handling, it is preferred that butanamide and one or more or any further additives used for stabilization are provided in the respective collection device, e.g. in form of a single composition. However, they may also be present as separate components or compositions in the collection device. According to one embodiment, butanamide and one or more or all of the further additives used for stabilization are not contained in a single stabilization composition. In an advantageous embodiment, butanamide, at least one caspase inhibitor, and optionally a compound according to formula 1 as described above and optionally further additive(s) such as e.g. an anticoagulant such as EDTA, are present in the collection device prior to adding the cell-containing biological sample. This ensures that the cell-containing biological sample is immediately stabilized upon contact with the stabilizing agents used according to the teachings of the present invention. The stabilization agents are present in the container in an amount effective to stabilize the amount of cell-containing biological sample to be collected, respectively contained in said container. As discussed above, butanamide, at least one caspase inhibitor, and optionally a compound according to formula 1 as described above and optionally further additive(s) such as e.g. an anticoagulant such as EDTA, can be present in a composition that is contained in the collection device. The same applies if at least one poly(oxyethylene) polymer is used in addition to butanamide. Suitable and preferred embodiments for a respective collection device are also described subsequently in conjunction with the fifth embodiment according to the invention and it is referred to said disclosure.

Preferably, the cell-containing biological sample is contacted with butanamide and optionally further additives directly after and/or during the collection of the cell-containing biological sample. Therefore, as described above, preferably, the agents used for stabilization are provided in form of a stabilizing composition. Preferably, said stabilizing composition is provided in a liquid form. It can be e.g. pre-filled in the sample collection device so that the cell-containing biological sample is immediately stabilized during collection. According to one embodiment, the stabilizing composition is contacted with the cell-containing sample in a volumetric ratio selected from 10:1 to 1:20, 5:1 to 1:15, 1:1 to 1:10 and 1:2 to 1:5. These rations are particularly useful for stabilizing blood samples. Suitable and preferred concentrations of the additives in the resulting mixture with the cell-containing sample, in particular a blood sample, were described above and it is referred to the respective disclosure. It is a particular advantage of the teachings of the present invention that stabilization of a large sample volume can be achieved with a small volume of the stabilizing composition according to the present invention. Therefore, preferably, the ratio of stabilizing composition to sample lies in a range from 1:2 to 1:7, more preferred 1:3 to 1:5. According to one embodiment, the stabilizing composition is contacted with the cell-containing sample in a volumetric ratio of 1:10 to 1:5. This ration is advantageous e.g. for the stabilization of blood.

The term "cell-containing biological sample", "cell-containing sample" and similar terms as used herein, in particular refers to a sample which comprises at least 50, 250, at least 500, at least 1000, at least 1500, at least 2000 or at least 5000 cells. Furthermore, also cell-containing samples comprising considerably more cells are encompassed by said term and can be stabilized with the teachings according to the present invention. However, the term "cell-containing biological sample" also refers to and thus encompasses cell-depleted samples, including cell-depleted samples that are commonly referred to as "cell-free" such as e.g. blood plasma as respective samples often include residual cells. At least, it can often not be fully excluded that even so-called "cell-free" samples such as blood plasma comprise residual amounts of cells which accordingly, pose a risk that the extracellular nucleic acid population becomes contaminated with intracellular nucleic acids released from said residual cells. Therefore, respective cell-depleted and "cell-free" samples are according to one embodiment also encompassed by the term "cell-containing biological sample". Thus, the "cell-containing sample" may comprise large amounts of cells, as is the case e.g. with whole blood, but may also only comprise merely minor amounts of cells. Hence, the term "cell containing biological sample" also encompasses samples that may only be suspected of or pose a risk of containing cells. As discussed above, also with respect to biological samples which only comprise minor, respectively residual amounts of cells such as e.g. blood plasma (blood plasma contains—depending on the preparation method—usually small residual amounts of cells, even though it is commonly referred to as being cell-free), the method according to the present invention has considerable advantages as these residual cells may also result in a undesired contamination of the comprised extracellular nucleic acids. Using the stabilizing technology of the present invention also ensures that respective biological samples which only comprise residual amounts of cells or are merely suspected of, or pose a risk of residual amounts of cells, are efficiently stabilized thereby preserving the extracellular nucleic acid population contained therein as is also described in detail above. According to one embodiment, the cellular portion makes up at least 1%, at least 2%, at least 2.5%, at least 5%, preferably at least 10%, at least 15%, at least 20%, more preferably at least 25%, at least 30%, at least 35% or at least 40% of the cell-containing biological sample. Cell-containing samples wherein the cellular fraction makes up more than 40% can also be stabilized using the teachings described herein. Using the stabilizing method according to the present invention has the advantage that substantially irrespective of the composition of the cell-containing biological sample and the number of cells contained therein, the extracellular nucleic acid population contained in said sample can be substantially preserved, respectively stabilized, thereby allowing for standardizing the subsequent isolation and/or analysis of the contained extracellular nucleic acids.

According to one embodiment, the cell-containing biological sample is selected from the group consisting of body fluids and cell-containing samples derived from body fluids, in particular, whole blood, samples derived from blood such as plasma or serum, buffy coat, urine, sputum, lachrymal fluid, lymphatic fluid, sweat, liquor, cerebrospinal fluid, ascites, milk, stool, bronchial lavage, saliva, amniotic fluid, nasal secretions, vaginal secretions, semen/seminal fluid, wound secretions, cell culture and swab samples. According to one embodiment, the cell-containing biological sample is a body fluid, a body secretion or body excretion, preferably a body fluid, most preferably urine, lymphatic fluid, whole blood, buffy coat, plasma or serum. In particular, the cell-containing biological sample can be a circulating body fluid such as blood or lymphatic fluid. Preferably, the cell-containing biological sample that is stabilized using the teachings described herein is a blood sample. According to one embodiment, the cell-containing biological sample was obtained from a human. The cell-containing biological sample comprises extracellular nucleic acids in the extracellular portion. Other examples of cell-containing biological samples that can be stabilized with the method according to the present invention include but are not limited to cell suspensions, cell cultures, supernatant of cell cultures and the like, which comprise extracellular nucleic acids.

According to one embodiment, the method according to the present invention is for stabilizing an extracellular nucleic acid population comprised in a blood sample and comprises contacting the blood sample with butanamide and an anticoagulant, wherein during the stabilization period, the release of genomic DNA from cells contained in the blood sample into the cell-free portion of the blood sample is reduced. In particular, the present invention provides a method for stabilizing an extracellular nucleic acid population comprised in a blood sample which comprises contacting the blood sample with butanamide, at least one caspase inhibitor and an anticoagulant and wherein the release of genomic DNA from nucleated cells contained in the blood sample into the cell-free portion of the blood sample is reduced. Furthermore, degradation of nucleic acids present in the sample is reduced due to the stabilization. As is shown in the examples, the caspase inhibitor can inhibit e.g. the fragmentation of genomic DNA. Particularly preferred is a combination with a poly(oxyethylene) polymer as described herein as this significantly supports the stabilizing effect on the white blood cells. In particular, the lysis of white blood cells is prevented/reduced during stabilization. According to one embodiment, the method is for stabilizing an extracellular nucleic acid population comprised in a blood sample and comprises contacting the blood sample with butanamide, at least one caspase inhibitor, a compound according to formula 1, preferably a tertiary carboxylic acid amide, in particular a N,N-dialkylpropanamide, more preferred N,N-dimethylpropanamide, and an anticoagulant, wherein the release of genomic DNA from cells contained in the blood sample into the cell-free portion of the blood sample is reduced. Preferably, said stabilization effect is achieved for at least 48 h, preferably at least 78 h. According to one embodiment, at least one poly(oxyethylene) polymer is used in combination with butanamide and a caspase inhibitor. As described, further stabilizing agents and additives can be used in addition.

A further advantage when stabilizing blood samples using the method according to the present invention is that hemolysis can be significantly reduced during the stabilization period. Thus, compared to unstabilized samples or standard EDTA blood samples, significantly less hemolysis occurs and can even be prevented. Hemolysis is the rupturing of erythrocytes and the release of their cytoplasm into surrounding extracellular fluid, e.g. blood plasma. The degree of hemolysis can be analysed e.g. by visual inspection, as the released hemoglobin will cause the serum or plasma to appear red. Most causes of in vitro hemolysis are related to specimen collection. However, in vitro hemolysis usually also occurs in a blood sample during ex vivo storage if no proper stabilization method is used. Depending on the extracellular nucleic acid of interest, hemolysis can be a considerable problem. If the extracellular nucleic acid of interest is DNA, hemolysis is less of a problem because red blood cells do not contain a nucleus and consequently, do not contain genomic DNA. Therefore, no intracellular DNA is released from the red blood cells during hemolysis. When the extracellular nucleic acid of interest is DNA, in particular the lysis or decay of white blood cells is a problem because in this case genomic DNA is released in addition to intracellular RNA. Therefore, when the extracellular nucleic acid of interest is extracellular DNA, in particular the lysis of white blood cells must be prevented. White blood cells may differ among each other in their stability characteristics. Thus, some types of white blood cells are more stable than others. However, generally, white blood cells are significantly more stable than red blood cells. Therefore, the lysis of red blood cells does not necessarily indicate that white blood cells were lysed. The different susceptibility of white blood cells and red blood cells to lysis is also used in the art to e.g. specifically lyse red blood cells, while preserving white cells in order to allow e. g. the collection of white blood cells. However, if the extracellular nucleic acid of interest is RNA, hemolysis and thus the lysis of red blood cells does constitute a problem. Mature red blood cells also do not contain RNA, however, their precursors (reticulocytes) do. Reticulocytes make up approximately 0.5% to 1% of the red blood cells and contain large amounts of globin RNA. Therefore, in particular when the extracellular nucleic acid of interest is RNA, a lysis of red blood cells and thus reticulocytes during storage should be prevented/reduced in order to reduce a dilution of the extracellular nucleic acid population, in particular the extracellular RNA population, with globin mRNA.

Furthermore, as described above, it is important to maintain the composition and thus profile of the extracellular nucleic acid population what is achieved using stabilization methods described herein as this is important for many diagnostic applications. As is shown by the examples, hemolysis is efficiently prevented/reduced when using the stabilization method according to the present invention. Thereby, the extracellular nucleic acid population is substantially preserved and furthermore, the stabilized blood sample, in particular the plasma or serum obtained from the stabilized blood sample, is due to the prevention of hemolysis and cell lysis in general also suitable for other standard laboratory analyses.

As is described above and as is demonstrated by the examples, using the methods of the present invention allows for stabilizing the cell-containing sample without refrigeration or freezing for a prolonged time period. Thus, the samples can be kept at room temperature or even at elevated temperatures e.g. up to 30° C. or even up to 40° C. According to one embodiment, a stabilization effect is achieved for at least two days, preferably at least three days, more preferred at least four days. According to one embodiment, the stabilization method according to the present invention achieves a stabilization of the extracellular nucleic acid population comprised in the cell-containing biological sample without refrigeration, preferably at room temperature, for a time period of at least two days to three days, at least two days to at least six days and/or at least two day to at least seven days. Preferably, during said stabilization periods the stabilization method according to the invention has the effect that cells contained in the sample are stabilized, that the release of genomic DNA from cells contained in the sample into the cell-free portion of the sample is reduced and/or that a degradation of nucleic acids present in the sample is reduced due to the stabilization. In particular, during the described stabilization periods, the stabilization reduces the dilution of the extracellular DNA population comprised in the biological sample with genomic DNA originating from cells contained in the stabilized sample during the stabilization period. The stabilizing effects that can be achieved with the method according to the present invention were described in detail above and it is referred to the above disclosure. Preferably, during said stabilization periods, the stabilization reduces the contamination of the extracellular nucleic acid population comprised in the biological sample with intracellular nucleic acids, in particular genomic DNA, originating from cells contained in the stabilized sample during the stabilization period. As is shown in the examples, blood samples could be stabilized up to 3 days or longer at room temperature. Even during longer storages at room temperature for up to 6 days or even longer, the extracellular nucleic acid population was substantially stabilized (in particular compared to non-stabilized samples or e.g. compared to samples that were stabilized using standard methods such as an EDTA treatment) when using butanamide in combination with a caspase inhibitor and/or a compound according to formula 1. Even though the stabilization effect may decrease over time, which may also depend on the source, e. g. the donor from which the cell-containing biological sample is derived, it is still sufficient to preserve the composition of the extracellular nucleic acid population to allow the analysis and/or further processing of the extracellular nucleic acids. Thus, cell-containing biological samples that were stabilized according to the methods of the present invention and in particular samples that were stabilized with butanamide and a caspase inhibitor were still suitable for isolating and analysing the extracellular nucleic acids contained therein even after prolonged storage at room temperature. The use butanamide in combination with at least one poly(oxyethylene) polymer and optionally at least one caspase inhibitor even further increases the stability of cell-containing biological samples and hence, further prolongs the suitable storage time significantly. Thus, even longer storage/shipping times are conceivable. However, usually, longer periods are not necessary, as the regular storage and e.g. shipping time to the laboratory, wherein the nucleic acid isolation and optionally the analysis is performed, usually does not exceed 6 or 7 days, but usually is even completed after two or three days. As is shown in the examples, the stabilization efficiency is particularly good during this time period. However, the long stabilization times and stabilization efficiencies that are achievable with the method according to the present invention provides an important safety factor.

The methods and also the subsequently described stabilizing compositions according to the present invention allow the stabilization of large volumes of cell-containing biological samples with small volumes/amounts of added stabilizer because butanamide and the described combinations of stabilizers used according to the teachings of the present invention for stabilization are highly active in particular in combination. This is an important advantage because the size/volume of the sample poses considerable restrains on the subsequent nucleic acid isolation procedure in particular when intending to use automated processes for isolating the extracellular nucleic acids contained in the samples. Furthermore, one has to consider that extracellular nucleic acids are usually only comprised in small amounts in the cell-containing biological sample. Thus, processing larger volumes of a cell-containing biological sample such as e.g. a blood sample has the advantage that more extracellular nucleic acids can be isolated from the sample and thus are available for a subsequent analysis.

The stabilization of the biological sample may either be followed directly by techniques for analysing nucleic acids, or nucleic acids may first be isolated from the stabilized sample. Hence, the cell-containing biological sample that was stabilized using the method of the present invention can be analysed in a nucleic acid analytic and/or detection method and/or may be further processed. E.g. extracellular nucleic acids can be isolated from the stabilized sample and can then be analysed in a nucleic acid analytic and/or detection method or may be further processed. Details regarding the nucleic acid isolation and analysis are described below in conjunction with the second aspect of the present invention and it is referred to said disclosure. As described, one important advantage of the stabilizing method according to the invention lies in that the subsequent isolation of nucleic acids is not hampered due to the stabilization as is, e.g., the case when using a cross-linking agent such as a formaldehyde releaser for stabilization.

B. Nucleic Acid isolation Method

According to a second aspect, a method for isolating nucleic acids from a cell-containing biological sample is provided, wherein said method comprises the steps of:

a) stabilizing a cell-containing sample according to the method described in the first aspect of the present invention;

b) isolating nucleic acids from the stabilized sample.

Preferably, said method is for isolating extracellular nucleic acids from a cell-containing biological sample and comprises the steps of:

a) stabilizing the extracellular nucleic acid population comprised in a cell-containing sample according to the method described in the first aspect of the present invention;

b) isolating extracellular nucleic acids.

As discussed above, the stabilization according to the present invention has the effect that the extracellular nucleic acid population contained in the sample is substantially preserved in the state it had shown at the time the biological sample was obtained, respectively collected. In particular, the usually observed high increase in nucleic acids that results from intracellular nucleic acids, in particular genomic DNA, more specifically fragmented genomic DNA, during storage/handling is efficiently reduced or even prevented as is demonstrated in the examples. Without being bound in theory, it is believed that the butanamide based stabilization described herein stabilizes cells and/or reduces the destruction of cells during the stabilization period, thereby reducing the release of intracellular nucleic acids. The method allows to separate a cell fraction from the stabilized sample after the desired stabilization period. Hence, extracellular nucleic acids obtained from a respectively stabilized sample comprise significantly less contamination with intracellular nucleic acids originating from degraded or dying cells and in particular comprise less amounts of fragmented genomic DNA compared to non-stabilized samples. Furthermore, the unique stabilization described herein allows to increase the amount of recoverable extracellular nucleic acids. As described above, the stabilization according to the present invention does not require the use of cross-linking agents. This is an important advantage over prior art methods which involve the use of cross-linking agents such as formaldehyde or formaldehyde releasers, because these reagents often reduce the recoverable amount of extracellular nucleic acids due to cross-linking when using standard nucleic acid isolation techniques. In contrast, the stabilization method of the invention, which does not require cross-linking agents, does not hamper the subsequent nucleic acid isolation. Thus, the method according to the present invention improves the diagnostic and prognostic capability of the extracellular nucleic acids. Furthermore, the stabilization described herein allows the sample to be stored and/or handled, e.g. transported, even at room temperature—for a prolonged period of time prior to separating the cells contained in the sample and/or prior to isolating nucleic acids comprised therein in step b). With respect to the details of the stabilization that is performed in step a), it is referred to the above disclosure which also applies here.

According to one embodiment, the cell-containing biological sample such as e.g. a whole blood sample is stabilized in step a) using butanamide and at least one apoptosis inhibitor, which preferably is a caspase inhibitor, and optionally, further stabilizing agents and/or additives. As described above, according to one embodiment, at least one poly(oxyethylene) polymer is used additionally for stabilization. Suitable and preferred embodiments of the stabilization method according to the present invention that is performed in step a) were described above and it is referred to the above disclosure which also applies here. Particularly preferred is the use of butanamide, at least one caspase inhibitor and optionally a compound according to formula 1 for stabilization. As described above, this also allows to achieve a stabilization of the transcriptome of contained cells. Therefore, the method may also comprise isolating intracellular nucleic acids from cells contained in the sample. As described above, the respective cells are preferably separated in advance. Preferred is the combination with an anticoagulant, preferably a chelating agent such as EDTA, when stabilizing a whole blood sample. As described above, also advantageous is the use of butanamide, at least one poly(oxyethylene) polymer and at least one caspase inhibitor, optionally in combination with one or more further additives described herein. The additional use of the poly(oxyethylene) polymer is advantageous, because it support the stabilization of the contained cells, thereby preventing the release of intracellular nucleic acids such as genomic DNA.

If the cell-containing biological sample comprises large amounts of cells as is e.g. the case with whole blood, the cells are separated from the remaining sample in order to obtain a cell-free, respectively cell-reduced or cell-depleted fraction of the stabilized sample from which the extracellular nucleic acids are then isolated in step b). Thus, according to one embodiment, cells are removed from the cell-containing sample between step a) and step b). This intermediate step is only optional and e.g. may be obsolete if samples are processed which merely comprise minor amounts of residual cells such as e.g. plasma or serum and/or wherein the extracellular nucleic acid of interest is DNA. Due to the stabilization of the invention, the release of genomic DNA during the stabilization period from the contained cells is reduced or even prevented and furthermore, in particular when using a caspase inhibitor in addition to butanamide, the fragmentation of genomic DNA is reduced. As described herein due to its considerably larger size, unfragmented genomic DNA can be distinguished from the smaller extracellular DNA. This allows to selectively isolate extracellular DNA even in the presence of unfragmented genomic DNA by using a size selective isolation protocol. However, in order improve the results, it is preferred that cells (or potentially remaining cells) are removed from the stabilized sample prior to isolating the extracellular nucleic acids in step b) in order to reduce contaminations of the extracellular nucleic acid population with intracellular nucleic acids that would otherwise be released from the cells during nucleic acid isolation. To remove the contained cells is in particular advantageous if the extracellular nucleic acids of interest are RNA, because it can be difficult to distinguish intracellular RNA from extracellular RNA and furthermore, a dilution of the extracellular RNA can thereby be prevented. However, a cell removal step prior to step b) is generally advantageous and thus preferred, also if the extracellular nucleic acid of interest is DNA, because this allows to use standard nucleic acid isolation procedures in step b). Depending on the type of cell-containing biological sample, cells, including residual cells, can be separated and removed e.g. by centrifugation, preferably high speed centrifugation, or by using means other than centrifugation, such as e.g. filtration, sedimentation or binding to surfaces e.g. on (optionally magnetic) particles if a centrifugation step is to be avoided. Respective cell separation methods are well-known in the prior art and thus, do not need to be described in detail. Respective cell removal steps can also be easily included into an automated sample preparation protocol. Respectively removed cells may also be processed further if desired. The cells can e.g. be stored, analysed and/or biomolecules such as e.g. nucleic acids or proteins can be isolated from the removed cells. Furthermore, it was found that intracellular nucleic acids such as intracellular RNA can be stabilized in particular when additionally using a compound according to formula 1 such as DMPA for stabilizing the cell-containing sample. The additional stabilization of the transcriptome is advantageous as it allows e.g. to analyse profiles of transcripts in the isolated intracellular nucleic acids which can also be important biomarkers for in vitro diagnostics.

Furthermore, it is also within the scope of the present invention to include further intermediate steps to work up the stabilized sample.

Extracellular nucleic acids are isolated in step b), preferably from the cell-free, respectively cell-depleted fraction of the stabilized sample, e.g. from supernatants or from plasma and/or serum in case the stabilized cell-containing sample sample was a blood sample. For isolating extracellular nucleic acids, any known nucleic acid isolation method can be used that is suitable for isolating nucleic acids from the stabilized sample, respectively the obtained cell-depleted sample. Examples for respective purification methods include but are not limited to extraction, solid-phase extraction, silica-based purification methods, magnetic particle-based purification, phenol-chloroform extraction, chromatography, anion-exchange chromatography (using anion-exchange surfaces), electrophoresis, filtration, precipitation and combinations thereof. It is also within the scope of the present invention to specifically isolate specific target extracellular nucleic acids, e.g. by using appropriate probes coupled to a solid support that enable a sequence specific binding. Also any other nucleic acid isolating technique known by the skilled person can be used. According to one embodiment, nucleic acids are isolated in step b) using a chaotropic agent and/or alcohol. Preferably, the nucleic acids are isolated by binding them to a solid phase, preferably a solid phase comprising silica or carrying anion exchange functional groups. Respective methods are well-known in the prior art and thus, do not need any detailed description. Suitable methods and kits for isolating extracellular nucleic acids are also commercially available such as the QIAamp® Circulating Nucleic Acid Kit (QIAGEN), the Chemagic Circulating NA Kit (Chemagen), the Nucleo-Spin Plasma XS Kit (Macherey-Nagel), the Plasma/Serum Circulating DNA Purification Kit (Norgen Biotek), the Plasma/Serum Circulating RNA Purification Kit (Norgen Biotek), the High Pure Viral Nucleic Acid Large Volume Kit (Roche) and other commercially available kits suitable for extracting and purifying extracellular nucleic acids.

According to one embodiment, total nucleic acids are isolated from the stabilized cell-containing sample that is obtained after step a) or optionally the sample that is obtained after cells were removed from the stabilized cell-containing sample in an intermediate step. Preferably, the nucleic acids are isolated from the, or a cell-free, respectively cell-depleted fraction of the stabilized sample. E.g. total nucleic acids can be isolated from plasma or serum and the extracellular nucleic acids will be comprised as portion in these extracted nucleic acids. If the cells contained in the stabilized sample are efficiently removed prior to nucleic acid isolation, the isolated total nucleic acids will predominantly comprise or even consist of extracellular nucleic acids.

It is also within the scope of the present invention to isolate at least predominantly a specific target nucleic acid. A target nucleic acid can be e.g. a certain type of extracellular nucleic acid, e.g. DNA or RNA, including mRNA, microRNA, other non-coding nucleic acids, epigenetically modified nucleic acids, and other nucleic acids. E.g. the target extracellular nucleic acid can be DNA and the non-target extracellular nucleic acid can be RNA or vice versa. Target specific nucleic acid isolation methods which specifically aim at isolating DNA or RNA are also well known in the prior art and thus, do not need any detailed description herein. According to one embodiment, the non-target nucleic acid is destroyed by adding an appropriate enzyme which specifically destroys the non-target nucleic acid, e.g. a RNase if the target nucleic acid is DNA or a DNase if the target nucleic acid is RNA. Said enzyme can be added to the lysis or binding mixture or can be added after extracellular nucleic acids were bound to a solid phase. Suitable embodiments for performing a respective non-target nucleic acid digestion step are known in the prior art and thus, do not need any further description herein. According to one embodiment which is feasible if DNA and RNA are bound to a solid support, elution conditions selective for the target nucleic acid can be applied to predominantly and thus selectively recover the target nucleic acid from the solid support. According to one embodiment, an isolation method is used, wherein the target nucleic acid, e.g. DNA, is selectively bound to a solid phase under conditions wherein non-target nucleic acids, e.g. RNA do not bind. Suitable binding conditions are well-known in the prior art and are e.g. described in WO 95/21849. According to one embodiment, the non-target nucleic acid is removed by binding at least a portion of the non-target nucleic acid under appropriate conditions to a solid phase and then separating the non-target nucleic acid bound to the solid phase from the remaining sample comprising the target extracellular nucleic acid. This can be achieved e.g. by the addition of a suitable solid phase under conditions wherein mainly the non-target nucleic acids e. g. DNA are bound to the solid phase while the non-target nucleic acid, e.g. RNA, remains in the sample and is recovered therefrom in a separate step. Suitable methods for selectively removing a non-target nucleic acid from a target nucleic acid are for example described in EP 0 880 537 and WO 95/21849, herein incorporated by reference. If desired, said non-target nucleic acid may also be further used, e.g. further processed such as e.g. eluted from the solid phase. However, it may also be discarded. It is also within the scope of the present invention to e.g. digest the non-target nucleic acid or remainders thereof using nucleases after isolation of the target nucleic acid.

The term target nucleic acid may also refer to a specific kind of nucleic acid, e.g. a specific extracellular nucleic acid that is known to be a certain disease marker. As discussed above, the isolation of extracellular nucleic acids may also comprise the specific isolation of a respective target nucleic acid e.g. by using appropriate capture probes which support the selective isolation of the target nucleic acid.

The term target nucleic acid may also refer to nucleic acids having a certain length, e.g. a nucleic acid having a length of 5000 nt or less, 2000 nt or less, 1000 nt or less, 900 nt or less, 800 nt or less, 700 nt or less, 600 nt or less, 500 nt or less, 400 nt or less or 350 nt or less. Isolating target nucleic acids of a certain maximum size can be advantageous in the context of the present invention. It is known that extracellular nucleic acids usually have a size of less than 2000 nt, less than 1000 nt and often even less than 500 nt. The sizes, respectively size ranges indicated herein refer to the chain length. I.e. in case of double-stranded nucleic acids such as double-stranded DNA it refers to bp. Selectively isolating smaller nucleic acids in step b) can increase the portion of extracellular nucleic acids obtained in the isolated nucleic acids. The stabilization methods according to the present invention allow, in particular due to the inhibition of the release of genomic DNA and/or the inhibition of the fragmentation of released genomic DNA, for a more efficient separation of such high molecular weight genomic DNA from the smaller extracellular nucleic acid population. As the substantial size difference between genomic DNA and extracellular nucleic acids is essentially preserved using the stabilization technology according to the present invention, genomic DNA can be removed more efficiently e.g. using a size selective nucleic acid isolation protocol. As the size difference between genomic DNA (usually larger than >10,000 bp) and extracellular nucleic acids (usually <1000 nt/bp) in a sample stabilized as described herein is usually relatively large due to the efficient stabilization, known methods for selectively isolating nucleic acids of a certain target length can be used. Thus, according to one embodiment, step b) comprises selectively isolating target nucleic acids having a length of 5000 nt or less, 2000 nt or less, 1500 nt or less, 1000 nt or less, 900 nt or less, 800 nt or less, 700 nt or less, 600 nt or less or 500 nt or less. Suitable methods to achieve a respective size selective isolation of nucleic acids e.g. by depleting high molecular weight genomic DNA, are known in the prior art and thus, need no detailed description herein. A classic method for isolating DNA of a target size involves the separation of the DNA in a gel, cutting out the desired gel band(s) and then isolating the DNA of the target size from the gel fragment(s). Another widely used technology is the size selective precipitation with polyethylene glycol based buffers (Lis and Schleif Nucleic Acids Res. 1975 March; 2(3):383-9) or the binding/precipitation on carboxyl-functionalized beads (DeAngelis et al, Nuc. Acid. Res. 1995, Vol 23(22), 4742-3; U.S. Pat. No. 5,898,071 and U.S. Pat. No. 5,705,628, commercialized by Beckman-Coulter (AmPure XP; SPRIselect) and U.S. Pat. No. 6,534,262). Furthermore, size selective isolation methods that are based on the use of solid supports comprising anion exchange groups and varying pH values are known. A size selective isolation provides further opportunities in order to reduce the amount of intracellular nucleic acids in the isolated extracellular nucleic acids. For example, when the target extracellular nucleic acid of interest is DNA, the removal of genomic DNA during nucleic acid isolation step b) could also supplement or even replace a separate high g-force centrifugation of a plasma sample before starting the nucleic acid extraction in order to remove residual cells. Genomic DNA that is released from said residual cells is prevented from becoming massively degraded due to the stabilization according to the present invention, in particular if a caspase inhibitor is used in addition to butanamide, and accordingly, said unfragmented or less fragmented genomic DNA can be depleted by using a size-selective nucleic acid isolation protocol in step b). This option is of particular advantage, as many clinical laboratories do not have a centrifuge capable of performing such a high g-force centrifugation or other means for removing in particular trace amounts of residual cells.

The isolated extracellular nucleic acids can then be analysed and/or further processed in a step c) using suitable assay and/or analytical methods. E.g. they can be identified, modified, contacted with at least one enzyme, amplified, reverse transcribed, cloned, sequenced, contacted with a probe, be detected (their presence or absence) and/or can be quantified. Respective methods are well-known in the prior art and are commonly applied in the medical, diagnostic and/or prognostic field in order to analyse extracellular nucleic acids (see also the detailed description in the background of the present invention). Thus, after extracellular nucleic acids were isolated in step b), optionally as part of total nucleic acids, total RNA and/or total DNA (see above), they can be analysed e.g. to identify the presence, absence or severity of a disease state including but not being limited to a multitude of neoplastic diseases, in particular premalignancies and malignancies such as different forms of tumors or cancers. E.g. the isolated extracellular nucleic acids can be analysed in order to detect diagnostic and/or prognostic markers (e.g., fetal- or tumor-derived extracellular nucleic acids) in many fields of application, including but not limited to non-invasive prenatal genetic testing respectively screening, disease screening, pathogen screening, oncology, cancer screening, early stage cancer screening, cancer therapy monitoring, genetic testing (genotyping), infectious disease testing, injury diagnostics, trauma diagnostics, transplantation medicine or many other diseases and, hence, are of diagnostic and/or prognostic relevance. According to one embodiment, the isolated extracellular nucleic acids are analyzed to identify and/or characterize a disease or a fetal characteristic. Thus, as discussed above, the isolation method described herein may further comprise a step c) of nucleic acid analysis and/or processing.

Therefore, according to one embodiment, the isolated extracellular nucleic acids are analysed in a step c) to identify, detect, screen for, monitor or exclude a disease and/or at least one fetal characteristic. The analysis/further processing of the isolated extracellular nucleic acids can be performed using any nucleic acid analysis/processing method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, next generation sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof. Respective technologies are well-known to the skilled person and thus, do not need further description here.

According to one embodiment, either or both of isolation step b) and analysis step c) occur at least one day up to 3 days or two days up to 7 days after the cell-containing biological sample has been collected, respectively was stabilized according to the teachings of the present invention. Suitable time periods for which the cell-containing biological sample, in particular a blood sample, respectively the extracellular nucleic acid population contained therein can be stabilized using the method according to the present invention are also described above in conjunction with the stabilization method and the respective disclosure also applies here. According to one embodiment, nucleic acid isolation step b) is performed at least one day, at least 2 days or at least 3 days after the cell-containing sample was collected and stabilized according to the method according to the present invention.

C. Stabilization Composition

Furthermore, according to a third aspect of the present invention a composition suitable for stabilizing a cell-containing biological sample is provided wherein the composition comprises butanamide and at least one further additive selected from the group consisting of an apoptosis inhibitor, an anticoagulant and a compound according to formula 1

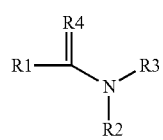

formula 1 wherein R1 is a hydrogen residue or an alkyl residue, preferably a C1-C5 alkyl residue, a C1-C4 alkyl residue or a C1-C3 alkyl residue, preferably a C1-C2 alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue, preferably R4 is oxygen.

As discussed above, the stabilizing compositions provided by the invention, in particular those comprising butanamide and an apoptosis inhibitor, are particularly effective in stabilizing a cell-containing biological sample, in particular blood, plasma and/or serum, by stabilizing comprised cells and the comprised extracellular nucleic acids thereby substantially preserving, respectively stabilizing the extracellular nucleic acid population at the time of stabilization. A respective stabilizing composition allows the storage and/or handling, e.g. shipping, of the cell-containing biological sample, which preferably is whole blood, at room temperature for at least two, preferably at least three days or even longer without substantially compromising the quality of the blood sample, respectively the extracellular nucleic acid population contained therein. Of course, it is not mandatory to make use of the full possible stabilization period. The samples may also be processed earlier if desired. Contacting the biological sample with the stabilizing composition allows the sample to be stored, and or handled, e.g. shipped, even at room temperature prior to isolating and optionally analysing and/or processing the contained extracellular nucleic acids. Thus, the time between the collection and stabilization of the cell-containing sample and the nucleic acid extraction can vary without substantially affecting the population, respectively the composition of the extracellular nucleic acid population, contained therein. In particular, dilutions, respectively contaminations of the extracellular nucleic acid composition with intracellular nucleic acids, in particular fragmented genomic DNA, are reduced or even prevented. Preferably, the stabilization composition is contacted with the cell-containing sample immediately after or during collection of the cell-containing biological sample.

According to one embodiment, the stabilization composition comprising butanamide additionally comprises a caspase inhibitor. The advantages of using a caspase inhibitor in combination with butanamide and suitable and preferred embodiments of the caspase inhibitor were described in detail above in conjunction with the stabilization method according to the first aspect and it is referred to the above disclosure which also applies here. Preferably, the caspase inhibitor is a pancaspase inhibitor. Preferably, the caspase inhibitor is a modified caspase specific peptide, preferably modified at the C-terminus with an O-phenoxy group such as Q-VD-OPh.

According to one embodiment, the composition additionally comprises at least one poly(oxyethylene) polymer. The advantages of using a poly(oxyethylene) polymer in combination with butanamide and suitable and preferred embodiments of the poly(oxyethylene) polymer were described in detail above in conjunction with the stabilization method according to the first aspect and it is referred to the above disclosure which also applies here. The molecular weight of the poly(oxyethylene) polymer may lie in a range of e.g. 100 to 40000. Preferably, the poly(oxyethylene) polymer is a high molecular weight poly(oxyethylene) polymer having a molecular weight of at least 1500. Preferably, the poly(oxyethylene) polymer is a polyethylene glycol, such as a unsubstituted polyethylene glycol. In certain embodiments, the molecular weight may lie in a range selected from 1500 to 40000, 2000 to 30000, 2500 to 25000, 3000 to 20000, 3500 to 15000, preferably 4000 to 10000, 4500 to 9000 and 5000 to 8000. Preferably, said composition comprising butanamide and at least one poly(oxyethylene) polymer additionally comprises a caspase inhibitor.

In specific embodiments, the stabilization composition comprising butanamide and a high molecular weight poly(oxyethylene) polymer additionally comprises at least one further poly(oxyethylene) polymer having a molecular weight that is at least 100, preferably at least 200, at least 300 or at least 400 below the molecular weight of the high molecular weight poly(oxyethylene) polymer. As described above in conjunction with the stabilization method according to the first aspect, using a combination of poly(oxyethylene) polymers that differ in their molecular weights is advantageous. Preferably, both poly(oxyethylene) polymers are polyethylene glycols such as unsubstituted polyethylene glycol. According to an advantageous embodiment, the stabilization composition comprising a high molecular weight poly(oxyethylene) polymer having a molecular weight of at least 1500 additionally comprises a low molecular weight poly(oxyethylene) polymer having a molecular weight of 1000 or less as further poly(oxyethylene) polymer. Details are described above in conjunction with the stabilization method according to the first aspect and it is referred to the respective disclosure which also applies here. The low molecular weight poly(oxyethylene) polymer is preferably a polyethylene glycol, such as a unsubstituted polyethylene glycol. The molecular weight of the low molecular weight poly(oxyethylene) polymer may lie in a range selected from 100 to 1000, 150 to 800 and preferably lies in the range of 200 to 600.

According to one embodiment, the stabilization composition comprising butanamide additionally comprises at least one compound according to formula 1

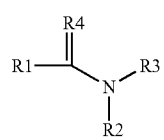

formula 1 wherein R1 is a hydrogen residue or an alkyl residue, preferably a C1-C5 alkyl residue, C1-C4 alkyl residue, C1-C3 alkyl residue, more preferred a C1-C2 alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue. Preferred embodiments were described above in conjunction with the stabilization method and it is referred to the above disclosure which also applies here. The compound according to formula 1 can be a primary, secondary or tertiary carboxylic acid amide. Preferably, the at least one compound according to formula 1 is a N,N-dialkyl-carboxylic acid amide. Preferably, a compound according to formula 1 is used which is not classified as toxic agent. According to one embodiment, the composition comprises butanamide and a N,N-dialkylpropanamide, preferably N,N-dimethylpropanamide. N,N-dimethylpropanamide is not classified as toxic agent. Furthermore, N,N-dimethylpropanamide has the advantageous effect that it is capable of stabilizing intracellular nucleic acids, and in particular may stabilize transcript profiles if used in an appropriate concentration. Preferably, said composition comprising butanamide and a compound according to formula 1 additionally comprises a caspase inhibitor. According to one embodiment, it additionally comprises at least one poly(oxyethylene) polymer.

According to one embodiment, the stabilization composition comprises butanamide and at least one anticoagulant. This embodiment is particularly suitable for stabilizing a blood sample or a cell-containing sample derived from blood. According to one embodiment, the stabilization composition comprises butanamide and a chelating agent. Suitable chelating agents which also function as anticoagulant as well as suitable concentrations for stabilization were described above in conjunction with the method according to the present invention and it is referred to the above disclosure which also applies here. Preferably, EDTA is used as anticoagulant, respectively as chelating agent. For stabilizing blood, the stabilization composition preferably comprises butanamide, at least one apotosis inhibitor, preferably a caspase inhibitor and an anticoagulant and optionally at least one compound according to formula 1. The compound according to formula 1 is preferably a N,N-dialkylpropanamide, preferably N,N-dimethlypropanamide. For stabilizing blood, the stabilization composition may also comprise butanamide, at least one apotosis inhibitor, preferably a caspase inhibitor, an anticoagulant and at least one poly(oxyethylene) polymer, preferably a polyethylene glycol, and optionally at least one compound according to formula 1. The compound according to formula 1 is preferably a N,N-dialkylpropanamide, preferably N, N-dimethlypropanamide.

The stabilization composition may also comprise further additives as described above.

Suitable and preferred embodiments of the apoptosis inhibitor, in particular the caspase inhibitor, the compound according to formula 1 and the anticoagulant were described in detail above in conjunction with the stabilization method and it is referred to the above disclosure which also applies here. The same applies with respect to the at least one poly(oxyethylene) polymer. Furthermore, suitable and preferred concentrations of the individual agents that can be used for stabilization in the stabilization mixture comprising the stabilizing composition and the cell-containing biological sample were described above and the skilled person can chose appropriate concentrations of said agents in the stabilization composition to achieve said concentrations in the mixture when the intended amount of the stabilization composition is mixed with the intended amount of cell-containing sample to be stabilized. It is referred to the above disclosure which also applies here with respect to the stabilization composition.

According to one embodiment, the stabilization composition of the invention has one or more, preferably at least two, at least three and more preferred all of the following characteristics:
i) the composition comprises butanamide in a concentration of 5% (w/v) to 50% (w/v), 7.5% (w/v) to 40% (w/v), 10% (w/v) to 35% (w/v), 12.5% (w/v) to 30% (w/v) or 15% (w/v) to 25% (w/v),
ii) the composition comprises at least one caspase inhibitor
iii) the composition comprises at least one compound according to formula 1, preferably N—N-dimethylpropanamide, in a concentration of 2% to 50%, 3% to 40%, 3.5% to 30%, 4% to 25%, 4.5% to 20% or 5% to 17.5% and/or
iv) the composition comprises an anticoagulant According to one embodiment, the stabilization composition of the invention has one or more, preferably at least two, at least three and more preferred all of the following characteristics:
i) the composition comprises butanamide in a concentration of 5% (w/v) to 50% (w/v), 7.5% (w/v) to 40% (w/v), 10% (w/v) to 35% (w/v), 12.5% (w/v) to 30% (w/v) or 15% (w/v) to 25% (w/v),
ii) the composition comprises at least one caspase inhibitor, preferably a pancaspase inhibitor, more preferred Q-VD-OPh;
iii) the composition comprises at least one poly(oxyethylene) polymer, preferably at least one high molecular weight poly(oxyethylene) polymer having a molecular weight of at least 1500, preferably in a range of 2000 to 40000, more preferred 3000 to 20000 or 4500 to 10000;
iv) the composition comprises at least one compound according to formula 1, preferably N—N-dimethylpropanamide, in a concentration of 2% to 50%, 3% to 40%, 3.5% to 30%, 4% to 25%, 4.5% to 20% or 5% to 17.5% and/or
v) the composition comprises an anticoagulant and/or a chelating agent, preferably EDTA.

As described above, according to one embodiment, a high molecular weight poly(oxyethylene) polymer is used in combination with at least one further poly(oxyethylene) polymer having a molecular weight that is at least 100, preferably at least 200, at least 300 or at least 400 below the molecular weight of the high molecular weight poly(oxyethylene) polymer used. Said further poly(oxyethylene) polymer may be a low molecular weight poly(oxyethylene) having a molecular weight of 1000 or less, preferably having a molecular weight in a range of 200 to 800 or 200 to 600. Details were described above in conjunction with the method according to the first aspect.

According to one embodiment, the stabilization composition is a liquid.

According to one embodiment, a liquid stabilization composition is provided which comprises butanamide and at least one poly(oxyethylene) polymer, which preferably is a polyethylene glycol. Subsequently, concentrations of individual agents are indicated if present in the stabilization composition that are particularly preferred for the stabilisation of blood samples. E.g. a liquid stabilisation composition of 0.5 ml to 2 ml, preferably 1 ml to 1.5 ml comprising the stabilizing agents in the concentrations indicated below, can be used for stabilizing 10 ml blood. According to one embodiment, the composition comprises butanamide and a high molecular weight poly(oxyethylene) polymer having a molecular weight of at least 1500 in a concentration selected from 0.4% to 35% (w/v), 0.8% to 25% (w/v), 1.5% to 20% (w/v), 3% to 15% (w/v) and 4% to 10% (w/v). According to one embodiment, said liquid stabilization composition comprises butanamide and a low molecular weight poly(oxyethylene) polymer having a molecular weight of 1000 or less which preferably is a polyethylene glycol in a concentration selected from 0.8% to 92.0%, 3.8% to 76.7%, 11.5% to 53.7% and 19.2% to 38.3%. The aforementioned concentrations refer to (w/v) or (v/v) depending on whether the low molecular weight poly(oxyethylene) polymer is a liquid or not. As described above, according to one embodiment, the stabilization composition comprises a high and a low molecular weight poly(oxyethylene) polymer. Examples of concentration ranges suitable when using a high molecular weight poly(oxyethylene) polymer in combination with a low molecular weight poly(oxyethylene) polymer include but are not limited to concentrations selected from 0.4% to 30.7%, 0.8% to 15.3%, 1% to 10%, 1.5% to 7.7% and 3.1% to 5.4%.

According to one embodiment, said liquid stabilization composition comprises butanamide in a concentration selected from 0.4% to 38.3%, 0.8% to 23.0%, 2.3% to 11.5% and 3.8% to 9.2%-all (w/v). According to one embodiment, said liquid stabilization composition comprises a caspase inhibitor in a concentration selected from 0.1 µM to 220 µM, 0.8 µM to 115.0 µM, 7.7 µM to 76.7 µM and 23.0 µM to 50 µM. According to one embodiment, said liquid composition comprises a chelating agent, preferably EDTA such as $K_2EDTA$ in a concentration selected from 9.5 mM to 1100 mM, 20 mM to 750 mM, 50 mM to 600 mM, 75 mM to 550 mM, 100 mM to 500 mM and 125 mM to 450 mM.

The stabilizing composition provided by the present invention stabilizes the cell-containing biological sample and thus, does not induce the lysis and/or disruption of nucleated cells and preferably also a nucleated cells, contained in the sample. Therefore, the stabilization composition does not comprise additives in a concentration wherein said additives would induce or promote cell lysis of respective cells and preferably cells in general. The stabilizing composition may reduce the damage of cells comprised in the sample as can be e.g. determined by the assay methods described in the example section. In particular, the stabilization composition described herein is capable of reducing the release of genomic DNA from cells contained in the cell-containing biological sample into the cell-free portion of the sample. Furthermore, in particular when comprising a caspase inhibitor, the stabilization composition may be capable of reducing the degradation of nucleic acids, in particular genomic DNA, present in the stabilized sample. As described, the stabilization composition is capable of reducing or preventing the contamination of the extracellular DNA population comprised in the biological sample with genomic DNA originating from cells contained in the stabilized sample. Preferably, it is capable of reducing or preventing the contamination of the extracellular nucleic acid population comprised in the biological sample with intracellular nucleic acids, in particular DNA and RNA, originating from cells contained in the stabilized sample. Preferably, the stabilization composition does not comprise a cross-linking agent that induces protein-DNA and/or protein-protein crosslinks. In particular, the stabilization composition does not comprise formaldehyde, formaline, paraformaldehyde or a formaldehyde releaser or similar crosslinking agents. Preferably, the stabilization composition does not comprise agents that are classified as toxic agents according to GHS. Preferably, the stabilization composition of the invention is capable of stabilizing the extracellular nucleic acid population comprised in the cell-containing biological sample without refrigeration, preferably at room temperature, for a time period selected from at least two days, at least three days, at least two days to three days, at least two days to six days and/or at least two day to seven days. In particular, one or more, preferably all of the above-described stabilizing effects are achieved during the defined stabilization periods.

According to one embodiment, the stabilizing composition consists essentially of the stabilizers, i.e. butanamide and one or more of an apoptosis inhibitor, which preferably is a caspase inhibitor, a compound according to formula 1 and an anticoagulant, which preferably is a chelating agent such as EDTA and optionally, a solvent and/or buffering agent. According to one embodiment, said stabilizing composition comprises one or more poly(oxyethylene) polymers.

The stabilization composition may be provided in a solid form, a semi-liquid form or as liquid. A solid composition is e.g. a suitable option if the cell-containing biological sample to be stabilized contains liquid to dissolve the solid (such as for example cell-containing body fluids, cells in medium, urine) or if liquid, e.g. water is added thereto to dissolve the solid composition. The advantage of using a solid stabilizing composition is that solids are usually chemically more stable. However, also a liquid stabilization composition may be used. Liquid compositions often have the advantage that the mixture with the sample to be stabilised can be quickly achieved, thereby basically providing an immediate stabilizing effect as soon as the sample comes into contact with the liquid stabilizing composition. Preferably, stabilizing agent(s) present in the liquid stabilizing composition remain stable in solution and require no pre-treatment-such as for example the dissolving of precipitates of limited solubility-by the user because pre-treatments of this kind pose a risk of variations in the stabilizing efficiency. An example of a respective storage stable liquid stabilization composition comprises butanamide, a caspase inhibitor and a compound according to formula 1, preferably a N,N-dialkylpropanamide such as N,N-dimethylpropanamide. A further example of a respective storage stable liquid stabilization composition comprises butanamide, a caspase inhibitor and at least one poly(oxyethylene) polymer.

The present invention also provides a mixture comprising the stabilizing composition according to the third aspect of the invention mixed with a cell-containing biological sample. Suitable and preferred examples of cell-containing biological samples as well as suitable concentrations of the stabilizing agent(s) when mixed with the cell-containing biological sample are described above inter alia in conjunction with the stabilizing method according to the invention. It is referred to the above disclosure which also applies here. As described, preferably the cell-containing sample is a blood sample.

According to one embodiment, the stabilizing composition of the invention is pre-filled in a sample collection device so that the sample is immediately stabilized upon or during collection. According to one embodiment, the stabilizing composition is contacted with the cell-containing biological sample in a volumetric ratio selected from 10:1 to 1:20, 5:1 to 1:15, 1:1 to 1:10 and 1:2 to 1:5. It is a particular advantage of the stabilizing composition of the present invention that stabilization of a large sample volume can be achieved with a small volume of the stabilizing composition. Therefore, preferably, the ratio of stabilizing composition to sample lies in a range from 1:2 to 1:7, more preferred 1:3 to 1:5. According to one embodiment, the stabilizing composition is contacted with the cell-containing biological sample in a volumetric ratio from 1:10 to 1:5.

The stabilizing composition according to the third aspect of the present invention can be used to stabilize the extracellular nucleic acid population comprised in a cell-containing sample, such as preferably a blood sample. Particularly advantageous is the additional use of at least one poly(oxyethylene) polymer. Furthermore, the stabilizing composition according to the third aspect of the present invention may also be used for stabilizing cells contained in a sample and/or intracellular nucleic acids. As described above, the stabilizing composition may stabilize cells and thereby inter alia reduce the release of genomic DNA and other intracellular nucleic acids from cells comprised in the cell-containing biological sample. Thereby, a contamination of the extracellular nucleic acid population with genomic DNA and other intracellular nucleic acids is reduced. Furthermore, in particular if the stabilization composition comprises a compound according to formula 1, such as in particular a carboxylic acid amid as is described above as being preferred, the transcriptome can be stabilized.

D. Use

According to fourth aspect, the present invention is directed to the use of butanamide and preferably the stabilizing composition according to the third aspect for stabilizing a cell-containing biological sample and in particular the extracellular nucleic acid population comprised in a cell-containing biological sample. In particular, the stabilizing composition can be used in the method according to the first aspect of the present invention. Details of said method were described above and it is referred to the above disclosure which also applies here. According to further aspect, the present invention is directed to the use of the composition according to the third aspect for stabilizing cells and/or the transcriptome in a cell-containing biological sample. Preferably, as described above, the composition comprises an anticoagulant if the cell-containing biological sample is blood what is a preferred embodiment.

G. Manufacturing Method

Also provided is a method of manufacturing a stabilizing composition according to the third aspect of the present invention, wherein the components of the stabilizing composition are mixed, preferably to provide a liquid solution.

E. Collection Device

The stabilizing composition of the present invention may also be incorporated into a sample collection device, in particular a blood collection assembly, such as a blood collection container thereby providing for a new and useful version of such a device. Such devices typically include a container having an open and a closed end. The container is preferably a blood collection tube. The container type also depends on the sample to be collected, other suitable formats are described below.

Furthermore, according to a fifth aspect, the present invention provides a container for collecting a cell-containing biological sample, wherein the container comprises butanamide and at least one further additive selected from the group consisting of
 an apoptosis inhibitor,
 an anticoagulant and
 a compound according to formula 1

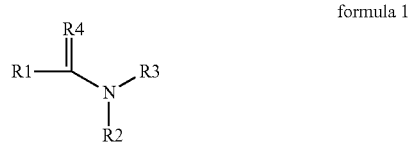

formula 1 wherein R1 is a hydrogen residue or an alkyl residue, preferably a C1-C5 alkyl residue, a C1-C4 alkyl residue or a C1-C3 alkyl residue, preferably a C1-C2 alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue, preferably R4 is oxygen.

Furthermore, the container may comprise at least one poly(oxyethylene) polymer, preferably at least one polyethylene glycol.

Providing a respective container, e.g. a sample collection tube, has the advantage that the sample is quickly stabilized when the sample is collected in the respective container. The container for collecting a cell-containing biological sample, preferably a blood sample, may comprise a stabilizing composition according to the present invention. Details with respect to the the use of butanamide and optionally the one or more further additives for stabilization as well as the stabilizing composition were described above, it is referred to the above disclosure which also applies here.

According to one embodiment, a collection container for receiving and collecting a cell-containing biological sample is provided wherein the container comprises:
 a) butanamide in concentration so that when the cell-containing biological sample is collected into the container, the concentration of butanamide in the resulting mixture is at least 0.25% (w/v), at least 0.3% (w/v), at least 0.4% (w/v), at least 0.5% (w/v), at least 0.75% (w/v) or at least 1% (w/v), at least 1.5% (w/v), at least 1.75% (w/v), at least 2% (w/v) or at least 2.5% (w/v) and wherein preferably, the resulting mixture comprises butanamide in a concentration that lies in the range of 0.25% (w/v) to 15% (w/v), 0.5% (w/v) to 12.5% (w/v), 0.75% (w/v) to 10% (w/v), 0.8% (w/v) to 9% (w/v), 0.9% (w/v) to 8% (w/v), 1% (w/v) to 7% (w/v), 1.1% (w/v) to 6% (w/v), 1.2% (w/v) to 6% (w/v), 1.3% (w/v) to 5.5% (w/v), 1.4% (w/v) to 5.25% (w/v), 1.5% (w/v) to 5% (w/v), 1.75% (w/v) to 4.75% (w/v), 2.0% (w/v) to 4.5% (w/v), 2.2% (w/v) to 4.25% (w/v), 2.3% (w/v) to 4% (w/v), 2.4% (w/v) to 3.75% (w/v) or 2.5% (w/v) to 3.5% (w/v); and
 b) at least one caspase inhibitor in a concentration so that when the cell-containing biological sample is collected into the container, the concentration of the caspase inhibitor in the resulting mixture is at least 0.01 µM, at least 0.1 µM, at least 0.25 µM, at least 0.5 µM, at least 0.6 µM, at least 0.7 µM, at least 0.8 µM, at least 0.9 µM or at least 1 µM and wherein preferably, the resulting mixture comprises the caspase inhibitor in a concentration that lies in the range of 0.01 µM to 100 µM, 0.1 µM to 75 µM, 0.25 µM to 50 µM, 0.5 µM to 40 µM, 0.6 µM to 30 µM, 0.7 µM to 35 µM, 0.8 µM to 30 µM, 0.9 µM to 25 µM, 1 µM to 20 µM, 1.1 µM to 17.5 µM, 1.25 µM to 15 µM or 1.5 µM to 12.5 µM.

According to one embodiment, the container additionally comprises
 c) a compound according to formula 1, preferably a non-toxic compound, preferably a N,N-dialkylpropanamide, more preferred N,N-dimethlypropanamide, in a concentration so that when the cell-containing biological sample is collected into the container, the concentration of the compound according to formula 1 in the resulting mixture is at least 0.1%, at least 0.5%, at least 0.75%, at least 1%, at least 1.25% or at least 1.5% and wherein preferably, the resulting mixture comprises the compound according to formula 1 in a concentration that lies in the range of 0.1% to 30%, 0.25% to 20%, 0.5% to 15%, 0.7% to 10%, 0.8% to 7.5%, 0.9% to 6% or 1% to 5%.

Suitable and preferred embodiments of the compound according to formula 1 were described above in conjunction with the stabilization method and the stabilization composition and it is referred to the above disclosure which also applies here. As is shown by the examples, a stabilizing composition comprising a caspase inhibitor, butanamide and N,N-dimethylpropanamide is very effective in stabilizing a cell-container biological sample, in particular a whole blood sample.

According to one embodiment, a collection container for receiving and collecting a cell-containing biological sample is provided wherein the container comprises:
 a) butanamide in concentration so that when the cell-containing biological sample is collected into the container, the concentration of butanamide in the resulting mixture is at least 0.25% (w/v), at least 0.3% (w/v), at least 0.4% (w/v), at least 0.5% (w/v) or at least 0.75% (w/v) and wherein preferably, the resulting mixture comprises butanamide in a concentration that lies in the range of 0.1% to 5%, 0.2% to 3.5%, 0.3% to 3%, 0.5% to 2.5% and 0.6% to 2%—all (w/v); and
 b) at least one caspase inhibitor in a concentration so that when the cell-containing biological sample is collected into the container, the concentration of the caspase inhibitor in the resulting mixture is at least 0.01 µM, at least 0.1 µM, at least 0.25 µM, at least 0.5 µM, at least 0.6 µM, at least 0.7 µM, at least 0.8 µM, at least 0.9 µM or at least 1 µM and wherein preferably, the resulting mixture comprises the caspase inhibitor in a concentration that lies in the range of 0.01 µM to 100 µM, 0.1 µM to 75 µM, 0.25 µM to 50 µM, 0.5 µM to 40 µM, 0.6 µM to 30 µM, 0.7 µM to 35 µM, 0.8 µM to 30 µM, 0.9 µM to 25 µM, 1 µM to 20 µM, 1.1 µM to 17.5 µM, 1.25 µM to 15 µM or 1.5 µM to 12.5 µM; and
 c) at least one poly(oxyethylene) polymer.

Suitable and preferred embodiments with respect to the poly(oxyethylene) polymer and also combinations of poly(oxyethylene) polymers were described in detail above and it is referred to the above disclosure which also applies here. According to one embodiment, a high molecular weight poly(oxyethylene) polymer is used which has a molecular weight of at least 1500, preferably in a range of 2000 to 40000, more preferred 3000 to 20000 or 4500 to 10000. Preferably, it is a polyethylene glycol such as an unsubstituted polyethylene glycol. It may be comprised in the container in a concentration so that when the cell-containing biological sample is collected into the container the concentration of the poly(oxyethylene) polymer in the resulting mixture lies in a range selected from 0.05% to 4% (w/v), 0.1% to 3% (w/v), 0.2% to 2.5% (w/v), 0.25% to 2% (w/v), 0.3% to 1.75% (w/v) and 0.35% to 1.5% (w/v), preferably in the range of 0.25% to 1.5% (w/v), 0.3% to 1.25% (w/v), 0.35% to 1% (w/v) or 0.4% to 0.75% (w/v).

According to one embodiment, the container additionally comprises at least one further additive, preferably an anticoagulant such as a chelating agent, preferably EDTA. This embodiment is particularly suitable if the container is for collecting blood or a sample derived from blood such as plasma or serum. The anticoagulant is comprised in a concentration wherein it is capable of preventing the coagulation of blood. Suitable anticoagulants were described above in conjunction with the method according to the first aspect and it is referred to the above disclosure which also applies here. According to one embodiment, the container comprises a chelating agent, preferably EDTA, in a concentration so that when the cell-containing biological sample is collected into the container, the concentration of the chelating agent in the resulting mixture lies in a concentration range selected from 0.05 mM to 100 mM, 0.1 mM to 50 mM, 0.5 mM to 30 mM, 1 mM to 20 mM, 1.5 mM to 15 mM or 2 mM to 15 mM. According to one embodiment, the container comprises a chelating agent, preferably EDTA, in a concentration so that when the cell-containing biological sample is collected into the container, the concentration of the chelating agent in the resulting mixture lies in a concentration range selected from 0.5 to 40 mg/ml, 1 to 30 mg/ml, 1.6 to 25 mg/ml, 5 to 20 mg/ml and 7.5 to 17.5 mg/ml.

The stabilizing composition and/or the individual compounds used for stabilization comprised in the collection container can be provided in a liquid; semi-liquid or in a dry form. As discussed above, butanamide and at least one further additive selected from the group consisting of an apoptosis inhibitor, an anticoagulant and a compound according to formula 1 may be provided in form of a stabilizing composition. The same applies if at least one polyoxyethylene) polymer is used in combination with butanamide to support the stabilization. The compounds used for stabilization may also be provided as separate entities in the container and may also be provided in different forms in the container. E.g. butanamide may be provided in dry form while the compound according to formula 1 may be provided as liquid. Other combinations are also feasible. Furthermore, it is within the scope to provide butanamide and e.g. the apoptosis inhibitor in form of a stabilization composition and the anticoagulant and/or a compound according to formula 1 separately in the container. Suitable formulation and manufacturing options are known to the skilled person.

For stabilizing whole blood it is preferred to encompass an anticoagulant such as EDTA into the container, e.g. in the stabilizing composition. A dry form is e.g. a suitable option if the biological sample to be stabilized contains liquid to dissolve the solid (such as for example cell-containing body fluids, cells in medium, urine) or if liquid, e.g. water or other solvent is added thereto to dissolve the solid. The advantage of using a solid stabilizing composition is that solids are usually chemically more stable than liquids. According to one embodiment, the inner wall of the container is treated/covered with a stabilizing composition according to the present invention or with individual components thereof, such as e.g. the anticoagulant. Said composition or component can be applied to the inner walls using e.g. a spray-dry-method. Liquid removal techniques can be performed on the stabilizing composition in order to obtain a substantially solid state protective composition. Liquid removal conditions may be such that they result in removal of at least about 50% by weight, at least about 75% by weight, or at least about 85% by weight of the original amount of the dispensed liquid stabilizing composition. Liquid removal conditions may be such that they result in removal of sufficient liquid so that the resulting composition is in the form of a film, gel or other substantially solid or highly viscous layer. For example it may result in a substantially immobile coating (preferably a coating that can be re-dissolved or otherwise dispersed upon contact with the cell-containing sample which preferably is a blood product sample). It is possible that lyophilization or other techniques may be employed for realizing a substantially solid form of the protective agent (e.g., in the form of one or more pellet). Thus, liquid removal conditions may be such that they result in a material that upon contact with the sample under consideration (e.g., a whole blood sample) the protective agent will disperse in the sample, and substantially preserve components (e.g., extracellular nucleic acids) in the sample. Liquid removal conditions may be such that they result in a remaining composition that is substantially free of crystallinity, has a viscosity that is sufficiently high that the remaining composition is substantially immobile at ambient temperature; or both.

However, also a liquid composition may be used and has advantages for the stabilization of blood. Liquid compositions often have the advantage that the mixture with the cell-containing biological sample to be stabilised can be quickly achieved, thereby basically providing an immediate stabilizing effect as soon as the sample comes into contact with the liquid stabilizing composition. Furthermore, liquid compositions are advantageous if larger amounts of stabilization compositions are used which accordingly, can not or are difficult to spray-dry or if the composition hampers providing a dry composition. Preferably, the stabilizing agents present in the liquid stabilizing composition remain stable in solution and require no pre-treatment—such as for example the dissolving of precipitates of limited solubility—by the user because pre-treatments of this kind pose a risk of variations in the stabilizing efficiency. As described herein, a stabilizing composition comprising butanamide and a compound according to formula 1, preferably a N,N-dialkylpropanamide, preferably N,N-dimethylpropanamide and optionally a caspase inhibitor optionally an anticoagulant such as EDTA, is storage stable. In particular, it is storage stable over a broad temperature range. For stabilizing blood, according to one embodiment, all compounds are present in the stabilizing composition. As described above, in advantageous embodiments the stabilizing composition additionally comprises at least one poly(oxyethylene) polymer, which preferably is a polyethylene glycol.

The stabilizing composition is comprised in the container in an amount effective to provide the stabilization of the amount of sample to be collected in said container. According to one embodiment, the liquid stabilizing composition is contacted with the biological sample in a volumetric ratio selected from 10:1 to 1:20, 5:1 to 1:15, 1:1 to 1:10 and 1:2 to 1:5. According one embodiment the liquid stabilizing composition is contacted with the biological sample in a volumetric ratio of 1:10 to 1:5. It is a particular advantage of the stabilizing composition of the present invention that stabilization of a large sample volume can be achieved with a small volume of the stabilizing composition. Therefore, preferably, the ratio of stabilizing composition to sample lies in a range from 1:2 to 1:7, more preferred 1:3 to 1:5.

According to one embodiment, the container is evacuated. The evacuation is preferably effective for drawing a specific volume of a fluid cell-containing biological sample into the interior. Thereby, it is ensured that the correct amount of sample is contacted with the pre-filled amount of the stabilizing composition comprised in the container, and accordingly, that the stabilization is efficient. According to one embodiment, the container comprises a tube having an open end sealed by a septum. E.g. the container is pre-filled with a defined amount of the stabilizing composition either in solid or liquid form and is provided with a defined vacuum and sealed with a septum. The septum is constructed such that it is compatible with the standard sampling accessories (e.g. cannula, etc.). When contacted with e.g. the canula, a sample amount that is predetermined by the vacuum is collected in the container. A respective embodiment is in particular advantageous for collecting blood. A suitable container is e.g. disclosed in U.S. Pat. No. 6,776,959.

The container according to the present invention can be made of glass, plastic or other suitable materials. Plastic materials can be oxygen impermeable materials or may contain an oxygen impermeable layer. Alternatively, the container can be made of air-permeable plastic material. The container according to the present invention preferably is made of a transparent material. Examples of suitable transparent thermoplastic materials include polycarbonates, polyethylene, polypropylene and polyethyleneterephthalate. The container may have a suitable dimension selected according to the required volume of the biological sample being collected. As described above, preferably, the container is evacuated to an internal pressure below atmospheric pressure. Such an embodiment is particularly suitable for collecting body fluids such as whole blood. The pressure is preferably selected to draw a predetermined volume of a biological sample into the container. In addition to such vacuum tubes also non-vacuum tubes, mechanical separator tubes or gel-barrier tubes can be used as sample containers, in particular for the collection of blood samples. Examples of suitable containers and capping devices are disclosed in U.S. Pat. No. 5,860,397 and US 2004/0043505. As container for collecting the cell-containing sample also further collection devices, for example a syringe, a urine collection device or other collection devices can be used. The type of the container may also depend on the sample type to be collected and suitable containers are also available to the skilled person.

According to one embodiment, the container has an open top, a bottom, and a sidewall extending therebetween defining a chamber, wherein butanamide and at least one further additive selected from the group consisting of an apoptosis inhibitor, an anticoagulant and a compound according to formula 1 or the stabilization composition according to the present invention is comprised in the chamber. It may be comprised therein in liquid or solid form. According to one embodiment, it is a liquid. According to one embodiment, additionally at least one poly(oxyethylene) polymer, preferably a polyethylene glycol is additionally comprised in the chamber. According to one embodiment the container is a tube, the bottom is a closed bottom, the container further comprises a closure in the open top, and the chamber is at a reduced pressure. The advantages of a reduced pressure in the chamber were described above. Preferably, the closure is capable of being pierced with a needle or cannula, and the reduced pressure is selected to draw a specified volume of a liquid sample into the chamber. According to one embodiment, the chamber is at a reduced pressure selected to draw a specified volume of a liquid sample into the chamber, and the stabilizing composition is a liquid and is disposed in the chamber such that the volumetric ratio of the stabilizing composition to the specified volume of the cell-containing sample is selected from 10:1 to 1:20, 5:1 to 1:15, 1:1 to 1:10 and 1:2 to 1:5. According to one embodiment the ratio is 1:10 to 1:5. The associated advantages were described above.

Preferably, the container is for drawing blood from a patient.

F. Method for Collecting a Cell Containing Sample

According to a sixth aspect, a method is provided comprising the step of collecting a cell-containing biological sample from a patient directly into a chamber of a container according to the fifth aspect of the present invention. Details with respect to the container and the cell-containing biological sample were described above. It is referred to the respective disclosure. According to one embodiment, a blood sample is collected, preferably it is drawn from the patient into the container.

The methods and compositions disclosed herein stabilize cell-containing biological samples and allow e.g. for the efficient preservation and isolation of extracellular nucleic acids while reducing the risk that after collection of the cell-containing biological sample the extracellular nucleic acid population becomes contaminated, in particular diluted with intracellular nucleic acids, in particular fragmented genomic DNA, which originate from cells comprised in the biological sample and which may be released due to cell damage, respectively cell lysis. The methods according to the present invention, as well as the compositions and the disclosed devices (e.g. the collection containers) allow to reduce the degradation of extracellular nucleic acids and also reduce cell lysis and/or release of genomic nucleic acids, in particular fragmented genomic DNA, from cells so that the extracellular nucleic acids contained in the sample do not become contaminated with intracellular nucleic acids, respectively a respective contamination is reduced by the teachings according to the present invention. As discussed above, an intermixing of extracellular nucleic acids and cellular nucleic acids, in particular fragmented genomic DNA, may reduce the accuracy of any measurement of the amount of extracellular nucleic acids in a biological sample. As discussed above, an important advantage of the present invention is the possibility for essentially simultaneous stabilizing both cells contained in the sample (in particular white blood cells or types of white blood cells in case of whole blood, plasma or serum) and the extracellular nucleic acids. This helps to prevent cellular nucleic acids such as genomic DNA from being released into the cell-free portion of the sample and diluting the comprised extracellular nucleic acids (and associated biomarkers) of interest. As discussed herein, contacting the cell-containing biological sample such as whole blood or plasma with the stabilizing agent(s) used according to the teachings of the present invention allows the sample to be stored for a period of time prior to isolating the extracellular nucleic acids. More preferably, the cell-containing biological sample, e.g. blood or plasma, may be drawn at one location (e.g., a health care facility), contacted with the stabilizing agent(s), and later transported to a different remote location (e.g., a laboratory) for the nucleic acid isolation and testing process. Furthermore, as described above, certain combinations of stabilizing agents are particularly effective in stabilizing additionally the transcriptome of contained cells, which has the above-described advantages.

Furthermore, the stabilization technologies, as disclosed in herein, provide an advantage over known state-of-the-art stabilization reagents which involve the use of cross-linking reagents, such as formaldehyde, formaldehyde releasers and the like, as the stabilization of samples according to the present invention does not require the use to such crosslinking reagents. Crosslinking reagents cause inter- or intramolecular covalent bonds between nucleic acid molecules or between nucleic acids and proteins. This effect can lead to a reduced recovery of such stabilized and partially crosslinked nucleic acids after a purification or extraction from a complex biological sample. As, for example, the concentration of circulating nucleic acids in a whole blood samples is already relatively low, any measure which further reduces the yield of such nucleic acids should be avoided. This may be of particular importance when detecting and analyzing very rare nucleic acid molecules derived from malignant tumors or from a developing fetus in the first trimester of pregnancy. Therefore, according to one embodiment, no cross-linking agents such as formaldehyde or formaldehyde releaser are comprised in the stabilizing composition, respectively are not additionally used for stabilization.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

The term "solution" as used herein in particular refers to a liquid composition, preferably an aqueous composition. It may be a homogenous mixture of only one phase but it is also within the scope of the present invention that a solution comprises solid additives such as e.g. precipitates, in particular of contained chemicals such as stabilizing agents.

The sizes, respectively size ranges indicated herein with reference to nucleotides (nt), refer to the chain length and thus are used in order to describe the length of single-stranded as well as double-stranded molecules. In double-stranded molecules said nucleotides are paired.

According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

Particularly preferred aspects and embodiments are described again in the following.

In a first aspect, the present invention is in particular directed to a method for stabilizing an extracellular nucleic acid population comprised in a cell-containing biological sample by contacting the cell-containing biological sample with butanamide. According to one embodiment, the cell-containing biological sample is additionally contacted with at least one apoptose inhibitor, preferably a caspase inhibitor. According to one embodiment, the sample is additionally contacted with a caspase inhibitor which is a pancaspase inhibitor and preferably, the pancaspase inhibitor is selected from the group consisting of Q-VD-OPh and Z-Val-Ala-Asp (OMe)-FMK, and the caspase inhibitor preferably is Q-VD-OPh.

According to one embodiment, the cell-containing biological sample is additionally contacted with at least one poly(oxyethylene) polymer. The poly(oxyethylene) polymer is preferably a polyethylene glycol, such as an unsubstituted polyethylene glycol. As described above, the at least one polymer may have a molecular weight in a range of 100 to 40000, suitable embodiments are described above. Preferably, the at least one poly(oxyethylene) polymer is a high molecular weight poly(oxyethylene) polymer or a combination of a high and a low molecular weight poly(oxyethylene) polymer. The high molecular weight poly(oxyethylene) polymer preferably has a molecular weight of at least 1500, more preferably in a range of 2000 to 40000, more preferred 3000 to 20000 or 4500 to 10000. Suitable concentrations are described above.

According to one embodiment, the cell-containing biological sample is additionally contacted with at least one compound according to formula 1

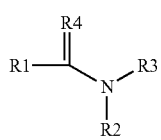

formula 1 wherein R1 is a hydrogen residue or an alkyl residue, preferably a C1-C5 alkyl residue, a C1-C4 alkyl residue or a C1-C3 alkyl residue, more preferred a C1-C2 alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue, preferably R4 is oxygen. The compound according to formula 1 preferably is a tertiary carboxylic acid amide, and wherein preferably, the compound according to formula 1 is a N,N-dialkyl-carboxylic acid amide. The compound according to formula 1 preferably is selected from the group consisting of N,N-dimethylacetamide, N,N-diethylacetamide, N,N-dimethylformamide, N,N-diethylformamide and N,N-dimethylpropanamide. The compound according to formula 1 preferably is a N,N-dialkylpropanamide, more preferably N,N-dimethylpropanamide. The compound according to formula 1 preferably is not a toxic agent. Using such compound according to formula 1 and a caspase inhibitor in addition to butanamide is particularly preferred.

According to one embodiment, the cell-containing biological sample is a blood sample or a sample derived from blood and said sample is additionally contacted with an anticoagulant, preferably a chelating agent, more preferably EDTA.

According to one embodiment, cells contained in the sample are stabilized and the release of genomic DNA from cells contained in the sample into the cell-free portion of the sample is reduced and/or the degradation of nucleic acids present in the sample is reduced due to the stabilization. According to one embodiment, the stabilization reduces the contamination of the extracellular DNA population comprised in the biological sample with genomic DNA originating from cells contained in the stabilized sample during the stabilization period. According to one embodiment, the stabilization reduces the contamination of the extracellular nucleic acid population comprised in the biological sample with intracellular nucleic acids originating from cells contained in the stabilized sample during the stabilization period.

According to one embodiment, after the cell-containing biological sample has been contacted with butanamide and optionally further additives used for stabilization, the resulting mixture comprises butanamide in a concentration of at least 0.25%, at least 0.3%, at least 0.4%, at least 0.5%, at least 0.75%, at least 1%, at least 1.5%, at least 1.75%, at least 2% or at least 2.5%. According to one embodiment, after the cell-containing biological sample has been contacted with butanamide and optionally further additives used for stabilization, the resulting mixture comprises butanamide in a concentration range of 0.25% to 15%, 0.5% to 12.5%, 0.75% to 10%, 1% to 9%, 1.25% to 8%, 1.5% to 7%, 1.75% to 6%, 1.8% to 5.5%, 1.9% to 5.25%, 2% to 5%, 2.1% to 4.75%, 2.2% to 4.5%, 2.3% to 4.25%, 2.4% to 4%, 2.5% to 3.75% or 0.75% to 2%. Concentrations for butanamide are preferably (w/v).

According to one embodiment, after the cell-containing biological sample has been contacted with butanamide, a caspase inhibitor and optionally further additives used for stabilization, the resulting mixture comprises the caspase inhibitor, which preferably is a pancaspase inhibitor as described above,
i) in a concentration of at least 0.01 NM, at least 0.1 NM, at least 0.25 μM, at least 0.5 μM, at least 0.6 μM, at least 0.7 μM, at least 0.8 μM, at least 0.9 μM or at least 1 μM, and/or
ii) in a concentration that lies in the range of 0.01 μM to 100 μM, 0.1 μM to 75 μM, 0.25 μM to 50 μM, 0.5 μM to 40 μM, 0.6 μM to 30 μM, 0.7 μM to 35 μM, 0.8 μM to 30 μM, 0.9 μM to 25 μM, 1 μM to 20 μM, 1.1 μM to 17.5 μM, 1.25 μM to 15 μM or 1.5 μM to 12.5 μM.

According to one embodiment, after the cell-containing biological sample has been contacted with butanamide, at least one high molecular poly(oxyethylene) polymer having a molecular weight of at least 1000 and optionally further additives used for stabilization, the resulting mixture comprises the at least one high molecular weight poly(oxyethylene) polymer
i) in a concentration that lies in the range of 0.05% to 4% (w/v), 0.1% to 3% (w/v), 0.2% to 2.5% (w/v), 0.25% to 2% (w/v), 0.3% to 1.75% (w/v) and 0.35% to 1.5% (w/v); and/or
ii) in a concentration that lies in the range of 0.25% to 1.5% (w/v), 0.3% to 1.25% (w/v), 0.35% to 1% (w/v) and 0.4% to 0.75% (w/v).

According to one embodiment, after the cell-containing biological sample has been contacted with butanamide, a compound according to formula 1 and optionally further additives used for stabilization, the resulting mixture comprises a compound according to formula 1
i) in a concentration of at least 0.1%, at least 0.25%, at least 0.5%, at least 0.75%, at least 1%, at least 1.25% or at least 1.5%; and/or
ii) in a concentration that lies in the range of 0.1% to 30%, 0.25% to 20%, 0.5% to 15%, 0.7% to 10%, 0.8% to 7.5%, 0.9% to 6% or 1% to 5%.

According to one embodiment, after the cell-containing biological sample has been contacted with butanamide, the anticoagulant and optionally further additives used for stabilization, the resulting mixture comprises the anticoagulant, which preferably is EDTA, in a concentration range selected from 0.05 mM to 100 mM, 0.05 mM to 50 mM, 0.1 mM to 30 mM, 0.5 mM to 25 mM, 1 mM to 20 mM, 1.5 mM to 15 mM and 2 mM to 10 mM.

According to one embodiment, for stabilization, the cell-containing sample is contacted with a stabilizing composition comprising:
a) butanamide;
b) at least one pancaspase inhibitor;
c) optionally at least one compound according to formula 1, preferably a N,N-dialkyl-carboxylic acid amide, more preferred a N,N-dialkylpropanamide; and
d) optionally an anticoagulant, preferably a chelating agent, more preferably EDTA and preferably, the cell-containing sample is contacted with a stabilizing composition as defined herein.

According to one embodiment, for stabilization, the cell-containing sample is contacted with a stabilizing composition comprising:
a) butanamide;
b) at least one poly(oxyethylene) polymer, preferably a polyethylene glycol;

c) optionally at least one caspase inhibitor, preferably a pancaspase inhibitor;

c) optionally at least one compound according to formula 1, preferably a N,N-dialkyl-carboxylic acid amide, more preferred a N,N-dialkylpropanamide; and d) optionally an anticoagulant, preferably a chelating agent, more preferably EDTA and preferably, the cell-containing sample is contacted with a stabilizing composition as defined herein.

Particularly advantageous is a stabilization with butanamide, at least one poly(oxyethylene) polymer and at least one caspase inhibitor.

According to one embodiment, the stabilization achieves a stabilization of the extracellular nucleic acid population comprised in the cell-containing biological sample without refrigeration, preferably at room temperature, for a time period selected from at least two days, at least three days, at least two days to three days, at least two days to six days and/or at least two days to seven days. According to one embodiment, the stabilization achieves a stabilization of cells contained in the cell-containing biological sample during the stabilization period and reduces a release of genomic DNA from said cells comprised in the stabilized sample. According to one embodiment, the stabilization does not involve the use of additives in a concentration wherein said additives would induce or promote lysis of nucleated cells. In particular, the stabilization does not involve the use of lytic agents such as chaotropic agents.

According to one embodiment, the stabilization does not involve the use of a cross-linking agent that induces protein-nucleic acid and/or protein-protein crosslinks; and/or the stabilization does not involve the use of toxic agents.

According to one embodiment, the cell-containing biological sample has one or more of the following characteristics:
  a) it is selected from the group consisting of body fluids, whole blood, samples derived from blood, plasma, serum, lymphatic fluid, urine, liquor, cerebrospinal fluid, ascites, milk, stool, bronchial lavage, saliva, amniotic fluid, semen/seminal fluid, swabs/smears, body secretions, nasal secretions, vaginal secretions, wound secretions and excretions and cell culture supernatants;
  b) it is a cell-depleted or cell-containing body fluid;
  c) it is a cell-containing body fluid;
  d) it is a circulating body fluid;
  e) it is selected from blood, plasma, serum or urine;
  f) it is blood.

According to one embodiment, the method is for stabilizing an extracellular nucleic acid population comprised in a blood sample, comprising contacting the blood sample with butanamide and an anticoagulant, wherein the release of genomic DNA from cells contained in the blood sample into the cell-free portion of the blood sample is reduced. According to one embodiment, the method is for stabilizing an extracellular nucleic acid population comprised in a blood sample, comprising contacting the blood sample with butanamide, at least one caspase inhibitor and an anticoagulant, wherein the release of genomic DNA from cells contained in the blood sample into the cell-free portion of the blood sample is reduced. According to one embodiment, the method is for stabilizing an extracellular nucleic acid population comprised in a blood sample, comprising contacting the blood sample with butanamide, at least one caspase inhibitor, at least one compound according to formula 1 and an anticoagulant, wherein the release of genomic DNA from cells contained in the blood sample into the cell-free portion of the blood sample is reduced.

According to one embodiment, the stabilization reduces hemolysis during the stabilization period. According to one embodiment, butanamide and optionally further additives used for stabilization are comprised in a stabilizing composition and wherein the volumetric ratio of the stabilizing composition to the specified volume of the cell-containing sample is selected from 10:1 to 1:20, 5:1 to 1:15, 1:1 to 1:10 and 1:2 to 1:5. According to one embodiment it is 1:10 to 1:5.

According to one embodiment, after the stabilization period, the method comprises one or more of the following
  a) the stabilized sample is subjected to a nucleic acid analysis and/or detection method;
  b) extracellular nucleic acids are isolated from the stabilized sample;
  c) extracellular nucleic acids are isolated from the stabilized sample and the isolated nucleic acids are analysed and/or detected;
  d) cells comprised in the stabilized sample are removed;
  e) cells comprised in the stabilized sample are removed prior to performing an nucleic acid isolation, analysis and/or detection step;
  f) cells are removed from the stabilized sample and extracellular nucleic acids are isolated from the cell-free or cell-depleted portion of the stabilized sample;
  g) (i) the stabilized sample, (ii) the stabilized sample from which cells have been removed and/or (iii) cells removed from the sample are stored;
  h) cells are removed from the stabilized sample and are discarded; and/or
  i) cells are removed from the stabilized sample and nucleic acids are isolated from cells that were removed from the stabilized sample;
  j) cells are removed from the stabilized sample and extracellular nucleic acids are isolated from the cell-free or cell-depleted portion of the stabilized sample using a size selective nucleic acid isolation method.

In a second aspect, the present invention in particular pertains to a method for isolating nucleic acids from a stabilized cell-containing biological sample comprising the steps of
  a) stabilizing the cell-containing biological sample according to the method according to the first aspect; and
  b) isolating nucleic acids from the stabilized sample.

In particular said second aspect provides a method for isolating extracellular nucleic acids from a stabilized cell-containing biological sample comprising the steps of
  a) stabilizing the extracellular nucleic acid population in the cell-containing biological sample according to the method for stabilizing an extracellular nucleic acid population according to the first aspect; and
  b) isolating extracellular nucleic acids.

According to one embodiment, the method comprises removing cells from the cell-containing biological sample between step a) and step b) and step b) comprises isolating extracellular nucleic acids from the cell-free or cell-depleted portion of the stabilized sample. According to one embodiment, the method comprises performing one or more of the following steps:
  a) the stabilized sample is subjected to a nucleic acid analysis and/or detection method;
  b) extracellular nucleic acids are isolated from the stabilized sample;

c) extracellular nucleic acids are isolated from the stabilized sample and the isolated nucleic acids are analysed and/or detected;
d) cells comprised in the stabilized sample are removed;
e) cells comprised in the stabilized sample are removed prior to performing an nucleic acid isolation, analysis and/or detection step;
f) cells are removed from the stabilized sample and extracellular nucleic acids are isolated from the cell-free or cell-depleted portion of the stabilized sample;
g) (i) the stabilized sample, (ii) the stabilized sample from which cells have been removed and/or (iii) cells removed from the sample are stored;
h) cells are removed from the stabilized sample and are discarded; and/or
i) cells are removed from the stabilized sample and nucleic acids are isolated from cells that were removed from the stabilized sample;
j) cells are removed from the stabilized sample and extracellular nucleic acids are isolated from the cell-free or cell-depleted portion of the stabilized sample using a size selective nucleic acid isolation method.

According to one embodiment, the cell-containing sample is a blood sample and wherein the stabilization in step a) is performed as defined for the method according to the first aspect.

According to one embodiment, the isolated extracellular nucleic acids are in a further step c) processed and/or analysed and preferably are
i) modified;
ii) contacted with at least one enzyme;
iii) amplified;
iv) reverse transcribed;
v) cloned;
vi) sequenced;
vii) contacted with a probe;
viii) detected;
ix) quantified; and/or
x) identified.

According to one embodiment, the extracellular nucleic acid population that is isolated in step b) has one or more of the following characteristics:
i) it is comprised as portion in the total nucleic acid that is isolated;
ii) it is a mixture of DNA and RNA;
iii) it predominantly comprises DNA;
iv) it predominantly comprises RNA;
v) it comprises mammalian extracellular nucleic acids;
vi) it comprises circulating extracellular nucleic acids;
vii) it comprises disease related nucleic acids;
viii) it comprises tumor-associated or tumor-derived nucleic acids;
ix) it comprises inflammation related nucleic acids:
x) it comprises viral nucleic acids;
xi) it comprises pathogen nucleic acids; and/or
xii) it comprises fetal nucleic acids.

According to one embodiment, the extracellular nucleic acid that is analysed and/or further processed, preferably detected, in step c), has one or more of the following characteristics:
i) it is DNA;
ii) it is RNA;
iii) it is a mammalian extracellular nucleic acid;
iv) it is circulating extracellular nucleic acid;
v) it is a disease related nucleic acid;
vi) it is a tumor-associated or tumor-derived nucleic acid;
vii) it is an inflammation related nucleic acid:
viii) it is a viral nucleic acid;
ix) it is a pathogen nucleic acid; and/or
x) it is a fetal nucleic acid.

In a third aspect, the present invention in particular pertains to a composition suitable for stabilizing a cell-containing biological sample wherein the composition comprises butanamide and at least one further additive selected from the group consisting of an apoptosis inhibitor, an anticoagulant and a compound according to formula 1

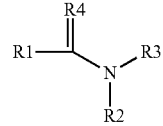

formula 1 wherein R1 is a hydrogen residue or an alkyl residue, preferably a C1-C5 alkyl residue, a C1-C4 alkyl residue or a C1-C3 alkyl residue, preferably a C1-C2 alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue, preferably R4 is oxygen.

According to one embodiment, the composition comprises an apoptosis inhibitor, preferably a caspase inhibitor. According to one embodiment, the composition comprises a pancaspase inhibitor which preferably is selected from the group consisting of Q-VD-OPh and Z-Val-Ala-Asp(OMe)-FMK and wherein the caspase inhibitor more preferably is Q-VD-OPh.

According to one embodiment, the composition additionally comprises at least one poly(oxyethylene) polymer. As described above, preferably, the at least one poly(oxyethylene) polymer is a high molecular weight poly(oxyethylene) polymer or a combination of a high and a low molecular weight poly(oxyethylene) polymer. The poly(oxyethylene) polymer is preferably a polyethylene glycol, such as an unsubstituted polyethylene glycol. The high molecular weight poly(oxyethylene) polymer preferably has a molecular weight of at least 1500, more preferably in a range of 2000 to 40000, more preferred 3000 to 20000 or 4500 to 10000. Preferably, the composition comprises additionally a caspase inhibitor.

According to one embodiment, the composition comprises at least one compound according to formula 1

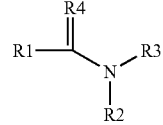

formula 1 wherein R1 is a hydrogen residue or an alkyl residue, preferably a C1-C5 alkyl residue, a C1-C4 alkyl residue or a C1-C3 alkyl residue, preferably a C1-C2 alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue, preferably R4 is oxygen. The compound according to formula 1 preferably is a tertiary carboxylic acid amide, and wherein preferably, the compound according to formula 1 is a N,N-dialkyl-carboxylic acid amide. The compound according to formula 1 preferably is selected from the group consisting of N,N-dimethylacetamide, N,N-diethylacetamide, N,N-dimethylformamide, N,N-diethylformamide and N,N-dimethylpropanamide. The compound according to formula 1 preferably is a N,N-dialkylpropanamide, more preferably N,N-dimethylpropanamide. The compound according to formula 1 preferably is not a toxic agent. Preferably, the compound according to formula 1 is used in combination with the caspase inhibitor and butanamide. According to one embodiment, the composition comprises at least one anticoagulant, preferably a chelating agent.

According to one embodiment, the composition has one or more of the following characteristics:
a) it is capable of stabilizing cells and reducing the release of genomic DNA from cells contained in the cell-containing biological sample into the cell-free portion of the sample;
b) it is capable of reducing the degradation of nucleic acids, in particular genomic DNA, present in the stabilized sample;
c) it is capable of reducing or preventing the contamination of the extracellular DNA population comprised in the biological sample with genomic DNA originating from cells contained in the stabilized sample;
d) it is capable of reducing or preventing the contamination of the extracellular nucleic acid population comprised in the biological sample with intracellular nucleic acids originating from cells contained in the stabilized sample;
e) the stabilization composition does not comprise additives in a concentration wherein said additives would induce or promote cell lysis;
f) the stabilization composition does not comprise a cross-linking agent that induces protein-DNA and/or protein-protein crosslinks;
g) the stabilization composition does not comprise formaldehyde, formaline, paraformaldehyde or a formaldehyde releaser;
h) the stabilization composition does not comprise a toxic agent and/or
i) it is capable of stabilizing extracellular nucleic acid population comprised in the cell-containing biological sample without refrigeration, preferably at room temperature, for a time period selected from at least two days, at least three days, at least two days to three days, at least two days to six days and/or at least two days to seven days.

According to one embodiment, the stabilizing composition comprises the stabilizing agents in a concentration that when mixed with the intended amount of cell-containing biological sample to be stabilized, which preferably is blood, the resulting mixture comprises
butanamide i) in a concentration of at least 0.25%, at least 0.3%, at least 0.4%, at least 0.5%, at least 0.75%, at least 1%, at least 1.5%, at least 1.75%, at least 2% or at least 2.5%; and/or ii) in a concentration range of 0.25% to 15%, 0.5% to 12.5%, 0.75% to 10%, 1% to 9%, 1.25% to 8%, 1.5% to 7%, 1.75% to 6%, 1.8% to 5.5%, 1.9% to 5.25%, 2% to 5%, 2.1% to 4.75%, 2.2% to 4.5%, 2.3% to 4.25%, 2.4% to 4%, 2.5% to 3.75% or 0.75% to 2%;
a caspase inhibitor, if present, i) in a concentration of at least 0.01 µM, at least 0.1 µM, at least 0.25 µM, at least 0.5 µM, at least 0.6 µM, at least 0.7 µM, at least 0.8 µM, at least 0.9 µM or at least 1 µM; and/or ii) in a concentration that lies in the range of 0.01 µM to 100 µM, 0.1 µM to 75 µM, 0.25 µM to 50 µM, 0.5 µM to 40 µM, 0.6 µM to 30 µM, 0.7 µM to 35 µM, 0.8 µM to 30 µM, 0.9 µM to 25 µM, 1 µM to 20 µM, 1.1 µM to 17.5 µM, 1.25 µM to 15 µM or 1.5 µM to 12.5 µM; and
a compound according to formula 1, if present, i) in a concentration of at least 0.1%, at least 0.5%, at least 0.75%, at least 1%, at least 1.25% or at least 1.5%; and/or ii) in a concentration that lies in the range of 0.1% to 30%, 0.25% to 20%, 0.5% to 15%, 0.7% to 10%, 0.8% to 7.5%, 0.9% to 6% or 1% to 5%; and/or
an anticoagulant, if present, in a concentration range selected from 0.05 mM to 100 mM, 0.05 mM to 50 mM, 0.1 mM to 30 mM, 0.5 mM to 25 mM, 1 mM to 20 mM, 1.5 mM to 15 mM and 2 mM to 10 mM.

According to one embodiment, the stabilizing composition comprises at least one poly(oxyethylene) polymer in a concentration that when mixed with the intended amount of cell-containing biological sample to be stabilized, which preferably is blood, the resulting mixture comprises the poly(oxyethylene) polymer i) in a concentration that lies in the range of 0.05% to 4% (w/v), 0.1% to 3% (w/v), 0.2% to 2.5% (w/v), 0.25% to 2% (w/v), 0.3% to 1.75% (w/v) and 0.35% to 1.5% (w/v); and/or ii) in a concentration that lies in the range of 0.25% to 1.5% (w/v), 0.3% to 1.25% (w/v), 0.35% to 1% (w/v) and 0.4% to 0.75% (w/v).

According to one embodiment, the composition has one or more of the following characteristics:
i) the composition comprises butanamide in a concentration of 5% to 50%, 7.5% to 40%, 10% to 35%, 12.5% to 30% or 15% to 25%,
ii) the composition comprises at least one caspase inhibitor,
iii) the composition comprises at least one compound according to formula 1, preferably N—N-dimethylpropanamide, in a concentration of 2% to 50%, 3% to 40%, 3.5% to 30%, 4% to 25%, 4.5% to 20% or 5% to 17.5% and/or
iv) the composition comprises an anticoagulant.

According to one embodiment, the composition comprises at least one poly(oxyethylene) polymer.

According to one embodiment, the composition is provided in a solid form, a semi-liquid form or in a liquid form. According to one embodiment, the stabilizing composition is present as mixture with a cell-containing biological sample and wherein said cell-containing biological sample has one or more of the following characteristics:
a) it is selected from the group consisting of body fluids, whole blood, samples derived from blood, plasma, serum, lymphatic fluid, urine, liquor, cerebrospinal fluid, ascites, milk, stool, bronchial lavage, saliva, amniotic fluid, semen/seminal fluid, swabs/smears, body secretions, nasal secretions, vaginal secretions, wound secretions and excretions and cell culture supernatants;
b) it is a cell-depleted or cell-containing body fluid;
c) it is a cell-containing body fluid;
d) it is a circulating body fluid;
e) it is selected from blood, plasma, serum or urine;
f) it is blood.

In particular, the mixture has one or more of the concentration characteristics as defined above. Furthermore, the volumetric ratio of the stabilizing composition to the specified volume of the cell-containing biological sample is selected from 10:1 to 1:20, 5:1 to 1:15, 1:1 to 1:10 and 1:2 to 1:5. According to one embodiment, it is 1:10 to 10:1.

In a fourth aspect, the present invention in particular is directed to the use of the composition according to the third aspect of the invention for stabilizing the extracellular nucleic acid population in a cell-containing biological sample. According to one embodiment, the composition comprises an anticoagulant and wherein the cell-containing biological sample is blood. According to one embodiment, the composition is used in a method according to the first or second aspect of the invention.

In a fifth aspect, the present invention in particular is directed to a container suitable for collecting a cell-containing biological sample, preferably blood, plasma or serum sample, comprising a stabilizing composition suitable for stabilizing an extracellular nucleic acid population comprised in the cell-containing biological sample, wherein said stabilizing composition comprises butanamide. According to one embodiment, the stabilizing composition further comprises
a) at least one apoptose inhibitor, preferably a caspase inhibitor; and/or
b) at least one compound according to formula 1

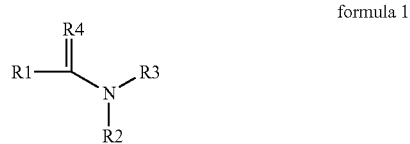

formula 1 wherein R1 is a hydrogen residue or an alkyl residue, preferably a C1-C5 alkyl residue, a C1-C4 alkyl residue or a C1-C3 alkyl residue, more preferred a C1-C2 alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue, preferably R4 is oxygen; and/or
c) an anticoagulant, preferably a chelating agent, more preferably EDTA.

According to one embodiment, the stabilization composition comprises at least one poly(oxyethylene) polymer, preferably a polyethylene glycol. According to one embodiment, the stabilization composition comprises butanamide, at least one poly(oxyethylene) polymer and an apoptose inhibitor, preferably a caspase inhibitor.

The compound according to formula 1 preferably is a N,N-dialkylpropanamide, more preferably N,N-dimethylpropanamide. The apoptose inhibitor preferably is a pancaspase inhibitor which preferably is selected from the group consisting of Q-VD-OPh and Z-Val-Ala-Asp(OMe)-FMK, and more preferably is Q-VD-OPh. According to one embodiment, the stabilizing composition comprises
a) butanamide;
b) at least one pancaspase inhibitor;
c) optionally at least one compound according to formula 1, preferably a N,N-dialkyl-carboxylic acid amide, more preferred a N,N-dialkylpropanamide; and
d) optionally an anticoagulant, preferably a chelating agent, more preferably EDTA.

According to one embodiment, the stabilizing composition or the container does not comprise a cross-linking agent that induces protein-nucleic acid and/or protein-protein crosslinks; and/or wherein the stabilizing composition or the container does not comprise toxic agents. According to one embodiment, the stabilizing composition is a composition according to the third aspect of the invention. According to one embodiment, the container has one or more of the features as defined herein for the other aspects of the invention.

In a sixth aspect, the invention is directed to a method comprising the step of collecting a sample from a patient into a chamber of the container according to the fifth aspect of the invention.

TABLE 1

Overview of apoptosis inhibitors

| Apoptosis inhibitor | Description |
|---|---|
| 1. Metabolic inhibitors | |
| AICA-Riboside, Acadesine, AICAr, 5-Aminoimidazole-4-carboxamide-1-β-riboside, Z-Riboside | Offers protection against cell death induced by glucose deprivation |
| Apoptosis Inhibitor II, diarylurea compound | prevents the active ~700-kDa apoptosome complex formation |
| Bax Channel Blocker, (±)-1-(3,6-Dibromocarbazol-9-yl)-3-piperazin-1-yl-propan-2-ol, bis TFA, iMAC1 | A cell-permeable dibromocarbazolo-piperazinyl derivative that displays anti-apoptotic properties. Effectively blocks Bid-induced cyctochrome c release from HeLa cell mitochondria (~80% inhibition at 5 µM) by inhibiting Bax channel-forming activity (IC50 = 520 nM in a liposome channel assay). |
| Bax-Inhibiting Peptide, V5 Peptide sequence: H-Val-Pro-Met-Leu-Lys-OH (SEQ ID NO: 1) | A cell-permeable pentapeptide based on the Ku70-Bax inhibiting domain that offers cytoprotection. Functions as effectively as the Caspase Inhibitor VI (Z-VAD-FMK; Cat. No. 219007) for Bax-mediated apoptosis (~50-200 µM). Also effectively blocks caspase-independent necrotic cell death. Shown to be Ku70 competitive, interact with Bax, prevent its conformational change and mitochondrial translocation. Displays extended stability in culture medium (~3 days). |
| Bcl-xL BH44-23, Human, Cell-Permeable | A cell-permeable peptide that prevents apoptotic cell death by directly binding to the voltage-dependent anion channel (VDAC) and blocking its activity. Leads to the inhibition of cytochrome c release and loss of mitochondrial membrane potential (ΔΨm). Contains the conserved N-terminal homology domain (BH4) of Bcl-xL (amino acids 4 - 23) that has been shown to be essential for inhibiting VDAC activity in liposomes and in isolated mitochondria. The BH4 domain is linked to a carrier peptide, a 10-amino acid HIV-TAT48-57 sequence with a β-alanine residue as a spacer for maximum flexibility. Following its uptake, it is mainly localized to the mitochondria |

TABLE 1-continued

Overview of apoptosis inhibitors

| Apoptosis inhibitor | Description |
| --- | --- |
| Bongkrekic Acid, Triammonium Salt | Acts as a ligand of the adenine nucleotide translocator. A potent inhibitor of mitochondrial megachannel (permeability transition pore). Significantly reduces signs of apoptosis induced by nitric oxide. Prevents the apoptotic breakdown of the inner mitochondrial transmembrane potential ($\Delta\Psi m$), as well as a number of other phenomena linked to apoptosis |
| Daunorubicin, Hydrochloride | Potent cell-permeable anticancer agent whose potential target site may be mitochondrial cytochrome c oxidase. Has been shown to inhibit RNA and DNA synthesis. Inhibits eukaryotic topoisomerases I and II. Induces DNA single-strand breaks. Also induces apoptosis in HeLa S3 tumor cells. According to one embodiment, said compound is not used as stabilizer according to the present invention. |
| Humanin, Human, Synthetic | A 24-residue anti-apoptotic peptide that, when expressed intracellularly, offers protection against neuronal apoptosis induced by presenilin and APP (amyloid precursor protein) mutants associated with familial Alzheimer's disease (AD). Shown to reduce cytochrome c release in vitro by directly binding to Bax (Bcl-2-associated X protein; Kd ~ 2 nM) and preventing its association with isolated mitochondria |
| Phorbol-12-myristate-13-acetate | Most commonly-used phorbol ester. Activates protein kinase C in vivo and in vitro, even at nM concentrations. Activates Ca2+-ATPase and potentiates forskolin-induced cAMP formation. Inhibits apoptosis induced by the Fas antigen, but induces apoptosis in HL-60 promyelocytic leukemia cells. |
| Pifithrin-α | A cell-permeable chemical inhibitor of p53. Reversibly inhibits p53-dependent transactivation of p53-responsive genes and reversibly blocks p53-mediated apoptosis. Inhibits p53-dependent growth arrest of human diploid fibroblasts in response to DNA damage but has no effect on p53-deficient fibroblasts. Protects normal tissues from the deleterious side effects of chemotherapy. Has been reported to protect neurons against β-amyloid peptide and glutamate-induced apoptosis |
| Pifithrin-μ | A cell-permeable sulfonamide that blocks p53 interaction with Bcl-xL and Bcl-2 proteins and selectively inhibits p53 translocation to mitochondria without affecting the transactivation function of p53. Effectively protects against γ radiation-induced cell death in vitro and animal lethality in vivo. Because Pifithrin-μ targets only the mitochondrial branch of the p53 pathway without affecting the important transcriptional functions of p53, it is superior to Pifithrin-a in in vivo studies. Shown to selectively interact with inducible HSP70 and disrupt its functions |
| Pifithrin-α, Cyclic- | A cell-permeable and very stable analog of Pifithrin-α, with similar biological function, but with reduced cytotoxicity. A chemical inhibitor of p53. Reversibly inhibits p53-dependent transactivation of p53-responsive genes; also reversibly blocks p53-mediated apoptosis. Acts as a P-gp modulator by changing relative substrate specificity of the transporter. This compound has been reported to be a potent STAT6 transcriptional inhibitor |
| Pifithrin-α, p-Nitro | A cell-permeable p53 inhibitor that serves as the prodrug form of Pifithrin-α, p-Nitro, Cyclic. Although its in vitro efficacy (ED50 = 0.3 μM in protecting etoposide-induced cortical neuron death) is similar to that of Pifithrin-α, it is 100-fold more potent than Pifithrin-α when adminstered in rats in vivo due to its long-lasting, steady conversion to the corresponding cyclic form of active compound in biological systems (t1/2 = 8h in neuron culture medium at 37° C.). |
| Pifithrin-α, p-Nitro, Cyclic | A cell-permeable p53 inhibitor that exhibits 10-fold higher potency (ED50 = 30 nM in protecting etoposide-induced cortical neuron death) and 50% longer half-life (t1/2 = 6h in neuron culture medium at 37° C.) than Pifithrin-α. It shows in vitro efficacy. |
| STAT3 Inhibitor Peptide Peptide sequence: Ac-Pro-Tyr(PO3H2)-Leu-Lys-Thr-Lys-OH (SEQ ID NO: 2) | A Stat3-SH2 domain binding phosphopeptide that acts as a selective inhibitor of Stat3 (signal transducers and activators of transcription 3) signaling with a DB50 of 235 μ(concentration of peptide at which DNA-binding activity is inhibited by 50%). Significantly lowers the DNA-binding activity of Stat3 by forming an inactive Stat3: peptide complex and reduces the levels of active Stat3:Stat3 dimers that can bind DNA. Displays greater affinity for Stat3, and to a lesser extent Stat1, over Stat5. Supplied as a trifluoroacetate salt. |
| STAT3 Inhibitor Peptide, Cell- Permeable Peptide sequence: Ac-Pro-Tyr(PO3H2)-Leu-Lys-Thr-Lys-OH (SEQ ID NO: 2) | A cell-permeable analog of the Stat3-SH2 domain-binding phosphopeptide that contains a C-terminal mts (membrane translocating sequence) and acts as a highly selective, potent blocker of Stat3 activation. Also suppresses constitutive Stat-3 dependent Src transformation with no effect on Stat-3 independent Ras transformation. The unphosphorylated inactive control peptide is also available. Supplied as a trifluoroacetate salt. |

TABLE 1-continued

Overview of apoptosis inhibitors

| Apoptosis inhibitor | Description |
|---|---|
| CAY10500, 6,7-dimethyl-3-{[methyl-[1-(3-trifluoromethyl-phenyl)-1H-indol-3-ylmethyl]-amino}-ethyl)-amino]-methyl}-chromen-4-one | Tumor necrosis factor α (TNFα) inhibitor that prevents binding to the TNF Receptor 1 (TNFR1).6 Binds to the biologically active TNFα trimer and promotes accelerated displacement of a single subunit to rapidly inactivate the cytokine. In a cell based assay, compound inhibited TNFα-mediated stimulation of IKB degradation. |
| Gambogic amide | A selective agonist for TrkA which mimics the actions of NGF. This compound possesses robust neurotrophic actvity, while it prevents neuronal cell death 1. |
| Maslinic Acid | A pentacyclic triterpene with antioxidant and anti-inflammatory properties. Shown to block the generation of nitric oxide, and inhibits the secretion of IL-6 and TNF-α induced by lipopolysaccharides |
| Naringin hydrate | A citrus bioflavonoid found to inhibit cytochrome P450 monooxygenase activity in mouse liver. It prevents toxin-induced cytoskeletal disruption and apoptotic liver cell death. |
| Necrostatin-1 | An inhibitor of necroptosis, a non-apoptotic cell death pathway. Does not affect Fas/TNFR-triggered apoptosis. According to one embodiment, said compound is not used as stabilizer according to the present invention. |
| NSC348884 hydrate, N1,N2-bis((3-imino-6-methyl-3H-indol-2-yl)methyl)-N1,N2-bis((6-methyl-1H-benzo[d]imidazol-2-yl)methyl)ethane-1,2-diaminehydrate | This product is a nucleolar phosphoprotein that displays several biological activities in ribosome biogenesis, cell proliferation, cytoplasmic/nuclear shuttle transportation, nucleic acid binding, ribonucleic cleavage, centrosome duplication and molecular chaperoning, and is found in higher levels in tumor cells. Overexpression has been shown to lead to inhibition of apoptosis. NSC34884 upregulates p53. |
| Orsellinic acid | Benzoic acid. Blocks PAF-mediated neuronal apoptosis. Shows free radical scavenging activity. |
| tetramethyl Nordihydroguaiaretic Acid | A synthetic derivative of NDGA and a non-selective lipoxygenase inhibitor. It inhibits Sp1 transcription factor binding at the HIV long terminal repeat promoter and at the α-ICP4 promoter (a gene essential for HSV replication). |
| GW 4869, 3,3'-(1,4-phenylene)bis[N-[4-(4,5-dihydro-1H-imidazol-2-yl)phenyl]-hydrochloride-2-propenamide | A cell-permeable, symmetrical dihydroimidazolo-amide compound that acts as a potent, specific, non-competitive inhibitor of N-SMase (neutral sphingomyelinase) [IC50 = ~ 1 µM, rat brain; Km for sphingomyelin ~13 µM]. Does not inhibit human A-SMase (acid sphingomyelinase) even at 150 µM. Weakly inhibits the activities of bovine protein phosphatase 2A and mammalian lyso-PAF PLC, while no inhibition is observed for bacterial phosphatidylcholine-specific PLC. Reported to offer complete protection against TNF-a or diamine-induced cell death in MCF7 breast cancer cells at 20 µM. Does not modify the intracellular glutathione levels or interfere with TNF-α or diamine-mediated signaling effects. |
| SP 600125, 1,9-Pyrazoloanthrone, Anthrapyrazolone | SP600125 is a JNK inhibitor (IC50 = 40 nM for JNK-1 and JNK-2 and 90 nM for JNK-3). This agent exhibits greater than 300-fold selectivity for JNK against related MAP kinases ERK1 and p38-2, and the serine threonine kinase PKA. SP600125 is a reversible ATP-com petitive inhibitor. |
| Mdivi-1, 3-(2,4-Dichloro-5-methoxyphenyl)-2,3-dihydro-2-thioxo-4(1H)-quinazolinone,3-(2,4-Dichloro-5-methoxyphenyl)-2-sulfanyl-4(3H)-quinazolinone | Mdivi-1 is a selective inhibitor of mitochondrial division in yeast and mammalian cells which acts via inhibiting the mitochondrial division dynamin. In cells, Mdivi-1 inhibits apoptosis by inhibiting mitochondrial outer membrane permeabilization. |
| Minocycline . hydrochloride | Tetracycline derivative with antimicrobial activity. Inhibitor of angiogenesis, apoptosis and poly(ADP-ribose) polymerase-1 (PARP-1). Anti-inflammatory and neuroprotective |
| Ro 08-2750 (C13H10N4O3) | Inhibitor of NGF-induced apoptosis. |
| RKTS-33 (C7H8O4) | selective inhibition of Fas ligand-dependent pathway alone |

2. Nucleic acids

| | |
|---|---|
| 3,4-Dichloroisocoumarin | Inhibitor of serine proteases →+0>granzyme B and blocks apoptotic internucleosomal DNA cleavage in thymocytes without the involvement of endonucleases. Does not affect thiol proteases and metalloproteases |
| Actinomycin D, *Streptomyces* sp. | Also acts as a competitive inhibitor of serine proteases; Classical anti-neoplastic drug. Cytotoxic inducer of apoptosis against tumor cells. A DNA dependent inhibitor of RNA synthesis, actinomycin promotes induction of apoptosis by some specific stimuli, for example, TRAIL and Fas (CD95). Actinomycin D can also alleviate or block the apoptotic process and decrease the cytotoxicity induced by several stimuli such as the dihydrofolate reductase inhibitor aminopterin and the prostaglandin derivative |

TABLE 1-continued

Overview of apoptosis inhibitors

| Apoptosis inhibitor | Description |
|---|---|
| | 15-deoxy-D12,14-prostaglandin J2, thus it can have both pro and anti-apoptotic activities in some systems. According to one embodiment, said compound is not used as stabilizer according to the present invention. |
| Aurintricarboxylic Acid | Inhibitor of DNA topoisomerase II |
| Baicalein | A cell-permeable flavone that inhibits the activity of 12-lipoxygenase (IC50 = 120 nM) and reverse transcriptase. Protects cortical neurons from (β-amyloid induced toxicity. Reduces leukotriene biosynthesis and inhibits the release of lysosomal enzymes. Also inhibits cellular Ca2+ uptake and mobilization, and adjuvant-induced arthritis. Reported to inhibit microsomal lipid peroxidation by forming an iron-baicalein complex. Inhibits topoisomerase II and induces cell death in hepatocellular carcinoma cell lines. Potentiates contractile responses to nerve stimulation. Inhibits protein tyrosine kinase and PMA-stimulated protein kinase C |
| Cam ptothecin, Cam ptotheca acuminata | A cell-permeable DNA topoisomerase I inhibitor. Exhibits anti-leukemic and antitumor properties. Induces apoptosis in HL-60 cells and mouse thymocytes. Arrests cells at the G2/M phase. According to one embodiment, said compound is not used. |
| Diisopropylfluorophosphate | serine protease inhibitor |
| Phenylmethylsulfonyl Fluoride (PMSF) | Irreversible inhibitor of serine proteases. Its mechanism of action is analogous to that of diisopropylfluorophosphate. PMSF causes sulfonylation of the active-site serine residues. Also reported to inhibit internucleosomal DNA fragmentation in immature thymocytes. For a related, more stable inhibitor, see AEBSF |
| (−)-Huperzine A | An inhibitor of AChE. Antagonist of NMDA receptors. Protects against glutamate-mediated excitotoxicity. |
| Razoxane | Inhibits topoisomerase II without inducing DNA strand breaks (topo II catalytic inhibitor). |
| Suptopin-2 | Suppressor of topoisomerase II inhibition. Reverses cell cycle arrest; bypass of checkpoint function. Has inherent fluorescence and a distinct advantage in identification of molecule targets; effective concentraion in the µM range. |

3. Enzymes
3.1. Caspases

| | |
|---|---|
| Apoptosis Inhibitor; 2-(p-Methoxybenzyl)-3,4-pyrrolidinediol-3-acetate | Effects attributable to the inhibition of caspase-3 activation |
| cIAP-1, Human, Recombinant, E. coli | Recombinant, human cIAP-1 (amino acids 1-618) fused to the peptide sequence MATVIDH10SSNG at the N-terminus and expressed in E. coli. cIAP is a member of the inhibitor of apoptosis family of proteins that inhibits proteolytic activity of mature caspases by interaction of the BIR domain with the active caspase |
| CrmA, Recombinant | CrmA (cowpox viral serpin cytokine response modifier A) is purified from E. coli transformed with a construct containing the full-length coding region of the CrmA gene and 7 additional amino acids that do not affect the activity. CrmA is a natural inhibitor of human caspase-1 and granzyme B, enzymes that are involved in apoptosis |
| Group III Caspase Inhibitor I Peptide sequence: Ac-Ile-Glu-Pro-Asp-CHO (SEQ ID NO: 3), Ac-IEPD-CHO (SEQ ID NO: 3), Caspase-8 inhibitor III | A potent, cell-permeable, and irreversible inhibitor of Group III caspases (caspase-6, -8, -9, and -10), although more effective towards caspases-6 and -8. Also inhibits caspase-1 and caspase-3. When using with purified native or recombinant enzyme, pretreatment with an esterase is required. |
| Kaempferol | A cell-permeable phytoestrogen that inhibits topoisomerase I-catalyzed DNA religation in HL-60 cells. Offers protection against Aβ25-35-induced cell death in neonatal cortical neurons. Its protective effects are comparable to that of estradiol. Blocks the Aβ-induced activation of caspase-2, -3, -8, and -9, and reduces NMDA-induced neuronal apoptosis. Reported to be a potent inhibitor of monoamine oxidases. Acts as an inhibitor of COX-1 activity (IC50 = 180 µM), and of transcriptional activation of COX-2 (IC50 < 15 µM |
| Q-VD-OPH | General, Pancaspase |
| Boc-D(OMe)-FMK | General, Pancaspase |
| Z-D(OMe)E(OMe)VD(OMe)-FMK (SEQ ID NO: 4) | Caspase 3, 7 |
| Z-LE(OMe)TD(OMe)-FMK (SEQ ID NO: 5) | Caspase 8 |
| Z-YVAD(OMe)-FMK (SEQ ID NO: 6) | Caspase 1, 4 |

TABLE 1-continued

Overview of apoptosis inhibitors

| Apoptosis inhibitor | Description |
| --- | --- |
| Z-FA-FMK | Inhibits Cathepsin B |
| Z-FF-FMK | Cathepsin B, L |
| Mu-PheHphe-FMK | Cathepsin B, L |
| Z-AE(OMe)VD(OMe)-FMK (SEQ ID NO: 7) | Caspase 10 |
| Z-ATAD(OMe)-FMK (SEQ ID NO: 8) | Caspase 12 |
| Z-VK(Biotin)-D(OMe)-FMK | General Caspase |
| Z-LE(OMe)VD(OMe)-FMK (SEQ ID NO: 9) | Caspase 4 |
| Z-VAM-FMK | Antiviral peptide inhibitor, Inhibits HRV2 and HRV14 |
| 4'-Azidocytidine | HCV Inhibitor |
| Caspase-13 Inhibitor I Peptide sequence: Ac-Leu-Glu-Glu-Asp-CHO (SEQ ID NO: 10) | A potent, reversible inhibitor of caspase-13 (ERICE). |
| Caspase-13 Inhibitor II Peptide sequence: Z-Leu-Glu(OMe)-Glu(OMe)-Asp(OMe)-FMK (SEQ ID NO: 11) | A cell-permeable, irreversible inhibitor of caspase-13. When using with purified native or recombinant enzyme, pretreatment with an esterase is required. |
| Caspase-1 Inhibitor I Peptide sequence: Ac-Tyr-Val-Ala-Asp-CHO (SEQ ID NO: 12) | A potent, specific, and reversible inhibitor of caspase-1 (Ki = 200 pM for human recombinant caspase-1), caspase-4, and caspase-5. Strongly inhibits anti-APO-1 induced apoptosis in L929-APO-1 cells. |
| Caspase-1 Inhibitor I, Cell-Permeable Peptide sequence: Ac-Ala-Ala-Val-Ala-Leu-Leu-Pro-Ala-Val-Leu-Leu-Ala-Leu-Leu-Ala-Pro-Tyr-Val-Ala-Asp-CHO (SEQ ID NO: 13) | A cell-permeable inhibitor of caspase-1 (ICE; Interleukin-1β Converting Enzyme), caspase-4, and caspase-5. The C-terminal YVAD-CHO (SEQ ID NO: 12) sequence of this peptide is a highly specific, potent, and reversible inhibitor of caspase-1 (Ki = 1 nM). The N-terminal sequence (amino acid residues 1-16) corresponds to the hydrophobic region (h-region) of the signal peptide of the Kaposi fibroblast growth factor (K-FGF) and confers cell-permeability to the peptide |
| Caspase-1 Inhibitor II Peptide sequence: Ac-Tyr-Val-Ala-Asp-CMK (SEQ ID NO: 14) | A cell-permeable and irreversible inhibitor of caspase-1 (Ki = 760 pM), caspase-4, and caspase-5. Inhibits Fas-mediated apoptosis and acidic sphingomyelinase activation |
| Caspase-1 Inhibitor IV Peptide sequence: Ac-Tyr-Val-Ala-Asp-AOM (SEQ ID NO: 15) (AOM = 2,6-dimethylbenzoyloxymethyl ketone) | A highly selective, competitive, cell-permeable, and irreversible inhibitor of caspase-1, caspase-4, and caspase-5. Inactivates the enzyme with a rate limited by diffusion and is relatively inert toward other bionucleophiles such as glutathione, making it an excellent candidate for in vivo studies of enzyme inhibition |
| Caspase-1 Inhibitor V Peptide sequence: Z-Asp-CH2-DCB | A potent inhibitor of caspase-1-like proteases. Blocks apoptotic cell death in human myeloid leukemia U937 cells and blocks etoposide-induced DNA fragmentation |
| Caspase-1 Inhibitor VI Peptide sequence: Z-Tyr-Val-Ala-Asp(OMe)-CH2F* (SEQ ID NO: 16) | A potent, cell-permeable, and irreversible inhibitor of caspase-1 (ICE), caspase-4, and caspase-5 |
| Caspase-2 Inhibitor I Peptide sequence: Z-Val-Asp(OMe)-Val-Ala-Asp(OMe)-CH2F* (SEQ ID NO: 17) | A cell-permeable and irreversible inhibitor of caspase-2 (ICH-1 |
| Caspase-2 Inhibitor II Peptide sequence: Ac-Leu-Asp-Glu-Ser-Asp-CHO (SEQ ID NO: 18) | A reversible inhibitor of caspase-2 and caspase-3 |
| Caspase-3/7 Inhibitor I Peptide sequence: 5-[(S)-(+)-2-(Methoxymethyl)pyrrolidino]sulfonylisatin | A potent, cell-permeable, and specific, reversible inhibitor of caspase-3 (Ki = 60 nM) and caspase-7 (Ki = 170 nM). |
| Caspase-3 Inhibitor I Peptide sequence: Ac-Asp-Glu-Val-Asp-CHO (SEQ ID NO: 19) | A very potent, specific, and reversible inhibitor of caspase-3 (IC50 = 200 pM), caspase-6, caspase-7, caspase-8, and caspase-10. |
| Caspase-3 Inhibitor I, Cell-Permeable Peptide sequence: Ac-Ala-Ala-Val-Ala-Leu-Leu-Pro-Ala-Val-Leu-Leu-Ala-Leu-Leu-Ala-Pro-Asp-Glu-Val-Asp-CHO (SEQ ID NO: 20) | A cell-permeable inhibitor of caspase-3, as well as caspase-6, caspase-7, caspase-8, and caspase-10. The C-terminal DEVD-CHO (SEQ ID NO: 19) sequence of this peptide is a highly specific, potent, and reversible inhibitor of caspase-3 (Ki < 1 nM) that has also been shown to strongly inhibit PARP cleavage in cultured human osteosarcoma cell extracts (IC50 = 200 pM). The N-terminal sequence (amino acid residues 1-16) corresponds to the hydrophobic region (h-region) of the signal peptide of Kaposi fibroblast growth factor (K-FGF) and confers cell-permeability to |

TABLE 1-continued

Overview of apoptosis inhibitors

| Apoptosis inhibitor | Description |
|---|---|
| | the peptide. A 5 mM (1 mg/100 µl) solution of Caspase-3 Inhibitor I, Cell-permeable (Cat. No. 235427) in DMSO is also available. |
| Caspase-3 Inhibitor II Peptide sequence: Z-Asp(OCH3)-Glu(OCH3)-Val-Asp(OCH3)-FMK (SEQ ID NO: 21) | A potent, cell-permeable, and irreversible inhibitor of caspase-3 as well as caspase-6, caspase-7, caspase-8, and caspase-10. When using with purified native or recombinant enzyme, pretreatment with an esterase is required. A 5 mM (250 µg/75 µl) solution of Z-DEVD-FMK (SEQ ID NO: 72) (Cat. No. 264156) in DMSO is also available |
| Caspase-3 Inhibitor III Peptide sequence: Ac-Asp-Glu-Val-Asp-CMK (SEQ ID NO: 22) | A potent, cell-permeable, and irreversible inhibitor of caspase-3 as well as caspase-6, caspase-7, caspase-8, and caspase-10 |
| Caspase-3 Inhibitor IV Peptide sequence. Ac-Asp-Met-Gln-Asp-CHO (SEQ ID NO: 23) | A specific inhibitor of caspase-3. This tetrapeptide inhibitor has been used with the caspase-6 inhibitor Ac-VEID-CHO (SEQ ID NO: 73) to dissect the pathway of caspase activation in Fas-stimulated Jurkat cells |
| Caspase-3 Inhibitor V Peptide sequence: Z-Asp(OMe)-Gln-Met-Asp(OMe)-CH2F* (SEQ ID NO: 24) | A potent, cell-permeable, and irreversible inhibitor of caspase-3, also recognizes caspase-1. When using with purified native or recombinant enzyme, pre-treatment with an esterase is required |
| Caspase-3 Inhibitor VII Peptide sequence: 2-(4-Methyl-8-(morpholin-4-ylsulfonyl)-1,3-dioxo-1,3-dihydro-2H-pyrrolo[3,4-c]quinolin-2-ypethyl acetate | A cell-permeable, non-peptidyl pyrroloquinoline compound that acts as a potent, reversible, and non-competitive inhibitor of caspase-3 (IC50 = 23 nM) with 10-100-fold greater selectivity. Shown to display higher anti-apoptotic activity than Z-VAD-FMK (Cat. No. 627610) in a model of Staurosporine- (Cat. No. 569397) induced apoptosis in human Jurkat T cells. |
| Caspase-4 Inhibitor I Peptide sequence: Ac-Leu-Glu-Val-Asp-CHO (SEQ ID NO: 25) | A reversible caspase-4 inhibitor |
| Caspase-4 Inhibitor I, Cell-Permeable Peptide sequence: Ac-Ala-Ala-Val-Ala-Leu-Leu-Pro-Ala-Val-Leu-Leu-Ala-Leu-Leu-Ala-Pro-Leu-Glu-Val-Asp-CHO (SEQ ID NO: 26) | A potent, cell-permeable, and reversible inhibitor of caspase-4. The N-terminal sequence (amino acid residues 1-16) corresponds to the hydrophobic region of the signal peptide of Kaposi fibroblast growth factor and confers cell permeability to the peptide. |
| Caspase-5 Inhibitor I Peptide sequence: Z-Trp-Glu(OMe)-His-Asp(OMe)-CH2F* (SEQ ID NO: 27) | A potent, cell-permeable, and irreversible inhibitor of caspase-5. Strongly inhibits caspase-1. Also inhibits caspase-4 and caspase-8 |
| Caspase-6 Inhibitor I Peptide sequence: Z-Val-Glu(OMe)-1Ie-Asp(OMe)-CH2F* (SEQ ID NO: 28) | A cell-permeable, irreversible inhibitor of caspase-6. When using with purified native or recombinant enzyme, pretreatment with an esterase is required |
| Caspase-6 Inhibitor II, Cell-Permeable Peptide sequence: Ac-Ala-Ala-Val-Ala-Leu-Leu-Pro-Ala-Val-Leu-Leu-Ala-Leu-Leu-Ala-Pro-Val-Gludle-Asp-CHO (SEQ ID NO: 29) | A potent, cell-permeable, and reversible inhibitor of caspase-6. The N-terminal sequence (amino acids 1-16) corresponds to the hydrophobic region of the signal peptide of Kaposi fibroblast growth factor and confers cell permeability to the peptide |
| Caspase-8 Inhibitor I, Cell-Permeable Peptide sequence: Ac-Ala-Ala-Val-Ala-Leu-Leu-Pro-Ala-Val-Leu-Leu-Ala-Leu-Leu-Ala-Pro-lle-Glu-Thr-Asp-CHO (SEQ ID NO: 30) | A potent, cell-permeable, and reversible inhibitor of caspase-8 and Granzyme B. The N-terminal sequence (amino acids 1-16) corresponds to the hydrophobic region of the signal peptide of Kaposi fibroblast growth factor and confers cell permeability to the peptide |
| Caspase-8 Inhibitor II Peptide sequence: Z-Ile-Glu(OMe)-Thr-Asp(OMe)-CH2F* (SEQ ID NO: 31) | A potent, cell-permeable, and irreversible inhibitor of caspase-8 and granzyme B. Effectively inhibits influenza virus-induced apoptosis in HeLa cells. Also inhibits granzyme B. When using with purified native or recombinant enzyme, pretreatment with an esterase is required. A 5 mM (250 µg/76 µl) solution of Z-IETD-FMK (SEQ ID NO: 74) (Cat. No. 218840) in DMSO is also available. |
| Caspase-9 Inhibitor I Peptide sequence: Z-Leu-Glu(OMe)-His-Asp(OMe)-CH2F* (SEQ ID NO: 32) | A potent, cell-permeable, and irreversible inhibitor of caspase-9. May also inhibit caspase-4 and caspase-5. When using with purified native or recombinant enzyme, pretreatment with an esterase is required. A 5 mM (250 µg/72 µl) solution of Z-LEHD-FMK (SEQ ID NO: 75) (Cat. No. 218841) in DMSO is also available |
| Caspase-9 Inhibitor II, Cell-Permeable | A potent, cell-permeable, and reversible inhibitor of caspase-9. May also inhibit caspase-4 and caspase-5. The N-terminal |

TABLE 1-continued

Overview of apoptosis inhibitors

| Apoptosis inhibitor | Description |
|---|---|
| Peptide sequence:<br>Ac-Ala-Ala-Val-Ala-Leu-Leu-<br>Pro-Ala-Val-Leu-Leu-Ala-Leu-<br>Leu-Ala-Pro-Leu-Glu-His-Asp-<br>CHO (SEQ ID NO: 33) | sequence (amino acids 1-16) corresponds to the hydrophobic region of the signal peptide of Kaposi fibroblast growth factor and confers cell permeability to the peptide |
| Caspase-9 Inhibitor III<br>Peptide sequence:<br>Ac-Leu-Glu-His-Asp-CMK<br>(SEQ ID NO: 34) | A potent, irreversible inhibitor of caspase-9. Reported to reduce myocardial infarct size during reperfusion (~70 nM). |
| Caspase Inhibitor I<br>Peptide sequence:<br>Z-Val-Ala-Asp(OMe)-CH2F* | A cell-permeable, irreversible, pan-caspase inhibitor. Inhibits Fas-mediated apoptosis in Jurkat cells and staurosporine-induced cell death in corneal epithelial cells. When using with purified native or recombinant enzyme, pre-treatment with an esterase is required. |
| Caspase Inhibitor II<br>Peptide sequence:<br>Ac-Val-Ala-Asp-CHO | A potent and reversible pan-caspase inhibitor. |
| Caspase Inhibitor II, Cell-Permeable<br>Peptide sequence:<br>Ac-Ala-Ala-Val-Ala-Leu-Leu-<br>Pro-Ala-Val-Leu-Leu-Ala-Leu-<br>Leu-Ala-Pro-Val-Ala-Asp-CHO<br>(SEQ ID NO: 35) | A cell-permeable, reversible pan-caspase inhibitor produced by attaching the N-terminal sequence (amino acids 1-16) of the Kaposi fibroblast growth factor signaling peptide, which imparts cell-permeability to VAD peptide. |
| Caspase Inhibitor III<br>Peptide sequence:<br>Boc-Asp(OMe)-CH2F* | A cell-permeable, irreversible, broad-spectrum caspase inhibitor. |
| Caspase Inhibitor IV<br>Peptide sequence:<br>Boc-Asp(OBzl)-CMK | A general, irreversible caspase inhibitor. |
| Caspase Inhibitor VI<br>Peptide sequence:<br>Z-Val-Ala-Asp-CH2F* | An irreversible general caspase inhibitor. Useful for studies involving recombinant, isolated, and purified caspase enzymes. Unlike Caspase Inhibitor I (Cat. No. 627610), this inhibitor does not require pretreatment with esterase for in vitro studies. A 10 mM (1 mg/221 µl) solution of Caspase Inhibitor VI (Cat. No. 219011) in DMSO is also available |
| Caspase Inhibitor VIII<br>Peptide sequence:<br>Ac-Val-Asp-Val-Ala-Asp-CHO<br>(SEQ ID NO: 36) | A potent, reversible inhibitor of caspase-2 (Ki = 3.5 nM), caspase-3 (Ki = 1 nM) and caspase-7 (Ki = 7.5 nM). Also serves as an inhibitor of DRONC (*Drosophila caspase*), a glutamate/aspartate protease. |
| Caspase Inhibitor X<br>Peptide sequence:<br>BI-9B12 | A benzodioxane containing 2,4-disubstituted thiazolo compound that acts as a selective, reversible and competitive inhibitor of caspases (Ki = 4.3 µM, 6.2 µM and 2.7 µM for caspase-3, -7 and -8, respectively). The benzodioxane moiety is shown to fit in the 'aspartate hole' of the caspases and possibly disrupt caspase-8 assisted cleavage of BID, a proapoptotic protein. Weakly affects the activity of anthrax lethal factor, a metalloprotease, at ~20 µM |
| Caspase-1 Inhibitors | Including, but not limited to<br>Ac-N-Me-Tyr-Val-Ala-Asp-aldehyde (pseudo acid) (SEQ ID NO: 37)<br>Ac-Trp-Glu-His-Asp-aldehyde (pseudo acid) (SEQ ID NO: 38)<br>Ac-Tyr-Val-Ala-Asp-aldehyde (pseudo acid) (SEQ ID NO: 39)<br>Ac-Tyr-Val-Ala-Asp-chloromethylketone (SEQ ID NO: 40)<br>Ac-Tyr-Val-Ala-Asp-2,6-dimethylbenzoyloxymethylketone (SEQ ID NO: 41)<br>Ac-Tyr-Val-Ala-Asp(OtBu)-aldehyde-dimethyl acetal (SEQ ID NO: 42)<br>Ac-Tyr-Val-Lys-aldehyde (pseudo acid) (SEQ ID NO: 43)<br>Ac-Tyr-Val-Lys(biotinyl)-Asp-2,6-dimethylbenzoyloxymethylketone (SEQ ID NO: 76)<br>Biotinyl-Tyr-Val-Ala-Asp-chloromethylketone (SEQ ID NO: 77)<br>Biotinyl-Val-Ala-DL-Asp-fluoromethylketone<br>Fluorescein-6-carbonyl-Tyr-Val-Ala-DL-Asp(OMe)-fluoromethylketone (SEQ ID NO: 78)<br>Fluorescein-6-carbonyl-Val-Ala-DL-Asp(OMe)-fluoromethylketone<br>Z-Asp-2,6-dichlorobenzoyloxymethylketone<br>Z-Tyr-Val-Ala-Asp-chloromethyl ketone (SEQ ID NO: 79)<br>Z-Val-Ala-DL-Asp-fluoromethylketone<br>Z-Val-Ala-DL-Asp(OMe)-fluoromethylketone |
| Caspase-2 Inhibitors | Including, but not limited to<br>Ac-Val-Asp-Val-Ala-Asp-aldehyde (pseudo acid) (SEQ ID NO: 44)<br>Fluorescein-6-carbonyl-Val-Asp(OMe)-Val-Ala-DL-Asp(OMe)-fluoromethylketone (SEQ ID NO: 45)<br>Z-Val-Asp(OMe)-Val-Ala-DL-Asp(OMe)-fluoromethylketone (SEQ ID NO: 45) |
| Caspase-3 Precursor<br>Protease Inhibitors | Including, but not limited to<br>Ac-Glu-Ser-Met-Asp-aldehyde (pseudo acid) (SEQ ID NO: 46)<br>Ac-Ile-Glu-Thr-Asp-aldehyde (pseudo acid) (SEQ ID NO: 47) |

TABLE 1-continued

Overview of apoptosis inhibitors

| Apoptosis inhibitor | Description |
|---|---|
| Caspase-3 Inhibitors | Including, but not limited to<br>Ac-Asp-Glu-Val-Asp-aldehyde (pseudo acid) (SEQ ID NO: 48)<br>Ac-Asp-Met-Gln-Asp-aldehyde (pseudo acid) (SEQ ID NO: 49)<br>Biotinyl-Asp-Glu-Val-Asp-aldehyde (pseudo acid) (SEQ ID NO: 80)<br>Caspase-3/7 Inhibitor II<br>Fluorescein-6-carbonyl-Asp(OMe)-Glu(OMe)-Val-DL-Asp(OMe)-fluoromethylketone (SEQ ID NO: 81)<br>Z-Asp(OMe)-Gln-Met-DL-Asp(OMe)-fluoromethylketone (SEQ ID NO: 50)<br>Z-Asp-Glu-Val-Asp-chloromethylketone (SEQ ID NO: 51)<br>Z-Asp(OMe)-Glu(OMe)-Val-DL-Asp(OMe)-fluoromethylketone (SEQ ID NO: 52) |
| Caspase-4 Inhibitors | Including, but not limited to<br>Ac-Leu-Glu-Val-Asp-aldehyde (pseudo acid) (SEQ ID NO: 53)<br>Z-Tyr-Val-Ala-DL-Asp-fluoromethylketone (SEQ ID NO: 54) |
| Caspase-6 Inhibitors | Including, but not limited to<br>Ac-Val-Glu-Ile-Asp-aldehyde (pseudo acid) (SEQ ID NO: 55)<br>Fluorescein-6-carbonyl-Val-Glu(OMe)-1Ie-DL-Asp(OMe)-fluoromethylketone (SEQ ID NO: 56)<br>Z-Val-Glu(OMe)-Ile-DL-Asp(OMe)-fluoromethylketone (SEQ ID NO: 56) |
| Caspase-8 Inhibitors | Including, but not limited to<br>Ac-Ile-Glu-Pro-Asp-aldehyde (pseudo acid) (SEQ ID NO: 57)<br>Boc-Ala-Glu-Val-Asp-aldehyde (pseudo acid) (SEQ ID NO: 58)<br>Fluorescein-6-carbonyl-Ile-Glu(OMe)-Thr-DL-Asp(OMe)-fluoromethylketone (SEQ ID NO: 59)<br>Fluorescein-6-carbonyl-Leu-Glu(OMe)-Thr-DL-Asp(OMe)-fluoromethylketone (SEQ ID NO: 60)<br>Z-Ile-Glu(OMe)-Thr-DL-Asp(OMe)-fluoromethylketone (SEQ ID NO: 59)<br>Z-Leu-Glu(OMe)-Thr-DL-Asp(OMe)-fluoromethylketone (SEQ ID NO: 60)<br>Z-LE(OMe)TD(OMe)-FMK (SEQ ID NO: 60) |
| Caspase-9 Inhibitors | Including, but not limited to<br>Ac-Leu-Glu-His-Asp-aldehyde (pseudo acid) (SEQ ID NO: 61)<br>Ac-Leu-Glu-His-Asp-chloromethylketone (SEQ ID NO: 62)<br>Fluorescein-6-carbonyl-Leu-Glu(OMe)-His-DL-Asp(OMe)-fluoromethylketone (SEQ ID NO: 82) |
| Caspase-10 Inhibitors | Including, but not limited to<br>Fluorescein-6-carbonyl-Ala-Glu(OMe)-Val-DL-Asp(OMe)-fluoromethylketone (SEQ ID NO: 83)<br>Z-Ala-Glu-Val-DL-Asp-fluoromethylketone (SEQ ID NO: 63) |

3.2. Calpain

| | |
|---|---|
| Calpain Inhibitor III<br>Peptide sequence:<br>Z-Val-Phe-CHO | A potent, cell-permeable inhibitor of calpain I and II (Ki = 8 nM). Reduces capsaicin-mediated cell death in cultured dorsal root ganglion. Reported to block A23187-induced suppression of neurite outgrowth in isolated hippocampal pyramidal neurons. Exhibits neuroprotective effect in glutamate-induced toxicity. |
| Calpain Inhibitor IV<br>Peptide sequence:<br>Z-Leu-Leu-Tyr-CH2F | A potent, cell-permeable, and irreversible inhibitor of calpain II (k2 = 28,900 M-1s-1). Also acts as an inhibitor of cathepsin L (k2 = 680,000 M-1s-1). |
| Calpain Inhibitor V<br>Peptide sequence:<br>Mu-Val-HPh-CH2F<br>(Mu = morpholinoureidyl;<br>HPh = homophenylalanyl) | A potent, cell-permeable, and irreversible inhibitor of calpain |
| Ac-Leu-Leu-Nle-al | Cell-permeable, peptide aldehyde inhibitor of calpain I (Ki = 190 nM), calpain II (Ki = 150 nM), cathepsin L (Ki = 0.5 nM) and other neutral cysteine proteases. Inhibits cell cycle progression at G1/S and metaphase/anaphase in CHO cells by inhibiting cyclin B degradation. Also stimulates HMG-CoA synthase transcription by inhibiting degradation of active SREBP-1 (sterol regulatory element-binding protein 1). Protects against neuronal damage caused by hypoxia and ischemia. Inhibits apoptosis in thymocytes and metamyelocytes. Also prevents nitric oxide production by activated macrophages by interfering with the transcription of inducible nitric oxide synthase (iNOS; NOS II). Inhibits proteolytic degradation of IkBalpha and IkBβ in RAW macrophages induced with LPS. It also prolong association of MHC class I molecules with the transporters associated with antigen processing |
| Z-LLY-FMK | Calpain |
| N-Acetyl-Leu-Leu-Met | Calpain I |
| N-Acetyl-Leu-Leu-Nle-CHO | Calpain I |

3.3. others

| | |
|---|---|
| BAPTA/AM | Membrane-permeable form of BAPTA. Can be loaded into a wide variety of cells, where it is hydrolyzed by cytosolic esterases and is trapped intracellularly as the active chelator BAPTA. Prevents cocaine-induced ventricular fibrillations. Abolishes vitamin D3-induced increase in intracellular Ca2+. Induces inactivation of |

TABLE 1-continued

Overview of apoptosis inhibitors

| Apoptosis inhibitor | Description |
|---|---|
| | protein kinase C. Also inhibits thapsigargin-induced apoptosis in rat thymocytes. |
| Granzyme B Inhibitor I Peptide sequence: Z-Ala-Ala-Asp-CH2Cl | A weak inhibitor of the human and murine granzyme B. Also inhibits the apoptosis-related DNA fragmentation in lymphocytes by fragmentin 2, a rat lymphocyte granule protease homologous to granzyme B (ID50 = 300 nM). |
| Granzyme B Inhibitor II Peptide sequence: Ac-Ile-Glu-Thr-Asp-CHO (SEQ ID NO: 64) | A potent, reversible inhibitor of granzyme B and caspase-8 (Ki = 1 nM). Also inhibits caspase-1 (<6 nM), caspase-6 (5.6 nM), and caspase-10 (27 nM). |
| Granzyme B Inhibitor IV Peptide sequence: Ac-Ile-Glu-Pro-Asp-CHO (SEQ ID NO: 65) | A reversible inhibitor of granzyme B and caspase-8 |
| Leupeptin, Hemisulfate, Microbial | A reversible inhibitor of trypsin-like proteases and cysteine proteases. Also known to inhibit activation-induced programmed cell death and to restore defective immune responses of HIV+ donors |
| N-Ethylmaleimide | Sulfhydryl alkylating reagent that inhibits H+-ATPase and suppresses the short circuit current (IC50 = 22 µM) in pancreatic duct cells. Inactivates NADP-dependent isocitrate dehydrogenase. Also a potent inhibitor of both Mg2+ and Ca2+/Mg2+-stimulated DNA fragmentation in rat liver nuclei. Stimulates arachidonic acid release through activation of PLA2 in endothelial cells |
| Nα-Tosyl-Lys Chloromethyl Ketone, Hydrochloride (TLCK) | Inhibits trypsin-like serine proteinases. Irreversibly inactivates trypsin without affecting chymotrypsin. Prevents nitric oxide production by activated macrophages by interfering with transcription of the iNOS gene. Blocks cell-cell adhesion and binding of HIV-1 virus to the target cells. In macrophages, blocks nitric oxide synthase induced by interferon-γ and lipopolysaccharides (EC50 = 80 µM). Prevents endonucleolysis accompanying apoptotic death of HL-60 leukemia cells and normal thymocytes |
| Omi/HtrA2 Protease Inhibitor, Ucf-101 | A cell-permeable furfurylidine-thiobarbituric acid compound that acts as a potent, specific, competitive, and reversible inhibitor of the pro-apoptotic, heat-inducible, mitochondrial serine protease Omi/HtrA2 (IC50 = 9.5 µM for His-Omi34-458). Shows very little activity against various other serine proteases tested (IC50 ≥ 200 µM). Reported to block Omi/HtrA2 induced cell death in caspase-9 (−/−) null fibroblasts. |
| Phenylarsine Oxide | A membrane-permeable protein tyrosine phosphatase inhibitor (IC50 = 18 µM). Stimulates 2-deoxyglucose transport in insulin-resistant human skeletal muscle and activates p56lck protein tyrosine kinase. Blocks TNF-α-dependent activation of NF-κB in human myeloid ML-1a cells. PAO inhibits the protease activities of recombinant human caspases as well as endogenous caspases that are active in extracts of pre-apoptotic chicken DU249 cells (S/M extracts). |
| Phorbol-12,13-dibutyrate | Activates protein kinase C. Stimulates the phosphorylation of Na+, K+− ATPase, thereby inhibiting its activity. Promotes the expression of inducible NOS in cultured hepatocytes. |
| Hypericin | Inhibits PKC, CKII, MAP Kinase, Insulin R, EGFR, PI-3 Kinase and also noted to possess antiviral activity. |
| Butyrolactone I | A cell-permeable and highly selective inhibitor of cyclin-dependent protein kinases (Cdks) that inhibits cell cycle progression at the G1/S and G2/M transitions. Inhibits p34cdk1/cyclinB (Cdk1; IC50 = 680 nM). Also selectively inhibits Cdk2 and Cdk5 kinases. Has little effect on casein kinase I, casein kinase II, EGF receptor kinase, MAP kinase, PKA, and PKC. Shown to prevent the phosphorylation of retinoblastoma protein and H1 histone. Also blocks Fas-induced apoptosis in HL-60 cells and shows antitumor effects on human lung cancer cell lines |
| Nilotinib | Specific BCR-ABL-Tyrosinkinase-Inhibitor |
| Quercetin(Sophoretin) | Quercetin is a PI3K and PKC inhibitor with IC50 of 3.8 µM and 15 µg/ml. It strongly abrogated PI3K and Src kinases, mildly inhibited Akt1/2, and slightly affected PKC, p38 and ERK1/2. [1][2] Quercetin is a naturally-occurring polar auxin transport inhibitor with IC50 of 0.8, 16.7, 6.1, 11.36 µM for the inhibition of LDH % release, the inhibition of TNF-induced PMN-EC adhesion, TNF-induced inhibition of DNA synthesis and proliferation |

EXAMPLES

It should be understood that the following examples are for illustrative purpose only and are not to be construed as limiting this invention in any manner.

Several different compounds were tested for their ability to stabilize a cell-containing biological sample, here a whole blood sample, either alone or in combination with a caspase inhibitor and/or different compounds according to formula 1. Compared to the reference samples (EDTA stabilized blood), butanamide (BA) was found to be able to efficiently stabilize blood samples and in particular, was found to inhibit the release of genomic DNA from cells comprised in the stabilized blood sample into the extracellular nucleic acid population. Furthermore, it was found that using butanamide in combination with a caspase inhibitor significantly improves the achieved stabilization effect. In particular, using a combination of butanamide and a caspase inhibitor for stabilization resulted in a prolonged stabilization effect and furthermore, showed less variation in the stabilization effect achieved with blood samples obtained from different donors. This is an important advantage, as it provides a uniform, reliable stabilization method for blood samples.

Example 1

In example 1, the stabilization effect of butanamide either alone or in combination with a caspase inhibitor on EDTA stabilized blood samples was tested and compared to EDTA stabilized blood as reference.

Blood Collection and Stabilization

Blood from two different donors was collected into 10 ml K2 EDTA tubes (BD). 4.5 ml of the respectively collected blood was mixed with 0.9 ml of two different stabilization solutions A and B. Said stabilization solutions contained (per ml of stabilization solution):

A: 34.2 mg K2 EDTA and 0.15 g or 0.18 g butanamide in water When using stabilization solution A, the following final concentration in the blood/stabilization mixture was obtained: 7.2 mg K2 EDTA/ml and 2.5% (w/v) or 3% (w/v) butanamide.

B: 34.2 mg K2 EDTA, 0.18 g butanamide and 1.2 µl Quinoline-Val-Asp-CH2-OPH (caspase inhibitor) solution (1 mg dissolved in 388 µl DMSO). When using stabilization solution B, the following final concentration in the blood/stabilization mixture was obtained: 7.2 mg K2 EDTA/ml, 3% (w/v) butanamide and 1 µM Quinoline-Val-Asp-CH2-OPH (caspase inhibitor).

All stabilized blood samples were set up in triplicates per condition and test time point. At time point 0 (reference), immediately after mixing the stabilization solution and blood, plasma was generated and the circulating extracellular DNA was extracted. The residual stabilized blood sample was stored for three days and six days at room temperature.

As a reference control, the EDTA stabilized blood sample (collected in K2 EDTA tubes without further additives) was also stored for 3 and 6 days.

Extracellular Nucleic Acid Isolation and Analysis

Plasma was generated from the stabilized and unstabilized (EDTA) blood samples by inverting the blood containing tubes for four times. Then, the tubes were centrifuged for 10 minutes at 1900×g at 4° C. 2.5 ml of the plasma fraction was transferred into a fresh 15 ml falcon tube and centrifuged for 10 minutes at 16.000×g at 4° C. 2 ml of the respectively cleared plasma was used for extracellular nucleic acid isolation using the QIAamp circulating nucleic acid kit (QIAGEN) according to the manufacturer's instructions.

The isolated extracellular DNA was analyzed using two different qPCR assays, targeting different fragment lengths of the 18S ribosomal DNA:

18S ribosomal DNA: 66 bp amplicon
18S ribosomal DNA: 500 bp amplicon

TABLE 2 summarizes the information of the used DNA target sequences detected by qPCR

| Target description | position | position | Sequence 5' - 3' | dye |
|---|---|---|---|---|
| h 18S rDNA 66 BP amplicon | p12 - region of chromosome 13, 14, 15, 21, 22 | Forward | GCCGCTAGAGGTGAAATTCTTG (SEQ ID NO: 66) | 5' Cy5 - BHQ 3' |
| | | reverse | CATTCTTGGCAAATGCTTTCG (SEQ ID NO: 67) | |
| | | probe | ACCGGCGCAAGACGGACCAGA (SEQ ID NO: 68) | |
| h18S rDNA 500 bp amplicon | p12 - region of chromosome 13, 14, 15, 21, 22 | forward | GTCGCTCGCTCCTCTCCTACTT (SEQ ID NO: 69) | 5' FAM - BHQ 3' |
| | | reverse | GGCTGCTGGCACCAGACTT (SEQ ID NO: 70) | |
| | | probe | CTAATACATGCCGACGGGCGCTGAC (SEQ ID NO: 71) | |

Cycle thresholds of the individual samples were translated into amount of gDNA in the eluate, according to a gDNA standard curve. The gDNA amount of the storage time points was compared to the time zero gDNA level from the same donor and is shown as fold increase in the figures. Especially the increase of the 500 bp fragment in the plasma fraction of the blood sample after storage is an indication for a lysis/destruction of white blood cells. Thus, the lower the amount of released 500 bp DNA, the better the performance of the stabilization method.

Results

Figure 2:
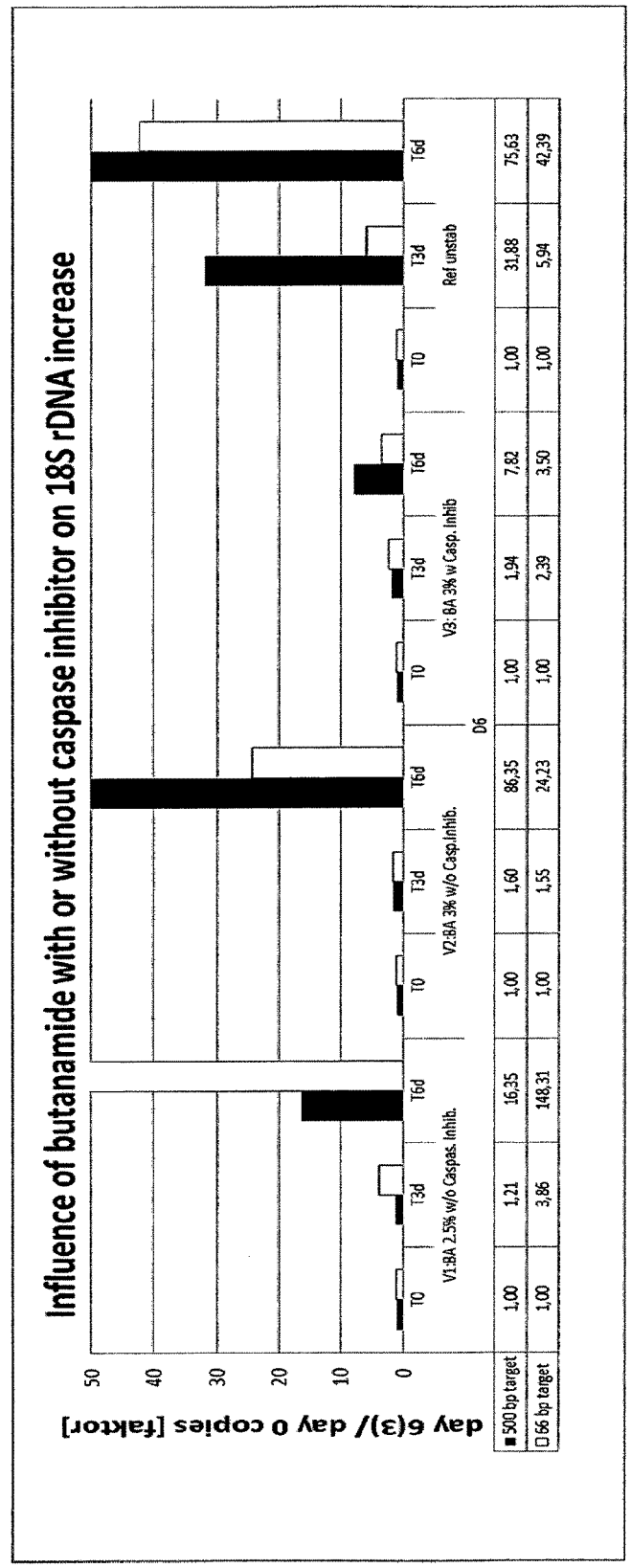

The results are shown in shown in FIGS. 1 and 2. Shown is the increase of DNA relative to time point 0 with the different stabilization solutions (fold change) using different amplicon lengths of 18S rRNA gene. Bars indicate the mean of the triplicate samples per condition and test time point. All stabilization solutions according to the present invention which accordingly comprise butanamide show significantly lower amounts of released DNA after storage for 3 days at room temperature compared to the unstabilized EDTA blood. As can be seen, the addition of stabilizing solutions A achieved in the tested samples stabilization for at least three days. The stabilization effect was significantly improved compared to the EDTA stabilized reference samples. A stabilization effect for three days is sufficient for many applications as this covers the regular shipping/storage time for blood samples. Furthermore, stabilization solution B according to the invention which additionally comprised a caspase inhibitor achieved a prolonged stabilization effect for at least 6 days. Furthermore, when testing the stabilization solutions on blood samples from several different donors, it was found that the stabilization effect that is achieved with the combination of butanamide and a caspase inhibitor showed less variations in the achieved stabilization effect (data not shown). Therefore, the stabilization was significantly improved when using butanamide in combination with a caspase inhibitor.

Example 2

In example 2, the stabilization effect of butanamide in combination with a caspase inhibitor on EDTA stabilized blood samples was tested and compared to the stabilization effect of a caspase inhibitor in combination with N,N-dimethylacetamide (DMAA) and EDTA stabilized blood as reference.

Blood Collection and Stabilization

Blood from four different donors was collected into 10 ml K2EDTA tubes (BD). 4.5 ml blood was mixed with 0.9 ml of different stabilization solutions containing (per ml of stabilization solution):

34.2 mg K2EDTA 1.2 µl Quinoline-Val-Asp-CH2-OPH (caspase inhibitor) solution (1 mg dissolved in 388 µl DMSO)

0.15 g, 0.18 g or 0.21 g butanamide or 0.3 ml DMAA, respectively.

Thereby, the following final concentrations in the blood/stabilization mixtures were obtained:

7.2 K2EDTA/ml

1 µM Quinoline-Val-Asp-CH2-OPH (caspase inhibitor)

2.5, 3 or 3.5% (w/v) butanamide or 5% (v/v) DMAA, respectively.

All stabilized blood samples were set up in triplicates per condition and test time point. At time point 0 (reference), immediately after mixing the stabilization solution and blood, plasma was generated and the circulating extracellular DNA was extracted. The residual stabilized blood sample was stored for three days and six days at room temperature.

As a reference control, the EDTA stabilized blood sample (without further additives) was also stored for 3 and 6 days.

Extracellular Nucleic Acid Isolation and Analysis

Plasma was prepared and extracellular nucleic acids were isolated and analysed as described in example 1.

Results

Figure 3:
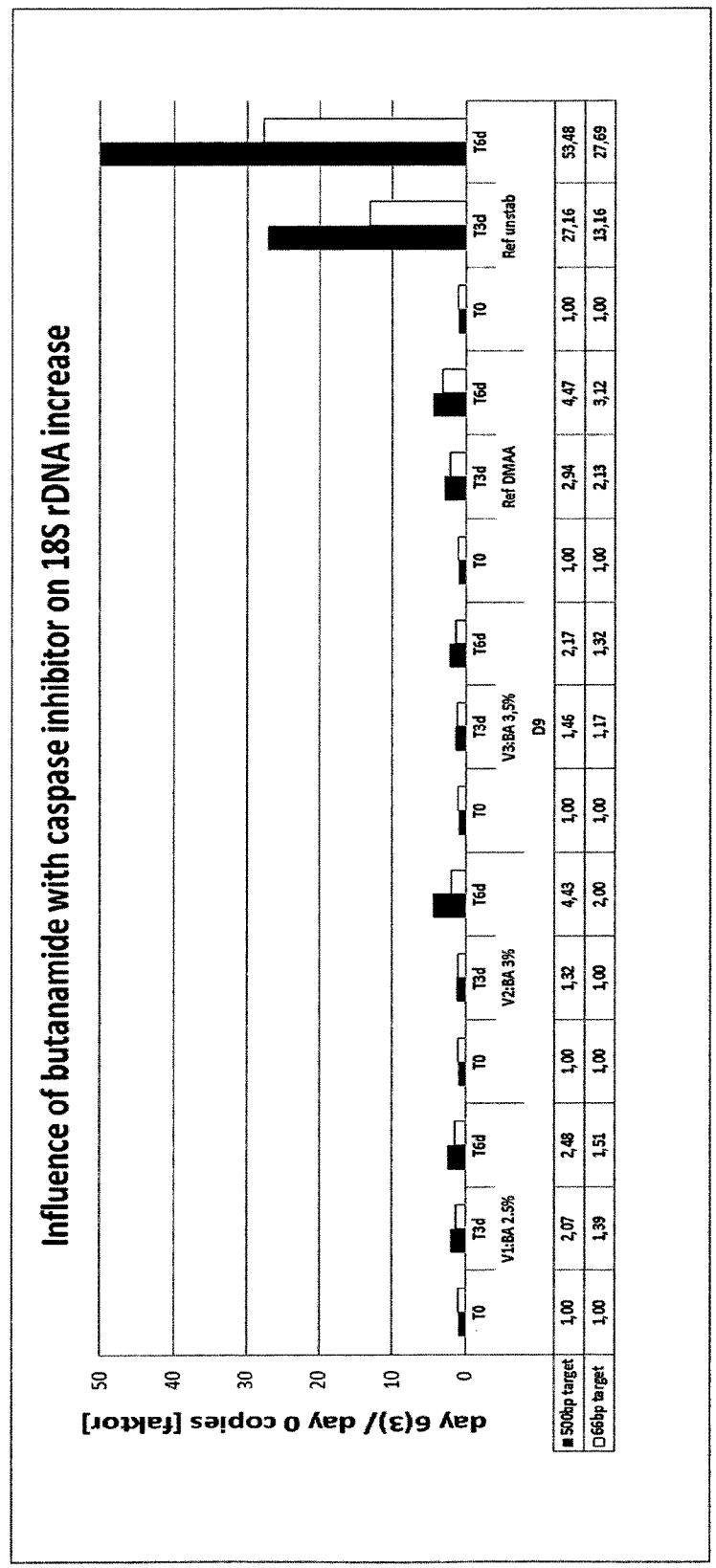
FIGS. 3-5 show the influence of butanamide with caspase inhibitor on 18S rDNA increase as described in Example 2.
Figure 4:
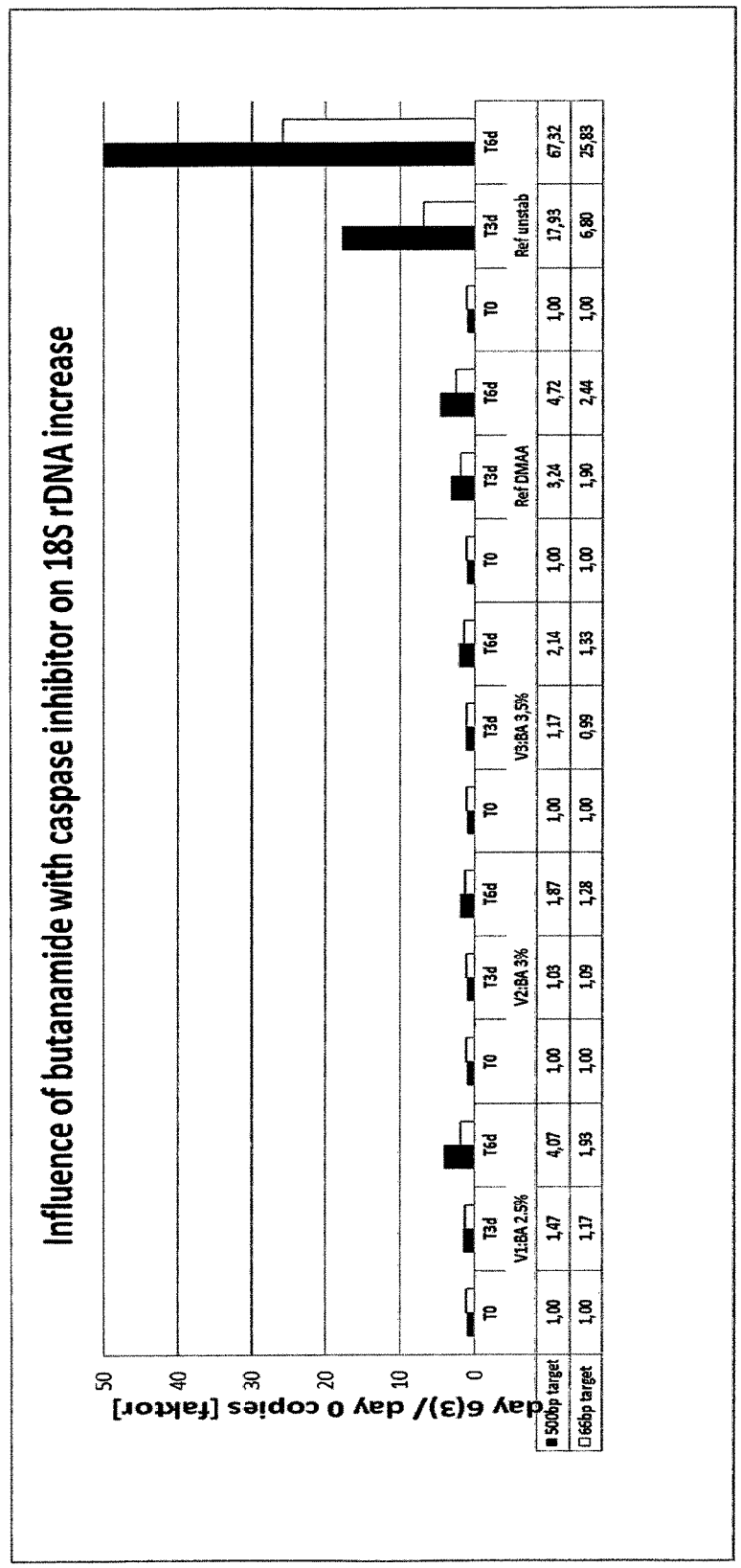
Figure 5:
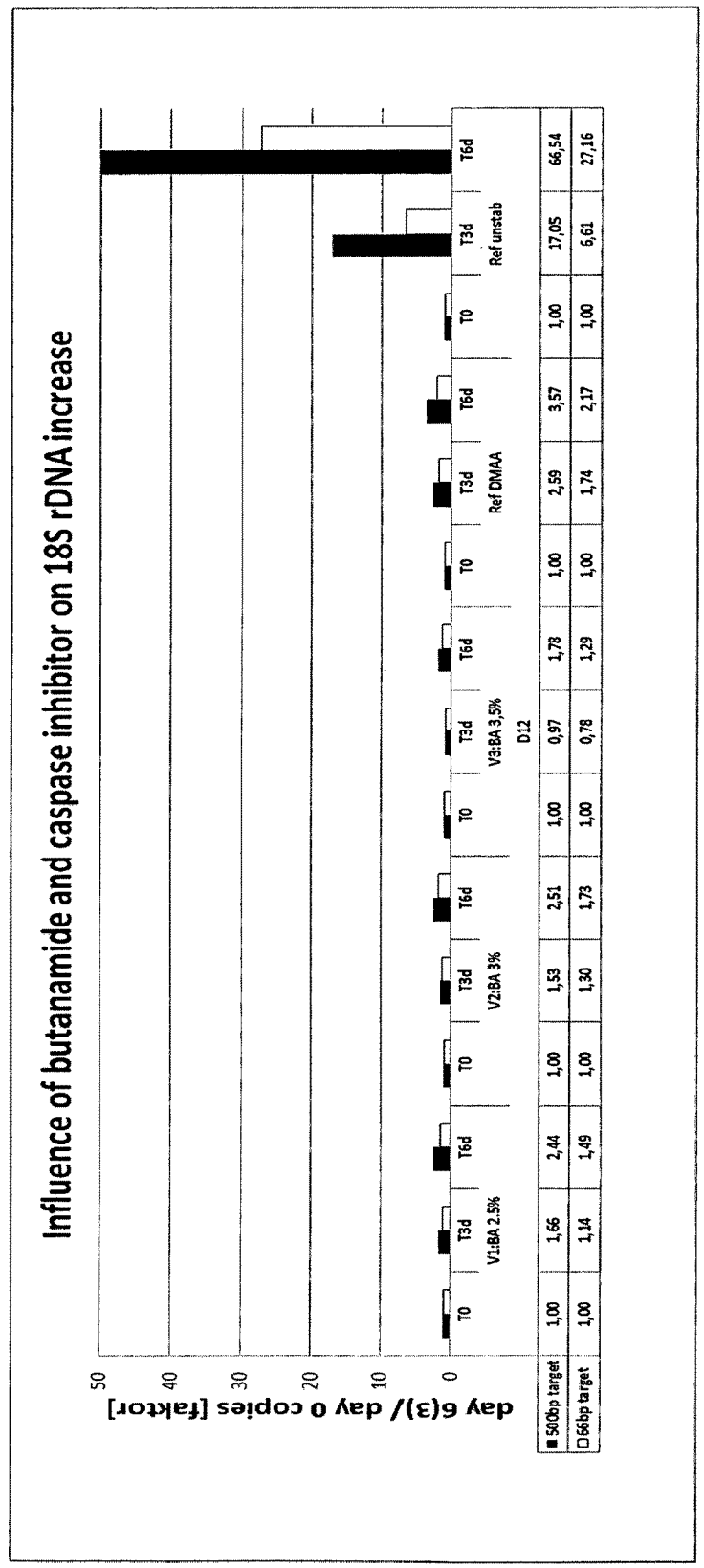

The results of qPCR analyses from four different donors are shown in FIGS. 3 to 5. The increase of DNA relative to time zero with 2.5%, 3% and 3.5% butanamide or 5% DMAA (fold change) using different amplicon lengths of the 18SrRNA gene is shown. Barrs indicate mean of triplicate samples per condition and test timepoint. All stabilization solutions used showed significant lower amounts of released DNA after storage for 3 and 6 days at room temperature compared to the reference EDTA blood sample. All three tested concentrations of butanamide showed at least comparable stabilization capabilities to DMAA and clear advantages compared to EDTA blood. DMAA is a stabilizer for blood samples, in particular in combination with a caspase inhibitor (see unpublished PCT/EP2012/070211 and PCT/EP2012/068850). As is shown by the present examples, butanamide is at least equally effective regarding its stabilization properties. Furthermore, butanamide has the significant advantage over DMAA, that butanamide is not toxic and also not harmful or irritant. Therefore, the present invention allows providing a stabilization composition that is not toxic or harmful. This simplifies the handling of the stabilization composition, as well as the handling of the stabilized samples for the user.

Figure 6:
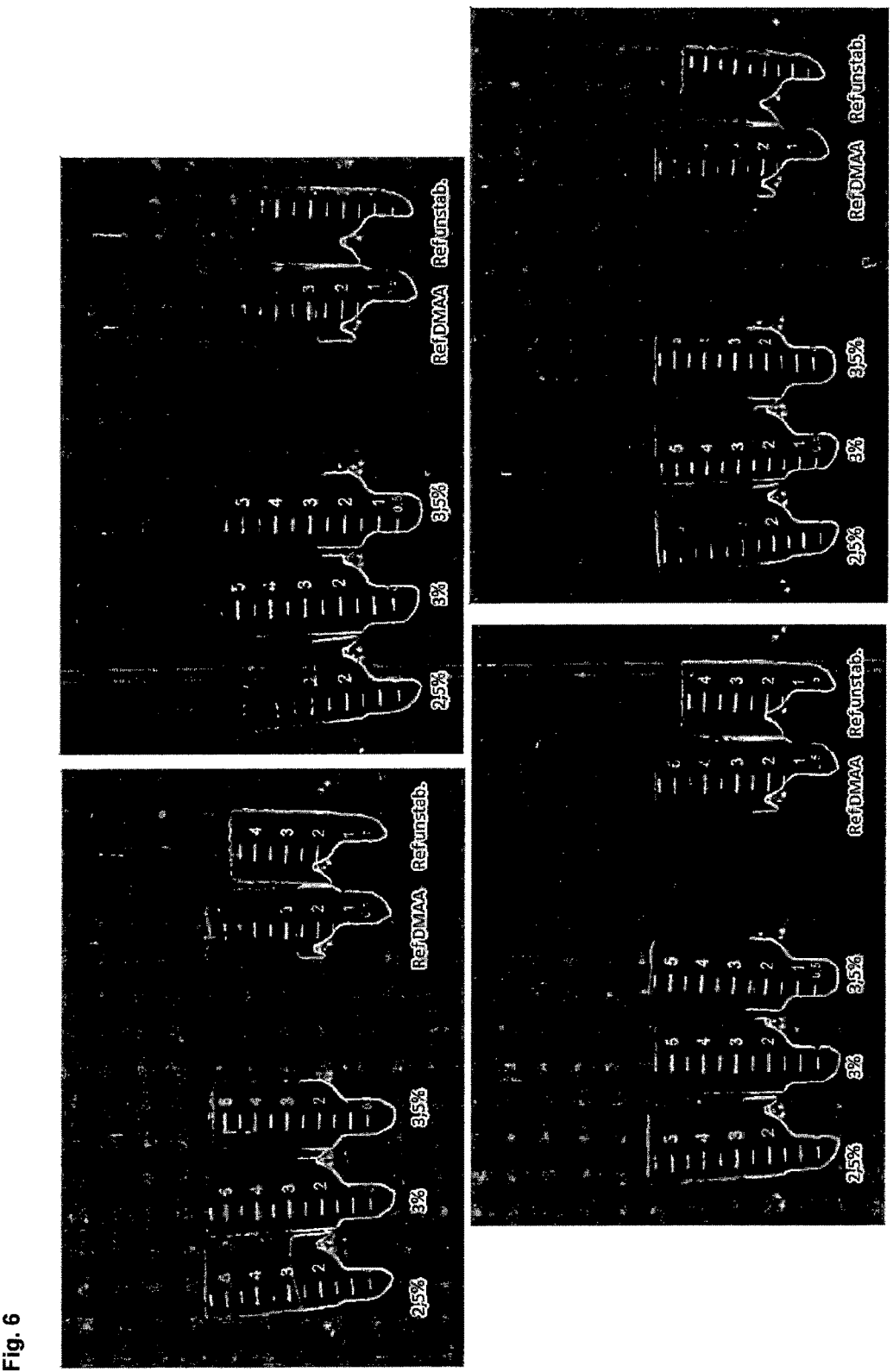
FIG. 6 shows the effects of different stabilization solutions on hemolysis (visible as an increased red color of the plasma fraction) after 6 days of storage as described in Example 2.
Figure 7:
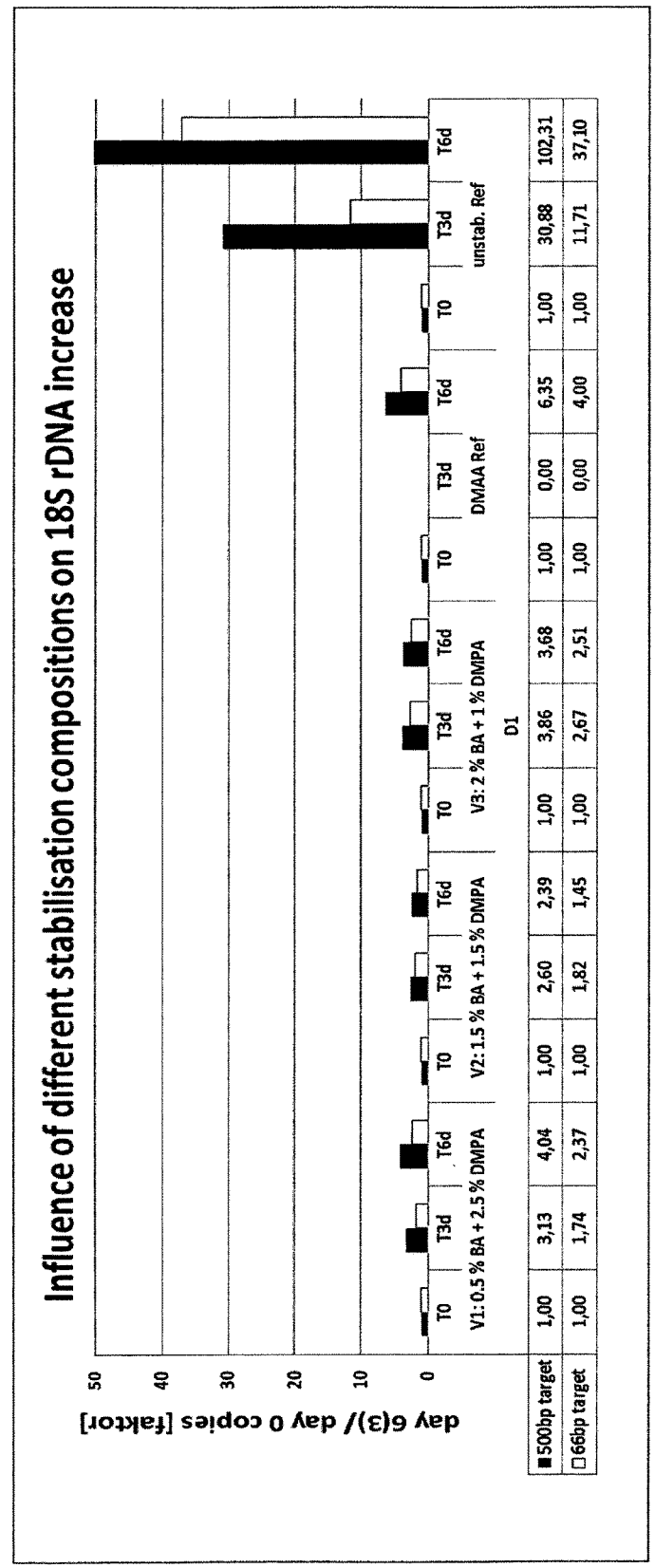
FIGS. 7-10 show influence of different stabilization compositions on 18S rDNA increase as described in Example 3.
Figure 8:
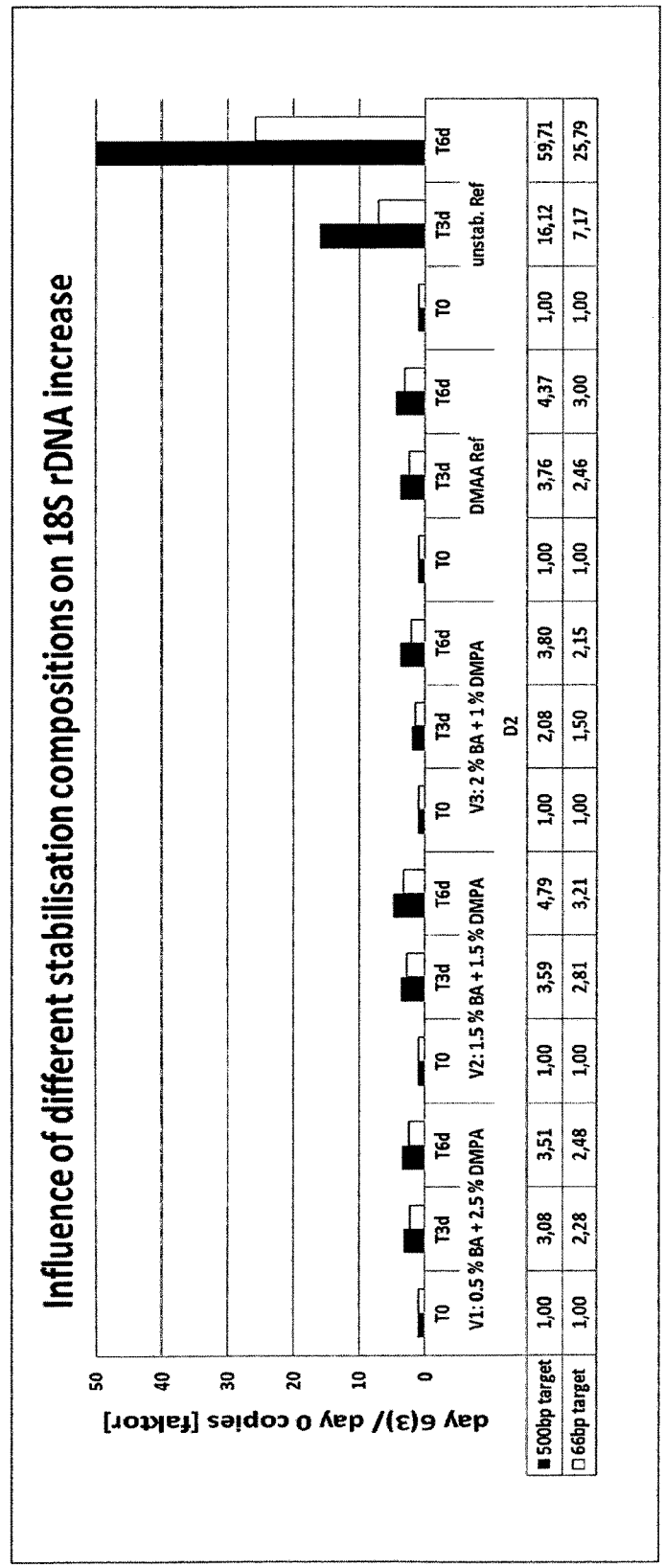
Figure 9:
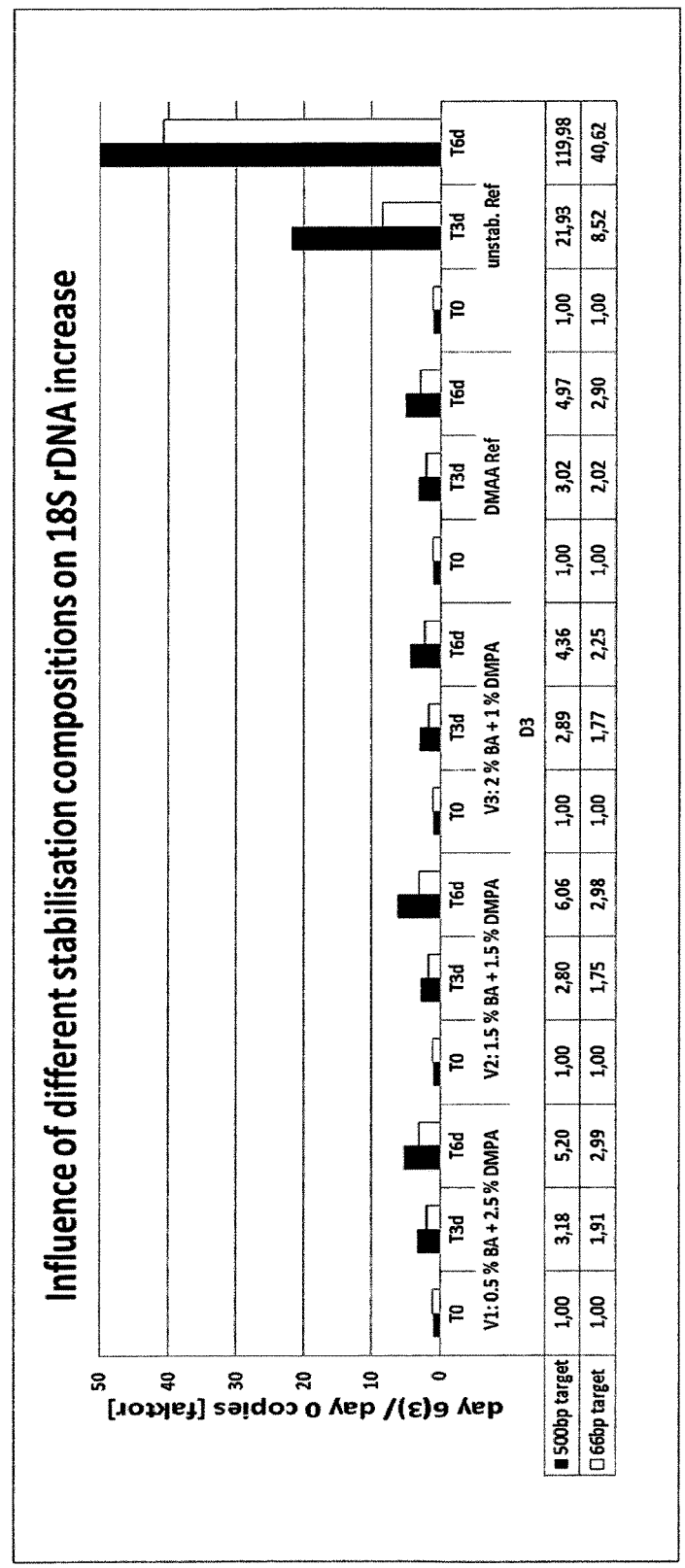
Figure 10:
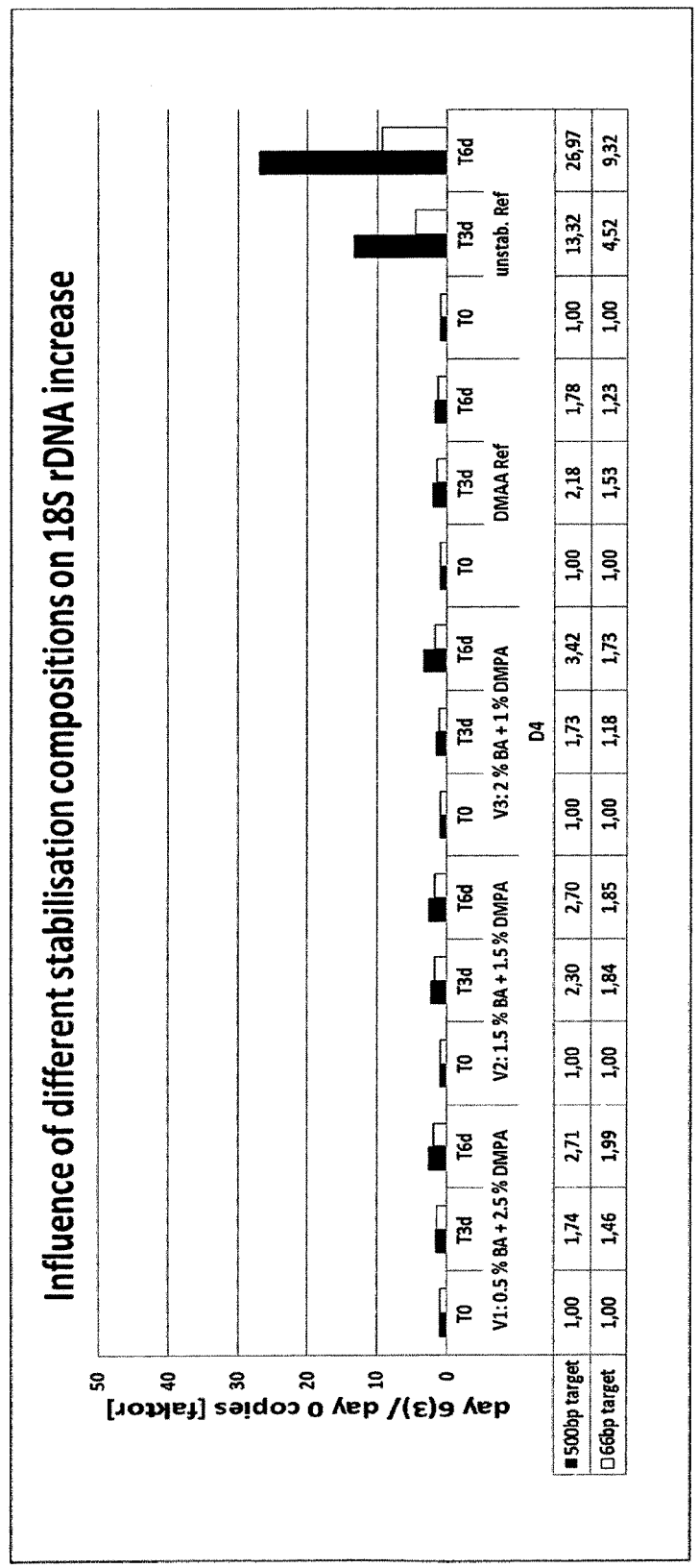
Figure 11:
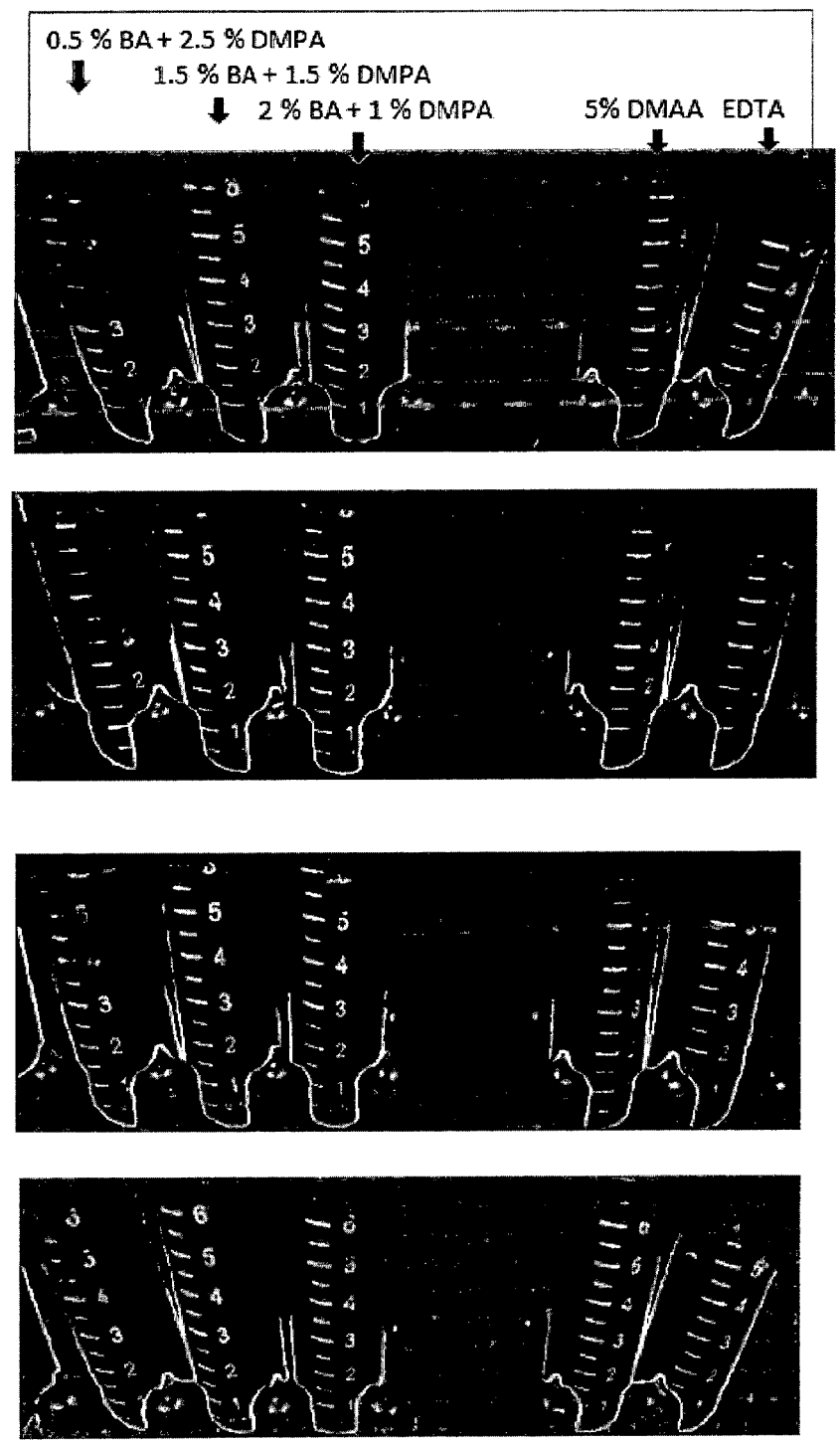
FIG. 11 shows the effects of different stabilization solutions on hemolysis (visible as an increased red color of the plasma fraction) after 6 days of storage as described in Example 3.

Furthermore, the effect of the different stabilization solutions on hemolysis (visible as an increased red color of the plasma fraction) was analyzed after 6 days of storage by visual inspection of the stabilized samples. The results shown in FIG. 6 demonstrate that the prevention of hemolysis was clearly better with the stabilization solutions according to the invention than in the EDTA control for all four donors and furthermore was comparable to the DMAA stabilized samples.

Example 3

In example 3, the stabilization effect of butanamide, a caspase inhibitor and N,N-dimethylpropanamide (DMPA) on EDTA stabilized blood samples was tested and compared to the stabilization effect of a caspase inhibitor in combination with N,N-dimethylacetamide (DMAA) and EDTA blood as reference.

Blood Collection and Stabilization

Blood collection and stabilization was generally performed as described in example 2, however, using different stabilization solutions. The following final concentrations in the blood/stabilization mixtures were set up 7.2 mg K2EDTA/ml (all samples)

1 µM Quinoline-Val-Asp-CH2-OPH (caspase inhibitor) (all samples) and 0.5% (w/v) butanamide and 2.5% (v/v) DMPA; or 1.5% (w/v) butanamide and 1.5% (v/v) DMPA; or 2% (w/v) butanamide and 1% (v/v) DMPA; or 5% (v/v) DMAA.

Extracellular Nucleic acid Isolation and Analysis

Plasma was prepared and extracellular nucleic acids were isolated and analysed as described in example 1.

Results

The results are shown in FIGS. 7 to 11. Shown is the increase of DNA relative to time zero (fold change) with stabilization solutions according to the invention (which comprised besides a caspase inhibitor (1 µM Quinoline-Val-Asp-CH2-OPH) and EDTA as anticoagulant (i) 0.5% butanamide and 2.5% DMPA, (ii) 1.5% butanamide and 1.5% DMPA or (iii) 2% butanamide and 1% DMPA) based on different amplicon length of the 18SrRNA gene. Bars indicate mean of triplicate samples per condition and test time point. All stabilization solutions according to the invention showed significant lower amounts of released DNA after storage for 3 and 6 days at room temperature compared to the reference EDTA blood. All three tested concentrations of butanamide showed in combination with DMPA comparable stabilization capabilities (compared to the stabilization solution comprising DMAA) and clear advantages compared to the reference EDTA blood. Using a combination of butanamide and DMPA allows to use lower concentrations of butanamide while preserving the stabilization effect. This is an advantage because a stabilization solution comprising butanamide in a high concentration may result in a precipitation of butanamide if the stabilization composition is stored at low temperatures. Thus, using a combination of butanamide and a compound according to formula 1 such as DMPA allows to provide a highly effective, storage- and in particular temperature stable stabilization composition which can also be shipped at lower temperatures. The combination of butanamide and N,N-dimethylpropanamide in such a stabilization composition is advantageous, because of the good stabilization properties that are achieved and furthermore, because both butanamide and N,N-dimethylpropanamide are not toxic. Furthermore, the effect of the different stabilization solutions on hemolysis (visible as an increased red color of the plasma fraction) was analyzed after 6 days of storage by visual inspection of the stabilized samples. The results shown in FIG. 11 demonstrate that the prevention of hemolysis was clearly better with the stabilization solutions according to the invention than in the EDTA control for all four donors and it was comparable to the DMAA stabilized samples. Therefore, hemolysis is efficiently reduced and can even be prevented.

Example 4

In example 4, different concentrations of butanamide were used in combination with a caspase inhibitor for stabilizing blood samples. The focus of the analysis was again the stabilization of the extracellular nucleic acid population as determined by analyzing the increase of 18S rDNA. Stabilization and processing of the samples were performed as described in example 2. When adding the tested stabilization solutions to the blood sample, the following final concentrations were obtained in the blood/stabilization solution mixture:

7.2 mg K2 EDTA/ml, 1 µM Quinoline-Val-Asp-CH2-OPH (caspase inhibitor) and different concentrations of butanamide (0.5% (w/v), 1.5% (w/v) and 2.5% (w/v)).

Figure 12:
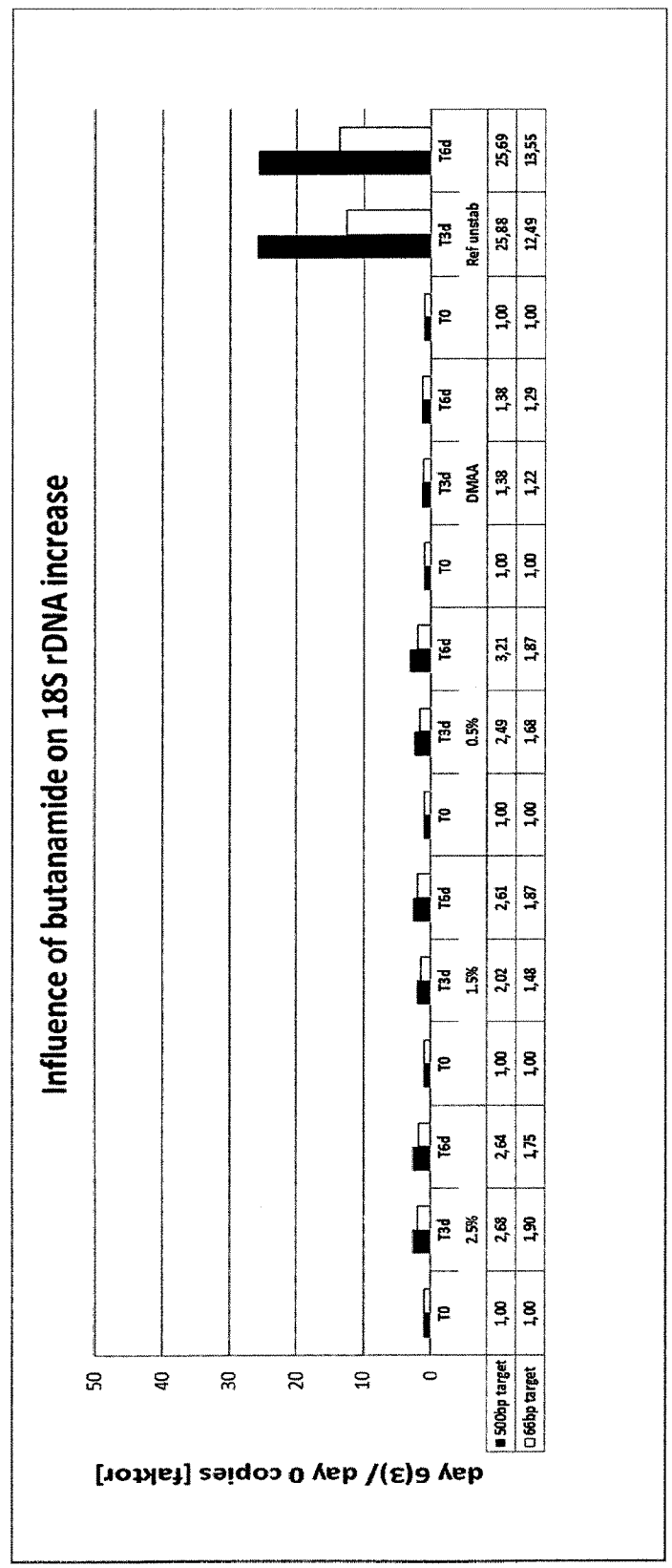
FIG. 12 shows the influence of butanamide on 18S rDNA increase as described in Example 4.

FIG. 12 shows the stabilization results obtained. As can be seen, butanamide was also in lower concentrations in combination with the caspase inhibitor effective to stabilize the extracellular nucleic acid population as can be seen from the significantly reduced increase in 18S rDNA in butanamide stabilized samples.

Example 5

In example 5, the stabilization effect of the caspase inhibitor alone and in combination with DMAA on blood samples is shown.

1. Materials and Methods
1.1 Separation of Blood Plasma

To separate the blood plasma from the whole blood, the blood samples were centrifuged for 15 min at 5000 rpm, and the obtained plasma samples were again centrifuged for 10 min at 16.000×g at 4° C.

The resulting blood plasma was used for isolating the nucleic acids contained therein.

1.2 Nucleic Acid Purification

The circulating, extracellular nucleic acids were purified from the obtained plasma samples using the QIAamp® Circulating NA Kit (QIAGEN, according to the handbook). In brief:

10 ml sample input;
lysis: 1 ml Proteinase K and 8 ml Buffer ACL (QIAGEN)
binding: 18 ml Buffer ACB (QIAGEN)
wash-steps: unchanged and according to handbook
elution in 60 µl Buffer AVE (QIAGEN)

1.3 Analysis of the Eluates

The eluates obtained after nucleic acid purification were stored at −20° C. till all samples (including day 6/7 samples) were purified. Afterwards, eluates of the same condition were pooled and treated as follows:

1.3.1 Measurement of the blood cell stability/DNA release by the determination of DNA size distribution using a chip gel electrophoresis (2100 Bioanalyzer; Agilent Technologies; Inc., USA) according to manufacturer's instruction (see handbook Agilent DNA 7500 and DNA 12000 Kit Guide), but 1.5 µl instead of 1 µl sample were transferred to the wells.

1.3.2 DNA quantification with a real time PCR assay, sensitive for DNA degradation (target: 500 and 66 bp long ribosomal 18S DNA coding sequences).

The DNA duplex assay was carried out according to the QuantiTect® Multiplex PCR handbook (Qiagen) with the following adaptions:

Primer concentration was up scaled from 8 µM to 16 µM.
Annealing/extension step was extended from 1 to 2 min. (samples were diluted 1:10 before amplification)
For details on the qPCR it is referred to example 1.

2. Performed Experiments and Results

Subsequently, the details on the performed experiments are explained. Details to the methods used in the examples were described above under 1.

2.1. Stabilization by the Addition of a Caspase-Inhibitor

Two different oligopeptides, Q-VD-OPh and Z-Val-Ala-Asp(OMe)-FMK which act as broad spectrum caspase-inhibitors, were tested:

TABLE 3

Tested caspase inhibitors

| inhibitor name | moleculare weight | solubility | structure |
|---|---|---|---|
| Q-VD-OPH | 513, 49 | 20 mM, add 97 µl DMSO 10 mM, add 194 µl DMSO 5 mM, add 388 µl DMSO | 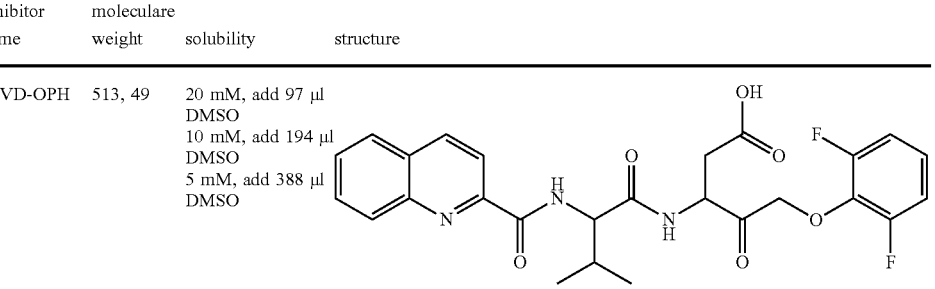 |

TABLE 3-continued

Tested caspase inhibitors

| inhibitor name | moleculare weight | solubility | structure |
|---|---|---|---|
| Z-Val-Ala-Asp(Ome)-FMK | 467, 49 | 20 mM, add 107 µl DMSO<br>10 mM, add 214 µl DMSO<br>5 mM, add 428 µl DMSO | 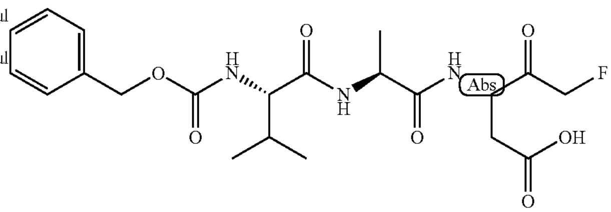 |

Each tested caspase inhibitor was added to whole blood samples (20 µM end concentration in 10 ml blood; blood was collected into Vacutainer K2E Tubes; BD). The whole blood sample was processed as described in section 1 (plasma preparation and nucleic acid isolation).

Results of the Chip Gel Electrophoresis

Figure 13:
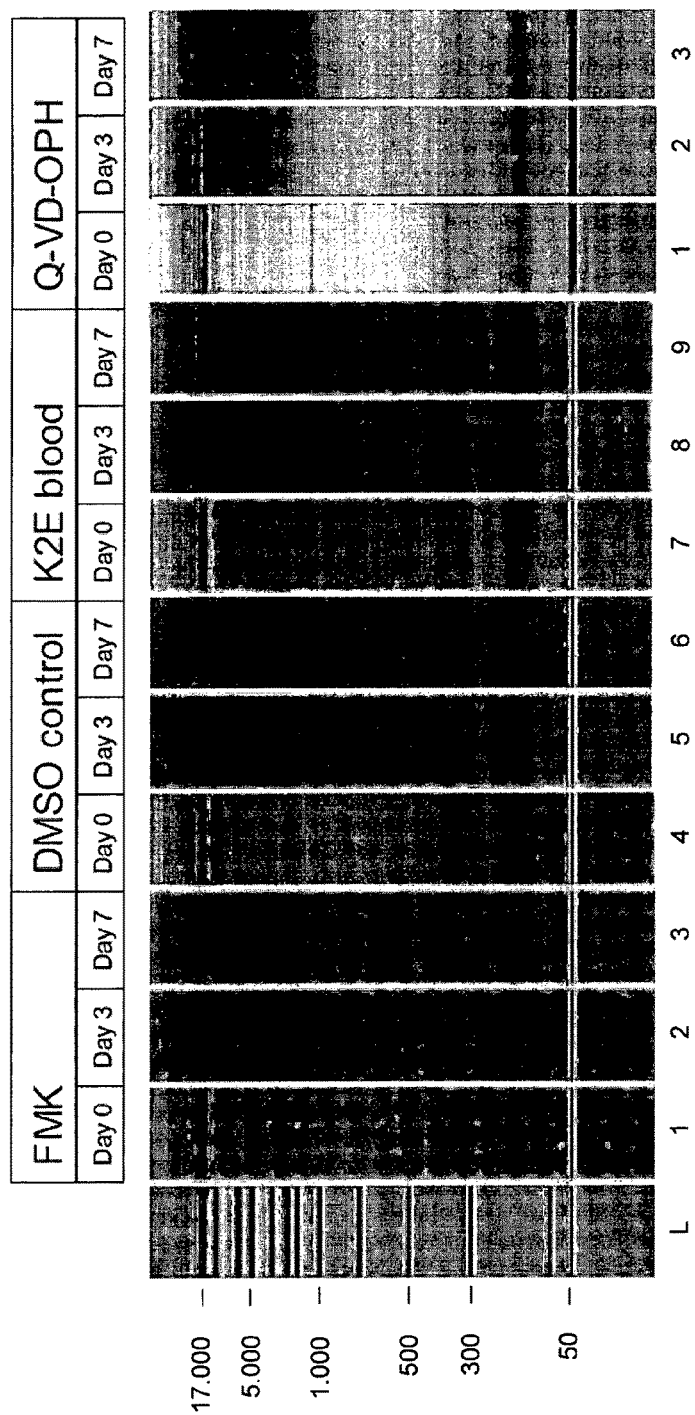
FIG. 13 shows circulating cell-free DNA isolated from stabilized samples and control samples and separated by size using chip gel electrophoresis as described in Example 5, Section 2.1.

The eluted circulating cell-free DNA was separated by size using chip gel electrophoresis (for details on the method see above). FIG. 13 shows the obtained results. The DMSO control and the K2E blood (not treated according to the teachings of the present invention) show the same ladder-like pattern of bands. This pattern occurs in samples where apoptosis takes place. During apoptosis, endonucleases degrade genomic DNA at inter-nucleosomal linker regions and produce DNA fragments of circa 180 bp or multiples of 180 bp. Thus, apoptosis occurs in samples which show a clear ladder-like pattern. Furthermore, the strength (darkness) of the pattern is decisive. The darker the bands, the more genomic DNA was released from the cells and thus contaminates the extracellular nucleic acid population.

FIG. 13 shows that the DMSO control and the K2E blood samples show a strong ladder-like pattern already on day 3, which becomes even stronger on day 7. Thus, genomic DNA was released from the cells contained in the sample and was also degraded. This released and degraded DNA contaminates the cell-free nucleic acids contained in the sample. Hence, no acceptable stabilization is achieved with these samples.

In contrast, whole blood samples treated with Z-Val-Ala-Asp(OMe)-FMK show a reduced ladder-like pattern in particular on day 7 compared to the controls, indicating an inhibition of the release of genomic DNA, respectively genomic DNA fragmentation caused by apoptosis. This effect is confirmed by the results shown in FIG. 14 (see below). The effect is even more prominent in the blood samples treated with Q-VD-OPh, which show significantly reduced ladder-like patterns already on day 3 and day 7. Thus, the release and degradation in particular fragmentation of genomic DNA is effectively prevented, respectively reduced by the addition of the caspase inhibitor Q-VD-OPh.

Results of the DNA Quantification

Figure 14:
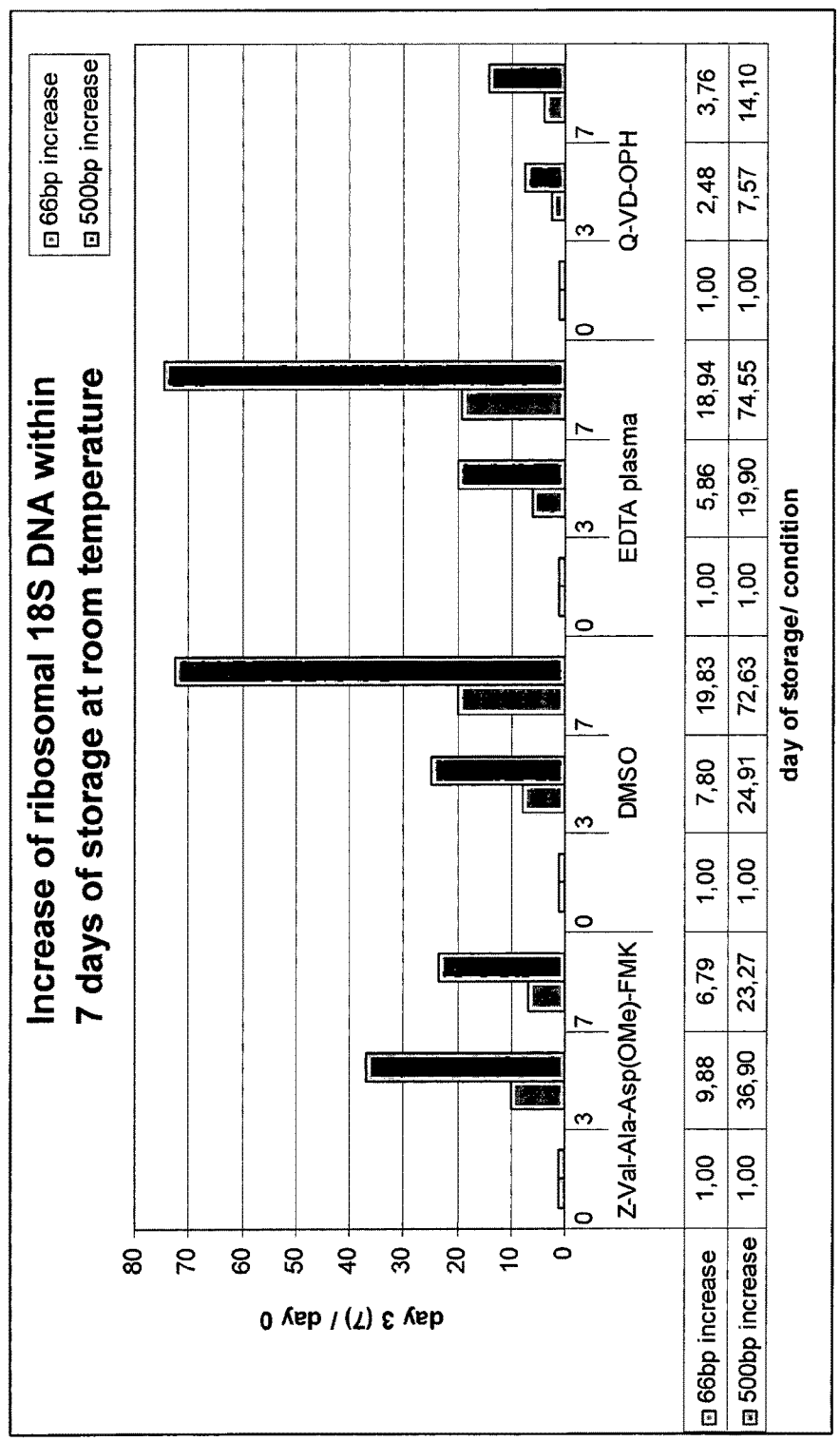
FIG. 14 shows the effect of various caspase-inhibitors on the stabilization of 18S DNA within 7 days of storage at room temperature as described in Example 5, Section 2.1.

The eluted circulating cell-free DNA was also quantified with the real time PCR assay that is sensitive for DNA degradation (for details on the method see example 1). FIG. 14 shows the effect of the tested caspase-inhibitors on the stabilization of the extracellular nucleic acid population (18S DNA duplex assay) within 7 days of storage at RT, here the increase in DNA.

Detection of ribosomal 18S DNA by quantitative real-time PCR, makes it possible to calculate the x-fold increase of DNA from day 0 to day 3 or 7 (calculation: division of day 3 (or 7) copies by day 0 copies). Thw results shown in FIG. 14 demonstrate a reduced increase of DNA when a caspase-inhibitor, especially Q-VD-OPh, was added to whole blood samples. The stabilizing effect of Z-Val-Ala-Asp(OMe)-FMK compared to the standard samples was more prominent on day 7, thereby confirming the results shown in FIG. 13.

Summary

Summarizing the results of the real time PCR and the gel electrophoresis, it was demonstrated that the addition of Q-VD-OPh or Z-Val-Ala-Asp(OMe)-FMK inhibits DNA fragmentation and furthermore, reduces the release of genomic DNA into blood plasma. Thus, adding a caspase inhibitor to whole blood is effective in stabilizing the sample and in particular the extracellular nucleic acid population even at room temperature. Therefore, it is preferred to use butanamide in combination with a caspase inhibitor. Both stabilizing agents in combination significantly improve and prolong the stabilization effect. Thus, using the stabilization method according to the present invention which involves the use of butanamide and a caspase inhibitor improves the stabilization and allows to ship whole blood samples even at room temperature without jeopardizing the quality of the sample. To completely prevent release of genomic DNA also during longer storage periods, the concentration of Q-VD-OPh may also be increased.

2.2. Stabilization by the Addition of N,N-dimethylacetamide (DMAA)

Two different concentrations of DMAA along with K$_2$EDTA were tested and compared to EDTA alone (K2E BD; 18 mg K$_2$EDTA).

DMAA was added to replicates of whole blood samples (0.75% and 1.5% end concentration in 10 ml blood; blood was collected into Vacutainer K2E Tubes; BD).

Blood samples were incubated for up to 6 days at room temperature. On day 0, 3 and 6, whole blood samples were centrifuged at 1912×g for 15 min at room temperature, followed by a centrifugation of the plasma samples at 16.000×g for 10 min at 4° C. 1 ml of the sample input was used for DNA isolation following the protocol described in the materials & methods section. DNA was eluted in 80 µl EB buffer and quantified with the RT PCR assay described in example 1.

Results of the DNA Quantification

Figure 15:
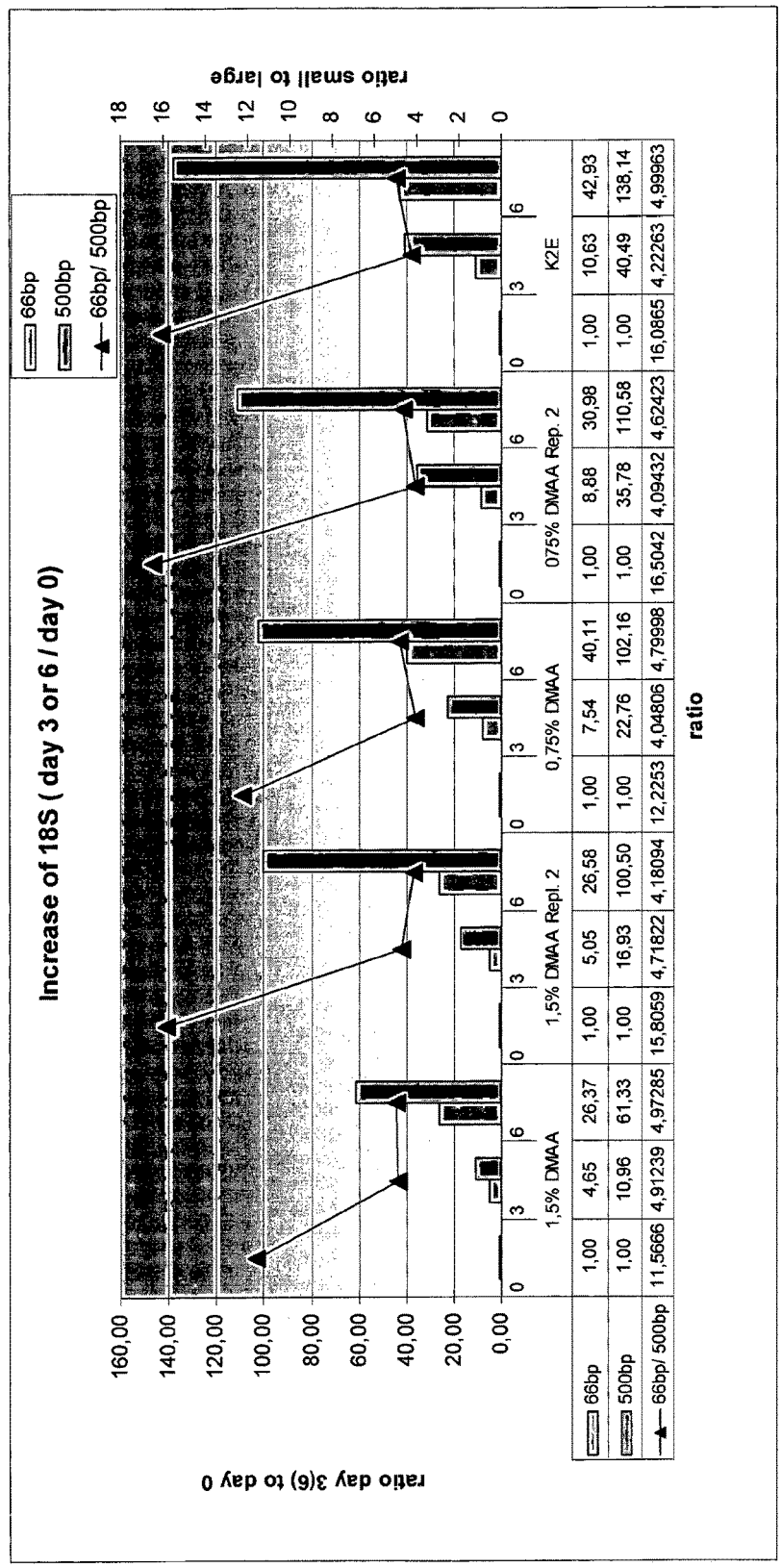
FIG. 15 shows the effect of various tested concentrations of DMAA on the increase of genomic DNA in the plasma as described in Example 5, Section 2.2.

FIG. 15 shows the effects of the tested concentrations of DMAA on the increase of genomic DNA in the plasma. Addition of DMAA significantly reduces the release of genomic DNA into plasma. The more DMAA is added to whole blood, the less DNA is released. Only a minor increase of cell-free DNA within 3 days of storage was observed if DMAA was added to the whole blood sample.

In summary, the addition of DMAA reduces the release of genomic DNA into blood plasma. Thus, adding DMAA to a blood sample is effective in stabilizing the sample even at room temperature. However, DMAA is a toxic agent.

2.3. Influence of Combinations of DMAA and OPH (Caspase Inhibitor) Concentrations on ccfDNA Levels.

10 ml whole blood samples were first collected in BD Vacutainer K2E-EDTA (4.45 mM EDTA=reference). Then, 2 ml of the following solutions were added (given concentrations represent final concentration in stabilized blood solution). Each condition was tested with six tubes from different donors.

1: EDTA reference (BD Vacutainer K2E);
2: 50 mg EDTA, 1 µM OPH;
3: 50 mg EDTA, 2 µM OPH;
4: 50 mg EDTA, 1 µM OPH, 5% DMAA;
5: 50 mg EDTA, 1 µM OPH, 10% DMAA;
6: 50 mg EDTA, 2 µM OPH, 5% DMAA;
7: 50 mg EDTA; 2 µM OPH and 10% DMAA.

Figure 16:
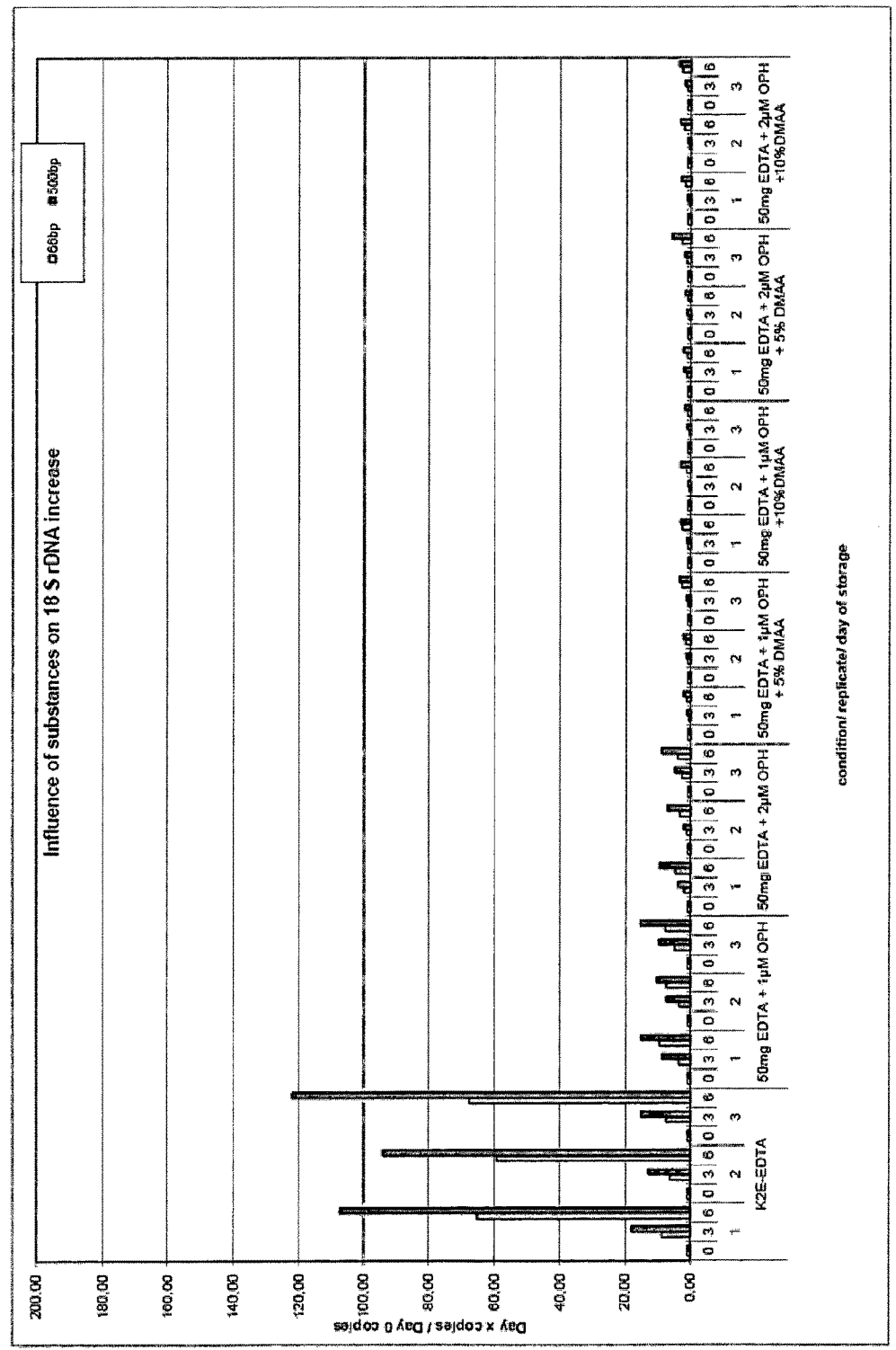
FIGS. 16 and 17 show the influence of various stabilization compositions on 18S rDNA increase as described in Example 5, Section 2.3.
Figure 17:
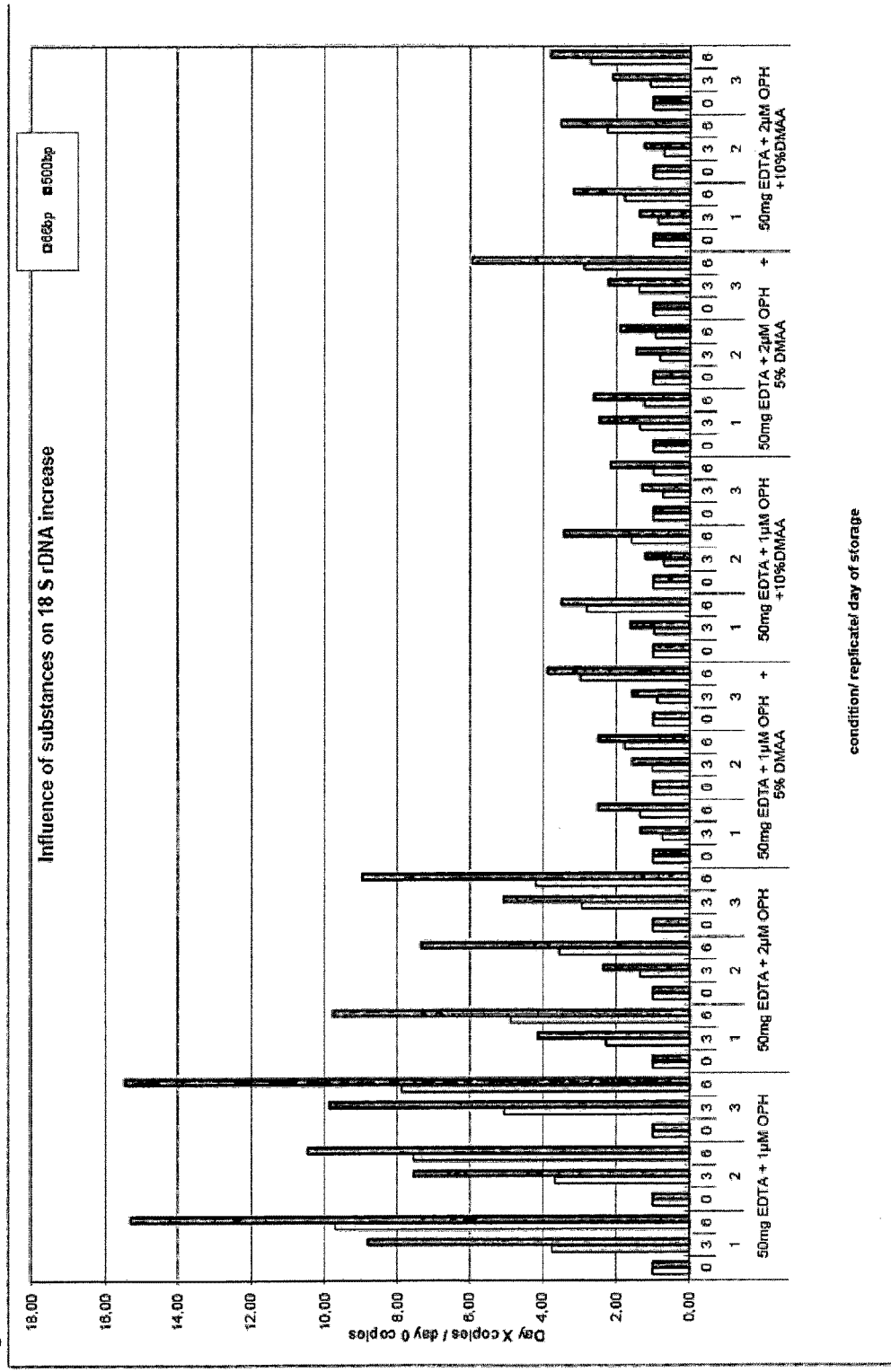

The sample incubation, isolation of plasma and isolation from nucleic acids from the cleared plasma fraction were performed as described in example 1. However, after the first centrifugation step at 3.000 rpm, plasma samples of identical stabilization conditions were pooled before the second centrifugation step for plasma clearing (16.000×g) was carried out. The results are shown in FIG. 16. As can be seen, the combination using a caspase inhibitor and DMAA is more effective than the caspase inhibitor alone. Furthermore, as is shown by the above examples, the non-toxic agent butanamide is equally effective as DMAA and therefore, provides an non-toxic stabilization alternative. FIG. 17 shows the same results as FIG. 16, however, in a different scaling due to enclosure of reference data.

2.4. Limit of Detection (LoD)

Extracellular nucleic acids are often comprised in very small amounts in the sample. Therefore, it is important to have a stabilization procedure which not only efficiently preserves the extracellular nucleic acids within the stabilized sample, but additionally allows to subsequently isolate the extracellular nucleic acids with high yield from the stabilized sample. Example 5. (2.4) demonstrates that a stabilization method which does not involve the use of formaldehyde releasers is superior to prior art stabilization methods in that the extracellular nucleic acids can be isolated with higher yield from the stabilized samples. This advantageously reduces the limit of detection and thus, allows to reliably determine also rare target nucleic acids within the population of extracellular nucleic acids.

The following stabilization solutions/tubes were compared:

1. Cell-free RNA BCT (Streck Inc, cat. #:218976—comprises a formaldehyde releaser as stabilizer)
2. BD Vacutainer K2E (BD, Cat. #: 367525—comprises EDTA)=reference
3. QGN stabilization (5% DMAA, 14 mM EDTA, 2 µM OPH (caspase inhibitor))

Whole blood samples were collected in cell-free RNA BCT and BD Vacutainer K2E tubes. To one half of blood collected in BD tubes, the QGN stabilization solution was added. Thus, the sample stabilized according to the invention comprise an additional amount of EDTA that is contributed by the BD Vacutainer stabilization. The samples were centrifuged at 3.000×rpm for 10 minutes, and the obtained plasma was aliquoted to 1.5 ml replicates. Afterwards, the following amounts of DNA spike-in control (1.000 bp) were added per sample: 1.000 copies, 5000 copies, 100 copies, 50 copies and 10 copies.

8 replicates of 500 to 10 copies/sample, 4 replicates of 1.000 copies/sample and 5 copies/sample were prepared. The samples were incubated for 3 days at room temperature. The sample preparation was done on the QIAsymphony SP automated system, using the QIAsymphony virus/bacteria Cell-free 1000 application which allows isolating extracellular nucleic acids from plasma samples. The nucleic acids were eluted in 60 µl; the subsequent PCR was performed in triplicates.

Figure 18:
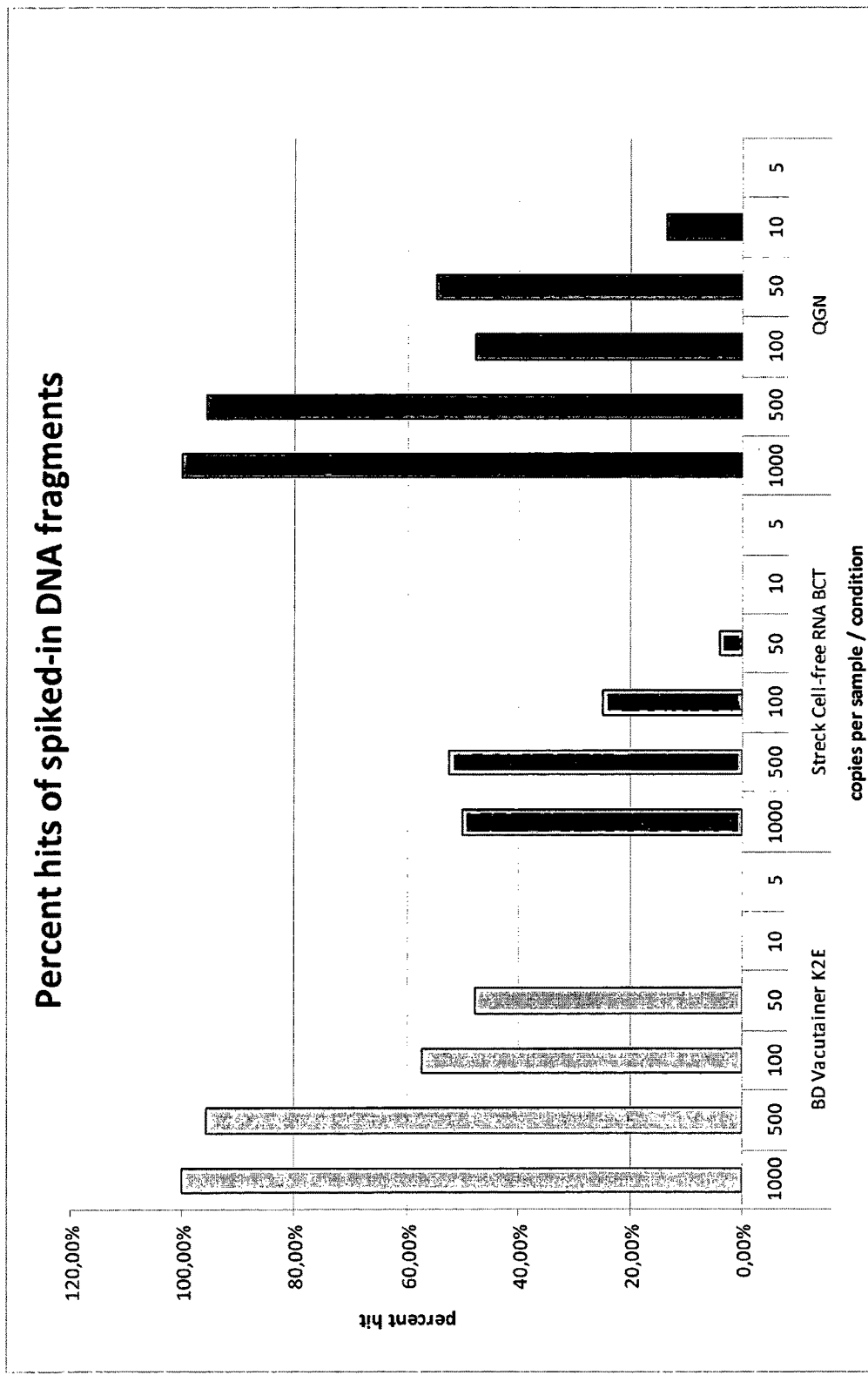
FIG. 18 shows percent hits of spiked-in DNA fragments as described in Example 5, Section 2.4.

The results are shown in FIG. 18. As can be seen, 100% hit≥1.000 copies per sample was obtained when using either the BD EDTA tubes or the stabilization solution according to the present invention. This shows that the isolation of nucleic acids is not impaired when using a stabilization solution comprising a caspase inhibitor and DMAA. In contrast, the stabilization that is based on the use of a formaldehyde releaser (Streck) shows a strong inhibition of the nucleic acid isolation. As can be seen, significantly less nucleic acids could be isolated from the respective samples, even with those samples wherein 500 or even 1.000 copies were spiked in. Furthermore, FIG. 18 shows that the best sensitivity was obtained with a sample stabilized using a caspase inhibitor and DMAA. Even for those embodiments wherein only 10 copies per sample were spiked in, still 13% positive PCR hits were obtained. Thus, a stabilization method which does not use formaldehyde releasers allows the subsequent recovery of even very low-abundant extracellular nucleic acids. This is an important advantage over cross-linking based stabilization because it makes such a method particularly suitable for diagnostic applications and e.g. the detection of rare target extracellular nucleic acids such as e.g. tumor derived extracellular nucleic acids or fetal nucleic acids. In particular, in the lower copy numbers, a stabilization solution that is based on the use of formaldehyde releasers had a very low performance and showed the highest limit of detection. This is also confirmed by table 4.

TABLE 4

Effect of stabilization method on nucleic acid isolation

| DNA Fragment | Tube/stabilizing | Dose for centile 95 [copies] | 95% confidence interval | |
|---|---|---|---|---|
| | | | min [copies] | max [copies] |
| 1000 bp | BD K2E | 386 | 230 | 995 |
| | Streck RNA | 9902 | 2909 | 164606 |
| | QGN | 599 | 319 | 1749 |

As can be seen from said table, for the 1000 bp fragment, the results achieved with EDTA sample and a stabilization solution comprising DMAA and a caspase inhibitor is comparable. Thus, the stabilization does not impair the subsequent isolation of nucleic acids. Stabilization using a formaldehyde releaser showed the highest limit of detection and thus demonstrates that the subsequent isolation of the nucleic acid was strongly impaired.

Figure 19:
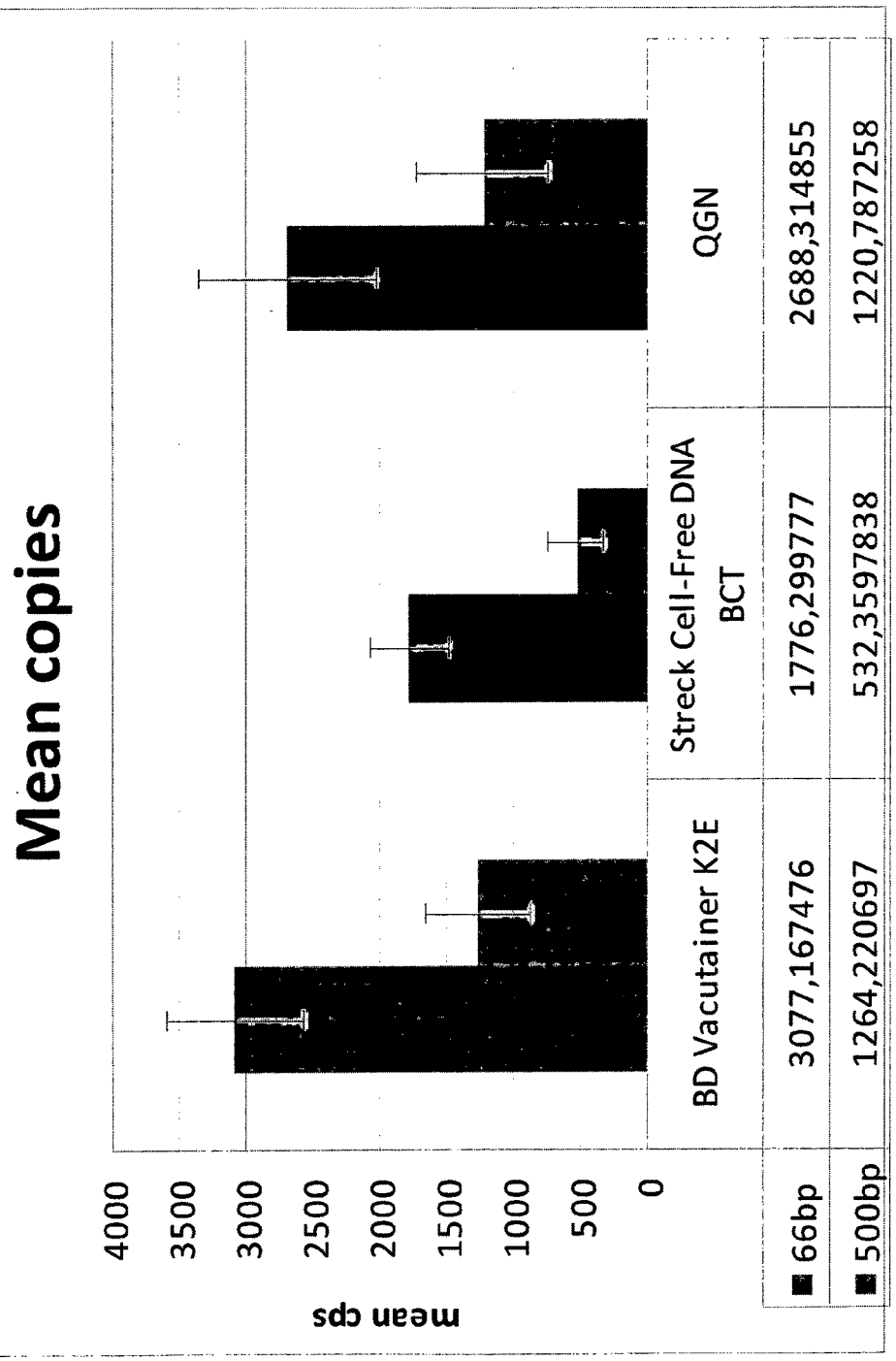
FIG. 19 shows mean copies of ccfDNA obtained from differently stabilized samples as described in Example 5, Section 2.4.
Figure 20:
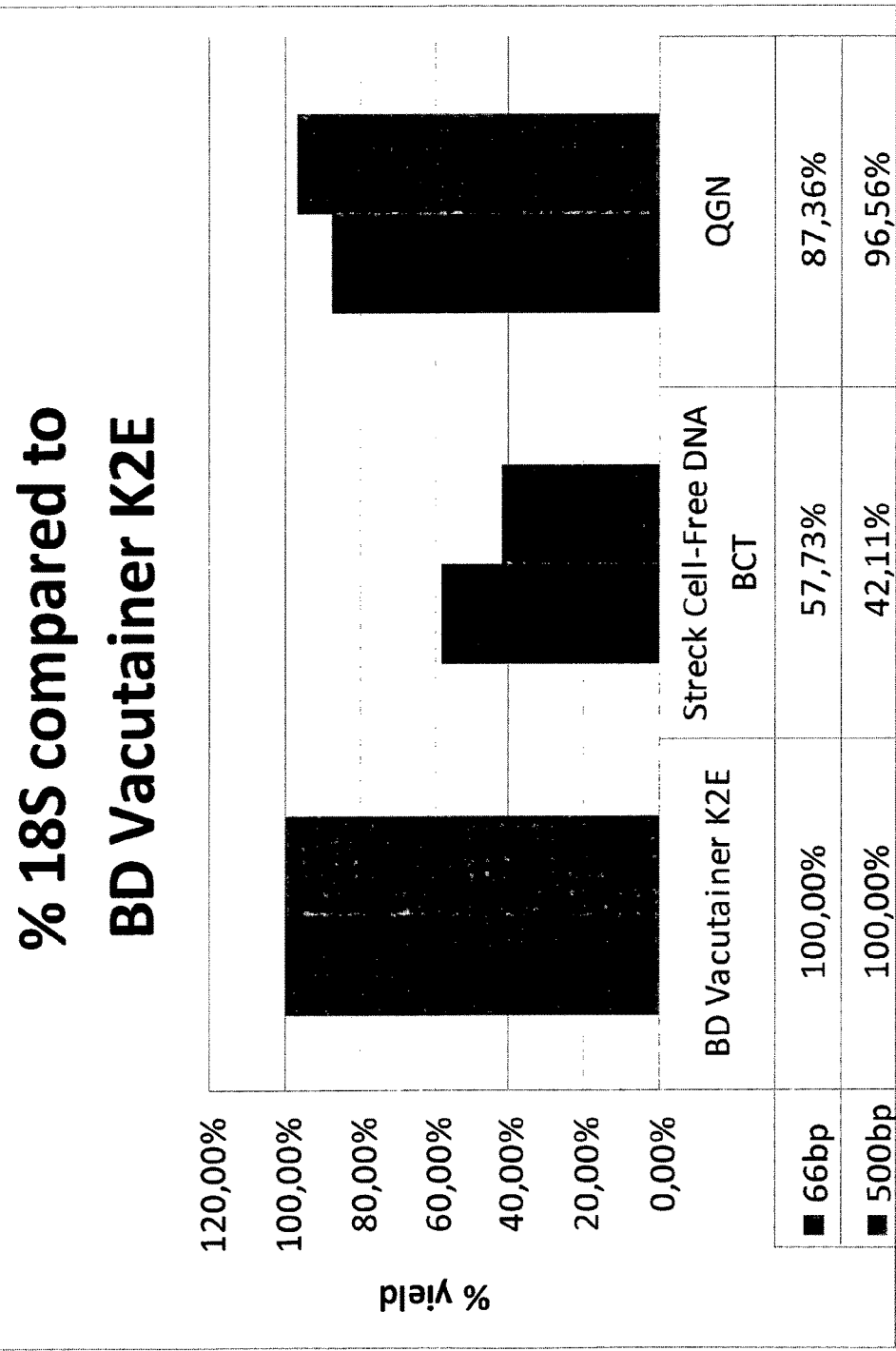
FIG. 20 shows percentage 18S isolated from differently stabilized samples compared to BD Vacutainer K2E as described in Example 5, Section 2.4.

This is also confirmed by the results shown in FIGS. 19 and 20. As can be seen, comparable ccfDNA yields are obtained for EDTA stabilized samples and samples stabilized with a caspase inhibitor and DMAA (measured by 18 S rDNA qPCR). However, reduced ccfDNA yields were obtained for the stabilization, which involves the use of formaldehyde releasers (Streck tubes). The yield of formaldehyde stabilized samples was reduced by approximately 50% compared to the EDTA stabilized samples. In contrast, the stabilization reagent not involving a formaldehyde releaser did not show an adverse effect on ccfDNA yield, when using conventional nucleic acid isolation methods. As can be seen by the above examples 1 to 4, the stabilizing method using butanamide as stabilizing agent shows an equal performance with respect to the downstream nucleic acid isolation as DMAA. Therefore, an indirect comparison with the formaldehyde releaser based stabilization can be made. Thus, also the butanamide based stabilization which does not involve the use of cross-linking agents does not have an adverse effect on ccf DNA yield. This is an important advantage as it allows integrating such stabilization method into existing nucleic acid isolation procedures and workflows. Similar results are achieved with the method according to the present invention which is based on the use of butanamide. As also no cross-linking agents are used, the nucleic acid isolation is not impaired.

Example 6

Abbreviations Used

BA: Butanamide
ccfDNA: circulating, cell free DNA
DMPA: Dimethylpropionamide
EDTA: Ethylenediaminetetraacetic acid
PEG: Polyethylene glycol In example 6, polyethylene glycol (PEG) was tested for its ability to stabilize a cell-containing biological sample, here a blood sample, either alone or in combination with butanamide and optionally including a caspase inhibitor and/or a tertiary amide. Compared to the reference samples (EDTA blood), PEG was found to be able to efficiently stabilize white blood cells in whole blood samples in a way, that it prevents the release of genomic DNA into the extracellular nucleic acid population. This stabilization effect was demonstrated for PEG of different molecular weights and when used in different concentrations. It is demonstrated that PEG can be added as a water-free powder or liquid, as pure reagent or dissolved in an aqueous solution. PEG alone has a strong stabilization effect on its own, but it also significantly improves the stabilization in combination with butanamide. Preferably, additionally a caspase inhibitor is used. It is demonstrated that using this advantageous combination achieves that the increase of DNA released from white blood cells into plasma between day 0 (directly after blood draw) and day 6 (6 days of storage at room temperature) is reproducible reduced to 2fold or even lower. Therefore, the stabilization effect can also be prolonged up to 6 days or even longer. This achieved prolonged, efficient stabilization is an important advantage, as it provides a uniform, reliable stabilization method for cell-containing samples such as blood samples. Furthermore, the examples demonstrate that it is advantageous to use a combination of a high molecular weight PEG and a low molecular weight PEG as strong stabilizing effects are achieved and extracellular nucleic acids can be efficiently isolated from stabilized samples using e.g. silica column based nucleic acid isolation methods.

Materials and Methods

The following procedure was followed in example 6 if not indicated otherwise.

Blood Collection and Stabilization

Blood was drawn into 10 ml spray dried EDTA tubes (BD) with 1.8 mg K2EDTA per ml of whole blood. Within 30 min after draw, stabilization reagents were either directly added or the blood was decanted into a new tube containing stabilization reagents. Blood and reagents were mixed by inverting the tube ten times. Stabilized blood samples were stored at room temperature standing in an upright position.

Preparation of Plasma

Whole blood samples were centrifuged at ambient temperature for 15 min at 3.000 rpm (resolutions per minute). Clear plasma fraction was removed by pipetting and transferred into a fresh centrifuge tube. In a second round, plasma samples were centrifuged at 4° C. for 10 min at 16.000×g. Supernatant was transferred into a new tube and either directly used for purification of ccfDNA or stored at −20° C. until use.

Purification of ccfDNA

DNA from plasma was isolated with the QIAamp circulating nucleic acid kit (QIAGEN GmbH), using the protocol for "purification of circulating nucleic acids from 1 ml, 2 ml, or 3 ml serum or plasma". If not stated otherwise, 2 ml of plasma was mixed with proteinase K and lysis buffer ACL, incubated for 30 min at 60° C., mixed with buffer ACB, bound on QIAamp Mini columns (which comprise a silica solid phase for binding the nucleic acids) with the use of a QIAvac 24 Plus vaccum manifold, washed and eluted with 60 µl elution buffer AVE, according to the manufactures recommendations.

Quantitative, real time PCR assay for analyzing the isolated extracellular DNA The isolated extracellular DNA was analysed in a real time PCR assay on Abi Prism HT7900 (Life technologies) using 3 µl of eluate. In a 20 µl assay volume using QuantiTect Multiplex PCR Kit reagents (QIAGEN GmbH) two fragments of the human 18S rDNA gene, 66 bp and 500 bp, were amplified in a multiplex PCR. Cycle thresholds (Ct values) of the individual samples were translated into amount of gDNA in the eluate according to a gDNA standard curve: total quantification was achieved by comparison with a standard curve generated with human genomic DNA diluted from 3000 to 0.3 genome equivalents (1 genome equivalent equates to around 6.6 pg of human genomic DNA). The gDNA amount of the storage time point (in general 6 days after blood withdrawal) was compared to the time zero gDNA level from the same donor. Details regarding the used DNA target sequences detected by quantitative real time PCR Target are summarized above in Table 2.

Quantification of the 66 bp fragment was again used to deflect the total amount of 18S rDNA copies in the plasma. Quantification of the 500 bp was used to determine the amount of 18S rDNA copies which derived from apoptotic or mechanically lysed leucocytes from whole blood. Cell free DNA has a typically lengths of 140-170 bp. Therefore, 500 bp fragments are believed to be derived from apoptotic, lysed or otherwise destructed blood cells. The increase of copy numbers from the 500 bp fragment between T0 and 6 days storage, was used as a measurement of stability efficiency. Thus, the lower the amount of released 500 bp DNA, the better the performance of the stabilization method. A higher amount of released 500 bp DNA indicates that lysis of white blood cells occurs and hence, that the extracellular nucleic acid population was contaminated with intracellular genomic DNA.

For the subsequent experiments with different stabilization compositions blood samples from a plurality of different individual donors were used. The average fold change of copy numbers of 66 bp and 500 bp fragments of the 18S rDNA gene in stabilized or unstabilized blood stored for different time points (days) at room temperature to time point 0 (day 0) after blood draw was single calculated for each individual donor sample. The average of the corresponding single calculated mean values (fold changes) was used as a measure of stabilization efficacy of the different stabilization compositions used. As blood samples underlie natural individual variations in their composition and in the amount of contained extracellular nucleic acids depending on the donor, this may result in elevated standard deviations.

5. Measurement of Haemoglobin

Absorbance at 414 nm, found to be linearly correlated with hemolytical discoloration of plasma, was measured on a spectramax photometer.

Conditions Tested in Example 6

6.1. Example 6.1

In example 6.1, the stabilization effect of polyethylene glycol (PEG) with different molecular weights in combination with BA, EDTA and a caspase inhibitor (Q-VD-OPh) in the absence of water was tested and compared to a combined BA, EDTA and caspase inhibitor (Q-VD-OPh) approach. Moreover, the effect on hemolysis of such stabilization mixtures in plasma samples was measured in parallel. An EDTA blood sample served as unstabilized reference control.

Blood Collection and Stabilization

Samples of 10 ml whole blood from eight donors, collected in 10 ml spray dry K2EDTA tubes, were stabilized with mixtures of butanamide (BA) and EDTA with or without PEG from different molecular weights without addition of water. Caspase inhibitor (Q-VD-OPh) dissolved in DMSO was added by pipetting. Plasma was directly generated from 5 ml of stabilized or unstabilized blood samples. Residual blood was stored for additional 6 days at room temperature before plasma generation. ccfDNA was purified from 2 ml plasma, copy numbers of 18S rDNA gene were determined in triplicates by real time PCR.

All stabilized blood samples were set up in triplicates per condition and test time point. At time point 0 (reference time point), immediately after mixing the stabilization solution and blood, plasma was generated and the circulating extracellular DNA was extracted. As a reference control, the EDTA stabilized blood sample (collected in K2 EDTA tubes without further additives) was also stored for 0 or 6 days and analyzed in triplicates.

Composition of stabilization reagent mixtures (for 10 ml K2EDTA whole blood each):
  unstabilized: 1.8 mg/ml K2EDTA
  BA, EDTA, Q-VD-OPh: 100 mg BA, 132 mg K2EDTA, 10 µl Q-VD-OPh (1 mg dissolved in 388 µl DMSO), water ad 2 ml
  PEG (600, 1000 or 3000), BA, EDTA, Q-VD-OPh: 250 mg PEG (600, 1000 or 3000), 100 mg BA, 132 mg K2EDTA, 10 µl Q-VD-OPh (1 mg dissolved in 388 µl DMSO) (no water)

Figure 21:
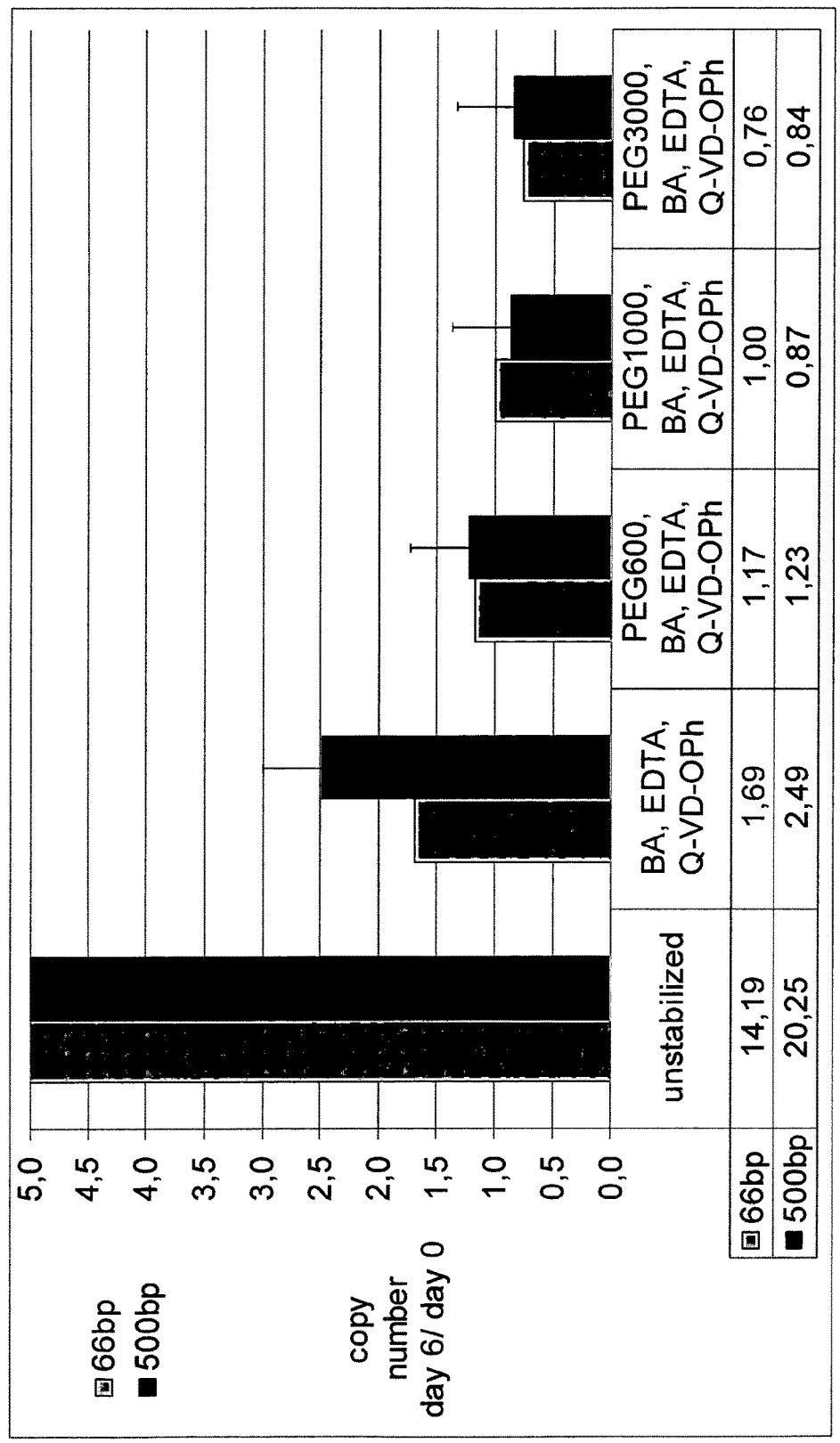
FIG. 21 shows average fold change of copy numbers of 66 bp and 500 bp fragments of the 18S rDNA gene 6 days after blood withdrawal relative to time zero in various stabilized or unstabilized blood from 8 donors as described in Example 6.1.

Thereby, the following final concentrations of the different components in the mixture are obtained after contact with blood:
  unstabilized: 1.8 mg/ml K2EDTA
  BA, EDTA, Q-VD-OPh: 1% (w/v) BA, 15 mg/ml K2EDTA, 5 µM Q-VD-OPh
  PEG(600, 1000 or 3000), BA, EDTA, Q-VD-OPh: 2.5% (w/v) PEG (600, 1000 or 3000), 1% (w/v) BA, 15 mg/ml K2EDTA, 5 µM Q-VD-OPh Results The average change of copy numbers (x fold change) of 66 bp and 500 bp fragments of the 18S rDNA gene in stabilized or unstabilized blood from 8 donors stored for 6 days at room temperature to time point 0 (day 0) after blood draw was single calculated for each of the eight blood donors. FIG. 21 shows the corresponding average fold change of copy numbers from 8 donors per condition. All stabilization compositions show significantly lower amounts of released genomic DNA after storage for 6 days at room temperature compared to the unstabilized control (EDTA blood) as the average fold change increases significantly less. Thus, a stabilization effect was achieved even throughout this long stabilization period of 6 days. FIG. 21 demonstrates that contacting the blood samples additionally with polyethylene glycol significantly improved the stabilization effect achieved. Therefore, PEG of different molecular weights were highly effective in improving the stabilization effect as the average fold change increase was consistently reduced below 2-fold and in embodiments even below 1-fold. I.e. the DNA levels at day 6 are comparable to that of the basal time point (day 0).

To summarize, the stabilization effect of a stabilization composition comprising a caspase inhibitor and butanamide, can be significantly increased when used in combination with a polyethylene glycol. Polyethylene glycol was effective in different molecular weights.

Moreover, the results indicate that the stabilization properties of PEG increased with increasing molecular weight of PEG, indicating that there is a positive correlation between the molecular weight of used PEG and the resulting sample stabilization effect. Higher molecular weights improved the achieved stabilization effect.

6.2. Example 6.2

In example 6.2, the stabilization effect of a combination of EDTA, BA and a caspase inhibitor (Q-VD-OPh) in the absence of water was tested and compared to corresponding compositions additionally including different amounts (0.2 g, 0.3 g or 0.4 g) of PEG with a molecular weight of 600 (PEG600). EDTA blood served as unstabilized reference.

Blood Collection and Stabilization

Samples of 10 ml whole blood from six donors, collected in 10 ml spray dry K2EDTA tubes, were stabilized with mixtures of butanamide (BA) and EDTA with or without different amounts of PEG with a molecular weight of 600 (PEG600) without addition of water. In addition, a caspase inhibitor (Q-VD-OPh) dissolved in DMSO was added by pipetting. Plasma was directly generated from 5 ml of stabilized or unstabilized blood samples. Residual blood was stored for additional 6 days at room temperature before plasma generation. ccfDNA was purified from 2 ml plasma, copy numbers of 18S rDNA gene were determined in triplicates per condition and test time point by real time PCR. As a reference control, the EDTA stabilized blood sample (collected in K2 EDTA tubes without further additives) was also stored for 6 days.

Composition of stabilization reagent mixtures (for 10 ml K2EDTA whole blood each):
  BA, EDTA, Q-VD-OPh: 100 mg BA, 182 mg K2EDTA, 10 µl Q-VD-OPh (1 mg dissolved in 388 µl DMSO), ad 2 ml water
  PEG600 (0.2-0.4 g), BA, EDTA, Q-VD-OPh: 200, 300 and 400 mg PEG600, 100 mg BA, 188 mg K2EDTA, 10 µl Q-VD-OPh (1 mg dissolved in 388 µl DMSO)

Figure 22:
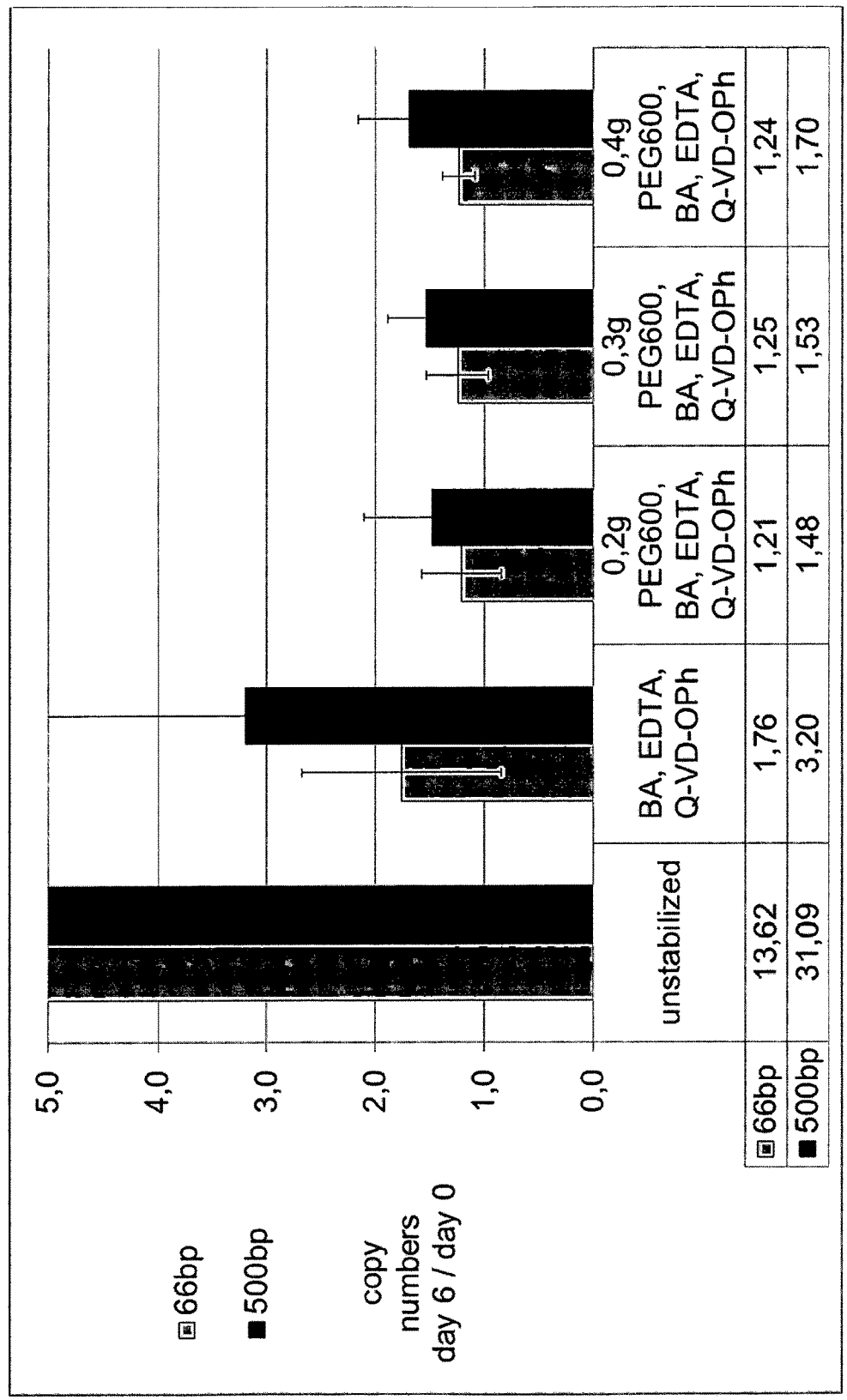
FIG. 22 shows average fold change of copy numbers of 66 bp and 500 bp fragments of the 18S rDNA gene 6 days after blood withdrawal relative to time zero in various stabilized or unstabilized blood from 6 donors as described in Example 6.2.

Thereby, the following final concentrations of the different components in the mixture are obtained after contact with blood:
  unstabilized: 1.8 mg/ml K2EDTA
  BA, EDTA, Q-VD-OPh: 1% (w/v) BA, 20 mg/ml K2EDTA, 5 µM Q-VD-OPh PEG600 (0.2-0.4 g), BA, EDTA, Q-VD-OPh: 2, 3 and 4% (w/v) PEG600, 1% (w/v) BA, 20 mg/ml K2EDTA, 5 µM Q-VD-OPh Results The results of the quantitative real time PCR analyses from six individual donor samples depicted as average fold change is shown in FIG. 22. The increase of DNA (66 bp and 500 bp fragment) relative to time zero with 0.2 g, 0.3 g or 0.4 g PEG600 (average fold change) is shown. All tested stabilization compositions showed significant lower amounts of released DNA after storage for 6 days at room temperature compared to the reference EDTA blood. The stabilization effect was significantly improved if the cell-containing sample was additionally contacted with polyethylene glycol. The average fold change of both 18S rDNA amplicon copy numbers was clearly smaller in all three PEG based stabilization approaches compared the composition not comprising PEG (BA, EDTA, Q-VD-OPh). The x fold change was in all cases below 2-fold. This example demonstrates that additionally using a polyethylene glycol in different quantities for stabilizing the extracellular nucleic acid population significantly improves the stabilization results that are achieved with the caspase inhibitor and butanamide.

6.3. Example 6.3

In example 6.3, the stabilization effect of reagent mixtures, including a high molecular weight PEG (PEG3000), EDTA, BA and caspase inhibitor (Q-VD-OPh), directly lyophilized into blood collection tubes in the presence of water was tested and compared to a sample concomitantly treated with a solution comprising BA, EDTA and a caspase inhibitor (Q-VD-OPh).

Blood Collection and Stabilization

Samples of 10 ml whole blood from eight donors, collected in 10 ml spray dry K2EDTA tubes, were stabilized with mixtures of butanamide (BA), EDTA, and caspase inhibitor (Q-VD-OPh) with or without PEG3000. For lyophilisation all components including caspase inhibitor, EDTA, BA and PEG were dissolved in water. Volumes of 1 ml (final concentrations see below) were lyophilized on a dry freezer Epsilon 2-25D (Christ GmbH) in 5 ml tubes. Blood was transferred from K2EDTA tubes into the 5 ml tubes with the lyophilized stabilization reagent and stabilized by 10 times inverting the tubes. As a reference, reagents were freshly prepared and caspase inhibitor (Q-VD-OPh) dissolved in DMSO was added by pipetting.

Plasma was directly generated from 5 ml of stabilized or unstabilized blood samples. Residual blood was stored for additional 6 days at room temperature before plasma generation. ccfDNA was purified from 2 ml plasma, copy numbers of 18S rDNA gene were determined in triplicates by real time PCR.

Composition of stabilization reagent mixtures (for 10 ml K2EDTA whole blood each):
  Freshly prepared BA, EDTA, Q-VD-OPh: 100 mg BA, 132 mg K2EDTA, 10 µl Q-VD-OPh (1 mg dissolved in 388 µl DMSO), ad 2 ml water
  Freshly prepared PEG3000, BA, EDTA, Q-VD-OPh: 250 mg PEG3000, 100 mg BA, 132 mg K2EDTA, 10 µl Q-VD-OPh (1 mg dissolved in 388 µl DMSO) (no water)

Composition of stabilization reagent mixtures in 0.5 ml for lyophilisation into 5 ml tubes:
  Lyophilized: 0.5 ml of stabilization reagent containing 125 mg PEG3000, 50 mg BA, 67.5 mg K2EDTA, 5 µl Q-VD-OPh (1 mg dissolved in 388 µl DMSO)

Figure 23:
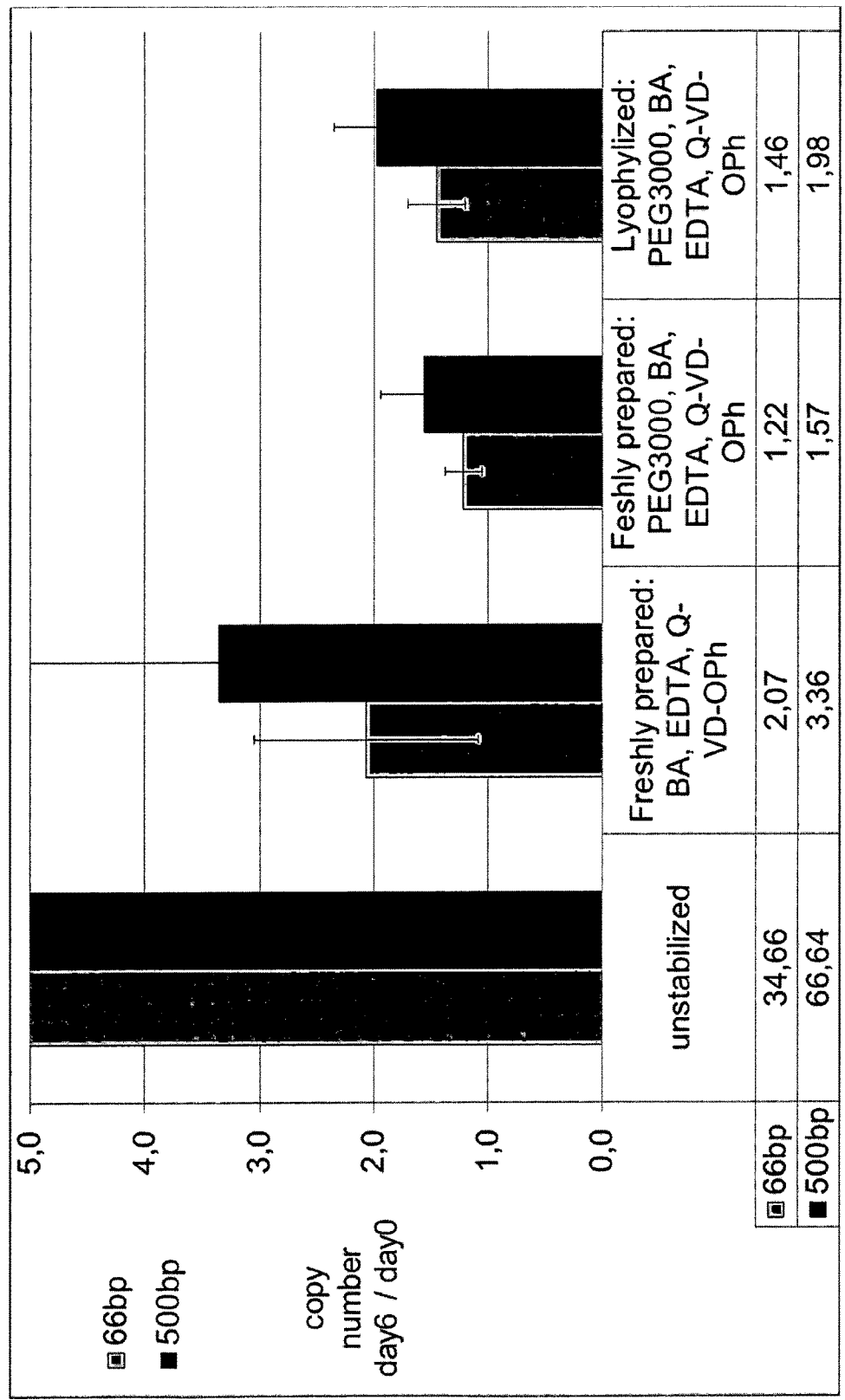
FIG. 23 shows average fold change of copy numbers of 66 bp and 500 bp fragments of the 18S rDNA gene 6 days after blood withdrawal relative to time zero in various stabilized or unstabilized blood as described in Example 6.3.

Thereby, the following final concentrations of the different components in the mixture are obtained after contact with blood:
  unstabilized: 1.8 mg/ml K2EDTA
  BA, EDTA, Q-VD-OPh: 1% (w/v) BA, 15 mg/ml K2EDTA, 5 µM Q-VD-OPh
  PEG3000, BA, EDTA, Q-VD-OPh: 1% (w/v) PEG 3000, 1% (w/v) BA, 15 mg/ml K2EDTA, 5 µM Q-VD-OPh Results The results are shown in FIG. 23. Shown is the increase (average fold change) of DNA 6 days after blood withdrawal relative to time zero based on different amplicon length of the 18S rDNA gene. The results again demonstrate that the stabilization effect is significantly improved if polyethylene glycol is additionally used for stabilization and that it enhances the stabilization effect that is achieved with BA, EDTA and a caspase inhibitor (Q-VD-OPh). Also during the prolonged stabilization periods tested (6 days), the x fold change was below 2-fold. Furthermore, the example demonstrates that these stabilization compositions may be used either freshly prepared or in lyophilized form.

6.4. Example 6.4

In example 6.4, the stabilization effect of PEG with different molecular weights (PEG300, PEG600, PEG1000) in an aqueous stabilization solutions further comprising BA, EDTA and a caspase inhibitor (Q-VD-OPh) was tested and compared to a sample co-treated with BA, dimethylpropionamide (DMPA), EDTA and caspase inhibitor (Q-VD-OPh). Unstabilized EDTA blood served as reference control.

Blood Collection and Stabilization

Samples of 10 ml whole blood from eight donors, collected in 10 ml spray dry K2EDTA tubes, were stabilized with mixtures of butanamide, EDTA and caspase inhibitor (Q-VD-OPh) in an aqueous solution with or without PEG of different molecular weights. Plasma was directly generated from 5 ml of stabilized or unstabilized blood samples. Residual blood was stored for additional 6 days at room temperature before plasma generation. ccfDNA was purified from 2 ml plasma, copy numbers of 18S rDNA gene were determined in triplicates by real time PCR.

Figure 24:
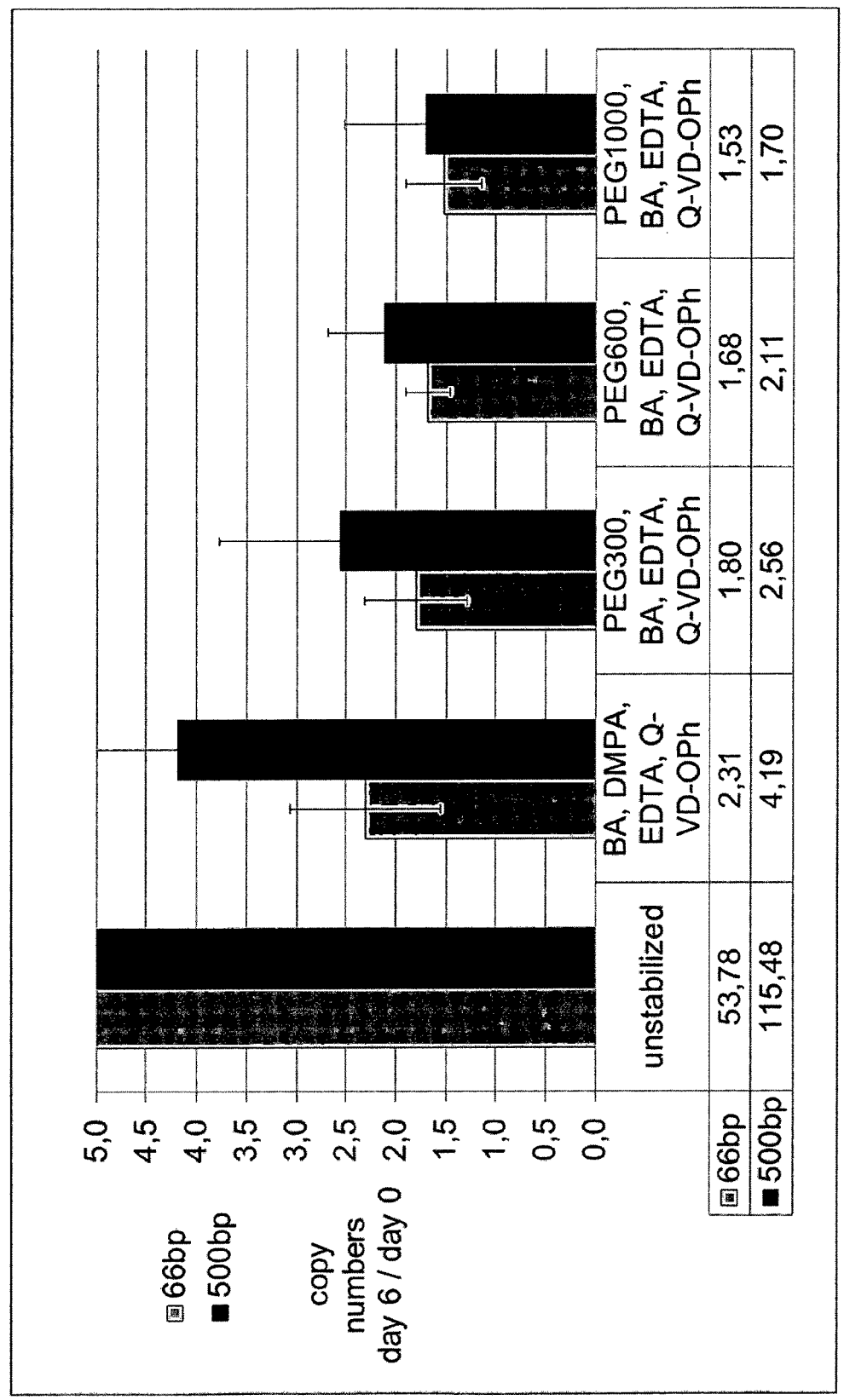
FIG. 24 shows average fold change of copy numbers of 66 bp and 500 bp fragments of the 18S rDNA gene 6 days after blood withdrawal relative to time zero in various stabilized or unstabilized blood as described in Example 6.4.

Composition of stabilization reagent mixtures (for 10 ml K2EDTA whole blood each):
  BA, DMPA, EDTA, Q-VD-OPh: 180 mg BA, 180 µl DMPA, 68.4 mg K2EDTA, 12 µl Q-VD-OPh (1 mg dissolved in 388 µl DMSO), water ad 2 ml
  PEG (300, 600 or 1000), BA, EDTA, Q-VD-OPh: 287.5 mg PEG (300, 600 or 1000), 115 mg BA, 154.5 mg K2EDTA, 11.5 µl Q-VD-OPh (1 mg dissolved in 388 µl DMSO), water ad 1.5 ml Thereby, the following final concentrations of the different components in the mixture are obtained after contact with blood:
  unstabilized: 1.8 mg/ml K2EDTA
  BA, DMPA, EDTA, Q-VD-OPh: 1.5% (w/v) BA, 1.5% (v/v) DMPA, 7.2 mg/ml K2EDTA, 5 µM Q-VD-OPh
  PEG (300, 600 or 1000), BA, EDTA, Q-VD-OPh: 2.5% (w/v) PEG, 1% (w/v) BA, 15 mg/ml K2EDTA, 5 µM Q-VD-OPh Results FIG. 24 shows the achieved stabilization results. As can be seen, the aqueous stabilization compositions comprising PEG of different molecular weight increased the stabilization effect that was achieved with butanamide and the caspase inhibitor. The stabilization of white blood cells was significantly improved as can be seen from the reduced amount of contaminating genomic DNA. The results also demonstrate that the stabilization effect increases with increasing molecular weight of the used PEG. The increase of the 500 bp fragment was reduced below 2-fold when using polyethylene glycol having a molecular weight of 1000.

6.5. Example 6.5

Here, the stabilization effect of decreasing PEG concentrations (2%, 1.5%, 1% or 0.7%) in an aqueous stabilization solution was tested in combination with butanamide, EDTA and a caspase inhibitor (Q-VD-OPh). Unstabilized EDTA blood served as reference control. A composition comprising BA, EDTA and Q-VD-OPh was tested in parallel.

Blood Collection and Stabilization

Samples of 10 ml whole blood from eight donors, collected in 10 ml spray dry K2EDTA tubes, were stabilized with mixtures of butanamide, EDTA and caspase inhibitor (Q-VD-OPh) in an aqueous solution with or without different concentrations of PEG6000. Plasma was directly generated from 5 ml of stabilized or unstabilized blood samples. Residual blood was stored for additional 6 days at room temperature before plasma generation. ccfDNA was purified from 2 ml plasma, copy numbers of 18S rDNA gene were determined in triplicates by real time PCR.

Composition of stabilization reagent mixtures (for 10 ml K2EDTA whole blood each):

BA, EDTA, Q-VD-OPh: 110 mg BA, 147 mg K2EDTA, 11 µl Q-VD-OPh (1 mg dissolved in 388 µl DMSO), water ad 1 ml PEG6000 (2-0.7%), BA, EDTA, Q-VD-OPh: 220, 165, 110, 77 mg PEG6000, 110 mg BA, 147 mg K2EDTA, 11 µl Q-VD-OPh (1 mg dissolved in 388 µl DMSO), water ad 1 ml Thereby, the following final concentrations of the different components in the mixture are obtained after contact with blood:

unstabilized: 1.8 mg/ml K2EDTA

BA, EDTA, Q-VD-OPh: 1% (w/v) BA, 15 mg/ml K2EDTA, 5 µM Q-VD-OPh

PEG6000 (2-0.7%), BA, EDTA, Q-VD-OPh: 2, 1.5, 1, 0.7% (w/v) PEG6000, 1% (w/v) BA, 15 mg/ml K2EDTA, 5 µM Q-VD-OPh

Results

Figure 25:
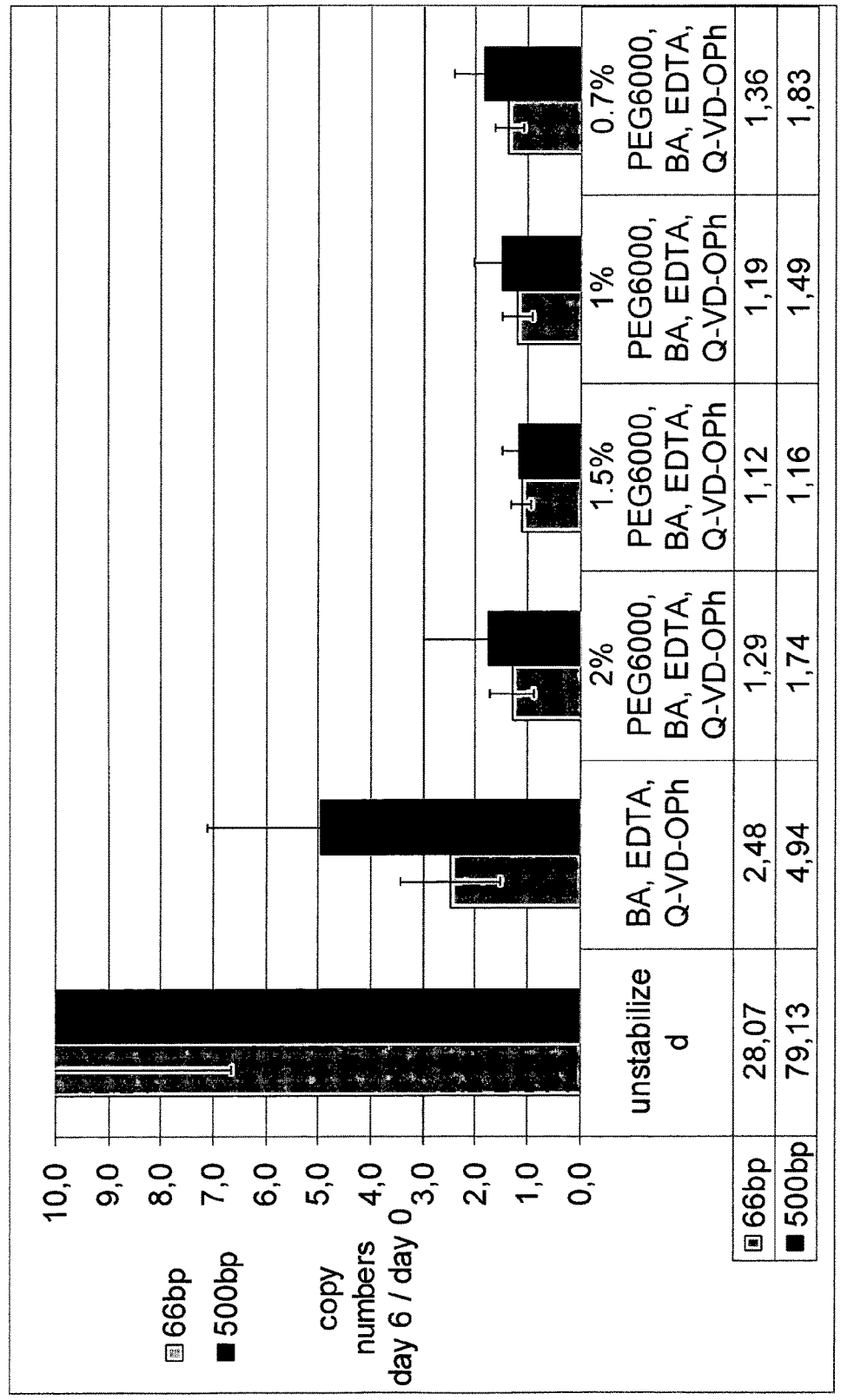
FIG. 25 shows average fold change of copy numbers of 66 bp and 500 bp fragments of the 18S rDNA gene 6 days after blood withdrawal relative to time zero in various stabilized or unstabilized blood as described in Example 6.5.

In example 6.5, decreasing concentrations of higher molecular PEG6000 were tested for their influence on the stabilization of white blood cells when applied in combination with butanamide, EDTA and a caspase inhibitor. FIG. 25 depicts the obtained stabilization result of the extracellular nucleic acid population as determined by analyzing the increase of 18S rDNA via quantitative real time PCR. All stabilization compositions according to the present invention comprising PEG show significantly lower amounts of released DNA after storage for 6 days at room temperature thereby improving the stabilization approach involving butanamide, EDTA and a caspase inhibitor during such long stabilization periods. Moreover, as can be seen, the high molecular weight polyethylene glycol can be used in different concentrations to stabilize white blood cells in aqueous solutions thereby reducing contaminations of the extracellular nucleic acid population with genomic DNA. Furthermore, it is again shown that PEG increases the stabilization effect of butanamide and the caspase inhibitor thereby providing a very effective stabilization approach.

6.6. Example 6.6

In example 6.6, the stabilization effect of PEG in an aqueous stabilization solution with different volumes and in combination with EDTA, a caspase inhibitor (Q-VD-OPh) and BA were tested. Unstabilized EDTA blood served as reference control. A composition comprising BA, DMPA, EDTA and Q-VD-OPh was tested in parallel.

Blood Collection and Stabilization

Samples of 10 ml whole blood from eight donors, collected in 10 ml spray dry K2EDTA tubes, were stabilized with mixtures of PEG6000, butanamide, EDTA and caspase inhibitor (Q-VD-OPh) in an aqueous solution with different volumes 0.8 and 1.2 ml. Plasma was directly generated from 5 ml of stabilized or unstabilized blood samples. Residual blood was stored for additional 6 days at room temperature before plasma generation. ccfDNA was purified from 2 ml plasma, copy numbers of 18S rDNA gene were determined in triplicates by real time PCR.

Composition of stabilization reagent mixtures (for 10 ml K2EDTA whole blood each):

BA, DMPA, EDTA, Q-VD-OPh: 180 mg BA, 180 µl DMPA, 68.4 mg K2EDTA, 12 µl Q-VD-OPh (1 mg dissolved in 388 µl DMSO), water ad 2 ml PEG6000, BA, EDTA, Q-VD-OPh: 112 mg PEG6000, 56 mg BA, 150 mg K2EDTA, 2.23 µl Q-VD-OPh (1 mg dissolved in 388 µl DMSO), water ad 1.2 or 0.8 ml Thereby, the following final concentrations of the different components in the mixture are obtained after contact with blood:

unstabilized: 1.8 mg/ml K2EDTA

BA, DMPA, EDTA, Q-VD-OPh: 1.5% (w/v) BA, 1.5% (v/v) DMPA, 7.2 mg/ml K2EDTA, 5 µM Q-VD-OPh

PEG6000, BA, EDTA, Q-VD-OPh ad 1.2 ml: 1% (w/v) PEG6000, 0.5% (w/v) BA, 15 mg/ml K2EDTA, 1 µM Q-VD-OPh

PEG6000, BA, EDTA, Q-VD-OPh ad 0.8 ml: 1.04% (w/v) PEG6000, 0.52% (w/v) BA, 15.6 mg/ml K2EDTA, 1.03 µM Q-VD-OPh

Results

Figure 26:
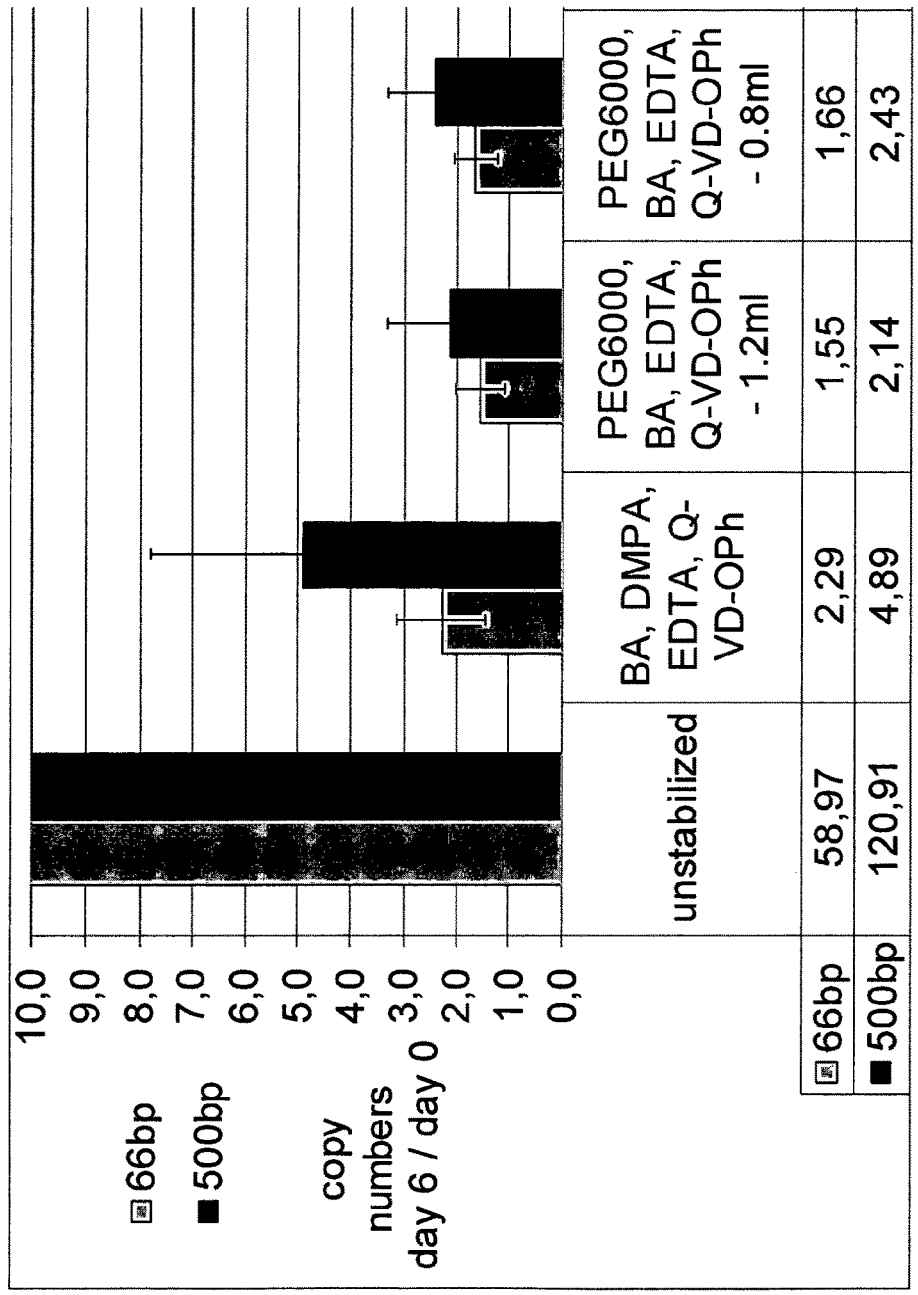
FIG. 26 shows average fold change of copy numbers of 66 bp and 500 bp fragments of the 18S rDNA gene 6 days after blood withdrawal relative to time zero in various stabilized or unstabilized blood as described in Example 6.6.

FIG. 26 shows the results of these stabilization assays. Shown is the average change of copy numbers (fold change) of DNA copies of different 18S rDNA gene amplicons (66 bp or 500 bp) in stabilized or unstabilized blood stored for 6 days at room temperature relative to time point 0 (day 0) after blood withdrawal. The results demonstrate that polyethylene glycol can be combined with different amides to stabilize white blood cells in different volumes of aqueous solutions, thereby providing stabilized blood samples wherein the extracellular nucleic acid population is preserved by preventing a dilution with intracellular nucleic acids.

6.7. Example 6.7

In example 6.7, the effect of stabilization reagents in aqueous stabilization solutions is tested by means of hemolysis assays.

Blood Collection and Stabilization

Samples of 10 ml whole blood from eight donors, collected in 10 ml spray dry K2EDTA tubes, were stabilized with mixtures of butanamide or butanamide and DMPA combined and EDTA with or without PEG with addition of water. Caspase inhibitor (Q-VD-OPh) dissolved in DMSO was added by pipetting. Plasma was directly generated from 5 ml of stabilized or unstabilized blood samples. Residual blood was stored for additional 3, 6 and 10 days at room temperature before plasma generation. Hemoglobin content was determined by measuring absorbance at 414 nm on a spectrophotometer.

Figure 27:
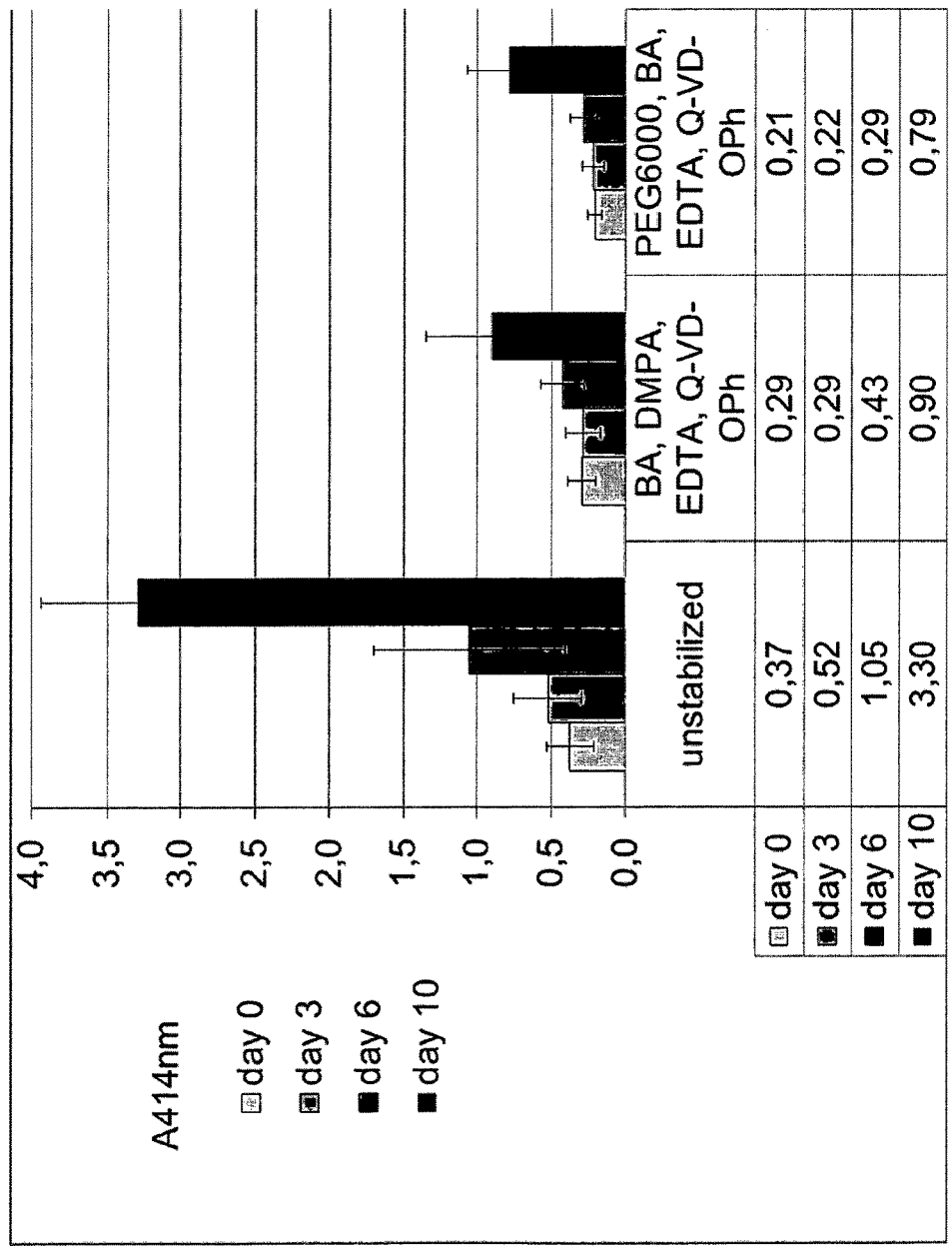
FIG. 27 shows the effect on hemolysis in plasma samples from 8 different donors after 0, 3, 6 and 10 days of storage as described in Example 6.7.

Composition of stabilization reagent mixtures (for 10 ml K2EDTA whole blood each):
  BA, DMPA, EDTA, Q-VD-OPh: 180 mg BA, 180 µl DMPA, 68.4 mg K2EDTA, 12 µl Q-VD-OPh (1 mg dissolved in 388 µl DMSO), water ad 2 ml
  PEG6000, BA, EDTA, Q-VD-OPh: 137.5 mg PEG6000, 55 mg BA, 165 mg K2EDTA, 11 µl Q-VD-OPh (1 mg dissolved in 388 µl DMSO), water ad 1.0 ml Thereby, the following final concentrations of the different components in the mixture are obtained after contact with blood:
  unstabilized: 1.8 mg/ml K2EDTA
  BA, DMPA, EDTA, Q-VD-OPh: 1.5% (w/v) BA, 1.5% (v/v) DMPA, 7.2 mg/ml K2EDTA, 5 µM Q-VD-OPh
  PEG6000, BA, EDTA, Q-VD-OPh: 1.25% (w/v) PEG6000, 0.5% (w/v) BA, 15 mg/ml K2EDTA, 5 µM Q-VD-OPh Results FIG. 27 shows the effect on hemolysis in plasma samples from 8 different donors after 0, 3, 6 and 10 days of storage. FIG. 27 depicts the average increase of hemolysis from the eight donors as increase of absorbance at 414 nm in the plasma fraction.

Whereas in EDTA control experiments hemolysis is elevated over storage time, hemolysis was reduced in the analyzed time points with the aqueous stabilization solutions according to the invention containing PEG6000 combined with EDTA and BA compared to the EDTA reference as can be seen in FIG. 27. Noteworthy, the increase of hemolysis from storage day 6 to storage day 10 seen in the EDTA control is essentially reduced in all tested solutions comprising the inventive stabilization reagent composition and water. The extent of reduced hemolysis in PEG containing aqueous solutions was comparable to the combined BA, DMPA, EDTA, caspase inhibitor (Q-VD-OPh) stabilized samples. Therefore, an aqueous stabilization composition is advantageous as it efficiently reduces hemolysis.

6.8. Example 6.8

In example 6.8 the effect of using different molecular weight PEGs (PEG300, PEG600, PEG1000, PEG3000) on the ccfDNA copy numbers is tested in combination with BA, EDTA and a caspase inhibitor (Q-VD-OPh) and compared to unstabilized EDTA control blood. A BA, DMPA, EDTA and caspase inhibitor (Q-VD-OPh) containing composition was tested in parallel.

Blood Collection and Stabilization

Samples of 10 ml whole blood from eight donors, collected in 10 ml spray dry K2EDTA tubes, were stabilized with combinations of butanamide, EDTA and caspase inhibitor (Q-VD-OPh) in an aqueous solution comprising PEG of increasing molecular weights. Plasma was directly generated from 5 ml of stabilized or unstabilized blood samples, one hour after blood collection. ccfDNA was purified from 2 ml plasma, copy numbers of 18S rDNA gene were determined in triplicates by real time PCR.

Figure 28:
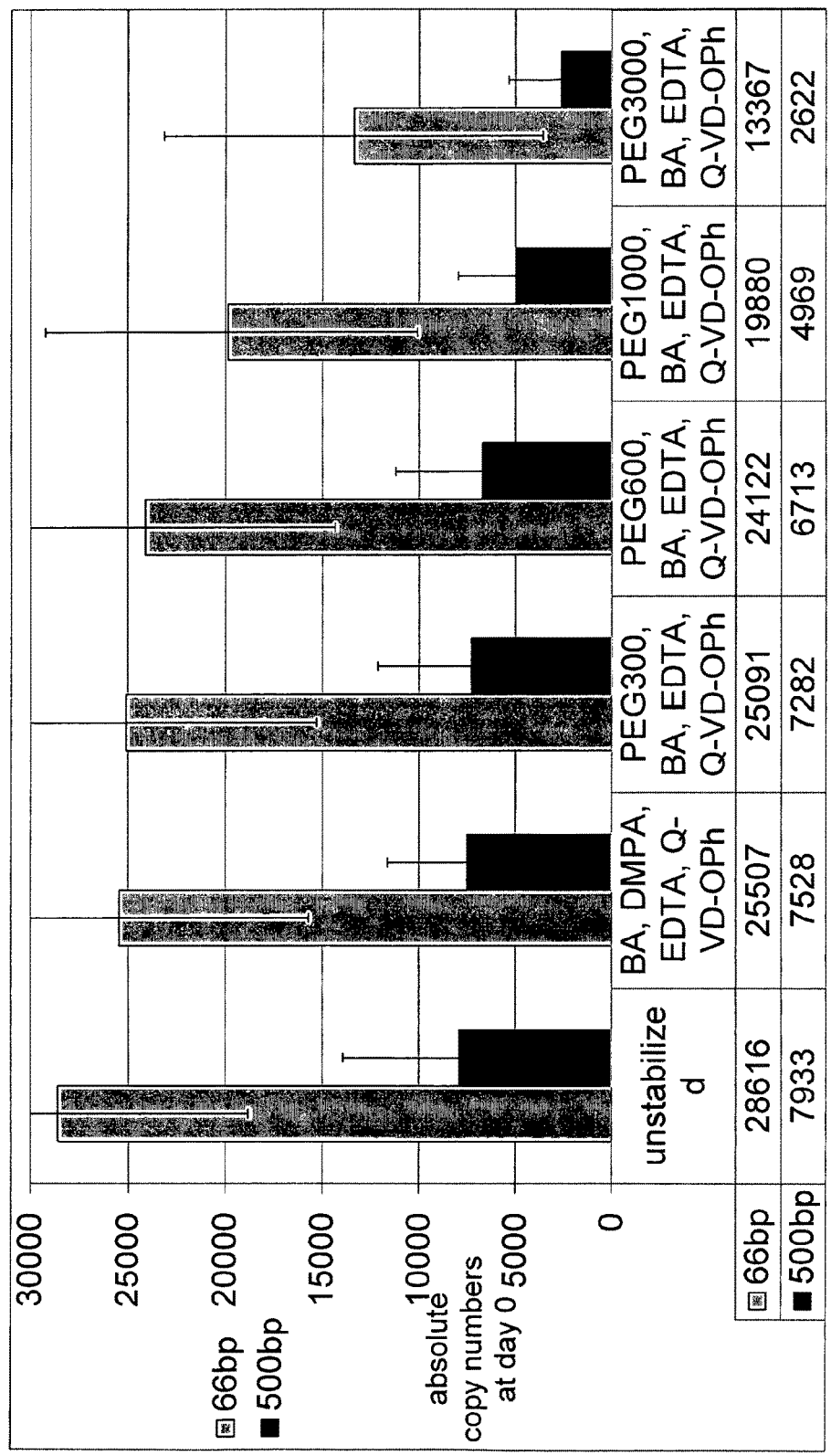
FIG. 28 shows the average of absolute copy numbers of DNA of different 18S rDNA gene amplicons (66 bp or 500 bp) in stabilized or unstabilized blood samples of 8 donors at day 0 after blood withdrawal as described in Example 6.8.

Composition of stabilization reagent mixtures (for 10 ml K2EDTA whole blood each):
  BA, DMPA, EDTA, Q-VD-OPh: 180 mg BA, 180 µl DMPA, 68.4 mg K2EDTA, 12 µl Q-VD-OPh (1 mg dissolved in 388 µl DMSO), water ad 2 ml
  PEG (300, 600, 1000 or 3000), BA, EDTA, Q-VD-OPh: 287.5 ml PEG 300 or 287.5 mg PEG (600, 1000 or 3000), 115 mg BA, 154.5 mg K2EDTA, 11.5 µl Q-VD-OPh (1 mg dissolved in 388 µl DMSO), water ad 1.5 ml Thereby, the following final concentrations of the different components in the mixture are obtained after contact with blood:
  unstabilized: 1.8 mg/ml K2EDTA
  BA, DMPA, EDTA, Q-VD-OPh: 1.5% (w/v) BA, 1.5% (v/v) DMPA, 7.2 mg/ml K2EDTA, 5 µM Q-VD-OPh
  PEG (300, 600, 1000 or 3000), BA, EDTA, Q-VD-OPh: 2.5% (v/v or w/v) PEG, 1% (w/v) BA, 15 mg/ml K2EDTA, 5 µM Q-VD-OPh Results The results of absolute quantitative real time PCR analyses from eight different donors are shown as average in FIG. 28. Particularly shown is the average of absolute copy numbers of DNA of different 18S rDNA gene amplicons (66 bp or 500 bp) in stabilized or unstabilized blood samples of the donors at day 0 after blood withdrawal. The aim was to test the effect of the used stabilization approach on the subsequent nucleic acid yield when using a silica column based nucleic acid isolation procedure. FIG. 28 shows that the addition of a higher molecular weight PEG led to a reduction of detectable amplicon gene copy numbers in plasma compared to either the EDTA reference samples (unstabilized approach) or the stabilized blood solution containing BA, DMPA, EDTA and a caspase inhibitor (Q-VD-OPh). The results indicates that for the use of PEG with increasing molecular weight or chain lengths for stabilization may lead when used in higher concentrations to a reduction of detectable ccfDNA gene copy numbers in plasma when using a silica column based nucleic acid isolation approach for isolating the extracellular nucleic acids from the stabilized samples.

6.9. Example 6.9

In example 6.9 PEG6000 was tested in different concentrations (1.0%, 1.25% or 1.5%) in in combination with BA, EDTA and a caspase inhibitor (Q-VD-OPh). An EDTA stabilized blood sample served as reference control. BA, DMPA, EDTA and a caspase inhibitor (Q-VD-OPh) containing blood mixture was analyzed in parallel.

Blood Collection and Stabilization

Samples of 10 ml whole blood from eight donors, collected in 10 ml spray dry K2EDTA tubes, were stabilized with combinations of amides (DMPA and/or BA), EDTA, caspase inhibitor (Q-VD-OPh) with or without PEG6000 in a volume of 1.5 ml to 10 ml blood with increasing concentration of PEG. Plasma was generated from 5 ml of stabilized or unstabilized blood samples, one hour after blood collection. ccfDNA was purified from 2 ml plasma, copy numbers of 18S rDNA gene were determined in triplicates by real time PCR.

Figure 29:
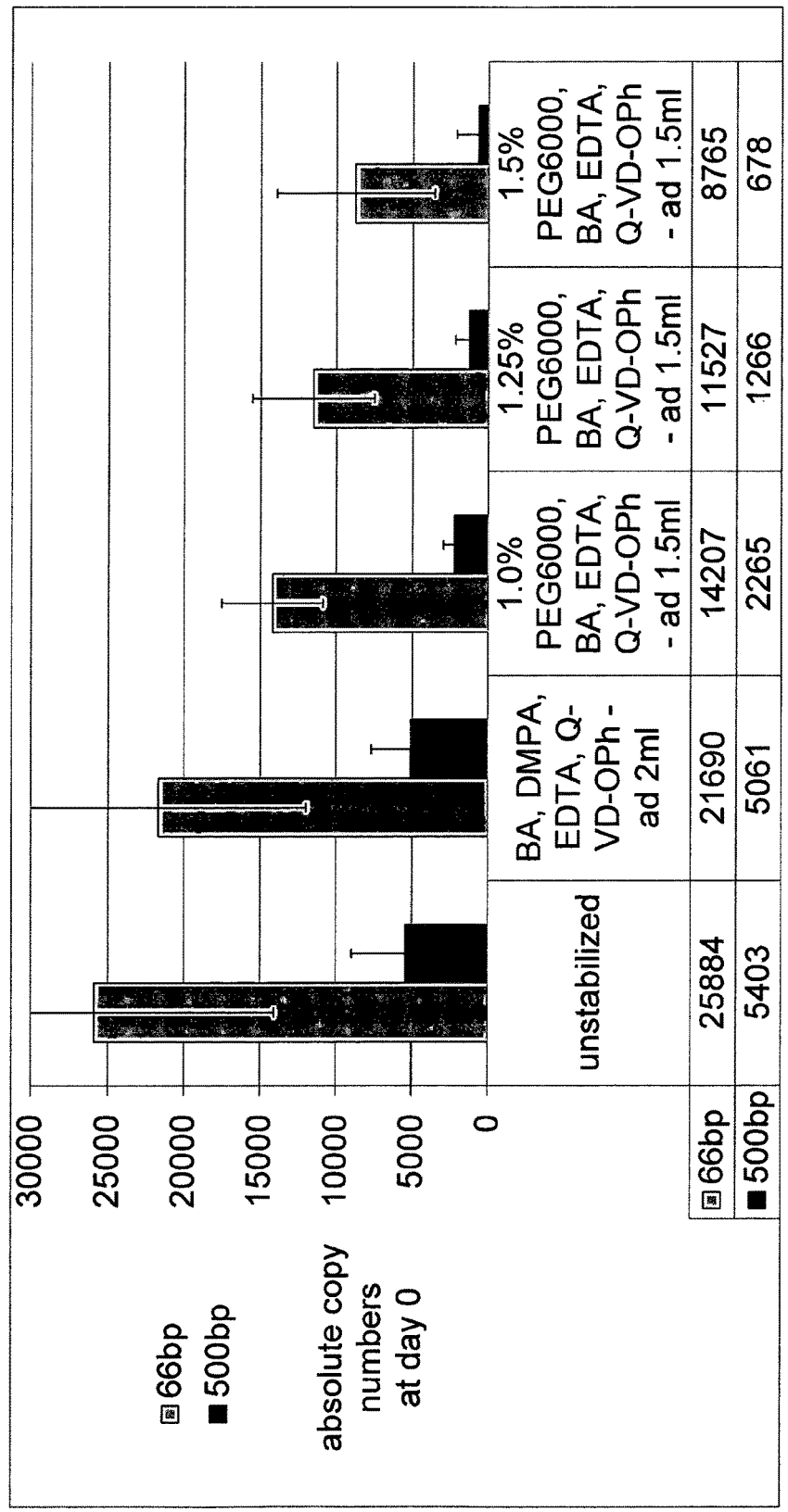
FIG. 29 shows the average decrease of absolute copy numbers of ccfDNA 0 day after blood draw from 8 donors based on different amplicon length of the 18S rDNA gene with stabilization compositions comprising PEG6000 in different concentrations (1.0%, 1.25% or 1.5%), BA, EDTA and a caspase inhibitor (Q-VD-OPh) as described in Example 6.9.

Composition of stabilization reagent mixtures for 10 ml K2EDTA whole blood each:
  BA, DMPA, EDTA, Q-VD-OPh: 180 mg BA, 180 µl DMPA, 68.4 mg K2EDTA, 12 µl Q-VD-OPh (1 mg dissolved in 388 µl DMSO), water ad 2 ml PEG6000 (1-1.5%), BA, EDTA, Q-VD-OPh-ad 1.5 ml: 115, 144 and 172 mg PEG6000, 115 mg BA, 155 mg K2EDTA, 11.5 µl Q-VD-OPh (1 mg dissolved in 388 µl DMSO), water ad 1.5 ml Thereby, the following final concentrations of the different components in the mixture are obtained after contact with blood:
unstabilized: 1.8 mg/ml K2EDTA
BA, DMPA, EDTA, Q-VD-OPh: 1.5% (w/v) BA, 1.5% (v/v) DMPA, 7.2 mg/ml K2EDTA, 5 µM Q-VD-OPh
PEG6000, BA, EDTA, Q-VD-OPh: 1, 1.25 and 1.5% (w/v) PEG6000, 1% (w/v) BA, 15 mg/ml K2EDTA, 5 µM Q-VD-OPh Results The results of example 6.9 are shown in FIG. 29. Shown is the average decrease of absolute copy numbers of ccfDNA 0 days after blood draw from 8 donors based on different amplicon length of the 18S rDNA gene with stabilization compositions according to the invention comprising PEG6000 in different concentrations (1.0%, 1.25% or 1.5%) and BA, EDTA and a caspase inhibitor (Q-VD-OPh). FIG. 29 shows that the reduction of absolute copy numbers of the 66 bp and 500 bp fragment of the 18S rDNA gene in stabilized blood-plasma containing PEG occurs in a PEG concentration dependent fashion. This demonstrates that increasing concentrations of higher molecular PEG (PEG6000) in the stabilization solution, leads to a reduction of detectable ccfDNA gene copy numbers in plasma when using a silica column based nucleic acid isolation approach.

6.10. Example 6.10

In example 6.10, the stabilization effect of different volumes of an aqueous stabilization composition comprising a high molecular weight PEG (PEG6000) in combination with BA, EDTA and a caspase inhibitor (Q-VD-OPh) was analyzed. Blood incubated with a stabilization solution comprising a combination of two amides (DMPA, BA), EDTA and a caspase inhibitor (Q-VD-OPh) was analyzed in parallel. EDTA blood served as unstabilized reference.

Blood Collection and Stabilization

Samples of 10 ml whole blood from eight donors, collected in 10 ml spray dry K2EDTA tubes, were stabilized with combinations of amides (DMPA and/or BA), EDTA, caspase inhibitor (Q-VD-OPh) with or without PEG6000 in different volumes of an aqueous solution. Plasma was generated from 5 ml of stabilized or unstabilized blood samples, one hour after blood collection. ccfDNA was purified from 2 ml plasma, copy numbers of 18S rDNA gene were determined in triplicates by real time PCR.

Figure 30:
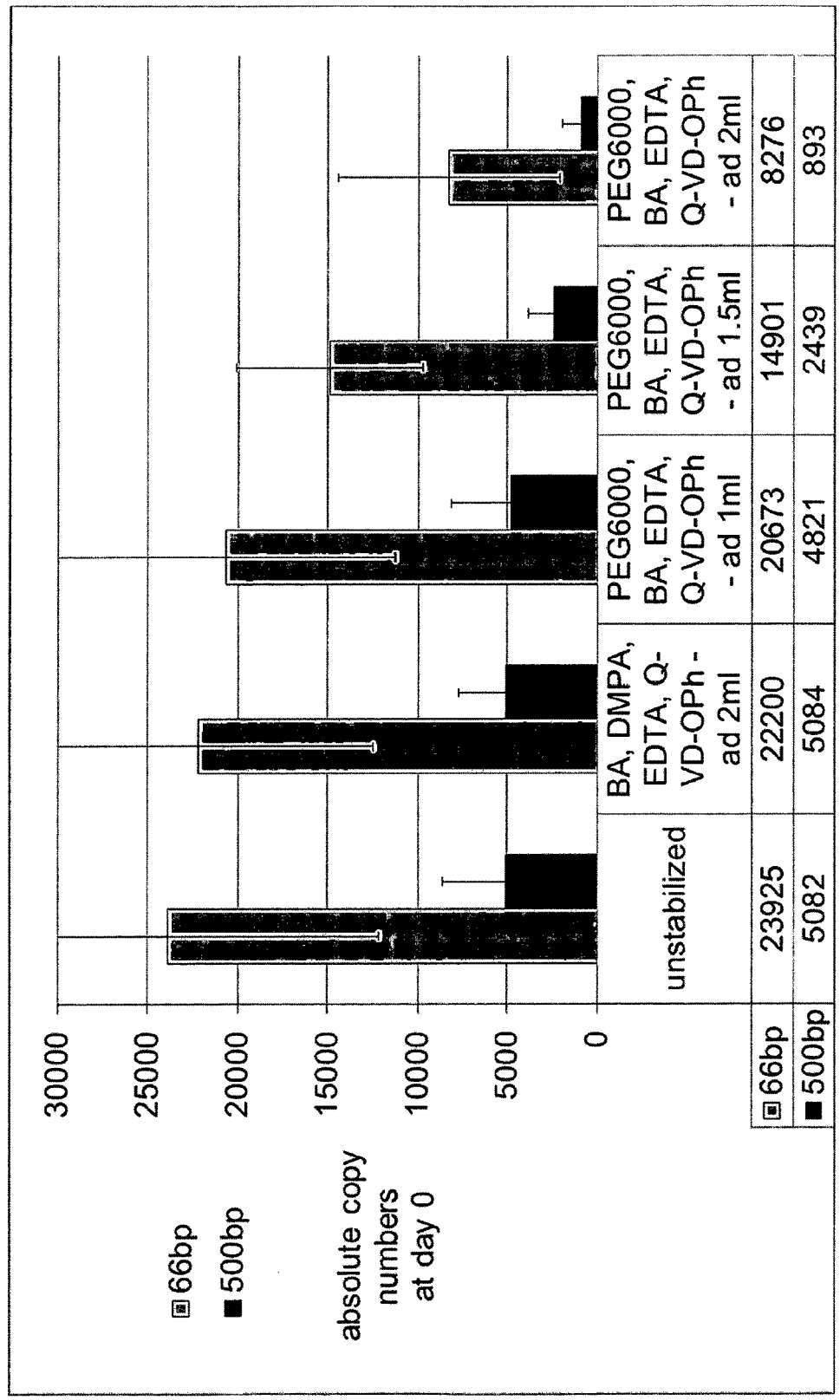
FIG. 30 shows the reduction of absolute copy numbers of the two tested fragments of the 18S rDNA gene in the stabilized samples with the increase in the stabilization reagent volume as described in Example 6.10.

Composition of stabilization reagent mixtures for 10 ml K2EDTA whole blood each:
BA, DMPA, EDTA, Q-VD-OPh: 180 mg BA, 180 µl DMPA, 68.4 mg K2EDTA, 12 µl Q-VD-OPh (1 mg dissolved in 388 µl DMSO), water ad 2 ml
PEG6000, BA, EDTA, Q-VD-OPh-ad 1 ml: 110 mg PEG6000, 110 mg BA, 147 mg K2EDTA, 11 µl Q-VD-OPh (1 mg dissolved in 388 µl DMSO), water ad 1 ml
PEG6000, BA, EDTA, Q-VD-OPh-ad 1.5 ml: 115 mg PEG6000, 115 mg BA, 155 mg K2EDTA, 11.5 µl Q-VD-OPh (1 mg dissolved in 388 µl DMSO), water ad 1.5 ml
PEG6000, BA, EDTA, Q-VD-OPh-ad 2 ml: 120 mg PEG6000, 120 mg BA, 162 mg K2EDTA, 12 µl Q-VD-OPh (1 mg dissolved in 388 µl DMSO), water ad 2 ml Thereby, the following final concentrations of the different components in the mixture are obtained after contact with blood:
unstabilized: 1.8 mg/ml K2EDTA
BA, DMPA, EDTA, Q-VD-OPh: 1.5% (w/v) BA, 1.5% (v/v) DMPA, 7.2 mg/ml K2EDTA, 5 µM Q-VD-OPh
PEG6000, BA, EDTA, Q-VD-OPh ad 1, 1.5 or 2 ml: 1% (w/v) PEG6000, 1% (w/v) BA, 15 mg/ml K2EDTA, 5 µM Q-VD-OPh Results In example 6.10, different volumes of stabilization solutions (1 ml, 1.5 ml or 2 ml) according to the invention comprising PEG6000 in combination with BA, EDTA and a caspase inhibitor (Q-VD-OPh) were tested. The results shown in FIG. 30 demonstrate that the reduction of absolute copy numbers of the two tested fragments of the 18S rDNA gene in the stabilized samples is dependent on the stabilization reagent volume. Thus, increasing the volume of the stabilization composition (and accordingly increasing the ratio of stabilization composition to blood) containing the high molecular weight PEG lead to a reduction of detectable ccfDNA gene copy numbers in plasma. The copy number was not significantly reduced when using a lower volume as in apparent from the results shown for 1 ml stabilization solution.

6.11. Example 6.11

In example 6.11 the stabilization effect of a combination of a high molecular weight PEG (0.5% PEG6000) and a low molecular weight PEG (2.5% or 5% PEG300) combined in aqueous stabilization solutions with BA, EDTA and a caspase inhibitor (Q-VD-OPh) were analyzed. Blood incubated with a stabilization solution comprising a mixture of two amides (DMPA, BA), EDTA and a caspase inhibitor (Q-VD-OPh) was co-analyzed. EDTA blood served as unstabilized reference control.

Blood Collection and Stabilization

Samples of 10 ml whole blood from eight donors, collected in 10 ml spray dry K2EDTA tubes, were stabilized with mixtures of PEG300 and PEG6000, BA, EDTA and caspase inhibitor (Q-VD-OPh) in an aqueous solution with a volume of 1.5 ml. Plasma was directly generated from 5 ml of stabilized or unstabilized blood samples. Residual blood was stored for additional 6 days at room temperature before plasma generation. ccfDNA was purified from 2 ml plasma, copy numbers of 18S rDNA gene were determined in triplicates by real time PCR.

Figure 31:
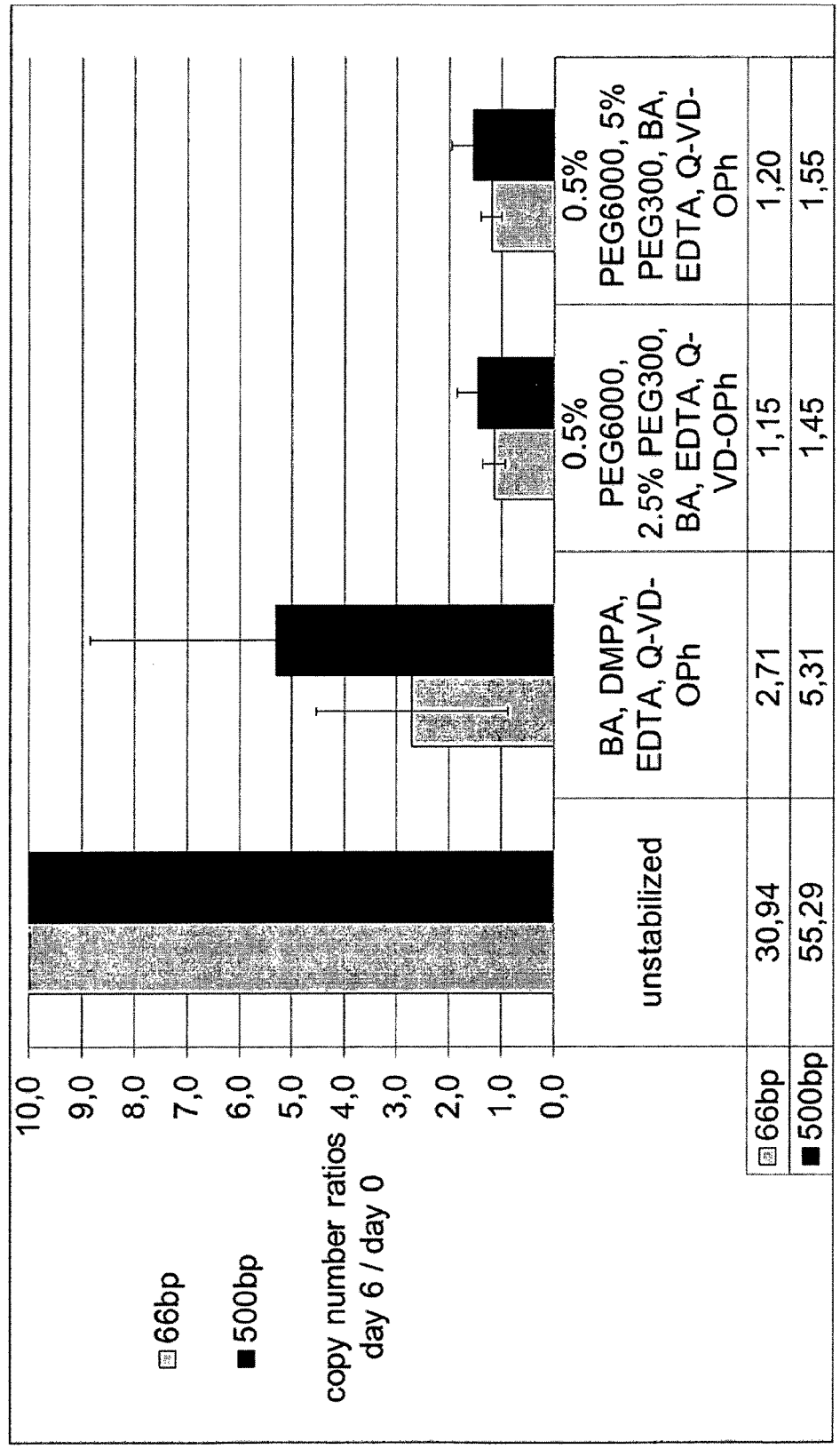
FIG. 31 shows the results of qPCR analyses from eight donors as average change of copy numbers (x fold change) of the tested 66bp or 500bp long 18S rDNA gene amplicons in stabilized or unstabilized blood from the donors stored for 6 days at room temperature to time point 0 (day 0) after blood withdrawal as described in Example 6.11.

Composition of stabilization reagent mixtures (for 10 ml K2EDTA whole blood each):
BA, DMPA, EDTA, Q-VD-OPh: 180 mg BA, 180 µl DMPA, 68.4 mg K2EDTA, 12 µl Q-VD-OPh (1 mg dissolved in 388 µl DMSO), water ad 2 ml
0.5% PEG6000, 2.5 or 5% PEG300, BA, EDTA, Q-VD-OPh-1.5 ml: 57.5 mg
PEG6000, 287.5 µl or 575 µl PEG300, 115 mg BA, 155 mg K2EDTA, 11.5 µl Q-VD-OPh (1 mg dissolved in 388 µl DMSO), water ad 1.5 ml Thereby, the following final concentrations of the different components in whole blood/stabilization mixtures were obtained:
unstabilized: 1.8 mg/ml K2EDTA
BA, DMPA, EDTA, Q-VD-OPh: 1.5% (w/v) BA, 1.5% (v/v) DMPA, 7.2 mg/ml K2EDTA, 5 µM Q-VD-OPh
PEG6000, PEG300, BA, EDTA, Q-VD-OPh-1.5 ml: 0.5% (w/v) PEG6000, 2.5 or 5% (v/v) PEG300, 1% (w/v) BA, 15 mg/ml K2EDTA, 5 µM Q-VD-OPh Results FIG. 31 shows the results of qPCR analyses from eight donors as average change of copy numbers (x fold change) of the tested 66 bp or 500 bp long 18S rDNA gene amplicons in stabilized or unstabilized blood from the donors stored for 6 days at room temperature to time point 0 (day 0) after blood withdrawal. Whereas the unstabilized EDTA blood control manifested an elevation in average fold change in copy numbers, all stabilization compositions containing PEG showed only a low increase with respect to the average x fold change of 18S rDNA gene amplicons copy numbers. The results indicate a similar stabilization capability of the tested PEG containing stabilization compositions. The achieved stabilization increased the stabilization compositions comprising BA, DMPA, EDTA and the caspase inhibitor thereby again demonstrating the important advantages that are achieved when using polyethylene glycol in addition.

Figure 32:
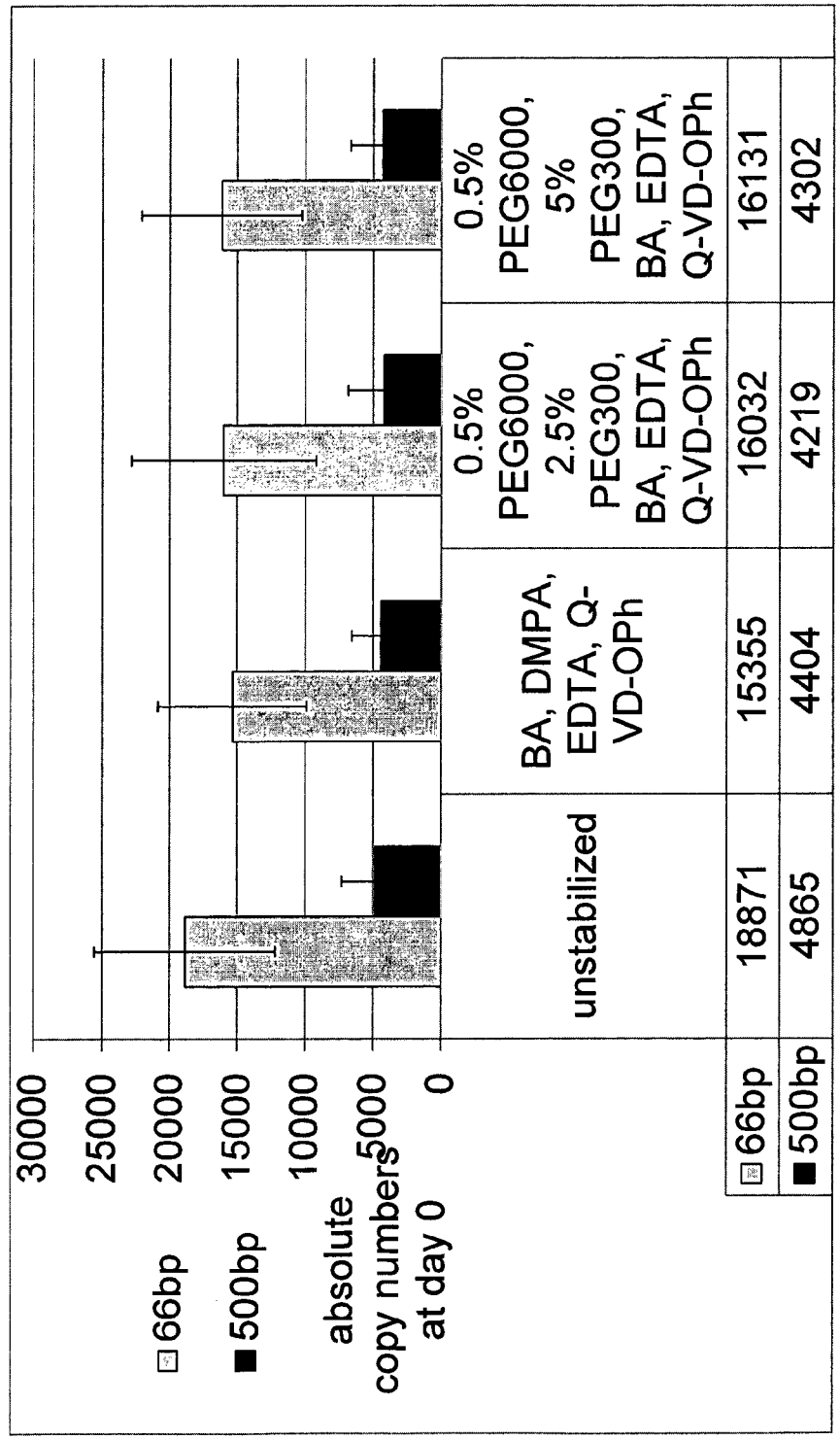
FIG. 32 shows the change of absolute copy numbers of 18S rDNA amplicons at day 0 in plasma after blood draw as described in Example 6.11.

Additionally, it was confirmed that the described advantageous stabilization capability of the used stabilization solutions with combinations of high and low molecular weight PEG is not accompanied by a reduction of ccfDNA copy numbers. This was analyzed by testing the same solutions for change of absolute copy numbers of 18S rDNA amplicons at day 0 in plasma after blood draw. FIG. 32 shows the obtained results. The obtained absolute copy number was similar to the stabilization composition comprising BA, DMPA, EDTA and the caspase inhibitor. Therefore, no significant reduction in the absolute ccfDNA copy number was detected in this assay. Thus, combinations of different molecular weight PEGs, particularly of a high and low molecular weight PEG can be combined in different volumes of aqueous solutions containing BA to effectively stabilize the extracellular nucleic acid population of blood samples, in particular by stabilizing white blood cells without significant reduction of absolute ccfDNA copy numbers when using a standard nucleic acid isolation procedure involving a silica membrane.

6.12. Example 6.12

In example 6.12, the effect of aqueous stabilization solutions was tested by hemolysis assays. Here, a combination of a high molecular weight PEG (0.5% PEG6000) and a low molecular weight PEG (2.5% or 5% PEG300) in combination with BA, EDTA and a caspase inhibitor (Q-VD-OPh) was analyzed. Blood incubated with a stabilization solution comprising a mixture of two amides (DMPA, BA), EDTA and a caspase inhibitor (Q-VD-OPh) was co-analyzed. EDTA blood served as unstabilized reference control.

Blood Collection and Stabilization

Samples of 10 ml whole blood from eight donors, collected in 10 ml spray dry K2EDTA tubes, were stabilized with mixtures of PEG300 and PEG6000, BA, EDTA and caspase inhibitor (Q-VD-OPh) in an aqueous solution with a volumes of 1.5 ml. Plasma was directly generated from 5 ml of stabilized or unstabilized blood samples. Residual blood was stored for additional 6 days at room temperature before plasma generation. Hemoglobin content was determined by measuring absorbance at 414 nm on a spectrophotometer.

Figure 33:
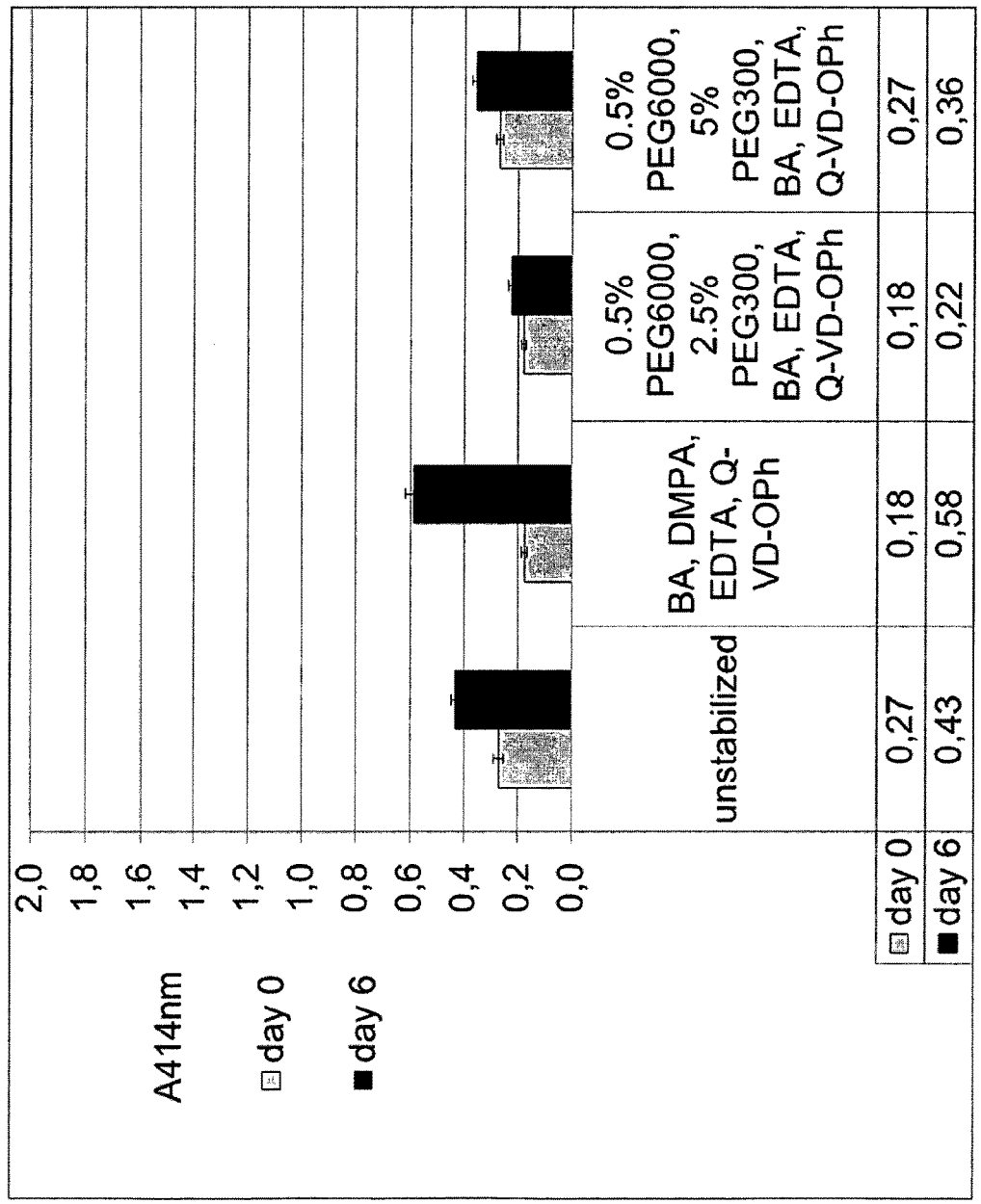
FIG. 33 shows the change in hemolysis (increase of absorption at 414 nm) after 6 days of blood sample storage compared to the initial time point at 0 day after storage under unstabilized or various stabilized conditions as described in Example 6.12.

Composition of stabilization reagent mixtures (for 10 ml K2EDTA whole blood each):
  BA, DMPA, EDTA, Q-VD-OPh: 180 mg BA, 180 µl DMPA, 68.4 mg K2EDTA, 12 µl Q-VD-OPh (1 mg dissolved in 388 µl DMSO), water ad 2 ml
  0.5% PEG6000, 2.5 or 5% PEG300, BA, EDTA, Q-VD-OPh: 57.5 mg PEG6000, 287.5 µl or 575 µl PEG300, 115 mg BA, 155 mg K2EDTA, 11.5 µl Q-VD-OPh (1 mg dissolved in 388 µl DMSO), water ad 1.5 ml Thereby, the following final concentrations of the different components in whole blood/stabilization mixtures were obtained:
  unstabilized: 1.8 mg/ml K2EDTA
  BA, DMPA, EDTA, Q-VD-OPh: 1.5% (w/v) BA, 1.5% (v/v) DMPA, 7.2 mg/ml K2EDTA, 5 µM Q-VD-OPh
  PEG6000, PEG300, BA, EDTA, Q-VD-OPh: 0.5% (w/v) PEG6000, 2.5 or 5% (v/v) PEG300, 1% (w/v) BA, 15 mg/ml K2EDTA, 5 µM Q-VD-OPh Results FIG. 33 shows the effect of the analyzed aqueous solutions comprising different molecular PEGs with BA on hemolysis in plasma samples from 8 different donors after 0 and 6 days of blood storage after draw. FIG. 33 shows the increase of hemolysis as increase of absorbance at 414 nm in the plasma fraction after 0 and 6 days of blood storage.

As can be seen in FIG. 33, EDTA control experiments reveal an increase in hemolysis (increase of absorption at 414 nm) after 6 days of blood sample storage compared to the initial time point at 0 days after storage. With the stabilization compositions comprising mixtures of 0.5% PEG6000 (higher molecular PEG) and a PEG300 concentration of 5% (lower molecular PEG) in combination with EDTA, caspase inhibitor (Q-VD-OPh) and BA, hemolysis was similar to the EDTA reference sample. In contrast, a stabilization composition according to the present invention using lower concentrations of PEG300 (here: 2.5%) in combination with 0.5% PEG6000, EDTA, caspase inhibitor (Q-VD-OPh) and BA reduced hemolysis following blood storage for 6 days. This demonstrates that hemolysis may be prevented in stabilization compositions containing a balanced composition of high and low molecular weight PEG when dissolved in an aqueous solution.

6.13. Example 6.13

A stabilization composition comprising PEG6000, BA, EDTA and a caspase inhibitor (Q-VD-OPh) pre-filled in vacuumized blood collection tubes (Alpha tubes) was compared to commercially available Streck Cell-Free DNA BCT tubes which comprise a stabilization composition that is based on the use of a formaldehyde releaser as stabilizing agent.

Blood Collection and Stabilization

Samples of 10 ml whole blood from eight donors were collected in 10 ml spray dry K2EDTA, Alpha tubes pre-filled with amounts of stabilization composition of the invention comprising PEG6000, EDTA, a caspase inhibitor (Q-VD-OPh) and BA in Streck Cell-Free DNA BCT tubes. Plasma was directly generated from 5 ml of stabilized or unstabilized blood samples. Residual blood was stored for additional 3, 6 and 10 days at room temperature before plasma generation. ccfDNA was purified from 2 ml plasma, copy numbers of 18S rDNA gene were determined in triplicates by real time PCR.

Composition of stabilization reagent mixtures in different tubes (all with a draw volume of 10 ml blood):
  EDTA-10 ml spray dried EDTA
  Alpha1-Tube (PEG6000, BA, EDTA, Q-VD-OPh): 137.5 mg PEG6000, 55 mg BA, 165 mg K2EDTA, 11 µl Q-VD-OPh (1 mg dissolved in 388 µl DMSO), water ad 1.0 ml Streck Cell-Free DNA BCT tube: comprises a formaldehyde releaser as stabilizer Thereby, the following final concentrations of the different components in whole blood/stabilization mixtures were obtained:

EDTA tube: 1.8 mg/ml K2EDTA

Figure 34:
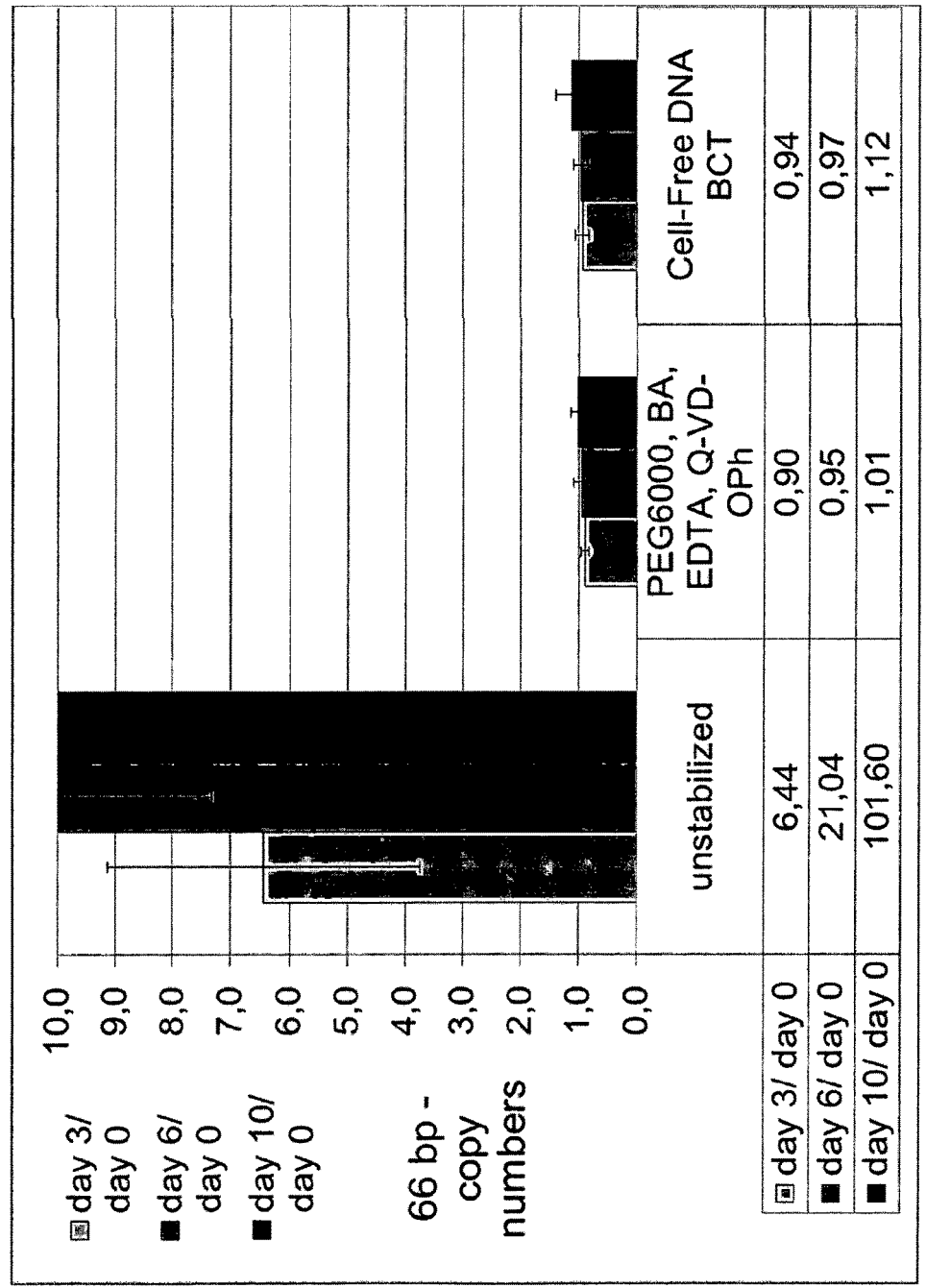
FIG. 34 shows the average change in copy numbers (x fold change) of 66 bp fragment of the 18S rDNA gene in stabilized or unstabilized blood from 8 donors stored for 3, 6 or 10 days at room temperature relative to time point 0 (day 0) after blood draw from the eight blood donors as described in Example 6.13.
Figure 35:
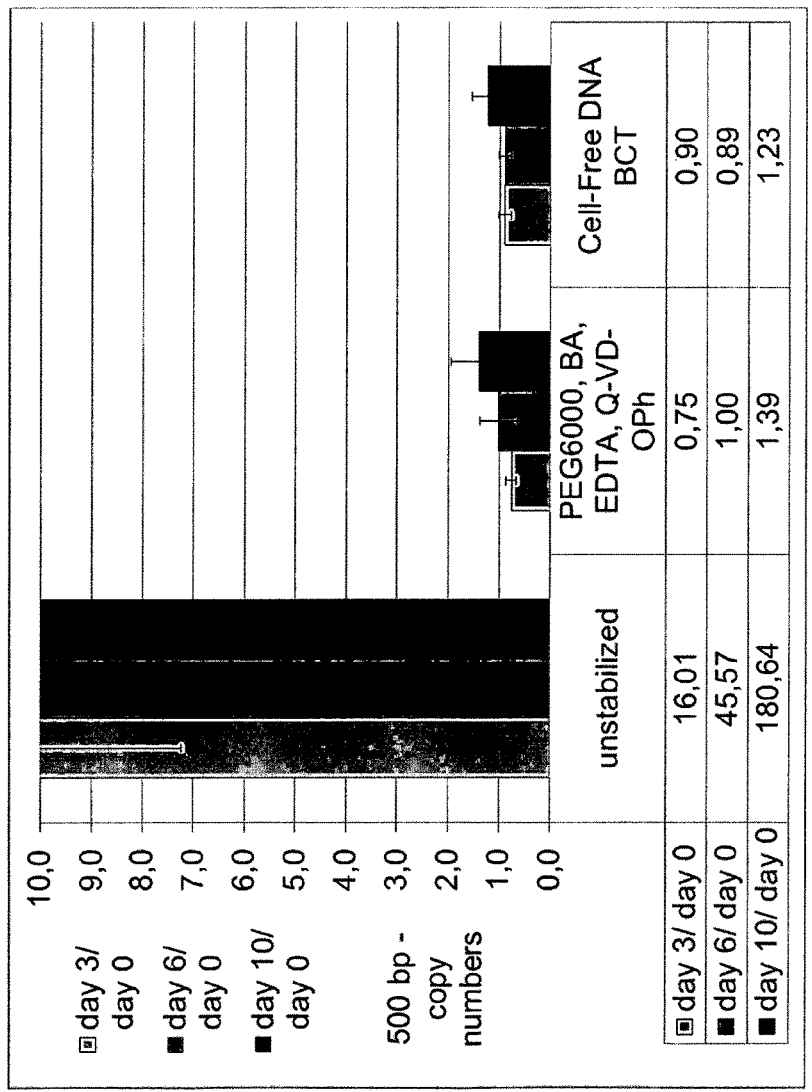
FIG. 35 shows the average change in copy numbers (x fold change) of 500 bp fragment of the 18S rDNA gene in stabilized or unstabilized blood from 8 donors stored for 3, 6 or 10 days at room temperature relative to time point 0 (day 0) after blood draw from the eight blood donors as described in Example 6.13.

Alpha1-tube (PEG6000, BA, EDTA, Q-VD-OPh): 1.25% (w/v) PEG6000, 0.5% (w/v) BA, 15 mg/ml K2EDTA, 5 µM Q-VD-OPh Streck Cell-Free DNA BCT tube: concentrations not applicable Results The results are shown in FIGS. 34 and 35. The average change in copy numbers (x fold change) of 66 bp fragment (FIG. 34) and 500 bp fragment (FIG. 35) of the 18S rDNA gene in stabilized or unstabilized blood from 8 donors stored for 3, 6 or 10 days at room temperature relative to time point 0 (day 0) after blood draw from the eight blood donors was analyzed. Bars indicate the corresponding standard deviation of the average fold change of the copy numbers from the eight donors per condition. As shown in FIGS. 34 and 35, both tested stabilization compositions comprising PEG6000, EDTA, a caspase inhibitor (Q-VD-OPh) and BA are highly efficient in stabilizing the extracellular nucleic acid population in blood. The average fold change of copy numbers of the 66 bp fragment of the 18S rDNA stayed on the basal level of time point zero for all tested time points (fold change at around 1.0). FIG. 35 shows comparable results for the 500 bp fragment levels of the 18S rDNA gene i.e. the test fragment for cellular nucleic acids released during cell breakage substantially stayed at the status of time point zero over the tested time period. This stabilization effect was comparable to the results where Streck Cell-Free DNA BCT tubes were used. Thus, the stabilization composition according to the present invention efficiently stabilizes the extracellular nucleic acid population in a blood sample by reducing the release from intracellular nucleic acids such as in particular genomic DNA from white blood cells similar to Streck Cell-Free DNA BCT tubes which comprise formaldehyde releasers. However, as explained above, the use of formaldehyde-releasing substances has drawbacks, as they compromise the efficacy of extracellular nucleic acid isolation by induction of cross-links between nucleic acid molecules or between proteins and nucleic acids. Therefore, specific nucleic acid isolation methods must be used. The stabilization composition according to the invention which does not involve the use of such cross-linking substances has important advantages over cross-linking based stabilization techniques.

The invention claimed is:

1. A method for stabilizing and treating an extracellular nucleic acid population comprised in a cell-containing biological sample, comprising:
   a) stabilizing the cell-containing biological sample by contacting the cell-containing biological sample with butanamide; and
   b) analyzing, detecting and/or further processing the extracellular nucleic acids either with or without previous isolation of the extracellular nucleic acids.

2. The method according to claim 1, comprising additionally contacting the cell-containing biological sample with a caspase inhibitor.

3. The method according to claim 1, comprising additionally contacting the cell-containing biological sample with at least one compound according to formula 1

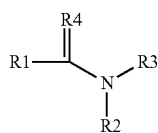

formula 1 wherein R1 is a hydrogen residue or an alkyl residue, R2 and R3 are identical or different and are selected from a hydrogen residue and a hydrocarbon residue with a length of the carbon chain of 1-20 atoms arranged in a linear or branched manner, and R4 is an oxygen, sulphur or selenium residue.

4. The method according to claim 3, wherein the compound according to formula 1 has one or both of the following characteristics:
   (i) it is a N,N-dialkylpropanamide;
   (ii) it is N,N-dimethylpropanamide.

5. The method according to claim 1, wherein after contacting the cell-containing biological sample with butanamide and optionally further additives used for stabilization, the resulting mixture comprises butanamide in a concentration range of 0.25% (w/v) to 15% (w/v), 0.5% (w/v) to 12.5% (w/v), 0.75% (w/v) to 10% (w/v), 1% (w/v) to 9% (w/v), 1.25% (w/v) to 8% (w/v), 1.5% (w/v) to 7% (w/v), 1.75% (w/v) to 6% (w/v), 1.8% (w/v) to 5.5% (w/v), 1.9% (w/v) to 5.25% (w/v), 2% (w/v) to 5% (w/v), 2.1% (w/v) to 4.75% (w/v), 2.2% (w/v) to 4.5% (w/v), 2.3% (w/v) to 4.25% (w/v), 2.4% (w/v) to 4% (w/v), 2.5% (w/v) to 3.75% (w/v) or 0.75% (w/v) to 2% (w/v).

6. The method according to claim 2, comprising contacting for stabilization the cell-containing sample with
   A) a stabilizing composition comprising:
   a) butanamide;
   b) at least one pancaspase inhibitor;
   or
   B) a stabilizing composition comprising:
   a) butanamide;
   b) at least one pancaspase inhibitor; and
   c) at least one compound according to formula 1 and/or
   d) an anticoagulant;
   or
   C) a stabilizing composition comprising:
   a) butanamide;
   b) at least one pancaspase inhibitor; and
   c) a N,N-dialkylpropanamide and/or
   d) EDTA.

7. The method according to claim 1, wherein the stabilizing (i) does not involve use of additives in a concentration wherein said additives would induce or promote lysis of nucleated cells, (ii) wherein the stabilizing does not involve use of a cross-linking agent that induces protein-nucleic acid and/or protein-protein crosslinks and/or (iii) wherein the stabilizing does not involve use of toxic agents.

8. The method according to claim 3 for stabilizing an extracellular nucleic acid population comprised in a blood sample, comprising contacting the blood sample with butanamide, at least one caspase inhibitor, at least one compound according to formula 1 and an anticoagulant, wherein the release of genomic DNA from cells contained in the blood sample into the cell-free portion of the blood sample is reduced.

9. The method according to claim 1, comprising additionally contacting the cell-containing biological sample with at least one poly(oxyethylene) polymer.

10. The method according to claim 9, wherein:
a) the poly(oxyethylene) polymer is polyethylene glycol;
b) the poly(oxyethylene) polymer is a high molecular weight poly(oxyethylene) polymer having a molecular weight in a range of 1500 to 40000 or 3000 to 20000;
c) at least two poly(oxyethylene) polymers are used for stabilization which differ in their molecular weight, wherein the difference in the molecular weight is at least 100 or at least 500; and/or
d) the poly(oxyethylene) polymer is a high molecular weight poly(oxyethylene) polymer having a molecular weight in a range of 1500 to 40000 and the method comprises additionally contacting the cell-containing biological sample with a low molecular weight poly (oxyethylene) having a molecular weight in a range of 100 to 1000.

11. The method according to claim 1, wherein after the stabilizing, the method comprises one or more of the following:
a) the stabilized sample is subjected to a nucleic acid analysis and/or detection method;
b) extracellular nucleic acids are isolated from the stabilized sample and the isolated nucleic acids are analysed and/or detected;
c) cells comprised in the stabilized sample are removed;
d) cells comprised in the stabilized sample are removed prior to performing an nucleic acid isolation, analysis and/or detection step;
e) cells are removed from the stabilized sample and extracellular nucleic acids are isolated from the cell-free or cell-depleted portion of the stabilized sample;
f) (i) the stabilized sample, (ii) the stabilized sample from which cells have been removed and/or (iii) cells removed from the sample are stored;
g) cells are removed from the stabilized sample and are discarded; and/or
h) cells are removed from the stabilized sample and nucleic acids are isolated from cells that were removed from the stabilized sample;
i) cells are removed from the stabilized sample and extracellular nucleic acids are isolated from the cell-free or cell-depleted portion of the stabilized sample using a size selective nucleic acid isolation method.

12. The method according to claim 1, comprising removing cells from the cell-containing biological sample between step a) and step b) to yield a cell-free or cell-depleted portion of the stabilized sample and wherein step b) comprises isolating extracellular nucleic acids from the cell-free or cell-depleted portion of the stabilized sample.

13. The method according to claim 1, comprising isolating extracellular nucleic acids in step b) and processing and/or analyzing the isolated extracellular nucleic acids in a further step c).

14. A method for isolating extracellular nucleic acids from a cell-containing biological sample comprising the steps of
a) stabilizing the cell-containing biological sample by contacting the cell-containing biological sample with butanamide; and
b) isolating extracellular nucleic acids from the cell-containing biological sample stabilized in step a).

\* \* \* \* \*